US007067629B2

(12) United States Patent
Dib-Hajj et al.

(10) Patent No.: US 7,067,629 B2
(45) Date of Patent: Jun. 27, 2006

(54) SODIUM CHANNEL IN DORSAL ROOT GANGLIA

(75) Inventors: Sulayman Dib-Hajj, East Lyme, CT (US); Stephen G. Waxman, New Haven, CT (US)

(73) Assignee: Yale University, New Haven, CT (US)

( * ) Notice: Subject to any disclaimer, the term of this patent is extended or adjusted under 35 U.S.C. 154(b) by 559 days.

(21) Appl. No.: 10/388,470

(22) Filed: Mar. 17, 2003

(65) Prior Publication Data

US 2003/0228662 A1    Dec. 11, 2003

Related U.S. Application Data

(60) Division of application No. 09/354,147, filed on Jul. 16, 1999, now Pat. No. 6,573,067, which is a continuation-in-part of application No. PCT/US99/02008, filed on Jan. 29, 1999.

(60) Provisional application No. 60/072,990, filed on Jan. 29, 1998, provisional application No. 60/109,402, filed on Nov. 20, 1998, provisional application No. 60/109,666, filed on Nov. 20, 1998.

(51) Int. Cl.
*C07K 14/00* (2006.01)

(52) U.S. Cl. ...................... 530/350; 435/69.1; 435/325; 536/23.5

(58) Field of Classification Search ...................... None
See application file for complete search history.

(56) References Cited

U.S. PATENT DOCUMENTS 6,184,349 B1   2/2001   Herman et al. ............. 530/350

FOREIGN PATENT DOCUMENTS

GB    2 332 906     7/1999
WO    WO97/01577    1/1997
WO    WO99/47670    9/1999

OTHER PUBLICATIONS

Arbuckel et al. (1995) Expression of tetrodotoxin-resistant sodium channels in capsaicin-sensitive dorsal root ganglion neurons of adult rats, Neurosci. Lett. 185:70-73.
Dib-Hajj et al., (1998) NaN, a novel voltage-gated Na channel, is expressed preferentially in peripheral sensory neurons and down-regulated after axotomy, Proc. Natl. Acad. Sci. USA 95:8963-8968.
Rush et al. (1997) Phenytoin and carbamazepine: differential inhibition of sodium currents in small cells from adult rat dorsal root ganglia, Neurosci. Lett. 226:95-98.
Tate et al., (1998) Two sodium channels contribute to the TTX-R sodium current in primary sensory neurons, Nat. Neurosci. 1:653-655.

Waxman et al., (1996) Expression of mRNA for sodium channel in subfamily 2 in spinal sensory neurons, Neurochem. Res. 21:395-401.
Akopian, A.N. et al., "A tetrodotoxin-resistant voltage-gated sodium channel expressed by sensory neurons," Nature, 379: 257-262, 1996.
Akopian, A.N. et al, "Structure and distribution of a broadly expressed atypical sodium channel," FEBS Letters, 400: 183-187, 1997.
Beckh, S. et al, "Differential regulation of three sodium channel messenger RNA's in the rat central nervous system during development," EMBO J., 8: 3611-3616, 1989.
Black, J.A. et al., "Sodium channel mRNAs in cultured spinal cord astrocytes: in situ hybridization in identified cell types," Molecular Brain Research, 23: 235-245, 1994.
Cannon, S.C., "Ion-channel defects and aberrant excitability in myotonia and periodic paralysis," Trends Neurosci., 19(1): 3-10, 1996.
Cannon, S.C., "From mutation to myotonia in sodium channel disorders," Neuromuscul. Disord. 7: 241-249, 1997.
Catterall, W.A., "Structure and function of voltage-gated ion channels," Trends Neurosci., 16(12):500-508, 1993.
Cummins, T.R. et al., "Downregulation of tetrodotoxin-resistant currants and upregulation of a rapidly repriming tetrodotoxin-sensitive sodium current in small spinal sensory neurons after nerve injury," J. Neuroscience, 17: 3503-3514, 1997.
Dib-Hajj, S., "Down-regulation of transcripts for Na channel α-SNS in spinal sensory neurons following axotomy," Proc. Natl. Acad. Sci. USA, 93: 14950-14954, 1996.
Dib-Hajj, S.D. et al., "Insertion of a SNS-specific tetrapeptide in S3-S4 linker of D4 accelerates recovery from inactivation of skeletal muscle voltage-gated Na Channel μ1 in HEK 293 cells," FEBS Letters 416: 11-14, 1997.
England, S., "$PGE_2$ modulates the tetrodotoxin-resistant sodium current in neonatal rat dorsal root ganglion neurones via the cyclic AMP-protein kinase cascade," J. Physiology 495(2): 429-440, 1996.
Felipe, A. et al., "Primary structure and differential expression during development and pregnancy of a novel voltage-gated sodium channel in the mouse," J. Biol. Chem., 269: 30125-30131, 1994.

(Continued)

*Primary Examiner*—Michael Pak
(74) *Attorney, Agent, or Firm*—Morgan, Lewis & Bockius LLP

(57) ABSTRACT

A novel tetrodotoxin resistant sodium channel is described, along with isolated nucleotides that encode this receptor. Methods for identifying agents that modulate the $Na^+$ current through the receptor are provided, as well as related therapeutic and diagnostic methods.

19 Claims, 28 Drawing Sheets

OTHER PUBLICATIONS

Figure 4:
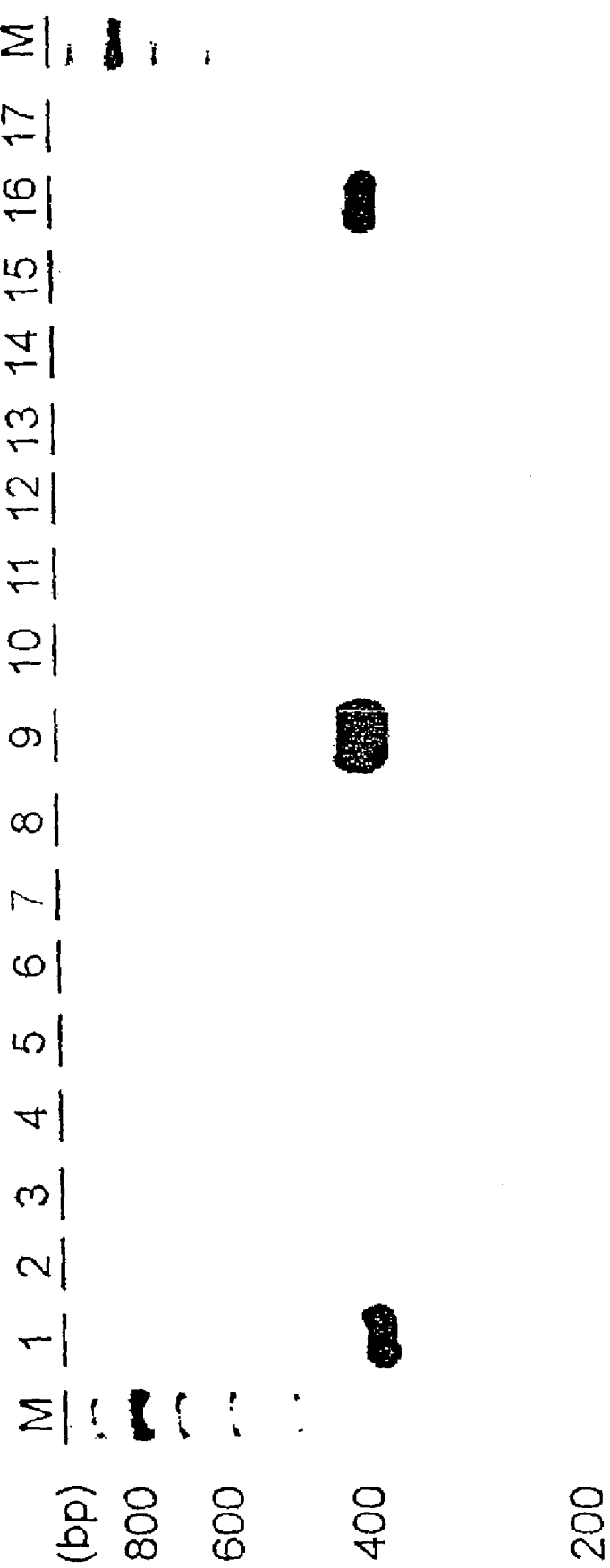

Fjell, J. et al., "Differential expression of sodium channel genes in retinal ganglion cells," Molecular Brain Research, 50: 197-204, 1997.

George, A.L., Jr. et al., "Genomic organization of the human skeletal muscle sodium channel gene," Genomics, 15: 598-606, 1993.

Gold, M.S. et al., "Hyperalgesic agents increase a tetrodotoxin-resistant $Na^+$ current in nociceptors," Proc. Natl. Acad. Sci. USA, 93: 1108-1112, 1996.

Goldin, A.L., Handbook of receptors and channels, pp. 73-100, North, R.A., Ed., CRC press, Boca Raton, FL, 1995.

Gu, X.Q., "TTX-sensitive and -resistant Na+ currents, and mRNA for the TTX-resistant rH1 channel, are expressed in B104 neuroblastoma c1ells," J. Neurophysiology, 77: 236-246, 1997.

Mandel, G., "Tissue-specific expression of the voltage-sensitive sodium channel," J. Membrane Biology, 125: 193-205, 1992.

McClatchey, A.I., "The genomic structure of the human skeletal muscle sodium channel gene," Hum. Mol. Genet., 1(7): 521-527, 1992.

Ptáček, L.J., "Channelopathies: ion channel disorders of muscle as a paradigm for paroxysmal disorders of the nervous system," Neuromuscul. Disord., 7: 250-255, 1997.

Rizzo, M.A. et al., "Slow sodium conductances of dorsal root ganglion neurons: intraneuronal homogeneity and interneuronal heterogeneity," J. Neurophysiology, 72(6): 2796-2815, 1994.

Rizzo, M.A. et al.,"Selective loss of slow and enhancement of fast $Na^+$currents in cutaneous afferent dorasal root ganglion neurones following axotomy," Neurobiol. Dis., 2: 87-96, 1995.

Rizzo, M.A., et al., "Mechanisms of paresthesiae, dysesthesia, and hyperesthesiae: role of Na+ channel heterogeneity," European Neurology, 36: 3-12, 1996.

Roden, D.M. et al., "Structure and function of cardiac sodium and potassium channels," Am. J. Physiol., 273: H511-525, 1997.

Sangameswaran, L. et al., "Structure and function of a novel voltage-gated, tetrodotoxin-resistant sodium channel specific to sensory neurons," J. Biol. Chem., 271(11): 5953-5956, 1996.

Sontheimer, H. et al., "Astrocyte $Na^+$ channels are required for maintenance of $Na^+/K^+$-ATPase activity," J. Neuroscience, 14(5): 2464-2475, 1994.

Sontheimer, H. et al., "Ion channels in spinal cord astrocytes in vitro. II. Biophysical and pharmacological analysis of two $Na^+$ current types," J. Neurophysiology, 68(4): 1001-1011. 1992.

Souslova, V.A. et al., "Cloning and characterization of a mouse sensory neuron tetrodotoxin-resistant voltage-gated sodium channel gene, Scn10a," Genomics, 41: 201-209, 1997.

Wang, Q. et al., "Genomic organization of the human SCN5A gene encoding the cardiac sodium channel," Genomics, 34: 9-16, 1996.

Waxman, S.G., et al., "Type III sodium channel mRNA is expressed in embryonic but not adult spinal sensory neurons, and is reexpressed following axotomy," J. Neurophysiology, 72: 466-470, 1994.

Zur, K.B. et al., "Differential up-regulation of sodium channel α- and β1-subunit mRNAs in cultured embryonic DGR neurons following exposure to NGF," Molecular Brain Research, 30: 97-105, 1995.

FIG. 1A

Nucleotide sequence of rat NaN. Translation initiation begins at position 41 (ATG). Reading frame ends at position 5336 (TGA).

```
   1  ACGGTGCCCT GATCCTCTGT ACCAGGAAGA CAGGGTGAAG ATGGAGGAGA
  51  GGTACTACCC GGTGATCTTC CCGGACGAGC GGAATTTCCG CCCCTTCACT
 101  TCCGACTCTC TGGCTGCCAT AGAGAAGCGG ATTGCTATCC AAAAGGAGAG
 151  GAAGAAGTCC AAAGACAAGG CGGCAGCTGA GCCCCAGCCT CGGCCTCAGC
 201  TTGACCTAAA GGCCTCCAGG AAGTTACCTA AGCTTTATGG TGACATTCCC
 251  CCTGAGCTTG TAGCGAAGCC TCTGGAAGAC CTGGACCCAT TCTACAAAGA
 301  CCATAAGACA TTCATGGTGT TGAACAAGAA GAGAACAATT TATCGCTTCA
 351  GCGCCAAGCG GGCCTTGTTC ATTCTGGGGC CTTTTAATCC CCTCAGAAGC
 401  TTAATGATTC GTATCTCTGT CCATTCAGTC TTTAGCATGT TCATCATCTG
 451  CACGGTGATC ATCAACTGTA TGTTCATGGC GAATTCTATG GAGAGAAGTT
 501  TCGACAACGA CATTCCCGAA TACGTCTTCA TTGGGATTTA TATTTTAGAA
 551  GCTGTGATTA AAATATTGGC AAGAGGCTTC ATTGTGGATG AGTTTTCCTT
 601  CCTCCGAGAT CCGTGGAACT GGCTGGACTT CATTGTCATT GGAACAGCGA
 651  TCGCAACTTG TTTTCCGGGC AGCCAAGTCA ATCTTTCAGC TCTTCGTACC
 701  TTCCGAGTGT TCAGAGCTCT GAAGGCGATT TCAGTTATCT CAGGTCTGAA
 751  GGTCATCGTA GGTGCCCTGC TGCGCTCGGT GAAGAAGCTG GTAGACGTGA
 801  TGGTCCTCAC TCTCTTCTGC CTCAGCATCT TTGCCCTGGT CGGTCAGCAG
 851  CTGTTCATGG GAATTCTGAA CCAGAAGTGT ATTAAGCACA ACTGTGGCCC
 901  CAACCCTGCA TCCAACAAGG ATTGTTTTGA AAAGGAAAAA GATAGCGAAG
 951  ACTTCATAAT GTGTGGTACC TGGCTCGGCA GCAGACCCTG TCCCAATGGT
1001  TCTACGTGCG ATAAAACCAC ATTGAACCCA GACAATAATT ATACAAAGTT
1051  TGACAACTTT GGCTGGTCCT TTCTCGCCAT GTTCCGGGTT ATGACTCAAG
1101  ACTCCTGGGA GAGGCTTTAC CGACAGATCC TGCGGACCTC TGGGATCTAC
1151  TTTGTCTTCT TCTTCGTGGT GGTCATCTTC CTGGCTCCT TCTACCTGCT
1201  TAACCTAACC CTGGCTGTTG TCACCATGGC TTATGAAGAA CAGAACAGAA
1251  ATGTAGCTGC TGAGACAGAG GCCAAGGAGA AAATGTTTCA GGAAGCCCAG
1301  CAGCTGTTAA GGGAGGAGAA GGAGGCTCTG GTTGCCATGG GAATTGACAG
1351  AAGTTCCCTT AATTCCCTTC AAGCTTCATC CTTTTCCCCG AAGAAGAGGA
1401  AGTTTTTCGG TAGTAAGACA AGAAAGTCCT TCTTTATGAG AGGGTCCAAG
1451  ACGGCCCAAG CCTCAGCGTC TGATTCAGAG GACGATGCCT CTAAAAATCC
1501  ACAGCTCCTT GAGCAGACCA AACGACTGTC CCAGAACTTG CCAGTGGATC
1551  TCTTTGATGA GCACGTGGAC CCCTCCACA GGCAGAGAGC GCTGAGCGCT
1601  GTCAGTATCT TAACCATCAC CATGCAGGAA CAAGAAAAAT TCCAGGAGCC
1651  TTGTTTCCCA TGTGGGAAAA ATTGGCCTC TAAGTACCTG GTGTGGGACT
```

FIG. 1B

```
1701  GTAGCCCTCA ATGGCTGTGC ATAAAGAAGG TCCTGCGGAC CATCATGACG
1751  GATCCCTTTA CTGAGCTGGC CATCACCATC TGCATCATCA TCAATACCGT
1801  TTTCTTAGCC GTGGAGCACC ACAACATGGA TGACAACTTA AAGACCATAC
1851  TGAAAATAGG AAACTGGGTT TTCACGGGAA TTTTCATAGC GGAAATGTGT
1901  CTCAAGATCA TCGCGCTCGA CCCTTACCAC TACTTCCGGC ACGGCTGGAA
1951  TGTTTTTGAC AGCATCGTGG CCCTCCTGAG TCTCGCTGAT GTGCTNTACA
2001  ACACACTGTC TGATAACAAT AGGTCTTTCT TGGCTTCCCT CAGAGTGCTG
2051  AGGGTCTTCA AGTTAGCCAA ATCCTGGCCC ACGTTAAACA CTCTCATTAA
2101  GATCATCGGC CACTCCGTGG GCGCGCTTGG AAACCTGACT GTGGTCCTGA
2151  CTATCGTGGT CTTCATCTTT TCTGTGGTGG CATGCGGCT CTTCGGCACC
2201  AAGTTTAACA AGACCGCCTA CGCCACCCAG GAGCGGCCCA GGCGGCGCTG
2251  GCACATGGAT AATTTCTACC ACTCCTTCCT GGTGGTGTTC CGCATCCTCT
2301  GTGGGGAATG GATCGAGAAC ATGTGGGGCT GCATGCAGGA TATGGACGGC
2351  TCCCCGTTGT GCATCATTGT CTTTGTCCTG ATAATGGTGA TCGGGAAGCT
2401  TGTGGTGCTT AACCTCTTCA TTGCCTTGCT GCTCAATTCC TTCAGCAATG
2451  AGGAGAAGGA TGGGAGCCTG GAAGGAGAGA CCAGGAAAAC CAAAGTGCAG
2501  CTAGCCCTGG ATCGGTTCCG CCGGGCCTTC TCCTTCATGC TGCACGCTCT
2551  TCAGAGTTTT TGTTGCAAGA AATGCAGGAG GAAAAACTCG CCAAAGCCAA
2601  AAGAGACAAC AGAAAGCTTT GCTGGTGAGA ATAAAGACTC AATCCTCCCG
2651  GATGCGAGGC CCTGGAAGGA GTATGATACA GACATGGCTT TGTACACTGG
2701  ACAGGCCGGG GCTCCGCTGG CCCCACTCGC AGAGGTAGAG GACGATGTGG
2751  AATATTGTGG TGAAGGCGGT GCCCTACCCA CCTCACAACA TAGTGCTGGA
2801  GTTCAGGCCG GTGACCTCCC TCCAGAGACC AAGCAGCTCA CTAGCCCGGA
2851  TGACCAAGGG GTTGAAATGG AAGTATTTTC TGAAGAAGAT CTGCATTTAA
2901  GCATACAGAG TCCTCGAAAG AAGTCTGACG CAGTGAGCAT GCTCTCGGAA
2951  TGCAGCACAA TTGACCTGAA TGATATCTTT AGAAATTTAC AGAAAACAGT
3001  TTCCCCCAAA AAGCAGCCAG ATAGATGCTT TCCCAAGGGC CTTAGTTGTC
3051  ACTTTCTATG CCACAAAACA GACAAGAGAA AGTCCCCCTG GGTCCTGTGG
3101  TGGAACATTC GGAAAACCTG CTACCAAATC GTGAAGCACA GCTGGTTTGA
3151  GAGTTTCATA ATCTTTGTTA TTCTGCTGAG CAGTGGAGCG CTGATATTTG
3201  AAGATGTCAA TCTCCCCAGC CGGCCCAAG TTGAGAAATT ACTAAGGTGT
3251  ACCGATAATA TTTTCACATT TATTTTCCTC CTGGAAATGA TCCTGAAGTG
3301  GGTGGCCTTT GGATTCCGGA GGTATTTCAC CAGTGCCTGG TGCTGGCTTG
3351  ATTTCCTCAT TGTGGTGGTG TCTGTGCTCA GTCTCATGAA TCTACCAAGC
3401  TTGAAGTCCT TCCGGACTCT GCGGGCCCTG AGACCTCTGC GGGCGCTGTC
3451  CCAGTTTGAA GGAATGAAGG TTGTCGTCTA CGCCCTGATC AGCGCCATAC
3501  CTGCCATTCT CAATGTCTTG CTGGTCTGCC TCATTTTCTG GCTCGTATTT
3551  TGTATCTTGG GAGTAAATTT ATTTTCTGGG AAGTTTGGAA GGTGCATTAA
3601  CGGGACAGAC ATAAATATGT ATTTGGATTT TACCGAAGTT CCGAACCGAA
```

FIG. IC

```
3651  GCCAATGTAA CATTAGTAAT TACTCGTGGA AGGTCCCGCA GGTCAACTTT
3701  GACAACGTGG GGAATGCCTA TCTCGCCCTG CTGCAAGTGG CAACCTATAA
3751  GGGCTGGCTG GAAATCATGA ATGCTGCTGT CGATTCCAGA GAGAAAGACG
3801  AGCAGCCGGA CTTTGAGGCG AACCTCTACG CGTATCTCTA CTTTGTGGTT
3851  TTTATCATCT TCGGCTCCTT CTTTACCCTG AACCTCTTTA TCGGTGTTAT
3901  TATTGACAAC TTCAATCAGC AGCAGAAAAA GTTAGGTGGC AAGACATTT
3951  TTATGACAGA AGAACAGAAG AAATATTACA ATGCAATGAA AAAGTTAGGA
4001  ACCAAGAAAC CTCAAAAGCC CATCCCAAGG CCCCTGAACA ANTGTCAAGC
4051  CTTTGTGTTC GACCTGGTCA CAAGCCATGT CTTTGACGTC ATCATTCTGG
4101  GTCTTATTGT CTTAAATATG ATTATCATGA TGGCTGAATC TGCCGACCAG
4151  CCCAAAGATG TGAAGAAAAC CTTTGATATC CTCAACATAG CCTTCGTGGT
4201  CATCTTTACC ATAGAGTGTC TCATCAAAGT CTTTGCTTTG AGGCAACACT
4251  ACTTCACCAA TGGCTGGAAC TTATTTGATT GTGTGGTCGT GGTTCTTTCT
4301  ATCATTAGTA CCCTGGTTTC CGCTTGGAG GACAGTGACA TTTCTTTCCC
4351  GCCCACGCTC TTCAGAGTCG TCCGCTTGGC TCGGATTGGT CGAATCCTCA
4401  GGCTGGTCCG GGCTGCCCGG GGAATCAGGA CCCTCCTCTT TGCTTTGATG
4451  ATGTCTCTCC CCTCTCTCTT CAACATCGGT CTGCTGCTCT TCCTGGTGAT
4501  GTTCATTTAC GCCATCTTTG GGATGAGCTG GTTTTCCAAA GTGAAGAAGG
4551  GCTCCGGGAT CGACGACATC TTCAACTTCG AGACCTTTAC GGGCAGCATG
4601  CTGTGCCTCT TCCAGATAAC CACTTCGGCT GGCTGGGATA CCCTCCTCAA
4651  CCCCATGCTG GAGGCAAAAG AACACTGCAA CTCCTCCTCC CAAGACAGCT
4701  GTCAGCAGCC GCAGATAGCC GTCGTCTACT TCGTCAGTTA CATCATCATC
4751  TCCTTCCTCA TCGTGGTCAA CATGTACATC GCTGTGATCC TCGAGAACTT
4801  CAACACAGCC ACGGAGGAGA GCGAGGACCC TCTGGGAGAG GACGACTTTG
4851  AAATCTTCTA TGAGGTCTGG GAGAAGTTTG ACCCCGAGGC GTCGCAGTTC
4901  ATCCAGTATT CGGCCCTCTC TGACTTTGCG GACGCCCTGC CGGAGCCGTT
4951  GCGTGTGGCC AAGCCGAATA AGTTTCAGTT TCTAGTGATG GACTTGCCCA
5001  TGGTGATGGG CGACCGCCTC CATTGCATGG ATGTTCTCTT TGCTTTCACT
5051  ACCAGGGTCC TCGGGGACTC CAGCGGCTTG GATACCATGA AAACCATGAT
5101  GGAGGAGAAG TTTATGGAGG CCAACCCTTT TAAGAAGCTC TACGAGCCCA
5151  TAGTCACCAC CACCAAGAGG AAGGAGGAGG AGCAAGGCGC CGCCGTCATC
5201  CAGAGGGCCT ACCGGAAACA CATGGAGAAG ATGGTCAAAC TGAGGCTGAA
5251  GGACAGGTCA AGTTCATCGC ACCAGGTGTT TTGCAATGGA GACTTGTCCA
5301  GCTTGGATGT GGCCAAGGTC AAGGTTCACA ATGACTGAAC CCTCATCTCC
5351  ACCCCTACCT CACTGCCTCA CAGCTTAGCC TCCAGCCTCT GGCGAGCAGG
5401  CGGCAGACTC ACTGAACACA GGCCGTTCGA TCTGTGTTTT TGGCTGAACG
5451  AGGTGACAGG TTGGCGTCCA TTTTTAAATG ACTCTTGGAA AGATTTCATG
5501  TAGAGAGATG TTAGAAGGGA CTGCAAAGGA CACCGACCAT AACGGAAGGC
5551  CTGGAGGACA GTCCAACTTA CATAAAGATG AGAAACAAGA AGGAAAGATC
```

FIG. 1D

```
5601  CCAGGAAAAC TTCAGATTGT GTTCTCAGTA CATTCCCCAA TGTGTCTGTT
5651  CGGTGTTTTG AGTATGTGAC CTGCCACATG TAGCTCTTTT TTGCATGTAC
5701  GTCAAAACCC TGCAGTAAGT TAATAGCTTG CTACGGGTGT TCCTACCAGC
5751  ATCACAGAAT TGGGTGTATG ACTCAAACCT AAAAGCATGA CTCTGACTTG
5801  TCAGTCAGCA CCCCGACTTT CAGACGCTCC AATCTCTGTC CCAGGTGTCT
5851  AACGAATAAA TAGGTAAAAG AAAAA
```

FIG. 2A

Predicted amino acid sequence of rat NaN (1765 a.a).

```
  1  MEERYYPVIF  PDERNFRPFT  SDSLAAIEKR  IAIQKERKKS  KDKAAAEPQP

51  RPQLDLKASR  KLPKLYGDIP  PELVAKPLED  LDPFYKDHKT  FMVLNKKRTI
                                                    DI-S1
101  YRFSAKRALF  ILGPFNPLRS  LMIRISVHSV  FSMFIICTVI  INCMFMANSM
                             DI-S2                   DI-S3
151  ERSFDNDIPE  YVFIGIYILE  AVIKILARGF  IVDEFSFLRD  PWNWLDFIVI
                             DI-S4
201  GTAIATCFPG  SQVNLSALRT  FRVFRALKAI  SVISGLKVIV  GALLRSVKKL
                             DI-S5
251  VDVMVLTLFC  LSIFALVGQQ  LFMGILNQKC  IKHNCGPNPA  SNKDCFEKEK
                                                    DI-SS1
301  DSEDFIMCGT  WLGSRPCPNG  STCDKTTLNP  DNNYTKFDNF  GWSFLAMFRV
     DI-SS2                              DI-S6
351  MTQDSWERLY  RQILRTSGIY  FVFFFVVVIF  LGSFYLLNLT  LAVVTMAYEE

401  QNRNVAAETE  AKEKMFQEAQ  QLLREEKEAL  VAMGIDRSSL  NSLQASSFSP

451  KKRKFFGSKT  RKSFFMRGSK  TAQASASDSE  DDASKNPQLL  EQTKRLSQNL

501  PVDLFDEHVD  PLHRQRALSA  VSILTITMQE  QEKFQEPCFP  CGKNLASKYL
                                         DII-S1
551  VWDCSPQWLC  IKKVLRTIMT  DPFTELAITI  CIIINTVFLA  VEHHNMDDNL
                 DII-S2                  DII-S3
601  KTILKIGNWV  FTGIFIAEMC  LKIIALDPYH  YFRHGWNVFD  SIVALLSLAD
                                                    DII-S4
651  VLYNTLSDNN  RSFLASLRVL  RVFKLAKSWP  TLNTLIKIIG  HSVGALGNLT
     DII-S5                                          DII-SS1
701  VVLTIVVFIF  SVVGMRLFGT  KFNKTAYATQ  ERPRRRWHMD  NFYHSFLVVF
     DII-SS2                                         DII-S6
751  RILCGEWIEN  MWGCMQDMDG  SPLCIIVFVL  IMVIGKLVVL  NLFIALLLNS
```

FIG. 2B

```
 801  FSNEEKDGSL EGETRKTKVQ LALDRFRRAF SFMLHALQSF CCKKCRRKNS
 851  PKPKETTESF AGENKDSILP DARPWKEYDT DMALYTGQAG APLAPLAEVE

901  DDVEYCGEGG ALPTSQHSAG VQAGDLPPET KQLTSPDDQG VEMEVFSEED

951  LHLSIQSPRK KSDAVSMLSE CSTIDLNDIF RNLQKTVSPK KQPDRCFPKG
                                                         DIII-S1
1001  LSCHFLCHKT DKRKSPWVLW WNIRKTCYQI VKHSWFESFI IFVILLSSGA
                                       DIII-S2
1051  LIFEDVNLPS RPQVEKLLRC TDNIFTFIFL LEMILKWVAF GFRRYFTSAW
         DIII-S3              DIII-S4
1101  CWLDFLIVVV SVLSLMNLPS LKSFRTLRAL RPLRALSQFE GMKVVVYALI
              DIII-S5
1151  SAIPAILNVL LVCLIFWLVF CILGVNLFSG KFGRCINGTD INMYLDFTEV
                                        DIII-SS1   DIII-SS2
1201  PNRSQCNISN YSWKVPQVNF DNVGNAYLAL LQVATYKGWL EIMNAAVDSR
                              DIII-S6
1251  EKDEQPDFEA NLYAYLYFVV FIIFGSFFTL NLFIGVIIDN FNQQQKKLGG
                                                          DIV-S1
1301  QDIFMTEEQK KYYNAMKKLG TKKPQKPIPR PLNRCQAFVF DLVTSHVFDV

1351  IILGLIVLNM IIMMAESADQ PKDVKKTFDI LNIAFVVIFT IECLIKVFAL
                                                         DIV-S4
1401  RQHYFTNGWN LFDCVVVVLS IISTLVSRLE DSDISFPPTL FRVVRLARIG
                                                     DIV-S5
1451  RILRLVRAAR GIRTLLFALM MSLPSLFNIG LLLFLVMFIY AIFGMSWFSK
              DIV-SS1              DIV-SS2
1501  VKKGSGIDDI FNFETFTGSM LCLFQITTSA GWDTLLNPML EAKEHCNSSS
                                     DIV-S6
1551  QDSCQQPQIA VVYFVSYIII SFLIVVNMYI AVILENFNTA TEESEDPLGE

1601  DDFEIFYEVW EKFDPEASQF IQYSALSDFA DALPEPLRVA KPNKFQFLVM

1651  DLPMVMGDRL HCMDVLFAFT TRVLGDSSGL DTMKTMMEEK FMEANPFKKL
```

FIG. 2C

```
1701  YEPIVTTTKR KEEEQGAAVI QRAYRKHMEK MVKLRLKDRS SSSHQVFCNG

1751  DLSSLDVAKV KVHND*
```

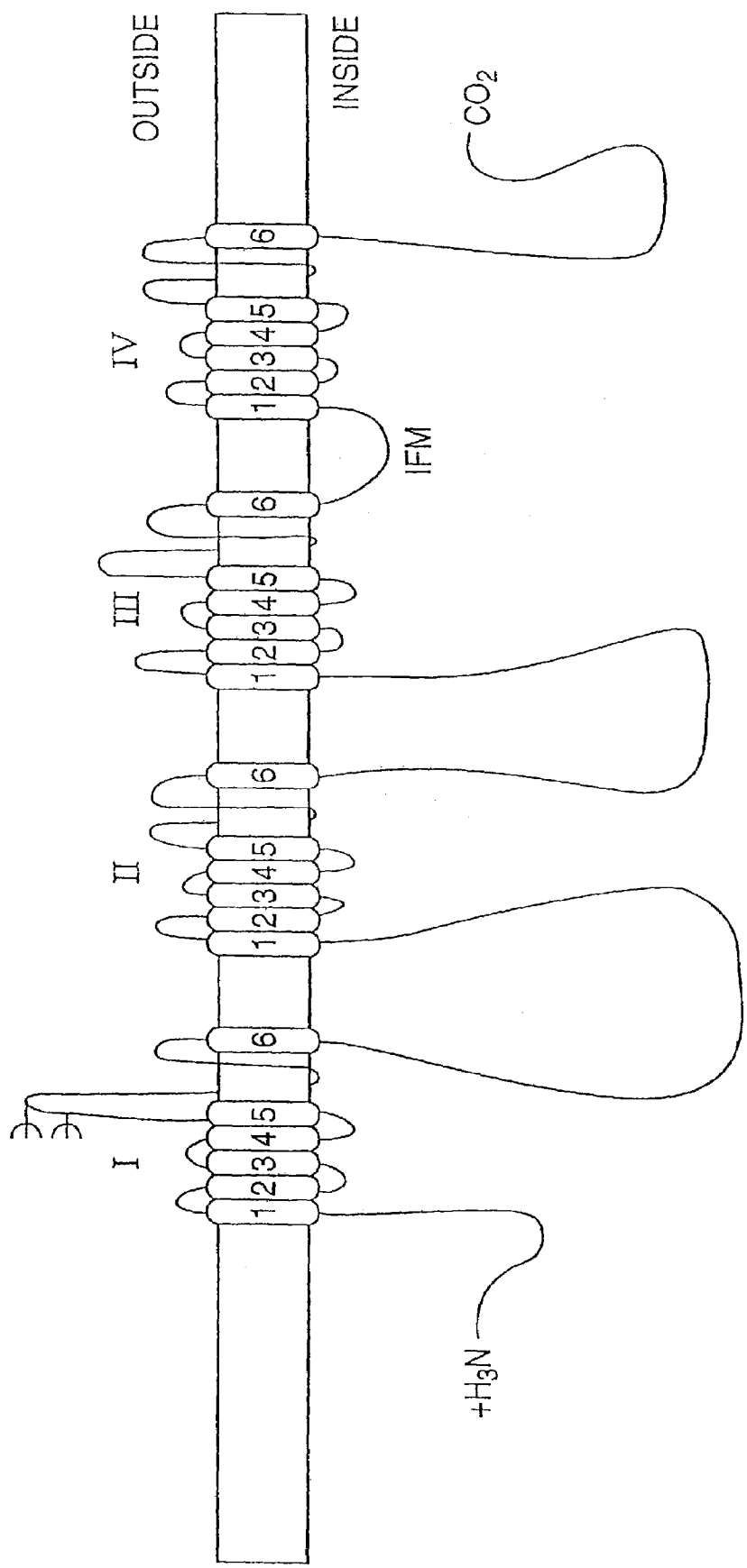

FIG. 6 RESTRICTION ENZYME ANALYSIS OF α-SUBUNIT PCR PRODUCTS FROM DOMAIN I USING THE FOLLOWING PRIMERS: NACHD1A.1-4 (FORWARD PRIMERS) AND NAAGEN.REV1-3 (REVERSE PRIMERS).

| Generic Primer pair | F1 R.1 | F2 R1 | F1 R1 | F1/F3 R1 | F1 R1 | F1/F3 R1 | F1 R1 | F2 R2 | F4 R3 | F2 R3 |
|---|---|---|---|---|---|---|---|---|---|---|
| | αI 558 bp | αII 561 bp | αIII 561 bp | αVI 507 bp | αrPN1 501 bp | αrH1 518 bp | αμI 602 bp | αSNS 479 bp | αNaG 501 bp | αNaN 468 bp |
| EcoR V | + 152, 406 | - | - | - | - | - | - | - | - | - |
| EcoN I | - | + 204, 357 | - | - | - | - | - | - | - | - |
| Ava I | - | - | + 279, 282 | - | - | - | - | - | - | - |
| Sph I | - | - | - | + 126, 381 | - | - | - | - | - | - |
| Bam H I | - | - | - | - | + 134, 367 | - | - | + 126, 353 | - | - |
| Acc I | - | - | - | - | - | + 173, 345 | - | - | - | + 185, 283 |
| Ngo M I | - | - | - | - | - | - | + 200, 402 | - | + 95, 406 | - |
| Afl II | - | - | - | - | - | - | - | + 224, 255 | - | - |
| Xba I | - | - | - | - | - | - | - | - | + 165, 336 | - |
| EcoR I | - | - | - | - | - | - | - | - | - | + 214, 254 |

FIG. 7A-1

Sequence of the mouse NaN cDNA.

```
   1  TCTGAGCCAA GGGTGAAGAT GGAGGAGAGG TACTATCCAG TGATCTTCCC AGACGAGAGG
  61  AATTTCCGCC CCTTCACTTT CGACTCTTTG GCTGCAATAG AGAAGCGGAT CACCATCCAA
 121  AAGGAGAAGA AGAAATCCAA AGACAAGGCA GCAACTGAGC CCCAGCCTCG GCCTCAGCTC
 181  GACCTAAAGG CCTCCAGGAA GTTACCTAAG CTCTATGGCG ACGTTCCCCC TGACCTTATA
 241  GCGAAGCCCC TGGAAGATCT GGACCCATTT TACAAAGACC ATAAGACATT CATGGTATTG
 301  AACAAGAAGA GAACAATCTA TCGCTTCAGC GCCAAGAGGG CCTTGTTCAT TCTGGGGCCT
 361  TTTAATCCCA TCAGAAGCTT CATGATTCGC ATCTCTGTCC ATTCAGTCTT CAGCATGTTC
 421  ATTATCTGCA CAGTGATCAT CAACTGTATG TTCATGGCTA ATAATTCTTC TGTGGACAGT
 481  CGTCCTAGCA GTAACATTCC CGAATACGTC TTCATTGGGA TTTATGTTTT AGAAGCTGTG
 541  ATTAAAATAT TGGCAAGAGG CTTCATTGTG GATGAGTTTT CCTACCTCCG AGATCCTTGG
 601  AACTGGCTGG ACTTCATTGT CATCGGAACA GCGATAGCGC CTTGTTTTCT CGGTAACAAA
 661  GTCAATAATC TTTCCACTCT ACGTACCTTC CGAGTGTTGA GAGCTCTGAA AGCCATTTCT
 721  GTAATCTCAG GTCTGAAGGT CATCGTGGGT GCCCTGCTGC GCTCCGTGAA GAAGCTAGTG
 781  GACGTGATGG TCCTCACTCT CTTTTGCCTC AGCATCTTTG CCCTGGTTGG TCAGCAGCTC
 841  TTCATGGGAA TTCTGAGCCA GAAATGTATT AAGGACGACT GTGGCCCTAA CGCTTTTTCC
 901  AACAAGGATT GCTTTGTAAA AGAAAATGAT AGCGAGGACT TCATAATGTG TGGCAACTGG
 961  CTCGGCAGAA GATCCTGCCC CGATGGTTCC ACGTGCAATA AAACCACATT TAACCCAGAT
1021  TATAATTATA CAAACTTTGA CAGCTTTGGC TGGTCTTTTC TCGCCATGTT CCGGGTTATG
1081  ACTCAAGACT CCTGGGAGAA GCTTTATCGA CAGATCCTTC GCACCTCCGG GATCTACTTT
1141  GTCTTCTTCT TCGTGGTCGT CATCTTCCTG GGCTCTTTCT ACCTGCTTAA CTTAACCCTG
1201  GCTGTCGTCA CCATGGCTTA CGAGGAACAG AACAGAAATG TCGCTGCCGA GACAGAGGCC
1261  AAGGAGAAGA TGTTTCAGGA AGCCCAGCAG CTGTTGAGGG AGGAAAAGGA GGCTCTGGTT
1321  GCCATGGGAA TTGACAGAAC TTCCCTTAAT TCCCTCCAAG CTTCGTCCTT TTCCCCAAAG
1381  AAGAGGAAGT TTTTTGGCAG TAAGACAAGA AAGTCCTTCT TTATGAGAGG GTCCAAGACA
1441  GCCCGAGCCT CAGCGTCCGA TTCAGAGGAC GATGCCTCTA AAAACCCACA ACTCCTTGAG
1501  CAAACAAAAC GACTATCCCA GAACTTGCCC GTAGAACTCT TTGATGAGCA CGTGGACCCC
1561  CTCCATAGGC AGAGAGCGCT GAGTGCCGTC AGTATCTTAA CCATCACCAT GCAGGAACAA
1621  GAAAAATCCC AGGAGCCTTG TTTCCCGTGT GGGAAAAACT TGGCATCCAA GTACCTGGTG
1681  TGGGAATGTA GCCCTCCGTG GCTGTGCATA AAGAAGGTCC TGCAGACTAT CATGACAGAC
1741  CCCTTCACTG AGCTGGCCAT CACCATCTGC ATCATCGTCA ATACTGTCTT CTTGGCCATG
1801  GAACACCACA ATATGGATAA CTCTTTAAAA GACATACTGA AAATAGGAAA CTGGGTTTTC
1861  ACTGGAATTT TCATAGCGGA AATGTGTCTC AAGATCATTG CGCTAGACCC TTACCACTAC
1921  TTCCGGCACG GCTGGAACAT CTTTGACAGC ATTGTGGCCC TTGTGAGTCT CGCTGACGTG
```

FIG. 7A-2

```
1981  CTCTTCCACA AACTGTCTAA AAACCTCTCC TTCTTGGCTT CCCTCAGAGT GCTGAGGGTC
2041  TTCAAGTTAG CCAAATCCTG GCCCACATTA AACACTCTCA TTAAGATCAT CGGCCACTCC
2101  GTGGGTGCGC TCGGAAACCT GACTGTGGTC CTAACGATCG TGGTCTTCAT CTTTTCCGTG
2161  GTTGGCATGC GGCTCTTTGG TGCCAAGTTT AACAAGACTT GCTCCACCTC TCCGGAGTCC
2221  CTCCGGCGCT GGCACATGGG TGATTTCTAC CATTCCTTCC TGGTGGTGTT CCGCATCCTC
2281  TGTGGGAGT GGATCGAGAA CATGTGGGAA TGCATGCAGG AGATGGAAGG CTCCCCGCTG
2341  TGTGTCATCG TCTTTGTGCT GATCATGGTG GTCGGGAAGC TCGTGGTGCT TAACCTCTTC
2401  ATTGCCTTGC TGCTCAATTC CTTCAGCAAT GAGGAAAAGG ATGGGAACCC AGAAGGAGAG
2461  ACCAGGAAAA CCAAAGTGCA GCTAGCCCTG GATCGGTTCA GCCGAGCGTT CTACTTCATG
2521  GCGCGCGCTC TTCAGAATTT CTGTTGCAAG AGATGCAGGA GGCAAAACTC GCCAAAGCCA
2581  AATGAGGCAA CAGAAAGCTT TGCTGGTGAG AGTAGAGACA CAGCCACCCT GGATACAAGG
2641  TCCTGGAAGG AGTATGATTC AGAAATGACT CTGTACACTG GGCAGGCCGG GGCTCCACTG
2701  GCCCCACTGG CAAAAGAAGA GGACGATATG GAATGTTGTG GTGAATGTGA TGCCTCACCT
2761  ACCTCACAGC CTAGTGAGGA AGCTCAGGCC TGTGACCTCC CTCTGAAGAC CAAGCGGCTC
2821  CCCAGCCCAG ATGACCACGG GGTTGAAATG GAAGTGTTTT CCGAAGAAGA TCCGAATTTA
2881  ACCATACAGA GTGCTCGAAA GAAGTCTGAT GCGGCAAGCA TGCTCTCAGA ATGCAGCACA
2941  ATAGACCTGA ATGATATCTT TAGAAATTTA CAGAAAACAG TTTCCCCCCA AAAGCAACCA
3001  GATCGATGCT TTCCCAAGGG CCTCAGTTGT ATCTTTCTAT GTTGCAAAAC AATCAAAAAA
3061  AAGTCCCCCT GGGTCCTGTG GTGGAATCTT CGGAAAACCT GCTACCAAAT CGTGAAGCAT
3121  AGCTGGTTTG AGAGCTTCAT AATTTTTGTC ATCCTGCTGA GCAGCGGAGC ACTGATATTC
3181  GAAGATGTCA ATCTTCCCAG CCGGCCCCAA GTTGAAAAAT TACTGAAAGTG TACCGATAAT
3241  ATTTTCACAT TTATTTTTCT CCTGGAAATG ATTTTGAAGT GGGTGGCCTT TGGATTCCGG
3301  AAGTATTTCA CCAGTGCCTG GTGCTGGCTC GATTTCCTCA TTGTGGTGGT GTCTGTGCTC
3361  AGCCTCACGA ACTTACCAAA CTTGAAGTCC TTCCGGAATC TGCGAGCGCT GAGACCTCTG
3421  CGGGCACTGT CTCAGTTTGA AGGAATGAAG GTTGTTGTCA ATGCCCTCAT GAGTGCCATA
3481  CCTGCCATCC TCAATGTCTT GCTGGTCTGC CTCATTTTCT GGCTCATATT TTGTATCCTG
3541  GGAGTAAATT TTTTTTCTGG GAAGTTTGGA AGATGCATTA ATGGAACAGA CATAAATAAA
3601  TATTTCAACG CTTCCAATGT TCCAAACCAA AGCCAATGTT TAGTTAGTAA TTACACGTGG
3661  AAAGTCCCGA ATGTCAACTT TGACAACGTG GGGAATGCCT ACCTTGCCCT GCTGCAAGTG
3721  GCGACCTATA AGGGCTGGCT GGACATTATG AATGCAGCTG TTGATTCCAG AGGGAAAGAT
3781  GAGCAGCCGG CCTTTGAGGC GAATCTATAC GCATACCTTT ACTTCGTGGT TTTTATCATC
3841  TTCGGCTCAT TCTTTACCCT GAACCTCTTT ATCGGTGTTA TTATTGACAA CTTCAATCAG
3901  CAGCAGAAAA AGTTAGGTGG CCAAGACATT TTATGACAG AAGAACAGAA GAAATATTAC
3961  AATGCAATGA AAAAGTTAGG AACCAAGAAG CCTCAAAAGC CCATCCCAAG GCCCCTGAAC
4021  AAATGTCAAG CCTTCGTGTT CGATTTGGTC ACAAGCCAGG TCTTTGACGT CATCATTCTG
4081  GGTCTTATTG TCACAAACAT GATTATCATG ATGGCTGAAT CTGAAGGCCA GCCCAACGAA
4141  GTGAAGAAAA TCTTTGATAT TCTCAACATA GTCTTCGTGG TCATCTTTAC CGTAGAGTGT
4201  CTCATCAAAG TCTTTGCTTT GAGGCAACAC TACTTCACCA ATGGCTGGAA CTTATTTGAT
```

FIG. 7A-3

```
4261  TGTGTGGTCG TGGTTCTTTC CATCATTAGT ACCTTGGTTT CTGGCTTGGA GAACAGCAAC
4321  GTCTTCCCGC CCACACTCTT CAGGATTGTC CGCTTGGCTC GGATCGGTCG AATCCTCAGA
4381  CTGGTCCGGG CGGCTCGAGG AATCAGGACA CTCCTTTTCG CGTTGATGAT GTCTCTCCCC
4441  TCTCTCTTCA ACATTGGTCT GCTTCTCTTT CTGGTGATGT TCATTTATGC CATCTTTGGG
4501  ATGAACTGGT TTTCCAAAGT GAAGAGAGGC TCTGGGATTG ATGACATCTT CAACTTTGAC
4561  ACTTTCTCGG GCAGCATGCT CTGCCTCTTC CAGATAACCA CTTCAGCCGG CTGGGATGCT
4621  CTCCTCAACC CCATGCTGGA ATCAAAAGCC TCTTGCAATT CCTCCTCCCA AGAGAGCTGT
4681  CAGCAGCCGC AGATAGCCAT AGTCTACTTC GTCAGCTACA TCATCATCTC CTTTCTCATT
4741  GTGGTTAACA TGTACATAGC TGTGATTCTA GAGAACTTCA ACACAGCCAC AGAGGAGAGC
4801  GAGGACCCCC TGGGCGAAGA CGACTTTGAG ATCTTCTATG AGATCTGGGA GAAGTTTGAC
4861  CCCGAAGCAA CACAGTTCAT CCAGTACTCA TCCCTCTCTG ACTTCGCCGA CGCCCTGCCC
4921  GAGCCGTTGC GTGTGGCCAA GCCCAACAGG TTTCAGTTTC TCATGATGGA CTTGCCCATG
4981  GTGATGGGTG ATCGCCTCCA TTGCATGGAT GTTCTCTTTG CTTTCACCAC CAGGGTCCTC
5041  GGGAACTCCA GCGGCTTGGA TACCATGAAA GCCATGATGG AGGAGAAGTT CATGGAGGCC
5101  AATCCTTTCA AGAAGTTGTA CGAGCCCATT GTCACCACCA CAAAGAGGAA GGAGGAGGAG
5161  GAATGTGCCG CTGTCATCCA GAGGGCCTAC CGGAGACACA TGGAGAAGAT GATCAAGCTG
5221  AAGCTGAAAG GCAGGTCAAG TTCATCGCTC CAGGTGTTTT GCAATGGAGA CTTGTCTAGC
5281  TTGGATGTGC CAAGATCAA GGTTCATTGT GACTGAAACC CCCACCTGCA CGCCTACCTC
5341  ACAGCCTCAC AGCTCAGCCC CCAGCCTCTG GCGAACAAGC GGCGGACTCA CCGAACAGGC
5401  CGTTCAACTT GTTTTTTTGG GTGAAAGAGG TGATAGGTTG GTGTCCATTT TTAAATGATT
5461  CTTGGAAAGA TTGAACGTCG GAACATGTTA GAAAGGACTG CCAAGGACAT CCACAGTAAC
5521  GGAAGGCCTG AAGGACAGTT CAAATTATGT AAAGAAACGA GAAGGAAAGG TCACATGTCT
5581  GTTCAGTTTT AAGTATGTGA CCTGCCACAT GTAGCTCCTT TGCATGTTAA GTGAGAAGTC
5641  AAAACCCTGC CATAAGTAAA TAGCTTTGTT GCAGGTGTTT CTACCAGTGC TGCGGATTTG
5701  GGTGTATGGC TCAAACCTGA AAGCATGACT CTGACTTGTC AGCACCCCAA CTTTCAGAAG
5761  CTCTGATCTC TGTCCTAGGT GTTTGACAAA TAAATACATA AAANAAAAAA AAAAAAAAA
5821  AA
```

FIG. 7B-1

Protein sequence of mNaN

Molecular Weight 201451.00 Daltons

1765 Amino Acids

198 Strongly Basic(+) Amino Acids (K,R)

177 Strongly Acidic(-) Amino Acids (D,E)

712 Hydrophobic Amino Acids (A,I,L,F,W,V)

453 Polar Amino Acids (N,C,Q,S,T,Y)

8.260 Isoelectric Point 22.540 Charge at PH 7.0

```
1    MEERYYPVIF PDERNFRPFT FDSLAAIEKR ITIQKEKKKS KDKAATEPQP RPQLDLKASR
21   KLPKLYGDVP PDLIAKPLED LDPFYKDHKT FMVLNKKRTI YRFSAKRALF ILGPFNPIRS
121  FMIRISVHSV FSMFIICTVI INCMFMANNS SVDSRPSSNI PEYVPIGIYV LEAVIKILAR
                DI-S1                              DI-S2
181  GFIVDEFSYL RDPWNWLDFI VIGTAIAPCF LGNKVNNLST LRTFRVLRAL KAISVISGLK
                   DI-S3                            DI-S4
241  VIVGALLRSV KKLVDVMVLT LFCLSIFALV GOOLFMGILS QKCIKDDCGP NAFSNKDCFV
                            DI-S5
301  KENDSEDFIM CGNWLGRRSC PDGSTCNKTT FNPDYNYTNF DSFGHSFLAM FRVMTQDSHE
                                                      DI-SS1      DI-SS2
361  KLYRQILRTS GIYFVFFFVV VIFLGSFYLL NLTLAVVTMA YEEQNRNVAA ETEAKEKMFQ
                         DI-S6
421  EAQQLLREEK EALVAMGIDR TSLNSLQASS FSPKKRKFFG SKTRKSFFMR GSKTARASAS
481  DSEDDASKNP QLLEQTKRLS QNLPVELFDE HVDPLHRQRA LSAVSILTIT MQEQEKSQEP
541  CFPCGKNLAS KYLVWECSPP WLCIKKVLQT IMTDPFTELA ITICIIVNTV FLAMEHHNMD
                                                     DII-S1
601  NSLKDILKIG NWVFTGIFIA EMCLKIIALD PYHYFRHGWN IFDSIVALVS LADVLFHKLS
                DII-S2                 DII-S3
661  KNLSFLASLR VLRVFKLAKS HPTLNTLIKI IGHSVGALGN LTVVLTIVVF IFSVVGMRLF
         DII-S4                                    DII-S5
721  GAKFNKTCST SPESLRRWHM GDFYHSFLVV FRILCGEWIE NMWECMQEME GSPLCVIVFV
                                     DII-SS1      DII-SS2
```

FIG. 7B-2

```
 781  LIMVVGKLVV LNLFIALLLN SFSNEEKDGN PEGETRKTKV QLALDRFSRA FYFMARALQN
           DII-S6
 841  FCCKRCRRQN SPKPNEATES FAGESRDTAT LDTRSWKEYD SEMTLYTGQA GAPLAPLAKE
 901  EDDMECCGEC DASPTSQPSE EAQACDLPLK TKRLPSPDDH GVEMEVFSEE DPNLTIQSAR
 961  KKSDAASMLS ECSTIDLNDI FRNLQKTVSP QKQPDRCFPK GLSCIFLCCK TIKKKSPWVL
1021  WWNLRKTCYQ IVKHSWFESF IIFVILLSSG ALIFEDVNLP SRPQVEKLLK CTDNIFTFIF
                    DIII-S1                              DIII-S2
1081  LLEMILKWVA FGFRKYFTSA WCWLDFLIVV VSVLSLTNLP NLKSFRNLRA LRPLRALSQF
          DIII-S2           DIII-S3               DIII-S4
1141  EGMKVVVNAL MSAIPAILNV LLVCLIFWLI FCILGVNFFS GKFGRCINGT DINKYFNASN
                               DIII-S5
1201  VPNQSQCLVS NYTWKVPNVN FDNVGNAYLA LLQVATYKGW LDIMNAAVDS RGKDEQPAFE
                                DIII-SS1    DIII-SS2
1261  ANLYAYLYFV VFIIFGSFFT LNLFIGVIID NFNQQQKKLG GQDIFMTEEQ KKYYNAMKKL
                    DIII-S6
1321  GTKKPQKPIP RPLNKCQAFV FDLVTSQVFD VIILGLIVTM MIIMMAESEG QPNEVKKIFD
                                              DIV-S1
1381  ILNIVFVVIF TVECLIKVFA LRQHYFTNGH NLFDCVVVVL SIISTLVSGL ENSNVFPPTL
          DIV-S2                       DIV-S3
1441  FRIVRLARIG RILRLVRAAR GIRTLLFALM MSLPSLFNIG LLLFLVMFIY AIFGMNWFSK
         DIV-S4                                           DIV-S5
1501  VKRGSGIDDI FNFDTFSGSM LCLFQITTSA GWDALLNPML ESKASCNSSS QESCQQPQIA
                 DIV-SS1    DIV-SS2
1561  IVYFVSYIII SFLIVVNMYI AVILENFNTA TEESEDPLGE DDFEIFYEIW EKFDPEATQF
          DIV-S6
1621  IQYSSLSDFA DALPEPLRVA KPNRFQFLMM DLPMVHGDRL HCMDVLFAFT TRVLGNSSGL
1681  DTMKAMMEEK FMEANPFKQL YEPIVTTTKR KEEEECAAVI QRAYRRHMEK MIKLKLGRS
1741  SSSLQVFCNG DLSSLDVPKI KVHCD.
```

FIG. 8A-1 Partial Human NaN Nucleotide Sequence

```
TCCATTGTCATTGGAATAGCGATTGTGTCATATATTCCAGGAATCACCATCAAACTATTGCCCC
TGCGTACCTTCCGTGTGTTCAGAGCTTTGAAAGCAATTTCAGTAGTTTCACGTCTGAAGGTCAT
CGTGGGGGCCTTGCTACGCTCTGTGAAGAAGCTGGTCAACGTGATTATCCTCACCTTCTTTTGC
CTCAGCATCTTTGCCCTGGTAGGTCAGCAGCTCTTCATGGGAAGTCTGAACCTGAAATGCATCT
CGAGGGACTGTAAAAATATCAGTAACCCGGAAGCTTATGACCATTGCTTTGAAAAGAAAGAAA
ATTCACCTGAATTCAAATGTGTGGCATCTGGATGGGTAACAGTGCCTGTTCCATACAATATGA
ATGTAAGCACACCAAAATTAATCCTGACTATAATTATACGAATTTTGACAACTTTGGCTGGTCT
TTTCTTGCCATGTTCCGGCTGATGACCCAAGATTCCTGGGAGAAGCTTTATCAACAGACCCTGC
GTACTACTGGGCTCTACTCAGTCTTCTTCTTCATTGTGGTCATTTTCCTGGGCTCCTTCTACCTGA
TTAACTTAACCCTGGCTGTTGTTACCATGGCATATGAGGAGCAGAACAAGAATGTAGCTGCAG
AGATAGAGGCCAAGGAAAAGATGTTTCAGGAAGCCCAGCAGCTGTTAAAGGAGGAAAAGGAG
GCTCTGGTTGCCATGGGAATTGACAGAAGTTCACTTACTTCCCTTGAAACATCATATTTTACCC
CAAAAAAGAGAAAGCTCTTTGGTAATAAGAAAAGGAAGTCCTTCTTTTTGAGAGAGTCTGGGA
AAGACCAGCCTCCTGGGTCAGATTCTGATGAAGATTGCCAAAAAAAGCCACAGCTCCTAGAGC
AAACCAAACGACTGTCCCAGAATCTATCAYTGGACCACTTTGATGAGCATGGAGATCCTCTCCA
AAGGCAGAGAGCACTGAGTGCTGTCAGCATCCTCACCATCACCATGAAGGAACAAGAAAAATC
ACAAGAGCCTTGTCTCCCTTGTGGAGAAAACCTGGCATCCAAGTACCTCGTGTGGAACTGTTGC
CCCCAGTGGCTGTGCGTTAAGAAGGTCCTGAGAACTGTGATGACTGACCCGTTTACTGAGCTGG
CCATCACCATCTGCATCATCATCAACACTGTCTTCTTGGCCATGGAGCATCACAAGATGGAGGC
CAGTTTTGAGAAGATGTTGAATATAGGGAATTTGGTTTTCACTAGCATTTTTATAGCAGAAATG
TGCCTAAAAATCATTGCGCTCGATCCCTACCACTACTTTCGCCGAGGCTGGAACATTTTTGACA
GCATTGTTGCTCTTCTGAGTTTTGCAGATGTAATGAACTGTGTACTTCAAAAGAGAAGCTGGCC
ATTCTTGCGTTCCTTCAGAGTGCTCAGGGTCTTCAAGTTAGCCAAATCCTGGCCAACTTTGAAC
ACACTAATTAAGATAATCGGCAACTCTGTCGGAGCCCTTGGAAGCCTGACTGTGGTCCTGGTCA
TTGTGATCTTTATTTTCTCAGTAGTTGGCATGCAGCTTTTTGGCCGTAGCTTCAATTCCCAAAAG
AGTCCAAAACTCTGTAACCCGACAGGCCCGACAGTCTCATGTTTACGGCACTGGCACATGGGG
GATTTCTGGCACTCCTTCCTAGTGGTATTCCGCATCCTCTGCGGGGAATGGATCGAAAATATGT
GGGAATGTATGCAAGAAGCGAATGCATCATCATCATTGTGTGTTATTGTCTTCATATTGATCAC
GGTGATAGGAAAACTTGTGGTGCTCAACCTCTTCATTGCCTTACTGCTCAATTCCTTTAGCAAT
GAGGAAAGAAATGGAAACTTAGAAGGAGAGGCCAGGAAAACTAAAGTCCAGTTAGCACTGGA
TCGATTCCGCCGGGCTTTTTGTTTTGTGAGACACACTCTTGAGCATTTCTGTCACAAGTGGTGCA
GGAAGCAAAACTTACCACAGCAAAAAGAGGTGGCAGGAGGCTGTGCTGCACAAAGCAAAGAC
ATCATTCCCCTGGTCATGGAGATGAAAAGGGGCTCAGAGACCCAGGAGGAGCTTGGTATACTA
ACCTCTGTACCAAAGACCCTGGGCGTCAGGCATGATTGGACTTGGTTGGCACCACTTGCGGAG
GAGGAAGATGACGTTGAATTTTCTGGTGAAGATAATGCACAGCGCATCACACAACCTGAGCCT
GAACAACAGGCCTATGAGCTCCATCAGGAGAACAAGAAGCCCACGAGCCAGAGAGTTCAAAG
TGTGGAAATTGACATGTTCTCTGAAGATGAGCCTCATCTGACCATACAGGATCCCCGAAAGAA
GTCTGATGTTACCAGTATACTATCAGAATGTAGCACCATTGATCTTCAGGATGGCTTTGGATGG
TTACCTGAGATGGTTCCCAAAAAGCAACCAGAGAGATGTTTGCCCAAAGGCTTTGGTTGCTGCT
TTCCATGCTGTAGCGTGGACAAGAGAAAGCCTCCCTGGGTCATTTGGTGGAACCTGCGGAAAA
```

FIG. 8A-2

CCTGCTACCAAATAGTGAAACACAGCTGGTTTGAGAGCTTTATTATCTTTGTGATTCTGCTGAG
CAGTGGGGCACTGATATTTGAAGATGTTCACCTTGAGAACCAACCCAAAATCCAAGAATTACT
AAATTGTACTGACATTATTTTTACACATATTTTTATCCTGGAGATGGTACTAAAATGGGTAGCC
TTCGGATTTGGAAAGTATTTCACCAGTGCCTGGTGCTGCCTTGATTTCATCATTGTGATTGTCTC
TGTGACCACCCTCATTAACTTAATGGAATTGAAGTCCTTCCGGACTCTACGAGCACTGAGGCCT
CTTCGTGCGCTGTCCCAGTTTGAAGGAATGAAGGTGGTGGTCAATGCTCTCATAGGTGCCATAC
CTGCCATTCTGAATGTTTTGCTTGTCTGCCTCATTTCTGGCTCGTATTTTGTATTCTGGGAGTAT
ACTTCTTTTCTGGAAAATTTGGGAAATGCATTAATGGAACAGACTCAGTTATAAATTATACCAT
CATTACAAATAAAAGTCAATGTGAAAGTGGCAATTTCTCTTGGATCAACCAGAAAGTCAACTTT
GACAATGTGGGAAATGCTTACCTCGCTCTGCTGCAAGTGGCAACATTTAAGGGCTGGATGGAT
ATTATATATGCAGCTGTTGATTCCACAGAGAAAGAACAACAGCCAGAGTTTGAGAGCAATTCA
CTCGGTTACATTTACTTCGTAGTCTTTATCATCTTTGGCTCATTCTTCACTCTGAATCTCTTCATT
GGCGTTATCATTGACAACTTCAACCAACAGCAGAAAAAGTTAGGTGGCCAAGACATTTTTATG
ACAGAAGAACAGAAGAAATACTATAATGCAATGAAAAAATTAGGATCCAAAAAACCTCAAAA
ACCCATTCCACGGCCTCTGAACAAATGTCAAGGTCTCGTGTTCGACATAGTCACAAGCCAGATC
TTTGACATCATCATCATAAGTCTCATTATCCTAAACATGATTAGCATGATGGCTGAATCATACA
ACCAACCCAAAGCCATGAAATCCATCCTTGACCATCTCAACTGGGTCTTTGTGGTCATCTTTAC
GTTAGAATGTCTCATCAAAATCTTTGCTTTGAGGCAATACTACTTCACCAATGGCTGGAATTTA
TTTGA

FIG. 8B

Partial Human NaNAmino Acid Sequence

SI VIGIAIVSYI PGITIKLLPL RTFRVFRALK AISVVSRLKV IVGALLRSVK KLVNVIILTF
FCLSIFALVG QQLFMGSLNL KCISRDCKNI SNPEAYDHCF EKKENSPEFK MCGIWMGNSA
CSIQYECKHT KINPDYNYTN FDNFGWSFLA MFRLMTQDSW EKLYQQTLRT TGLYSVFFFI
VVIFLGSFYL INLTLAVVTM AYEEQNKNVA AEIEAKEKMF QEAQQLLKEE KEALVAMGID
RSSLTSLETS YFTPKKRKLF GNKKRKSFFL RESGKDQPPG SDSDEDCQKK PQLLEQTKRL
SQNLSLDHFD EHGDPLQRQR ALSAVSILTI TMKEQEKSQE PCLPCGENLA SKYLVWNCCP
QWLCVKKVLR TVMTDPFTEL AITICIIINT VFLAMEHHKM EASFEKMLNI GNLVFTSIFI
AEMCLKIIAL DPYHYFRRGW NIFDSIVALL SFADVMNCVL QKRSWPFLRS
FRVLRVFKLAKSWPTLNTLI KIIGNSVGAL GSLTVVLVIV IFIFSVVGMQ LFGRSFNSQK
SPKLCNPTGP TVSCLRHWHM GDFWHSFLVV FRILCGEWIE NMWECMQEAN ASSSLCVIVF
ILITVIGKLV VLNLFIALLL NSFSNEERNG NLEGEARKTK VQLALDRFRR AFCFVRHTLE
HFCHKWCRKQ NLPQQKEVAG GCAAQSKDII PLVMEMKRGS ETQEELGILT SVPKTLGVRH
DWTWLAPLAE EEDDVEFSGE DNAQRITQPE PEQQAYELHQ ENKKPTSQRVQSVEIDMFSE
DEPHLTQDP RKKSDVTSIL SECSTIDLQD GFGWLPEMVP KKQPERCLPK GFGCCFPCCS
VDKRKPPWVI WWNLRKTCYQ IVKHSWFESF IIFVILLSSG ALIFEDVHLE NQPKIQELLN
CTDIIFTHIF ILEMVLKWVA FGFGKYFTSA WCCLDFIIVI VSVTTLINLM ELKSFRTLRA
LRPLRALSQF EGMKVVVNAL IGAIPAILNV LLVCLIFWLV FCILGVYFFS GKFGKCINGT
DSVINYTITT NKSQCESGNF SWINQKVNFD NVGNAYLALL QVATFKGWMD IIYAAVDSTE
KEQQPEFESN SLGYTYFVVF IIFGSFFTLN LFIGVIIDNF NQQQKKLGGQ DIFMTEEQKK
YYNAMKKLGS KKPQKPIPRP LNKCQGLVFD IVTSQIFDII IISLIILNMI SMMAESYNQP
KAMKSILDHL NWVFVVIFTL ECLIKIFALR QYYFTNGWNL FDCVVVLLSIV

NaN immunostaining in DRG neurons

FIG. 11A

Sequence of human NaN cDNA. Open reading frame (cdc)
Extends from position 31 (ATG) to the termination codon TGA at
Position 5400.

```
   1  ATCTGCTCAA GCCAGGAATC TCGGGTGAAG ATGGATGACA GATGCTACCC
  51  AGTAATCTTT CCAGATGAGC GGAATTTCCG CCCCTTCACT TCCGACTCTC
 101  TGGCTGCAAT TGAGAAGCGG ATTGCCATCC AAAAGGAGAA AAAGAAGTCT
 151  AAAGACCAGA CAGGAGAAGT ACCCCAGCCT CGGCCTCAGC TTGACCTAAA
 201  GGCCTCCAGG AAGTTGCCCA AGCTCTATGG CGACATTCCT CGTGAGCTCA
 251  TAGGAAAGCC TCTGGAAGAC TTGGACCCAT TCTACCGAAA TCATAAGACA
 301  TTTATGGTGT TAAACAGAAA GAGGACAATC TACCGCTTCA GTGCCAAGCA
 351  TGCCTTGTTC ATTTTGGGC CTTTCAATTC AATCAGAAGT TTAGCCATTA
 401  GAGTCTCAGT CCATTCATTG TTCAGCATGT TCATTATCGG CACCGTTATC
 451  ATCAACTGCG TGTTCATGGC TACAGGGCCT GCTAAAAACA GCAACAGTAA
 501  CAATACTGAC ATTGCAGAGT GTGTCTTCAC TGGGATTTAT ATTTTTGAAG
 551  CTTTGATTAA AATATTGGCA AGAGGTTTCA TTCTGGATGA GTTTTCTTTC
 601  CTTCGAGATC CATGGAACTG GCTGGACTCC ATTGTCATTG AATAGCGAT
 651  TGTGTCATAT ATTCCAGGAA TCACCATCAA ACTATTGCCC CTGCGTACCT
 701  TCCGTGTGTT CAGAGCTTTG AAAGCAATTT CAGTAGTTTC ACGTCTGAAG
 751  GTCATCGTGG GGCCTTGCT ACGCTCTGTG AAGAAGCTGG TCAACGTGAT
 801  TATCCTCACC TTCTTTTGCC TCAGCATCTT TGCCCTGGTA GGTCAGCAGC
 851  TCTTCATGGG AAGTCTGAAC CTGAAATGCA TCTCGAGGGA CTGTAAAAAT
 901  ATCAGTAACC CGGAAGCTTA TGACCATTGC TTTGAAAAGA AAGAAAATTC
 951  ACCTGAATTC AAAATGTGTG GCATCTGGAT GGGTAACAGT GCCTGTTCCA
1001  TACAATATGA ATGTAAGCAC ACCAAAATTA ATCCTGACTA TAATTATACG
1051  AATTTTGACA ACTTTGGCTG GTCTTTTCTT GCCATGTTCC GGCTGATGAC
1101  CCAAGATTCC TGGGAGAAGC TTTATCAACA GACCCTGCGT ACTACTGGGC
1151  TCTACTCAGT CTTCTTCTTC ATTGTGGTCA TTTTCCTGGG CTCCTTCTAC
1201  CTGATTAACT TAACCCTGGC TGTTGTTACC ATGGCATATG AGGAGCAGAA
```

FIG. 11A-2

```
1251  CAAGAATGTA GCTGCAGAGA TAGAGGCCAA GGAAAAGATG TTTCAGGAAG
1301  CCCAGCAGCT GTTAAAGGAG GAAAAGGAGG CTCTGGTTGC CATGGGAATT
1351  GACAGAAGTT CACTTACTTC CCTTGAAACA TCATATTTTA CCCCAAAAAA
1401  GAGAAAGCTC TTTGGTAATA AGAAAAGGAA GTCCTTCTTT TTGAGAGAGT
1451  CTGGGAAAGA CCAGCCTCCT GGGTCAGATT CTGATGAAGA TTGCCAAAAA
1501  AAGCCACAGC TCCTAGAGCA AACCAAACGA CTGTCCCAGA ATCTATCACT
1551  GGACCACTTT GATGAGCATG GAGATCCTCT CCAAAGGCAG AGAGCACTGA
1601  GTGCTGTCAG CATCCTCACC ATCACCATGA AGGAACAAGA AAAATCACAA
1651  GAGCCTTGTC TCCCTTGTGG AGAAAACCTG GCATCCAAGT ACCTCGTGTG
1701  GAACTGTTGC CCCCAGTGGC TGTGCGTTAA GAAGGTCCTG AGAACTGTGA
1751  TGACTGACCC GTTTACTGAG CTGGCCATCA CCATCTGCAT CATCATCAAC
1801  ACTGTCTTCT TGGCCATGGA GCATGACAAG ATGGAGGCCA GTTTTGAGAA
1851  GATGTTGAAT ATAGGGAATT TGGTTTTCAC TAGCATTTTT ATAGCAGAAA
1901  TGTGCCTAAA AATCATTGCG CTCGATCCCT ACCACTACTT TCGCCGAGGC
1951  TGGAACATTT TTGACAGCAT TGTTGCTCTT CTGAGTTTTG CAGATGTAAT
2001  GAACTGTGTA CTTCAAAAGA GAAGCTGGCC ATTCTTGCGT TCCTTCAGAG
2051  TGCTCAGGGT CTTCAAGTTA GCCAAATCCT GGCCAACTTT GAACACACTA
2101  ATTAAGATAA TCGGCAACTC TGTCGGAGCC CTTGGAAGCC TGACTGTGGT
2151  CCTGGTCATT GTGATCTTTA TTTTCTCAGT AGTTGGCATG CAGCTTTTTG
2201  GCCGTAGCTT CAATTCCCAA AAGAGTCCAA AACTCTGTAA CCCGACAGGC
2251  CCGACAGTCT CATGTTTACG GCACTGGCAC ATGGGGGATT TCTGGCACTC
2301  CTTCCTAGTG GTATTCCGCA TCCTCTGCGG GGAATGGATC GAAAATATGT
2351  GGGAATGTAT GCAAGAAGCG AATGCATCAT CATCATTGTG TGTTATTGTC
2401  TTCATATTGA TCACGGTGAT AGGAAAACTT GTGGTGCTCA ACCTCTTCAT
2451  TGCCTTACTG CTCAATTCCT TTAGCAATGA GGAAAGAAAT GGAAACTTAG
2501  AAGGAGAGGC CAGGAAAACT AAAGTCCAGT TAGCACTGGA TCGATTCCGC
2551  CGGGCTTTTT GTTTTGTGAG ACACACTCTT GAGCATTTCT GTCACAAGTG
```

FIG. 11A-3

```
2601  GTGCAGGAAG CAAAACTTAC CACAGCAAAA AGAGGTGGCA GGAGGCTGTG
2651  CTGCACAAAG CAAAGACATC ATTCCCCTGG TCATGGAGAT GAAAAGGGGC
2701  TCAGAGACCC AGGAGGAGCT TGGTATACTA ACCTCTGTAC CAAAGACCCT
2751  GGGCGTCAGG CATGATTGGA CTTGGTTGGC ACCACTTGCG GAGGAGGAAG
2801  ATGACGTTGA ATTTTCTGGT GAAGATAATG CACAGCGCAT CACACAACCT
2851  GAGCCTGAAC AACAGGCCTA TGAGCTCCAT CAGGAGAACA AGAAGCCCAC
2901  GAGCCAGAGA GTTCAAAGTG TGGAAATTGA CATGTTCTCT GAAGATGAGC
2951  CTCATCTGAC CATACAGGAT CCCCGAAAGA AGTCTGATGT TACCAGTATA
3001  CTATCAGAAT GTAGCACCAT TGATCTTCAG GATGGCTTTG GATGGTTACC
3051  TGAGATGGTT CCCAAAAAGC AACCAGAGAG ATGTTTGCCC AAAGGCTTTG
3101  GTTGCTGCTT TCCATGCTGT AGCGTGGACA AGAGAAAGCC TCCCTGGGTC
3151  ATTTGGTGGA ACCTGCGGAA AACCTGCTAC CAAATAGTGA AACACAGCTG
3201  GTTTGAGAGC TTTATTATCT TTGTGATTCT GCTGAGCAGT GGGGCACTGA
3251  TATTTGAAGA TGTTCACCTT GAGAACCAAC CCAAAATCCA AGAATTACTA
3301  AATTGTACTG ACATTATTTT TACACATATT TTTATCCTGG AGATGGTACT
3351  AAAATGGGTA GCCTTCGGAT TTGGAAAGTA TTTCACCAGT GCCTGGTGCT
3401  GCCTTGATTT CATCATTGTG ATTGTCTCTG TGACCACCCT CATTAACTTA
3451  ATGGAATTGA AGTCCTTCCG GACTCTACGA GCACTGAGGC CTCTTCGTGC
3501  GCTGTCCCAG TTTGAAGGAA TGAAGGTGGT GGTCAATGCT CTCATAGGTG
3551  CCATACCTGC CATTCTGAAT GTTTTGCTTG TCTGCCTCAT TTTCTGGCTC
3601  GTATTTTGTA TTCTGGGAGT ATACTTCTTT TCTGGAAAAT TTGGGAAATG
3651  CATTAATGGA ACAGACTCAG TTATAAATTA TACCATCATT ACAAATAAAA
3701  GTCAATGTGA AAGTGGCAAT TTCTCTTGGA TCAACCAGAA AGTCAACTTT
3751  GACAATGTGG GAAATGCTTA CCTCGCTCTG CTGCAAGTGG CAACATTTAA
3801  GGGCTGGATG GATATTATAT ATGCAGCTGT TGATTCCACA GAGAAAGAAC
3851  AACAGCCAGA GTTTGAGAGC AATTCACTCG GTTACATTTA CTTCGTAGTC
3901  TTTATCATCT TTGGCTCATT CTTCACTCTG AATCTCTTCA TTGGCGTTAT
3951  CATTGACAAC TTCAACCAAC AGCAGAAAAA GTTAGGTGGC CAAGACATTT
```

FIG. 11A-4

```
4001  TTATGACAGA AGAACAGAAG AAATACTATA ATGCAATGAA AAAATTAGGA
4051  TCCAAAAAAC CTCAAAAACC CATTCCACGG CCTCTGAACA AATGTCAAGG
4101  TCTCGTGTTC GACATAGTCA CAAGCCAGAT CTTTGACATC ATCATCATAA
4151  GTCTCATTAT CCTAAACATG ATTAGCATGA TGGCTGAATC ATACAACCAA
4201  CCCAAAGCCA TGAAATCCAT CCTTGACCAT CTCAACTGGG TCTTTGTGGT
4251  CATCTTTACG TTAGAATGTC TCATCAAAAT CTTTGCTTTG AGGCAATACT
4301  ACTTCACCAA TGGCTGGAAT TTATTTGACT GTGTGGTCGT GCTTCTTTCC
4351  ATTGTTAGTA CAATGATTTC TACCTTGGAA AATCAGGAGC ACATTCCTTT
4401  CCCTCCGACG CTCTTCAGAA TTGTCCGCTT GGCTCGGATT GGCCGAATCC
4451  TGAGGCTTGT CCGGGCTGCA CGAGGAATCA GGACTCTCCT CTTTGCTCTG
4501  ATGATGTCGC TTCCTTCTCT GTTCAACATT GGTCTTCTAC TCTTTCTGAT
4551  TATGTTTATC TATGCCATTC TGGGTATGAA CTGGTTTTCC AAAGTGAATC
4601  CAGAGTCTGG AATCGATGAC ATATTCAACT TCAAGACTTT TGCCAGCAGC
4651  ATGCTCTGTC TCTTCCAGAT AAGCACATCA GCAGGTTGGG ATTCCCTGCT
4701  CAGCCCCATG CTGCGATCAA AGAATCATG TAACTCTTCC TCAGAAAACT
4751  GCCACCTCCC TGGCATAGCC ACATCCTACT TTGTCAGTTA CATTATCATC
4801  TCCTTTCTCA TTGTTGTCAA CATGTACATT GCTGTGATTT TAGAGAACTT
4851  CAATACAGCC ACTGAAGAAA GTGAGGACCC TTTGGGTGAA GATGACTTTG
4901  ACATATTTTA TGAAGTGTGG GAAAAGTTTG ACCCAGAAGC AACACAATTT
4951  ATCAAATATT CTGCCCTTTC TGACTTTGCT GATGCCTTGC CTGAGCCTTT
5001  GCGTGTCGCA AAGCCAAATA AATATCAATT TCTAGTAATG GACTTGCCCA
5051  TGGTGAGTGA AGATCGCCTC CACTGCATGG ATATTCTTTT CGCCTTCACC
5101  GCTAGGGTAC TCGGTGGCTC TGATGGCCTA GATAGTATGA AGCAATGAT
5151  GGAAGAGAAG TTCATGGAAG CCAATCCTCT CAAGAAGTTG TATGAACCCA
5201  TAGTCACCAC CACCAAGAGA AAGGAAGAGG AAAGAGGTGC TGCTATTATT
5251  CAAAAGGCCT TTCGAAAGTA CATGATGAAG GTGACCAAGG GTGACCAAGG
5301  TGACCAAAAT GACTTGGAAA ACGGGCCTCA TTCACCACTC CAGACTCTTT
```

FIG. 11A-5

```
5351  GCAATGGAGA CTTGTCTAGC TTTGGGGTGG CCAAGGGCAA GGTCCACTGT

5401  GACTGAGCCC TCACCTCCAC GCCTACCTCA TAGCTTCACA GCCTTGCCTT

5451  CAGCCTCTGA GCTCCAGGGG TCAGCAGCTT AGTGTATCAA CAGGGAGTGG

5501  ATTCACCAAA TTAGCCATTC CATTTCTTT TCTGGCTAAA ATAAATGATA

5551  TTTCAATTTC ATTTAAATG ATACTTACAG AGATATAAGA TAAGGCTACT

5601  TGACAACCAG TGGTACTATT ATAATAAGGA AGAAGACACC AGGAAGGACT

5651  GTAAAAGGAC ATACCAATTT TAGGATTGAA ATAGTTCAGG CCGGGCGCAG

5701  TGGCTCATGC CTGTAATCCC AGCACTTTGA GAGGCCAAGG CAGGTGGATC

5751  ACGAGGTCAA GAGATCGAGA CCATCCTGGC CAACATGATG AAACTCCGTC

5801  TCTCTAAAAA TACAAAAATT AGCTGGGCAT GGTGGCGTGC GCCTGTAGTC

5851  CCACTACTTG
```

FIG. 11B

Sequence of human NaN.

```
   1  MDDRCYPVIF  PDERNFRPFT  SDSLAAIEKR  IAIQKEKKKS  KDQTGEVPQP
  51  RPQLDLKASR  KLPKLYGDIP  RELIGKPLED  LDPFYRNHKT  FMVLNRKRTI
 101  YRFSAKHALF  IFGPFNSIRS  LAIRVSVHSL  FSMFIIGTVI  INCVFMATGP
 151  AKNSNSNNTD  IAECVFTGIY  IFEALIKILA  RGFILDEFSF  LRDPWNWLDS
 201  IVIGIAIVSY  IPGITIKLLP  LRTFRVFRAL  KAISVVSRLK  VIVGALLRSV
 251  KKLVNVIILT  FFCLSIFALV  GQQLFMGSLN  LKCISRDCKN  ISNPEAYDHC
 301  FEKKENSPEF  KMCGIWMGNS  ACSIQYECKH  TKINPDYNYT  NFDNFGWSFL
 351  AMFRLMTQDS  WEKLYQQTLR  TTGLYSVFFF  IVVIFLGSFY  LINLTLAVVT
 401  MAYEEQNKNV  AAEIEAKEKM  FQEAQQLLKE  EKEALVAMGI  DRSSLTSLET
 451  SYFTPKKRKL  FGNKKRKSFF  LRESGKDQPP  GSDSDEDCQK  KPQLLEQTKR
 501  LSQNLSLDHF  DEHGDPLQRQ  RALSAVSILT  ITMKEQEKSQ  EPCLPCGENL
 551  ASKYLVWNCC  PQWLCVKKVL  RTVMTDPFTE  LAITICIIIN  TVFLAMEHHK
 601  MEASFEKMLN  IGNLVFTSIF  IAEMCLKIIA  LDPYHYFRRG  WNIFDSIVAL
 651  LSFADVMNCV  LQKRSWPFLR  SFRVLRVFKL  AKSWPTLNTL  IKIIGNSVGA
 701  LGSLTVVLVI  VIFIFSVVGM  QLFGRSFNSQ  KSPKLCNPTG  PTVSCLRHWH
 751  MGDFWHSFLV  VFRILCGEWI  ENMWECMQEA  NASSSLCVIV  FILITVIGKL
 801  VVLNLFIALL  LNSFSNEERN  GNLEGEARKT  KVQLALDRFR  RAFCFVRHTL
 851  EHFCHKWCRK  QNLPQQKEVA  GGCAAQSKDI  IPLVMEMKRG  SETQEELGIL
 901  TSVPKTLGVR  HDWTWLAPLA  EEEDDVEFSG  EDNAQRITQP  EPEQQAYELH
 951  QENKKPTSQR  VQSVEIDMFS  EDEPHLTIQD  PRKKSDVTSI  LSECSTIDLQ
1001  DGFGWLPEMV  PKKQPERCLP  KGFGCCFPCC  SVDKRKPPWV  IWWNLRKTCY
1051  QIVKHSWFES  FIIFVILLSS  GALIFEDVHL  ENQPKIQELL  NCTDIIFTHI
1101  FILEMVLKWV  AFGFGKYFTS  AWCCLDFIIV  IVSVTTLINL  MELKSFRTLR
1151  ALRPLRALSQ  FEGMKVVVNA  LIGAIPAILN  VLLVCLIFWL  VFCILGVYFF
```

FIG. 11B-2

```
1201  SGKFGKCING  TDSVINYTII  TNKSQCESGN  FSWINQKVNF  DNVGNAYLAL
1251  LQVATFKGWM  DIIYAAVDST  EKEQQPEFES  NSLGYIYFVV  FIIFGSFFTL
1301  NLFIGVIIDN  FNQQQKKLGG  QDIFMTEEQK  KYYNAMKKLG  SKKPQKPIPR
1351  PLNKCQGLVF  DIVTSQIFDI  IIISLIILNM  ISMMAESYNQ  PKAMKSILDH
1401  LNWVFVVIFT  LECLIKIFAL  RQYYFTNGWN  LFDCVVVLLS  IVSTMISTLE
1451  NQEHIPFPPT  LFRIVRLARI  GRILRLVRAA  RGIRTLLFAL  MMSLPSLFNI
1501  GLLLFLIMFI  YAILGMNWFS  KVNPESGIDD  IFNFKTFASS  MLCLFQISTS
1551  AGWDSLLSPM  LRSKESCNSS  SENCHLPGIA  TSYFVSYIII  SFLIVVNMYI
1601  AVILENFNTA  TEESEDPLGE  DDFDIFYEVW  EKFDPEATQF  IKYSALSDFA
1651  DALPEPLRVA  KPNKYQFLVM  DLPMVSEDRL  HCMDILFAFT  ARVLGGSDGL
1701  DSMKAMMEEK  FMEANPLKKL  YEPIVTTTKR  KEEERGAAII  QKAFRKYMMK
1751  VTKGDQGDQN  DLENGPHSPL  QTLCNGDLSS  FGVAKGKVHC  D.
```

SODIUM CHANNEL IN DORSAL ROOT GANGLIA

This application is divisional of U.S. application Ser. No. 09/354,147 (filed Jul. 16, 1999 now U.S. Pat. No. 6,573,067) which is a continuation-in-part of PCT International Application PCT/US99/02008 (filed Jan. 29, 1999) which claims the benefit under 35 U.S.C. 119(e) of U.S. Provisional Applications 60/072,990 (filed Jan. 29, 1998), 60/109,402 (filed Nov. 20, 1998) and 60/109,666 (also filed Nov. 20, 1998), all of which are herein incorporated by reference in their entirety.

FIELD OF THE INVENTION

BACKGROUND

A. Sodium Channels

Voltage-gated sodium channels are a class of specialized protein molecules that act as molecular batteries permitting excitable cells (neurons and muscle fibers) to produce and propagate electrical impulses. Voltage-gated $Na^+$ channels from rat brain are composed of three subunits, the pore-forming α subunit (260 KDa) and two auxiliary subunits, β1 (36 KDa) and β2 (33 KDa) that may modulate the properties of the α-subunit; the α subunit is sufficient to form a functional channel that generates a Na current flow across the membrane [references 1,2 as cited below]. Nine distinct α subunits have been identified in vertebrates and are encoded by members of an expanding gene family [3 and references therein, 4–6] and respective orthologues of a number of them have been cloned from various mammalian species including humans. Specific α subunits are expressed in a tissue- and developmentally-specific manner [7,8]. Aberrant expression patterns or mutations of voltage-gated sodium channel α-subunits underlie a number of human and animal disorders [9–13].

Voltage-gated sodium channel α-subunits consist of four domains (D1–4) of varying internal homology but of similar predicted structure, connected by three intracellular loops (L1–3). The four domains fold to form a channel that opens to both the cytoplasm and the extracellular space via a pore. The pore opens and closes depending upon the physiological state of the cell membrane.

Each domain consists of six transmembrane segments (S1–6) that allow the protein to weave through the membrane with intra- and extracellular linkers. The linkers of S5–S6 segments of the four domains contain sequences that line the pore of the channel, and a highly conserved subset of amino acids that acts as a filter to selectively allow sodium ions to traverse the channel pore into the cytoplasm, thus generating an electric current. The amphiphatic S4 segment, in each of the four domains, rich in basic residues repeated every third amino acid, acts as a voltage sensor and undergoes a conformational change as a result of. the change in the voltage difference across the cell membrane. This in turn triggers the conformational change of the protein to open its pore to the extracellular $Na^+$ ion gradient.

In most of the known voltage-gated sodium channel α-subunits the channels close and change into an inoperable state quickly (inactivate) within a few milliseconds after opening of the pore (activation); SNS-type channels, on the other hand, inactivate slowly and require a greater voltage change to activate. L3, the loop that links domains D3 and D4, contains a tripeptide which acts as an intracellular plug that closes the pore after activation, thus inducing the channel to enter the inactive state. After inactivation, these channels further undergo conformational change to restore their resting state and become available for activation. This period is referred to as recovery from inactivation (repriming). Different channels reprime at different rates, and repriming in SNS is relatively rapid.

Based on amino acid similarities, the voltage-gated sodium channel family has been further subdivided into two subfamilies [14]. Eight of the nine cloned channels belong to subfamily 1. They share many structural features, particularly in their S4 transmembrane segments. However, some of them have been shown to have distinct kinetic properties of inactivation and repriming. Only a single channel of subfamily 2, also referred to as atypical channels, has been identified in human, rat and mouse tissues. This subfamily is primarily characterized by reduced numbers of basic residues in its S4 segments, and thus is predicted to have different voltage-dependence compared to subfamily 1. The physiological function of subfamily 2 channels is currently unknown because its electrophysiological properties have not yet been elucidated.

The blocking of voltage-gated sodium channels by tetrodotoxin, a neurotoxin, has served to functionally classify these channels into sensitive (TTX-S) and resistant (TTX-R) phenotypes. Two mammalian TTX-R channels have so far been identified, one specific to the cardiac muscle and to very limited areas of the central nervous system (CNS) and the second, SNS, is restricted to peripheral neurons (PNS) of the dorsal root ganglia (DRG) and trigeminal ganglia. Specific amino acid residues that confer resistance or sensitivity to TTX have been localized to the ion selectivity filter of the channel pore. The SNS channel is also described in International Patent Application WO 97/01577

B. Role of Sodium Channels in Disease States

Because different $Na^+$ channel α-subunit isotypes exhibit different kinetics and voltage-dependence, the firing properties of excitable cells depend on the precise mixture of channel types that they express. Mutants of the cardiac and skeletal muscle α-subunit have been shown to cause a number of muscle disorders. Some examples are as follows: A change of a single basic amino acid residue in the S4 of the skeletal muscle channel is sufficient to change the kinetic properties of this channel and induce a disease state in many patients. A tripeptide deletion in L3 of the cardiac channel, proximal to the inactivation gate, induces a cardiac disorder called Long QT syndrome. A single amino acid change in the S5–S6 linker of domain 1 of Scn8a, the region lining the pore of the channel, causes the mouse mutant "jolting". The total loss of this channel by a different mutation causes motor end plate "med" disease in mice. This mutation is characterized by loss of motor neuron stimulation of the innervated muscle.

C. Sodium Channels and Pain

Axonal injury (injury to nerve fibers, also called axons) can produce chronic pain (termed neuropathic pain). A number of studies have demonstrated altered excitability of the neuronal cell body and dendrites after axonal injury [15–17], and there is evidence for a change in $Na^+$ channel density over the neuronal cell body and dendrites following axonal injury [18–20]. The expression of abnormal mixtures of different types of sodium channels in a neuronal cell can also lead to abnormal firing [13], and can contribute to hyperexcitability, paresthesia or pain.

Recent studies from our group on rat sensory DRG neurons have demonstrated a dramatic change in the expression profile of TTX-R and TTX-S currents and in a number of mRNA transcripts that could encode the channels responsible for these currents in DRG neurons following various insults [21–23]. We have, for example, shown an attenuation of the slowly inactivating, TTX-R current and simultaneous enhancement of the rapidly inactivating, TTX-S Na$^+$ currents in identified sensory cutaneous afferent neurons following axotomy [21]. We also have shown a loss of TTX-S, slowly repriming current and TTX-R current and a gain in TTX-S, rapidly repriming current in nociceptive (pain) neurons following axotomy [22], down-regulation of SNS transcripts and a simultaneous up-regulation of α-III Transcripts [23]. Also associated with axotomy is a moderate elevation in the levels of αI and αII mRNAs [24]. These changes in the sodium channel profile appear to contribute to abnormal firing that underlies neuropathic pain that patients suffer following axonal injury.

Inflammation, which is also associated with pain (termed inflammatory pain), also causes alteration in the sodium current profile in nociceptive DRG neurons. Inflammatory modulators up-regulate TTX-R current in small C-type nociceptive DRG neurons in culture [25,26]. The rapid action of these modulators suggests that their action include posttranslational modification of existing TTX-R channels. We have now determined that inflammation also increases a TTX-R Na$^+$ current and up-regulates SNS transcripts in C-type DRG neurons [58]. This data suggests that changes in the sodium current profile contribute to inflammation evoked-pain.

D. Therapies for Chronic Pain:

A variety of classes of drugs (anticonvulsants such as phenytoin and carbamazepine; anti-arrhythmics such as mexitine; local anesthetics such as lidocaine) act on Na$^+$ channels. Since the various Na$^+$ channels produce sodium currents with different properties, selective blockade or activation (or other modulation) of specific channel subtypes is expected to be of significant therapeutic value. Moreover, the selective expression of certain α-subunit isoforms (PN1, SNS, NaN) in specific types of neurons provides a means for selectively altering their behavior.

Nociceptive neurons of the DRG are the major source of the PNS TTX-R Na$^+$ current. Thus, the Na$^+$ channels producing TTX-R currents provide a relatively specific target for the manipulation of pain-producing neurons. The molecular structure of one TTX-R channel in these DRG neurons, SNS, has been identified but, prior to our research, it has not been determined whether there are other TTX-R channels in these neurons. If such channels could be identified, they would be ideal candidates as target molecules that are preferentially expressed in nociceptive neurons, and whose modulation would attenuate pain transmission.

SUMMARY OF THE INVENTION

The present invention includes an isolated nucleic acid which encodes a voltage gated Na$^+$ channel that is preferentially expressed in dorsal root ganglia or trigeminal ganglia (the NaN channel). (In our preceding U.S. Provisional Application 60/072,990, this NaN channel was referred to by its previous name "NaX.") In a preferred embodiment, the isolated nucleic acid comprises the sequence shown in FIG. 1, FIG. 7A, FIG. 8A, FIG. 11A (SEQ ID NO: 1, 4, 6 and 41, respectively), allelic variants of said sequences or nucleic acids that hybridize to the foregoing sequences under stringent conditions.

In another embodiment, the invention includes an expression vector comprising an isolated nucleic acid which encodes the voltage gated Na$^+$ channel that is preferentially expressed in dorsal root ganglia or trigeminal ganglia either alone or with appropriate regulatory and expression control elements. In a preferred embodiment, the expression vector comprises an isolated nucleic acid having the sequence shown in FIG. 1, FIG. 7A, FIG. 8A, FIG. 11A, allelic variants of said sequences or nucleic acids that hybridize to the foregoing sequences under stringent conditions.

The present invention further includes a host cell transformed with an expression vector comprising an isolated nucleic acid which encodes a voltage gated Na$^+$ channel that is preferentially expressed in dorsal root ganglia or trigeminal ganglia with appropriate regulatory and expression control elements. In a preferred embodiment, the expression vector comprises an isolated nucleic acid having the sequence shown in FIG. 1, FIG. 7A, FIG. 8A, FIG. 11A, allelic variants of said sequences or nucleic acids that hybridize to the foregoing sequences under stringent conditions.

The present invention also includes an isolated voltage gated Na$^+$ channel that is preterentially expressed in dorsal root ganglia or trigeminal ganglia. In a preferred embodiment, the channel has the amino acid sequence of FIGS. 2, 7B, 8B or 11B (SEQ ID NO: 3, 5, 8 and 42, respectively), or is encoded by a nucleic acid having the sequence shown in FIGS. 1, 7A, 8A or 11A, allelic variants of said sequences or nucleic acids that hybridize to the foregoing sequences under stringent conditions. Peptide fragments of the channel are also included.

Another aspect of the invention is a method to identify an agent that modulates the activity of the NaN channel, comprising the steps of bringing the agent into contact with a cell that expresses the Na$^+$ channel on its surface and measuring depolarization, or any resultant changes in the sodium current. The measuring step may be accomplished with voltage clamp measurements, by measuring depolarization, the level of intracellular sodium or by measuring sodium influx.

Another aspect of the invention is a method to identify an agent that modulates the transcription or translation of mRNA encoding the NaN channel. The method comprises the steps of bringing the agent into contact with a cell that expresses the Na$^+$ channel on its surface and measuring the resultant level of expression of the Na$^+$ channel.

The invention also includes a method to treat pain, paraesthesia and hyperexcitability phenomena in an animal or human subject by administering an effective amount of an agent capable of modulating, such as by inhibiting or enhancing, Na$^+$ current flow through NaN channels in DRG or trigeminal neurons. The method may include administering an effective amount of an agent capable of modulating the transcription or translation of mRNA encoding the NaN channel.

Another aspect of the invention is an isolated nucleic acid that is antisense to the nucleic acids described above. In a preferred embodiment, the antisense nucleic acids are of sufficient length to modulate the expression of NaN channel mRNA in a cell containing the mRNA.

Another aspect of the invention is a scintigraphic method to image the loci of pain generation or provide a measure the level of pain associated with DRG or trigeminal neuron mediated hyperexcitability in an animal or human subject by administering labeled monoclonal antibodies or other labeled ligands specific for the NaN Na$^+$ channel.

Another aspect of the invention is a method to identify tissues, cells and cell types that express the NaN sodium channel. This method comprises the step of detecting NaN on the cell surface, or en route to the cell surface, or the presence of NaN encoding mRNA.

The present invention further includes a method of producing a transformed cell that expresses an exogenous NaN encoding nucleic acid, comprising the step of transforming the cell with an expression vector comprising an isolated nucleic acid having the sequence shown in FIGS. 1, 7A, 8A or 11A, allelic variants of said sequences or nucleic acids that hybridize to the foregoing sequences under stringent conditions, together with appropriate regulatory and expression control elements. The invention also includes a method of producing recombinant NaN protein, comprising the step of culturing the transformed host under conditions in which the NaN sodium channel or protein is expressed, and recovering the NaN protein.

The invention also includes an isolated antibody specific for the NaN channel or polypeptide fragment thereof. The isolated antibody may be labeled.

Another aspect of the invention includes a therapeutic composition comprising an effective amount of an agent capable of decreasing rapidly repriming sodium current flow in axotomized, inflamed or otherwise injured DRG neurons or in normal DRG neurons that are being driven to fire at high frequency. The invention also includes a method to treat acute pain or acute or chronic neuropathic or inflammatory pain and hyperexcitability phenomena in an animal or a human patient by administering the therapeutic composition.

The present invention also includes a method to screen candidate compounds for use in treating pain and hyperexcitability phenomena by testing their ability to alter the expression or activity of an NaN channel mRNA or protein in axotomized, inflamed or otherwise injured DRG neurons.

BRIEF DESCRIPTION OF THE DRAWING FIGURES

FIG. 1 shows the sequence of the rat NaN cDNA (SEQ ID NO: 1).

FIG. 2 shows the putative amino acid sequence of the rat NaN cDNA (SEQ ID NO: 3). Predicted transmembrance segments of domains I–IV are underlined. The amino acid serine "S" in DI-SS2, implicated in the TTX-R phenotype, is in bold face type.

FIG. 3 presents a schematic diagram of predicted secondary structure of the NaN α-subunit.

FIG. 4 shows the results of RT-PCR analysis for α-NaN in extracts of various tissues using NaN-specific primers. NaN is abundantly expressed in dorsal root and trigeminal ganglia. Low levels of NaN are detected in cerebral hemisphere and retina tissues. No detectable NaN signal is seen in cerebellum, optic nerve, spinal cord, sciatic nerve, superior cervical ganglia, skeletal muscle, cardiac muscle, adrenal gland, uterus, liver and kidney.

Figure 5:
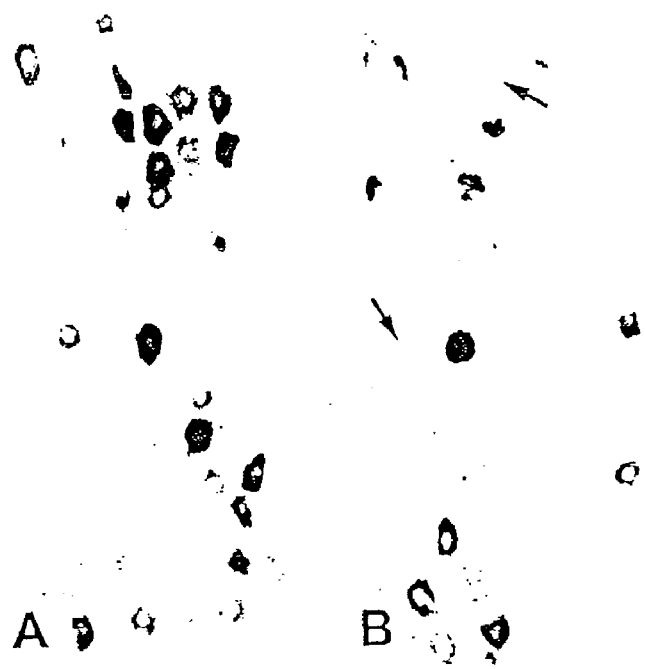

FIG. 5 shows the tissue distribution of α-NaN by in situ hybridization. A. Trigeminal ganglion neurons show moderate-to-high hybridization signal. B. Dorsal root ganglion neurons show moderate-to-high hybridization signal in small neurons. Hybridization signal is attenuated in large neurons (arrow). C. Sense probe shows no signal in DRG neurons. D., E., and F. No hybridization signal is seen in spinal cord, cerebellum and liver. All tissues are from adult Sprague-Dawley rat. Scale bars=50 micrometer.

FIG. 6 shows the predicted lengths of domain I amplification products of rat α-subunits and their subunit-specific restriction enzyme profile.

FIGS. 7A–7B set forth the nucleotide (SEQ ID NO: 4) and amino acid (SEQ ID NO: 5) sequences of the murine NaN.

FIG. 8A–FIG. 8B. FIG. 8A is a partial nucleotide sequence of the human NaN (SEQ ID NO: 6). FIG. 8B is a partial amino acid sequence of the human NaN protein (SEQ ID NO: 8).

Figure 9:
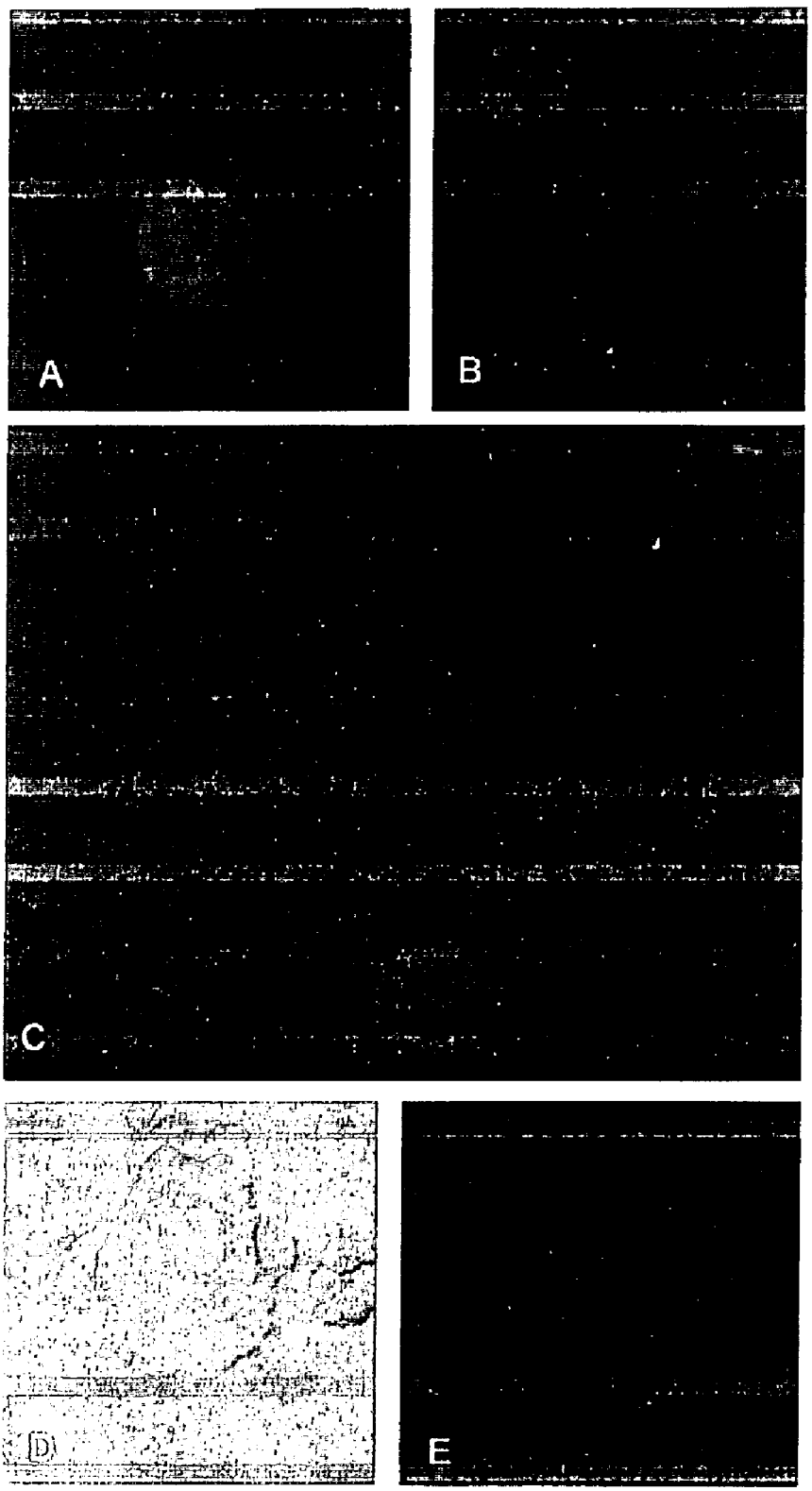

FIG. 9 shows cultures of DRG neurons obtained from L4/5 ganglia of adult rats that were reacted with antibody to NaN and then processed for immunofluorescent localization. a.,b. NaN immunostaining is prominent within the cell bodies of DRG neurons. c. NaN is present in the neuritic outgrowths, as well as the cell bodies, of DRG neurons. d., d'. Nomarski (d.) and fluorescent (d'.) images of a neuron that does not express NaN protein.

Figures 10A, 10B:
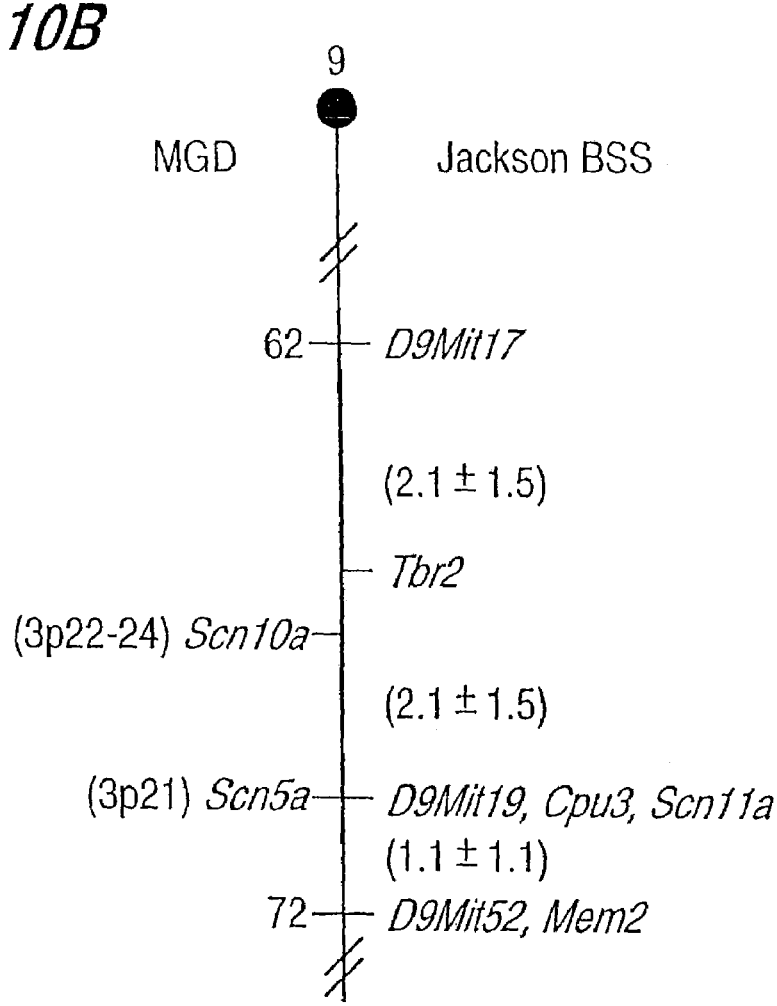

FIG. 10 shows the location of Scn1 1a and related genes on distal mouse chromosome 9. (A) Haplotypes from the Jackson BSS backcross. Black boxes represent C57BL/6J alleles and white boxes represent SPRET/Ei alleles. The number of animals with each haplotype is given below each column. Missing data was inferred from adjacent data when typing was ambiguous. (B) Map of distal chromosome 9 based on data in (A). Positions of Scn5a and Scn10a from the MGD consensus map and the locations of the human orthologs are indicated. Numbers are cM positions on the consensus map (http://www.informatics.jax.org/bin/ccr/index).

FIG. 11A–FIG. 11B. FIG. 11A shows the cDNA nucleotide sequence of the human NaN gene spanning the complete open reading frame (SEQ ID NO: 41). FIG. 11B sets forth the putative amino acid sequence of the full length human NaN protein (SEQ ID NO: 42).

DETAILED DESCRIPTION

The present invention relates to a novel gene that we have discovered, called NaN. NaN encodes a previously unidentified protein, referred to herein as NaN, that belongs to the α-subunit voltage-gated sodium channel protein family and that produces a TTX-R sodium current. Such channels underlie the generation and propagation of impulses in excitable cells like neurons and muscle fibers. NaN is a novel sodium channel, with a sequence distinct from other, previously identified, channels. The preferential expression of NaN on sensory, but not other neurons, makes it a very useful target for diagnostic and/or therapeutic uses in relation to acute and/or chronic pain pathologies.

Definitions:

This specification uses several technical terms and phrases which are intended to have the following meanings:

The phrase "modulate" or "alter" refers to up- or down-regulating the level or activity of a particular receptor, ligand or current flow. For example an agent might modulate $Na^+$ current flow by inhibiting (decreasing) or enhancing (increasing) $Na^+$ current flow. Similarly, an agent might modulate the level of expression of the NaN sodium channel or the activity of the NaN channels that are expressed.

The phrase "sodium current" or "$Na^+$ current" means the flow of sodium ions across a cell membrane, often through channels (specialized protein molecules) that are specifically permeable to certain ions, in this case sodium ions.

The phrase "voltage gated" means that the ion channel opens when the cell membrane is in a particular voltage range. Voltage-sensitive sodium channels open when the membrane is depolarized. They then permit $Na^+$ ions to flow into the cell, producing further depolarization. This permits the cell to generate electrical impulses (also known as "action potentials").

The phrase "rapidly repriming" means that the currents recover from inactivation more rapidly than do such currents in most other voltage gated sodium channel family members.

The terms "TTX-R" and "TTX-S" means that the flow of current through a cell membrane is, respectively, resistant or sensitive to tetrodotoxin (a neurotoxin produced in certain species) at a concentration of about 100 nM.

The phrase "peripheral nervous system (PNS)" means the part of the nervous system outside of the brain and spinal cord, i.e., the spinal roots and associated ganglia such as dorsal root ganglia (DRG) and trigeminal ganglia, and the peripheral nerves.

The phrase "inhibits $Na^+$ current flow" means that an agent has decreased such current flow relative to a control cell not exposed to that agent. A preferred inhibitor will selectively inhibit such current flow, without affecting the current flow of other sodium channels; or it will inhibit $Na^+$ current in the channel of interest to a much larger extent than in other channels.

The phrase "enhances $Na^+$ current flow" means that an agent has increased such current flow relative to a control cell not exposed to that agent. A preferred agent will selectively increase such current flow, without affecting the current flow of other sodium channels; or it will increase $Na^+$ current in the channel of interest to a much larger extent than in other channels.

The phrase "specifically hybridizes" refers to nucleic acids which hybridize under highly stringent or moderately stringent conditions to the nucleic acids encoding the NaN sodium channel, such as the DNA sequence of FIGS. 1, 7A, 8A or 11A (SEQ ID NO: 1, 4, 6 or 41).

The phrase "isolated nucleic acid" refers to nucleic acids that have been separated from or substantially purified relative to contaminant nucleic acids encoding other polypeptides. "Nucleic acids" refers to all forms of DNA and RNA, including cDNA molecules and antisense RNA molecules.

The phrase "RT-PCR" refers to the process of reverse transcription of RNA (RT) using the enzyme reverse transcriptase, followed by the amplification of certain cDNA templates using the polymerase chain reaction (PCR); PCR requires generic or gene-specific primers and thermostable DNA polymerase, for example, Taq DNA polymerase.

The phrase "preferentially expressed" means that voltage gated $Na^+$ channel is expressed in the defined tissues in detectably greater quantities than in other tissues. For instance, a voltage gated $Na^+$ channel that is preferentially expressed in dorsal root ganglia or trigeminal ganglia is found in detectably greater quantities in dorsal root ganglia or trigeminal ganglia when compared to other tissues or cell types. The quantity of the voltage gated $Na^+$ channel may be detected by any available means, including the detection of specific RNA levels and detection of the channel protein with specific antibodies.

Characterization of the NaN Sodium Channel:

The present invention relates to a previously unidentified, voltage-gated sodium channel a-subunit (NaN), predicted to he TTX-R, voltage-gated, and preferentially expressed in sensory neurons innervating the body (dorsal root ganglia or DRG) and the face (trigeminal ganglia). The predicted open reading frame (ORF), the part of the sequence coding for the NaN protein molecule, has been determined with the putative amino acid sequence from different species (rat, mouse, human) presented in FIGS. 2, 7B, 8B or 11B (SEQ ID NO: 3, 5, 8 or 42).

All of the relevant landmark sequences of voltage-gated sodium channels are present in NaN at the predicted positions, indicating that NaN belongs to the sodium channel family. But NaN is distinct from all other previously identified Na channels, sharing a sequence identity of less than 53% with each one of them. NaN is distinct from SNS, the only other TTX-R $Na^+$ channel subunit that has been identified, until our discovery, in PNS. We have identified and cloned NaN without using any primers or probes that are based upon or specific to SNS. Moreover, NaN and SNS share only 47% similarity of their predicted open reading frame (ORF), comparable to the limited similarity of NaN to all subfamily 1 members.

The low sequence similarity to existing α-subunits clearly identifies NaN as a novel gene, not simply a variant of an existing channel. Sequence variations compared to the other voltage-gated channels indicate that NaN may be the prototype of a novel and previously unidentified, third class of TTX-R channels that may possess distinct properties compared to SNS. NaN and SNS, which are present in nociceptive DRG and trigeminal neurons, may respond to pharmacological interventions in different ways. The preferential expression of NaN in sensory DRG and trigeminal neurons provides a target for selectively modifying the behavior of these nerve cells while not affecting other nerve cells in the brain and spinal cord. A further elucidation of the properties of NaN channels will be important to understand more fully the effects of drugs designed to modulate the function of the "TTX-R" currents which are characteristic of DRG nociceptive neurons and which contribute to the transmission of pain messages, and to abnormal firing patterns after nerve injury and in other painful conditions.

NaN Nucleic Acids:

Nucleic acid molecules of the invention include the nucleotide sequences set forth in FIG. 1, FIG. 7A, FIG. 8A, FIG. 11A as well as nucleotide sequences that encode the amino acid sequences of FIG. 2, FIG. 7B, FIG. 8B and 11B. Nucleic acids of the claimed invention also include nucleic acids which specifically hybridize to nucleic acids comprising the nucleotide sequences set forth in FIG. 1, FIG. 7A, 8A or FIG. 11A, or nucleotide sequences which encode the amino acid sequences of FIG. 2, FIG. 7B, FIG. 8B or FIG. 11B. A nucleic acid which specifically hybridizes to a nucleic acid comprising that sequence remains stably bound to said nucleic acid under highly stringent or moderately stringent conditions. Stringent and moderately stringent conditions are those commonly defined and available, such as those defined by Sambrook et al. [59] or Ausubel et al. [60]. The precise level of stringency is not important, rather, conditions should be selected that provide a clear, detectable signal when specific hybridization has occurred.

Hybridization is a function of sequence identity (homology), G+C content of the sequence, buffer salt content, sequence length and duplex melt temperature (T[m]) among other variables. See, Maniatis et al.[62]. With similar sequence lengths, the buffer salt concentration and temperature provide useful variables for assessing sequence identity (homology) by hybridization techniques. For example, where there is at least 90 percent homology, hybridization is commonly carried out at 68° C. in a buffer salt such as 6×SCC diluted from 20×SSC. See Sambrook et al. [59]. The buffer salt utilized for final Southern blot washes can be used at a low concentration, e.g., 0.1×SSC and at a relatively high temperature, e.g., 68° C., and two sequences will form a hybrid duplex (hybridize). Use of the above hybridization and washing conditions together are defined as conditions of high stringency or highly stringent conditions. Moderately stringent conditions can be utilized for hybridization where two sequences share at least about 80 percent homology. Here, hybridization is carried out using 6×SSC at a temperature of about 50–55° C. A final wash salt concentration of about 1–3×SSC and at a temperature of about 60–68° C. are used. These hybridization and washing conditions define moderately stringent conditions.

In particular, specific hybridization occurs under conditions in which a high degree of complementarity exists between a nucleic acid comprising the sequence of an isolated sequence and another nucleic acid. With specific hybridization, complementarity will generally be at least about 70%, 75%, 80%, 85%, preferably about 90–100%, or most preferably about 95–100%.

As used herein, homology or identity is determined by BLAST (Basic Local Alignment Search Tool) analysis using the algorithm employed by the programs blastp, blastn, blastx, tblastn and tblastx (Karlin et al. Proc. Natl. Acad. Sci. USA 87: 2264–2268 (1990) and Altschul, S. F. J. Mol. Evol. 36: 290–300(1993), both of which are herein incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (Nature Genetics 6: 119–129 (1994)) which is herein incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al. Proc. Natl. Acad. Sci. USA 89: 10915–10919 (1992), herein incorporated by reference). For blastn, the scoring matrix is set by the ratios of M (i.e., the reward score for a pair of matching residues) to N (i.e., the penalty score for mismatching residues), wherein the default values for M and N are 5 and −4, respectively.

The nucleic acids of the present invention can be used in a variety of ways in accordance with the present invention. For example, they can be used as nucleic acid probes to screen other cDNA and genomic DNA libraries so as to select by hybridization other DNA sequences that encode homologous NaN sequences. Contemplated nucleic acid probes could be RNA or DNA labeled with radioactive nucleotides or by non-radioactive methods (for example, biotin). Screening may be done at various stringencies (through manipulation of the hybridization Tm, usually using a combination of ionic strength, temperature and/or presence of formamide) to isolate close or distantly related homologs. The nucleic acids may also be used to generate primers to amplify cDNA or genomic DNA using polymerase chain reaction (PCR) techniques. The nucleic acid sequences of the present invention can also be used to identify adjacent sequences in the genome, for example, flanking sequences and regulatory elements of NaN. The nucleic acids may also be used to generate antisense primers or constructs that could be used to modulate the level of gene expression of NaN. The amino acid sequence may be used to design and produce antibodies specific to NaN that could be used to localize NaN to specific cells and to modulate the function of NaN channels expressed on the surface of cells.

Vectors and Transformed Host Cells:

The present invention also comprises recombinant vectors containing and capable of replicating and directing the expression of nucleic acids encoding a NaN sodium channel in a compatible host cell. For example, the insertion of a DNA in accordance with the present invention into a vector using enzymes such as T4 DNA ligase, may be performed by any conventional means. Such an insertion is easily accomplished when both the DNA and the desired vector have been cut with the same restriction enzyme or enzymes, since complementary DNA termini are thereby produced. If this cannot be accomplished, it may be necessary to modify the cut ends that are produced by digesting back single-stranded DNA to produce blunt ends, or by achieving the same result by filling in the single-stranded termini with an appropriate DNA polymerase. In this way, blunt-end ligation may be carried out. Alternatively, any site desired may be produced by ligating nucleotide sequences (linkers) onto the DNA termini. Such linkers may comprise specific oligonucleotide sequences that encode restriction site recognition sequences.

Any available vectors and the appropriate compatible host cells may be used [59, 60]. Commercially available vectors, for instance, those available from New England Biolabs Inc., Promega Corp., Stratagene Inc. or other commercial sources are included.

The transformation of appropriate cell hosts with an rDNA (recombinant DNA) molecule of the present invention is accomplished by well known methods that typically depend on the type of vector used and host system employed. Frog oocytes can be injected with RNA and will express channels, but in general, expression in a mammalian cell line (such as HEK293 or CHO cells) is preferred. With regard to transformation of prokaryotic host cells, electroporation and salt treatment methods are typically employed, see, for example, Cohen et al. [61]; and [62]. With regard to transformation of vertebrate cells with vectors containing rDNAs, electroporation, cationic lipid or salt treatment methods are typically employed [63, 64].

Successfully transformed cells, i.e., cells that contain an rDNA molecule of the present invention, can be identified by well known techniques. For example, cells resulting from the introduction of an rDNA of the present invention can be cloned to produce single colonies. Cells from those colonies can be harvested, lysed and their DNA content examined for the presence of the rDNA using conventional methods [65, 66] or the proteins produced from the cell assayed via an immunological method. If tags such as green fluorescent protein are employed in the construction of the recombinant DNA, the transfected cells may also be detected in vivo by the fluorescence of such molecules by cell sorting.

For transient expression of recombinant channels, transformed host cells for the measurement of $Na^+$ current or intracellular $Na^+$ levels are typically prepared by co-transfecting constructs into cells such as HEK293 cells with a fluorescent reporter plasmid (such as pGreen Lantern-1, Life Technologies, Inc.) using the calcium-phosphate precipitation technique [27]. HEK293 cells are typically grown in high glucose DMEM (Life Technologies, Inc) supplemented with 10% fetal calf serum (Life Technologies, Inc). After 48 hrs, cells with green fluorescence are selected for recording [28].

For preparation of cell lines continuously expressing recombinant channels, the NaN construct is cloned into other vectors that cany a selectable marker in mammalian cells. Transfections are carried out using the calcium phosphate precipitation technique [27]. Human embryonic kidney (HEK-293), chinese hamster ovary (CHO) cells, derivatives of either or other suitable cell lines are grown under standard tissue culture conditions in Dulbecco's modified Eagle's medium supplemented with 10% fetal bovine serum. The calcium phosphate-DNA mixture is added to the cell culture medium and left for 15–20 hr, after which time the cells are washed with fresh medium. After 48 hrs, antibiotic (G418, Geneticin, Life Technologies) is added to select for cells which have acquired neomycin resistance. After 2–3 weeks in G418, 10–20 isolated cell colonies are harvested using sterile 10 ml pipette tips. Colonies are grown for another 4–7 days, split and subsequently tested for channel expression using whole-cell patch-clamp recording techniques and RT-PCR.

Method of Measuring $Na^+$ Current Flow:

$Na^+$ currents are measured using patch clamp methods [29], as described by Rizzo et al. [30] and Dib-Hajj et al. [28]. For these recordings data are acquired on a Macintosh Quadra 950 or similar computer, using a program such as Pulse (v 7.52, HEKA, German). Fire polished electrodes typically (0.8–1.5 MW) are fabricated from capillary glass using a Sutter P-87 puller or a similar instrument. In the most rigorous analyses, cells are usually only considered for analysis if initial seal resistance is <5 Gohm, they have high leakage currents (holding current <0.1 nA at −80 mV), membrane blebs, and an access resistance <5 Mohm. Access resistance is usually monitored throughout the experiment and data are not used if resistance changes occur. Voltage errors are minimized using series resistance compensation and the capacitance artifact is canceled using computer controlled amplifier circuitry or other similar methods. For comparisons of the voltage dependence of activation and inactivation, cells with a maximum voltage error of ±10 mV after compensation are used. Linear leak subtraction is usually used for voltage clamp recordings. Membrane currents are typically filtered at 5 KHz and sampled at 20 KHz. The pipette solution contains a standard solution such as: 140 mM CsF, 2 mM $MgCl_2$, 1 mM EGTA, and 10 mM Na-HEPES (pH 7.3). The standard bathing solution is usually 140 nM NaCl, 3 mM KCl, 2 mM $MgCl_2$, 1 mM $CaCl_2$, 10 mM HEPES, and 10 mM glucose (pH 7.3).

Voltage clamp studies on transformed cells or DRG neurons, using methods such as intracellular patch-clamp recordings, can provide a quantitative measure of the sodium current density (and thus the number of sodium channels in a cell), and channel physiological properties. These techniques, which measure the currents that flow through ion channels such as sodium channels, are described in Rizzo et al. [21]. Alternatively, the blockage or enhancement of sodium channel function can be measured using optical imaging with sodium-sensitive dyes or with isotopically labeled Na. These methods which are described in Rose, et al., (J. Neurophysiology, 1997 in press) [67] and by Kimelberg and Walz [31], measure the increase in intracellular concentration of sodium ions that occurs when sodium channels are open.

Measurement of Intracellular Sodium ($[Na^+]_i$)

The effects of various agents on cells that express $Na^+$ can be determined using ratiometric imaging of $[Na^+]_i$ using SBFI or other similar ion-sensitive dyes. In this method, as described by Sontheimer et al. [32], cytosolic-free $Na^+$ is measured using an indicator for $Na^+$, such as SBFI (sodium-binding benzofuran isophthalate; [33]) or a similar dye. Cells are first loaded with the membrane-permeable acetoxymethyl ester form of the dye (which is dissolved in dimethyl sulfoxide (DMSO) at a stock concentration of 10 mM). Recordings are obtained on the stage of a microscope using a ratiometric imaging setup (e.g., from Georgia Instruments). Excitation light is provided at appropriate wavelengths (e.g., 340:385 nm). Excitation light is passed to the cells through a dichroic reflector (400 nm) and emitted light above 450 nm is collected. Fluorescence signals are amplified, e.g., by an image intensifier (GenIISyS) and collected with a CCD camera, or similar device, interfaced to a frame grabber. To account for fluorescence rundown, the fluorescence ratio 340:385 is used to assay cytosolic-free $Na^+$.

For calibration of SBFI's fluorescence, cells are perfused with calibration solutions containing known $Na^+$ concentrations (typically 0 and 30 mM, or 0, 30, and 50 mM $[Na^+]$), and with ionophones such as gramicidin and monensin (see above) after each experiment. As reported by Rose and Ransom [34], the 345/390 nm fluorescence ratio of intracellular SBFI changes monotonically with changes in $[Na^+]_i$. Experiments are typically repeated on multiple (typically at least 4) different coverslips, providing statistically significant measurements of intracellular sodium in control cells, and in cells exposed to various concentrations of agents that may block, inhibit or enhance $Na^+$.

Method to Measure $Na^+$ Influx via Measuring $^{22}Na$ or $^{86}Rb$.

$^{22}Na$ is a gamma emitter and can be used to measure $Na^+$ flux [31], and $^{86}Rb^+$ can be used to measure $Na^+/K^+$-ATPase activity [32]. $^{86}Rb^+$ ions are taken up by the $Na^+/K^+$-ATPase-like $K^+$ ions, but have the advantage of a much longer half-life than $^{42}K^+$[35]. Thus, measurement of the unidirectional ouabain-sensitive $^{86}Rb^+$ uptake provides a quantitative method for assaying $Na^+/K^+$-ATPase activity which provides another indicator of the electrical firing of nerve cells. Following incubation of cells expressing NaN with the isotope $^{22}Na^+$, the cellular content of the isotope is measured by liquid scintillation counting or a similar method, and cell protein is determined using a method such as the bicinchoninic acid protein assay [36] following the modifications described by Goldschmidt and Kimelberg [37] for cultured cells. $^{22}Na$ and $^{86}Rb^+$ fluxes are determined in the presence and absence of agents that may block, inhibit, or enhance NaN. This permits determination of the actions of these agents on NaN.

Method to Identify Agents that Modulate NaN-Mediated Current:

Several approaches can be used to identify agents that are able to modulate (i.e., block or augment) the $Na^+$ current through the NaN sodium channel. In general, to identify such agents, a model cultured cell line that expresses the NaN sodium channel is utilized, and one or more conventional assays are used to measure $Na^+$ current. Such conventional assays include, for example, patch clamp methods, the ratiometric imaging of $[Na^+]_i$, and the use of $^{22}Na$ and $^{86}Rb$ as described above.

In one embodiment of the present invention, to evaluate the activity of a candidate compound to modulate $Na^+$ current, an agent is brought into contact with a suitable transformed host cell that expresses NaN. After mixing or appropriate incubation time, the $Na^+$ current is measured to determine if the agent inhibited or enhanced $Na^+$ current flow.

Agents that inhibit or enhance $Na^+$ current are thereby identified. A skilled artisan can readily employ a variety of art-recognized techniques for determining whether a particular agent modulates the $Na^+$ current flow.

Because $Na^+$ is preferentially expressed in pain-signaling cells, one can also design agents that block, inhibit, or enhance $Na^+$ channel function by measuring the response of laboratory animals, treated with these agents, to acute or chronic pain. In one embodiment of this aspect of the invention, laboratory animals such as rats are treated with an agent for instance, an agent that blocks or inhibits (or is thought to block or inhibit) NaN. The response to various painful stimuli are then measured using tests such as the tail-flick test and limb withdrawal reflex, and are compared to untreated controls. These methods are described in Chapter 15 of Reference [38]. In another embodiment of this aspect of the invention, laboratory animals such as rats are subjected to localized injection of pain-producing inflammatory agents such as formalin [39], Freunds adjuvant [40] or carageenan, or are subjected to nerve constriction [41,42] or nerve transection [43] which produce persistent pain. The response to various normal and painful stimuli are then measured, for example, by measuring the latency to withdrawal from a warm or hot stimulus [38] so as to compare control animals and animals treated with agents that are thought to modify NaN.

The preferred inhibitors and enhancers of NaN preferably will be selective for the NaN $Na^+$ channel. They may be totally specific (like tetrodotoxin, TTX, which inhibits sodium channels but does not bind to or directly effect any other channels or receptors), or relatively specific (such as lidocaine which binds to and blocks several types of ion channels, but has a predilection for sodium channels). Total specificity is not required for an inhibitor or enhancer to be efficacious. The ratio of its effect on sodium channels vs. other channels and receptors, may often determine its effect and effects on several channels, in addition to the targeted one, may be efficacious [44].

It is contemplated that modulating agents of the present invention can be, as examples, peptides, small molecules, naturally occurring and other toxins and vitamin derivatives, as well as carbohydrates. A skilled artisan can readily recognize that there is no limit as to the structural nature of the modulating agents of the present invention. Screening of libraries of molecules may reveal agents that modulate NaN or current flow through it. Similarly, naturally occurring toxins (such as those produced by certain fish, amphibians and invertebrates) can be screened. Such agents can be routinely identified by exposing a transformed host cell or other cell which expresses a sodium channel to these agents and measuring any resultant changes in $Na^+$ current Recombinant Protein Expression, Synthesis and Purification:

Recombinant NaN proteins can be expressed, for example, in *E. coli* strains HB 101, DH5a or the protease deficient strain such as CAG-456 and purified by conventional techniques.

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Antibodies and Immunodetection:

Another class of agents of the present invention are antibodies immunoreactive with the $Na^+$ channel. These antibodies may block, inhibit, or enhance the $Na^+$ current flow through the channel. Antibodies can be obtained by immunization of suitable mammalian subjects with peptides, containing as antigenic regions, those portions of NaN, particularly (but not necessarily) those that are exposed extracellularly on the cell surface. Such immunological agents also can be used in competitive binding studies to identify second generation inhibitory agents. The antibodies may also be useful in imaging studies, once appropriately labeled by conventional techniques.

Production of Transgenic Animals:

Transgenic animals containing and mutant, knock-out or modified NaN genes are also included in the invention. Transgenic animals wherein both NaN and the SNS/PN3 gene are modified, disrupted or in some form modified are also included in the present invention. Transgenic animals are genetically modified animals into which recombinant, exogenous or cloned genetic material has been experimentally transferred. Such genetic material is often referred to as a "transgene". The nucleic acid sequence of the transgene, in this case a form of NaN, may be integrated either at a locus of a genome where that particular nucleic acid sequence is not otherwise normally found or at the normal locus for the transgene. The transgene may consist of nucleic acid sequences derived from the genome of the same species or of a different species than the species of the target animal.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals.

The alteration or genetic information may be foreign to the species of animal to which the recipient belongs, foreign only to the particular individual recipient, or may be genetic information already possessed by the recipient. In the last case, the altered or introduced gene may be expressed differently than the native gene.

Transgenic animals can be produced by a variety of different methods including transfection, electroporation, microinjection, gene targeting in embryonic stem cells and recombinant viral and retroviral infection (see, e.g., U.S. Pat. Nos. 4,736,866; 5,602,307; Mullins et al. (1993) Hypertension 22(4):630–633; Brenin et al. (1997) Surg. Oncol. 6(2)99–110; Tuan (ed.), *Recombinant Gene Expression Protocols*, Methods in Molecular Biology No. 62, Humana Press (1997)).

A number of recombinant or transgenic mice have been produced, including those which express an activated oncogene sequence (U.S. Pat. No. 4,736,866); express simian SV 40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720, 936); have a reduced capacity to mediate cellular adhesion (U.S. Pat. No. 5,602,307); possess a bovine growth hormone gene (Clutter et al. (1996) Genetics 143(4):1753–1760); or, are capable of generating a fully human antibody response (McCarthy (1997) The Lancet 349(9049):405).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al. (1997) Mol. Reprod. Dev. 46(4):515–526; Houdebine (1995) Reprod. Nutr. Dev.

35(6):609–617; Petters (1994) Reprod. Fertil. Dev. 6(5): 643–645; Schnieke et al. (1997) Science 278(5346):2130–2133; and Amoah (1997) J. Animal Science 75(2):578–585).

The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. Nos. 5,489,743 and 5,602,307.

The specific examples presented below are illustrative only and are not intended to limit the scope of the invention.

EXAMPLES

Example 1

Cloning and Characterization of the Rat NaN Coding Sequence a. RNA Preparation Dorsal root ganglia (DRG) from the lumber region (L4–L5) were dissected from adult Sprague-Dawley rats and total cellular RNA was isolated by the single step guanidinum isothiocyanate-acid phenol procedure [45]. For analytical applications, DRG tissues were dissected from a few animals at a time. The quality and relative yield of the RNA was assessed by electrophoresis in a 1% agarose gel. Because of the limited starting material (4 DRGs weigh on average 10 mg), quantifying the RNA yield was not attempted. PolyA+ RNA was purified from about 300 μg of total DRG RNA (28 animals) using the PolyATract isolation system according to the manufacturers recommendations (Promega). Half of the purified RNA was used for the preparation of Marathon cDNA (see below) without further quantification.

b. Reverse Transcription

For analytical applications, first strand cDNA was synthesized essentially as previously described [46]. Briefly, total RNA was reverse transcribed in a 25 μl final volume using 1 μM random hexamer (Boehringer Mannheim) and 500 units SuperScript II reverse transcriptase (Life Technologies) in the presence of 100 units of RNase Inhibitor (Boehringer Mannheim). The reaction buffer consisted of 50 mM Tris-HCl (pH 8.3), 75 mM KCl, 3 mM $MgCl_2$, 10 mM DTT and 125 μM dNTP. The reaction was allowed to proceed at 37° C. for 90 min., 42° C. for 30 min, then terminated by heating to 65° C. for 10 min.

c. First-Strand cDNA Synthesis

The Marathon cDNA synthesis protocol was followed according to the manufacturer's instruction as summarized below (all buffers and enzymes are purchased from the manufacturer (Clontech):

Combine the following reagents in a sterile 0.5-ml microcentrifuge tube: 1 μg (1–4 μl) PolyA+ RNA sample, 1 μl cDNA Synthesis Primer (10 μM) and sterile $H_2O$ to a final volume of 5 μl. Mix contents and spin the tube briefly in a microcentrifuge. Incubate the mixture at 70° C. for 2 min., then immediately quench the tube on ice for 2 min. Touch-spin the tube briefly to collect the condensation. Add the following to each reaction tube: 2 μl 5× First-Strand Buffer, 1 μl dNTP Mix (10 mM), 1 μl [$\alpha$-$^{32}$P]dCTP (1 μCi/μl), 1 μl AMV Reverse Transcriptase (20 units/μl) for a 10 μl volume. The radiolabeled dCTP is optional (used to determine yield of cDNA) and is replaced by sterile $H_2O$ if not used. Mix the contents of the tube by gently pipetting and touch-spin the tube to collect the contents at the bottom. Incubate the mixture at 42° C. for 1 hr in an air incubator to reduce condensation and enhance the yield of the first strand cDNA. Place the tube on ice to terminate first-strand synthesis.

d. Second-Strand cDNA Synthesis

Combine the following components in the reaction tube from above: b 48.4 μl Sterile $H_2O$, 16 μl 5× Second-Strand Buffer, 1.6 μl dNTP Mix (10 mM), 4 μl 20× Second-Strand Enzyme Cocktail for an 80 μl total volume. Mix the contents thoroughly with gentle pipetting and spin the tube briefly in a microcentrifuge. Incubate the mixture at 16° C. for 1.5 hr. then add 2 μl (10 units) of T4 DNA Polymerase, mix thoroughly with gentle pipetting and incubate the mixture at 16° C. for 45 min. Add 4 μl of the EDTA/Glycogen mix to terminate second-strand synthesis. Extract the mixture with an equal volume of buffer-saturated (pH 7.5) phenol:chloroform:isoamyl alcohol (25:24:1). Mix the contents thoroughly by vortexing and spin the tube in a microcentrifuge at maximum speed (up to 14,000 rpm or 13000 ×g), 4° C. for 10 min. to separate layers. Carefully transfer the top aqueous layer to a clean 0.5-ml tube. Extract the aqueous layer with 100 μl of chloroform:isoamyl alcohol (24:1), vortex, and spin the tube as before to separate the layers. Collect the top layer into a clean 0.5-ml microcentrifuge tube. Ethanol precipitate the double-stranded cDNA by adding one-half volume of 4 M Ammonium Acetate and 2.5 volumes of room-temperature 95% ethanol. Mix thoroughly by vortexing and spin the tube immediately in a microcentrifuge at top speed, room temperature for 20 min. Remove the supernatant carefully and wash the pellet with 300 μl of 80% ethanol. Spin the tube as before for 10 min. and carefully remove the supernatant. Air dry the pellet for up to 10 min. and dissolve the cDNA in 10 μl of sterile $H_2O$ and store at −20° C. Analyze the yield and size of cDNA by running 2 μl of the cDNA solution on a 1.2% agarose/EtBr gel with suitable DNA size markers (for example the 1 Kbp ladder, Gibco/BRL). If EtBr staining does not show a signal and [$\alpha$-$^{32}$P]dCTP was included in the reaction, dry the agarose gel on a vacuum gel drying system and expose an x-ray film to the gel overnight at −70° C.

e. Adaptor Ligation

Combine these reagents in a 0.5-ml microcentrifuge test tube, at room temperature, and in the following order: 5 μl ds cDNA, 2 μl Marathon cDNA Adaptor (10 μM), 2 μl 5×DNA Ligation Buffer, 1 μT4 DNA Ligase (1 unit/μl) for a 10 μl final volume. Mix the contents thoroughly with gentle pipetting and spin the tube briefly in a microcentrifuge. Incubate at either: 16° C. overnight; or room temperature (19–23° C.) for 3–4 hr. Inactivate the ligase enzyme by heating the mixture at 70° C. for 5 min. Dilute 1 μl of this reaction mixture with 250 μl of Tricine-EDTA buffer and use for RACE protocols. Store the undiluted adaptor-ligated cDNA at −20° C. for future use.

f. PCR

For the initial discovery of NaN, we used generic primers designed against highly conserved sequences in domain 1 (D1) of α-subunits I, II and III and later added more primers to accommodate the new α-subunits that were discovered. Thus, we used generic primers that recognize conserved sequences in all known Na+ channels. The middle of the amplified region shows significant sequence and length polymorphism (FIG. 6) and [47,48]. Due to codon degeneracy, 4 forward primers (F1–F4) and 3 reverse primers (R1–R3) were designed to ensure efficient priming from all templates that might have been present in the eDNA pool (Table 1); however, any of these primers may bind to multiple templates depending on the stringency of the reaction. Forward primer F1 matches subunits αI, αIII; αNa6; αPN1; αμ1, αrH1 and αSNS/PN3. Sequences of individual subunits show 1 or 2 mismatches to this primer: T to C at position 16 and A to G at position 18 (αNa6); C to R at position 6 (αμ1); A to G at position 18 (αrH1) and T to C at position 3 (αSNS). Forward primer F2 matches subunit αII. Forward primer F3 perfectly matches αNa6 and also matches αrH1 with a single mismatch of C to T at position 16. Reverse primer R1 matches subunits αI, αII, αIII, αNa6, αPN1, αμ1 and αrH1. This primer has mismatches compared to 4 subunits: G to A at position 3, A to G at position 4 and T to G at position 7 (αI); T to C at position 1 and A to G at position 19 (αPN1); G to A at position 3 and A to G at position 7 (αμ1); an extra G after position 3, GC to CT at positions 14–15, and A to T at position 21 (αrH1). Reverse primer R2 matches subunit αSNS/PN3.

units for reference). The sequence of the R5 primer is based on the amino acid sequence AWCWLDFL (SEQ ID NO: 43) which forms the N-terminal portion of domain III S3 segment.

Amplification was typically performed in 60 μl volume using 1 μl of the first strand cDNA, 0.8 mM of each primer and 1.75 units of Expand Long Template DNA polymerase enzyme mixture (Boehringer Mannheim). Compared to conventional and thermostable DNA polymerases, Expand Long Template enzyme mixture increases the yield of the PCR products without an increase in non-specific amplification [49,50]. The PCR reaction buffer consisted of 50 mM Tris-HCl (pH 9.2), 16 mM $(NH4)_2SO_4$, 2.25 mM $MgCl_2$, 2% (v/v) DMSO and 0.1% Tween 20. As described previously [46], amplification was carried out in two stages using a programmable thermal cycler (PTC-200, MJ Research,

TABLE 1

Generic and NaN-specific primers used for the identification and cloning of NaN. All primers except the marathon primers, were synthesized at the department of Pathology, Program for Critical Technologies in Molecular Medicine, Yale University.

| Forward Primers | Reverse Primers |
|---|---|
| 1. GACCCRTGGAATTGGTTGGA | 1. CAAGAAGGCCCAGCTGAAGGTGTC |
| 2. AATCCCTGGAATTGGTTGGA | 2. GAGGAATGCCCACGCAAAGGAATC |
| 3. GACCCGTGGAACTGGTTAGA | 3. AAGAAGGGACCAGCCAAAGTTGTC |
| 4. GATCTTTGGAACTGGCTTGA | 4. ACYTCCATRCANWCCCACAT |
| 5. AACATAGTGCTGGAGTTCAGG | 5. AGRAARTCNAGCCARCACCA |
| 6. GTGGCCTTTGGATTCCGGAGG | 6. TCTGCTGCCGAGCCAGGTA |
| 7. | 7. CTGAGATAACTGAAATCGCC |
| Marathon AP-1 CCATCCTAATACGACTCACTATAGGGC | |
| Marathon AP-2 ACTCACTATAGGGCTCGAGCGGC | |

We used the respective mouse atypical sodium channel $mNa_x2.3$ sequence to design forward primer F4 and reverse primer R3 to amplify the analogous sequence from αNaG, the presumed rat homolog of $mNa_x2.3$ [14]. The amplified sequence was cloned into the SrfI site of the vector pCR-SCRIPT (Stratagene). The nucleotide sequence of this fragment shows 88% identity to the respective sequence of $mNa_x2.3$ (Dib-Hajj and Waxman, unpublished [68]). The restriction enzyme Xba I was found to be unique to this subunit. Recently, the sequence of a full length cDNA clone of putative sodium channel, NaG-like (SCL-11:Y09164), subunit was published [5]. The published sequence is 99% identical to our sequence and confirms the size and restriction enzyme polymorphism of the NaG PCR product.

The predicted lengths of amplified products and subunit-specific restriction enzyme recognition sites are shown in FIG. 6. All subunit sequences are based on Genbank database (accession numbers: αI: X03638; αII: X03639; αIII: Y00766; αNa6: L39018; αhNE-Na: X82835; αμ1 M26643; αrH1 M27902 and αSNS X92184; mNa 2.3 L36719).

Subsequently, amplification of NaN sequences 3' terminal to the aforementioned fragment was achieved using NaN-specific primers and two generic reverse primers, R4 and R5. The sequence of the R4 primer was based on the amino acid sequence MWV/DCMEV (SEQ ID NO: 38) located just N-terminal to domain II S6 segment (see schematic diagram of FIG. 3 of voltage-gated sodium channel a-sub- Cambridge, Mass.). First, a denaturation step at 94° C. for 4 min, an annealing step at 60° C. for 2 min and an elongation step at 72° C. for 90 sec. Second, a denaturation step at 94° C. for 1 min, an annealing step at 60° C. for 1 min and an elongation step at 72° C. for 90 sec. The second stage was repeated 33 times for a total of 35 cycles, with the elongation step in the last cycle extended to 10 min.

Primary RACE amplification was performed in 50 μl final volume using 4 μl diluted DRG marathon cDNA template, 0.2 μM marathon AP-1 and NaN-specific primers, 3.5 U Expand Long Template enzyme mixture. Extension period was adjusted at 1 min/800 bp based on the expected product. 5' and 3' RACE amplification was performed using primer pairs marathon AP-1/NaN-specific R6 and NaN-specific F5/marathon AP-1, respectively. The PCR reaction buffer consisted of 50 mM Tris-HCl (pH 9.2), 16 mM $(NH4)_2SO_4$, 3.0 mM $MgCl_2$, 2% (v/v) DMSO and 0.1% Tween 20. Amplification in three stages was performed in a programmable thermal cycler (PTC-200, MJ Research, Cambridge, Mass.). An initial denaturation step at 92° C. was carried out for 2 min. This was followed by 35 cycles consisting of denaturation at 92° C. for 20 sec, annealing step at 60° C. for 1 min, and an elongation step at 68° C. Finally, an elongation step at 68° C. was carried out for 5 min. Nested amplification was performed using 2 μl of a 1/500 diluted primary RACE product in a final volume of 50 μl under similar conditions to the primary RACE reactions. Primer pairs AP-2/NaN-specific R7 and NaN-specific F6/marathon AP-2 were used for nested 5' and 3' RACE, respectively. Secondary RACE products were band isolated from 1% agarose gels and purified using Qiaex gel extraction kit (Qiagen Inc.).

A schematic diagram of the putative structure of NaN is shown in FIG. 3. The length of the intracellular loops is highly variable both in sequence and length among the various subunits. The exception is the loop between domains III and IV.

Example 2

Determination of the Putative Rat Amino Acid Sequence for the NaN Channel

NaN-related clones and secondary RACE fragments were sequenced at the W. M. Keck Foundation Biotechnology Resource Lab, DNA sequencing group at Yale University. Sequence analysis including determination of the predicted amino acid sequence was performed using commercial softwares, Lasergene (DNASTAR) and GCG, Inc. The putative amino acid sequence of NaN is shown in FIG. 2. Predicted transmembrane segments of domains I–IV are underlined.

Example 3

Determination of the Murine NaN Sequence

Total RNA extraction from trigeminal ganglia of mice, purification of polyA+RNA, and Marathon cDNA construction were done as previously described for the rat. The initial amplification was performed using rat NaN primers. The forward primer corresponds to nucleotides 765–787 of the rat sequence (5'CCCTGCTGCGCTCGGTGAAGAAG 3') (SEQ ID NO: 24), and the reverse primer corresponds to nucleotides 1156–1137 (negative strand) of the rat sequence (5'GACAAAGTAGATCCCAGAGG 3') (SEQ ID NO: 25). The amplification produced a fragment of the expected size. The sequence of this fragment demonstrated high similarity to rat NaN. Other fragments were amplified using different rat primers and primers designed based on the new mouse NaN sequence that was being produced. Finally, longer fragments were amplified using mouse Marathon cDNA template and mouse NaN-specific primers in combination with adaptor primers that were introduced during the Marathon cDNA synthesis. These fragments were sequenced using primer walking and assembled into FIG. 7A.

Mouse NaN nucleotide sequence, like rat NaN, lacks the out-of-frame ATG at the -8 position relative to the translation initiation codon ATG at position 19 (FIG. 7A). Translation termination codon TGA is at position 5313. A polyadenylation signal (AATAAA) is present at position 5789 and a putative 23 nucleotide polyA tail is present beginning at position 5800. The sequence encodes an ORF of 1765 a.a. (FIG. 7B), which is 90% similar to rat NaN. The gene encoding NaN has been named Scn11a.

Chromosomal Localization of Mouse Nan

A genetic polymorphism between strains C57BL/6J and SPRET/Ei was identified by SSCP analysis of a 274 bp fragment from the 3'UTR of Scn11a . Genotyping of 94 animals from the BSS backcross panel (Rowe et al., 1994) demonstrated linkage of Scn11a with markers on distal chromosome 9 (FIG. 10). No recombinants were observed between Scn11a and the microsatellite marker D9Mit19. Comparison of our data with the MGD consensus map of mouse chromosome 9 revealed close linkage of Scn11a with the two other TTX-R voltage-gated sodium channels, Scn5a (George et al., 1995; Klocke et al., 1992) and Scn10a (Kozak and Sangameswaran, 1996; Souslova et al., 1997).

Example 4

Determination of a Partial and Complete Human NaN Coding Sequence

Forward primer corresponds to sequence 310–294 (minus strand) of EST AA446878. The sequence of the primer is 5'CTCAGTAGTTGGCATGC 3'(SEQ ID NO: 26). Reverse primer corresponds to sequence 270–247 (minus strand) of EST AA88521 1. The sequence of the primer is 5'GGAAA-GAAGCACGACCACACAGTC 3'(SEQ ID NO: 27). Amplification was performed as previously described. PCR amplification was successful and a 2.1 Kbp fragment was obtained. This fragment was gel purified and sent for sequencing by primer walking, similar to what is done for mouse NaN. The sequence of the ESTs is extended in both directions; the additional sequence shows highest similarity to rat and mouse NaN, compared to the rest of the subunits.

The sequence of a human 2.1 kbp fragment was obtained using the PCR forward and reverse primers for sequencing from both ends of the fragment. Two additional primers were used to cover the rest of the sequence. The sequence was then extended in the 5' direction using forward primer 1 (above) and human NaN reverse primer (5'-GTGCCG-TAAACATGAGACTGTCG3') (SEQ ID NO: 44) near the 5' end of the 2.1 kb fragment. The partial amino acid sequence is set forth in FIG. 8B.

The partial ORF of the human NaN consists 1241 amino acids. The sequence is 64% identical to the corresponding sequence of rat NaN (73% similar, allowing for conservative substitutions) using the advanced BLAST program at NIH. Using the Clustal method of alignment (Lasergene software, DNAStar, Inc.) the human NaN is 68% and 69% similar to mouse and rat NaN, respectively. The respective mouse and rat sequences are 88% similar.

Further sequencing revealed the cDNA sequence spanning the full length open reading frame for the human NaN gene. This extended sequence is shown in FIG. 11A. (SEQ ID NO: 41). In addition to the features noted with regard to the partial cDNA sequence (FIG. 8A), notable features of the extended sequence include a translation start codon (ATG) at position 31 and a translation termination codon at position 5400. A recognizable polyadenylation signal has not been observed and presumably is located 3' of the disclosed sequence. The putative amino acid sequence of the human Nan protein is set forth in FIG. 11B. (SEQ ID NO: 42)

Example 5

Isolation of an Alternative Splicing Variant of Rat NaN

A rat NaN cDNA that encodes a C-terminal truncated version of the full-length rat NaN in FIGS. 1 and 2 was isolated by sequencing the insert of a rat cDNA clone. The variant NaN cDNA encodes an NaN protein lacking the 387 C-terminal amino acids of the full length NaN and containing a novel 94 amino acid stretch at the C-terminal end. The new sequence arises from the use of a cryptic donor splice site in exon 23 and a novel exon 23' which is located in intron 23. Thee novel C terminal amino acids are: AAGQAMRKQG DILGPNIHQF SQSSETPFLG CPQQRTCVSF VRPQRVLRVP WFPAWRTVTF LSR- PRSSESS AWLGLVESSG WSGLPGESGP SSLL. (SEQ ID NO: 28). The N-terminal amino acids of the truncated variant are identical to amino acids 1–1378 of the full length rat NaN of FIG. 2. The alternative exon and the splicing pattern was confirmed by comparing the cDNA sequence and the genomic sequence in the respective region.

Example 6

Methods to Isolate other NaN Sequences a. Isolation of NaN Sequences from Genomic DNA The genomic structure of 3 voltage-gated Na$^+$ channel α-subunits have already been determined [51–54]. These genes bear remarkable similarity in their organization and provide a predictable map of most of the exon/intron boundaries. Based on the available rat, mouse and human cDNA sequence of NaN, disclosed herein, PCR primers are designed to amplify NaN homologous sequences from other species using standard PCR protocols.

Alternatively, commercially available genomic DNA libraries are screened with NaN-specific probes (based on the rat, mouse, or more preferably, the human sequence) using standard library screening procedures [59, 60]. This strategy yields genomic DNA isolates that can then be sequenced and the exon/intron boundaries determined by homology to the rat, mouse or human cDNA sequence.

b. Isolation of Full Length NaN Sequences Such as Allelic Variants from Human Autopsy or Biopsy/Surgical Tissues b.1. Isolation of Human Ganglia Total RNA A full length NaN human cDNA homologue is isolated from human dorsal root ganglia or trigeminal ganglia or other cranial ganglia from post-mortem human material, foetuses or biopsy or surgical tissues. Total ribonucleic acid (RNA) is isolated from these tissues by extraction in guanidinium isothiocyanate [69] as described in Example 1.

b.2 Determination of the Full Length Transcript Size of the Human Homologue of the Rat NaN Sodium Channel cDNA.

The method of determining transcript size is as described in Example 9.

Example 7

Production of Human DRG cDNA Library

A cDNA library from human DRG or trigeminal ganglia polyA+ RNA was prepared in Example 4 using standard molecular biology techniques [59, 60].

PolyA+ mRNA is hybridized to an oligo(dT) primer and the RNA is copied by reverse transcriptase into single strand cDNA. Then, the RNA in the RNA-DNA hybrid is fragmented by RNase H as E. coli DNA polymerase I synthesizes the second-strand fragment. The ends of the double stranded cDNA are repaired, linkers carrying specific restriction enzyme site (for example, Eco RI) are ligated to the ends using E. coli DNA ligase. The pool of the cDNA insert is then ligated into one of a variety of bacteriophage vectors that are commercially available like Lambda-Zap (Stratagene). The procedures are summarized in more detail as follows:

a. First Strand cDNA Synthesis

Dissolve 10 µg poly(A)+RNA at a concentration of 1 µg/µl in sterile water. Heat the RNA for 2–5 min. at 65° C.–70° C., then quench immediately on ice. In a separate tube add in the following order (180 µl total):20 µl 5 mM dNTPs (500 uM final each), 40 µl 5×RT buffer (1×final), 10 µl 200 mM DTT (10 mM final), 20 µl 0.5 mg/ml oligo (dT)12–18 (50 µg/ml final), 60 µl H$_2$O, 10 µl (10 U) RNasin (50 U/ml final). Mix by vortexing, briefly microcentrifuge, and add the mixture to the tube containing the RNA. Add 20 µl (200 U) AMV or MMLV reverse transcriptase for a final concentration of 1000 U/ml in 200 µl. Mix by pipetting up and down several times and remove 10 µl to a separate tube containing 1 µl of α$^{32}$P dCTP. Typically, incubate both tubes at room temperature for 5 min., then place both tubes at 42° C. for 1.5 hr. This radiolabeled aliquot is removed to determine incorporation and permit an estimation of recovery; this reaction is stopped by adding 1 µl of 0.5 M EDTA, pH 8.0, and stored frozen at −20° C. The radiolabeled reaction will be used later to estimate the yield and average size of the cDNA inserts. The main reaction is stopped by adding 4 µl of 0.5 M EDTA, pH 8.0, and 200 µl buffered phenol. The mixture is vortexed well, microcentrifuged at room temperature for 1 min. to separate phases, and the upper aqueous layer is transferred to a fresh tube. Back extract the phenol layer with 1 ×TE buffer (10 mM Tris, 1 mM EDTA, pH 7.5) and pool the aqueous layers from the two extractions. This back extraction of the phenol layer improves the yield. The cDNA is ethanol precipitated using 7.5 M ammonium acetate (final concentration 2.0 to 2.5 M) and 95% ethanol. Place in dry ice/ethanol bath 15 min., warm to 4° C., and microcentrifuge at 10 min. at full speed, 4° C., to pellet nucleic acids. The small, yellow-white pellet is then washed with ice-cold 70% ethanol, and microcentrifuged for 3 min. at full speed, 4° C. Again, remove the supernatant, then briefly dry the pellet.

b. Second Strand Synthesis

Typically, the pellet from the first-strand synthesis is resuspended in 284 µl water and these reagents are added in the following order (400 µl total): 4 µl 5 mM dNTPs (50 uM final each), 80 µl 5×second-strand buffer (1×final), 12 µl 5 mM β-NAD (150 uM final), 2 µl 10 uCi/µl α-$^{32}$P dCTP (50 uCi/ml final). Mix by vortexing, briefly microcentrifuge, and add: 4 µl (4 U) RNase H (10 U/ml final), 4 µl (20 U) E. coli DNA ligase (50 U/ml final), and 10 µl (100 U) E. coli DNA polymerase I (250 U/ml final). Mix by pipetting up and down, briefly microcentrifuge, and incubate 12 to 16 hr at 14° C. After second-strand synthesis, remove 4 µl of the reaction to determine the yield from the incorporation of the radiolabel into acid-insoluble material. Extract the second-strand synthesis reaction with 400 µl buffered phenol and back extract the phenol phase with 200 µl TE buffer, pH 7.5, as described above. The double stranded cDNA is then ethanol precipitated as described above.

To complete the second-strand synthesis the double-stranded cDNA ends are rendered blunt using a mixture of enzymes. Resuspend the pellet in 42 µl water then add these reagents in the following order (80 µl total): 5 µl 5 mM dNTPs (310 uM final each), 16 µl 5×TA buffer (1×final), 1µl 5 mM β-NAD (62 uM final). Mix by vortexing, microcentrifuge briefly, and add: 4 µl of 2 µg/ml RNase A (100 ng/ml final), 4 µl (4 U) RNase H (50 U/ml final), 4 µl (20 U) E. coli. DNA ligase (250 U/ml final), and 4 µl (8 U) T4 DNA polymerase (100 U/ml final). Mix as above and incubate 45 min at 37° C. Add 120 µl TE buffer, pH 7.5, and 1 l of 10 mg/ml tRNA. Extract with 200 µl buffered phenol and back extract the phenol layer with 100 µl TE buffer as described above. Pool the two aqueous layers and ethanol precipitate as described above.

c. Addition of Linkers to Double Stranded cDNA

Combine these reagents in a 0.5-ml microcentrifuge test tube, at room temperature, and in the following order: 100 ng ds cDNA, 2 µl linkers/adaptors (10 µM), 2 µl 5×DNA Ligation Buffer, 1 µl T4 DNA Ligase ( unit/µl) for a 10 µl final volume. Mix the contents thoroughly with gentle pipetting and spin the tube briefly in a microcentrifuge. Incubate at either: 16° C. overnight; or room temperature (19–23° C.) for 3–4 hr. Inactivate the ligase enzyme by heating the mixture at 70° C. for 5 min. This cDNA is typically digested by Eco RI to prepare the cohesive ends of the cDNA for ligation into the vector and to cleave linker concatemers. Typically this reaction consists of the 10 µl of the cDNA, 2 µl of 10×Eco RI buffer (depending on the company of source), 2 µl of Eco RI (10 units/µl) and sterile H$_2$O to a final volume of 20 µl. The mixture is incubated at 37° C. for 2–4 hrs.

d. Size Fractionation of cDNA

Size exclusion columns are typically used to remove linker molecules and short cDNA fragments (350 bp). For example, a 1-ml Sepharose CL-4B column is prepared in a plastic column plugged with a small piece of sterilized glass wool (a 5 ml plastic pipet will work fine). The column is equilibrated with 0.1 M sodium chloride in 1×TE (10 mM Tris, 1 mM EDTA, pH 7.5). The cDNA is then loaded onto the column and 200 µl fractions are collected. 2 µl aliquots of each fraction are analyzed by gel electrophoresis and autoradiography to determine the peak of cDNA elution. Typically, fractions containing the first half of the peak are pooled and purified by ethanol precipitation and resuspending in 10 µl distilled water.

e. Cloning of cDNA Into Bacteriophage Vector

Bacteriophage vectors designed for the cloning and propagation of cDNA are provided ready-digested with Eco RI and with phosphatased ends from commercial sources (e.g., lambda gt10 from Stratagene). The prepared cDNA is ligated into lambda vectors following manufacturer's instructions. Ligated vector/cDNA molecules are packaged into phage particles using packaging extracts available commercially.

Example 8

Screening of Human cDNA Library a. Labeling of cDNA Fragments (Probes) for Library Screening An RNA probe is used that recognizes nucleotide sequences that are specific to NaN, such as 1371–1751 of NaN. Other nucleotide sequences can be developed on the basis of the NaN sequence (FIGS. 2, 7 and 8) such as nucleotides 765–1160 of the human nucleotide sequence. A Hind III/Bam HI fragment of NaN was inserted in pBluescript (SK+) vector (Stratagene). The sequence of the resulting construct was verified by sequencing. The orientation of the insert is such that the 5' and 3' ends of the construct delineated by the Hind III and Bam HI restriction enzyme sites, respectively, are proximal to T7 and T3 RNA polymerase promoters, respectively. Digoxigenin-labeled Sense (linearized at the Hind III site and transcribed by T7 RNA polymerase) and antisense (linearized at the Bam HI site and transcribed by T3 RNA polymerase) transcripts were prepared in vitro using MEGAscript transcription kit (Ambion) according to manufacturer specifications. Briefly, 1 µg linearized template was transcribed with the respective RNA polymerase in a 20 µl final volume containing the following reagents: 1×enzyme mixture containing the respective RNA polymerase and RNase inhibitor and reaction buffer (Ambion), 7.5 mM ATP, GTP and CTP nucleotides, 5.625 mM UTP and 1.725 mM Dig-11UTP (Boehringer Mannheim). In vitro transcription was carried out at 37° C. for 3 hrs in a water bath. DNA template was removed by adding 1 µl of RNase-free DNase I (2U/µl) to each reaction and incubating further at 37° C. for 15 min. The reaction was then stopped by adding 30 µl nuclease-free H$_2$) and 25 µl of LiCl precipitation solution (7.5 M Lithium Chloride, 50 mM EDTA).

The mixture was incubated at –20° C. for 30 min. The RNA transcripts were pelleted in a microfuge at 13000×g, 4° C. for 15 min. The supernatant was removed and the pellet washed once with 100 µl of 75% ethanol. The mixture was re-centrifuged at 13000×g, room temperature for 5 min. The pellet was then air-dried in a closed chamber and subsequently dissolved in 100 ml of RNase-free H$_2$O. The transcript yield and integrity were determined by comparison to a control DIG-labeled RNA on agarose-formaldehyde gel as described in the DIG/Genius kit according to manufacturer recommendations (Boehringer Mannheim). Alternatively, a skilled artisan can design radioactive probes for autoradiographic analysis.

Other regions of the rat, mouse or human NaN sodium channel cDNA, like 3' untranslated sequences, can also be used as probes in a similar fashion for cDNA library screening or Northern blot analysis. Specifically, a probe is made using commercially available kits, such as the Pharmacia oligo labeling kit, or Genius kit (Boehringer Mannheim).

b. cDNA Library Screening

Recombinant plaques containing full length human homologues of the NaN sodium channel are detected using moderate stringency hybridization washes (50–60° C., 5×SSC, 30 minutes), using non-radioactive (see above) or radiolabeled DNA or cRNA NaN-specific probes derived from the 3' untranslated or other regions as described above. Libraries are screened using standard protocols [59, 60] involving the production of nitrocellulose or nylon membrane filters carrying recombinant phages. The recombinant DNA is then hybridized to NaN-specific probes (see above). Moderate stringency washes are carried out.

Plaques which are positive on duplicate filters (i.e., not artefacts or background) are selected for further purification. One or more rounds of screening after dilution to separate the phage are typically performed. Resulting plaques are then purified, DNA is extracted and the insert sizes of these clones characterized. The clones are cross-hybridized to each other using standard techniques [59] and distinct positive clones identified.

Typically, overlapping clones that encode the channel are isolated. Standard cloning techniques are then used to produce a full length cDNA construct that contains any 5' untranslated sequence, the start codon ATG, the coding sequence, a stop codon and any 3' untranslated sequence, a poly A consensus sequence and possibly a poly A run. If overlapping clones do not produce sufficient fragments to assemble a full length cDNA clone, alternative methods like RACE (PCR-based) could be used to generate the missing pieces or a full length clone.

C. Characterization of a Human Homologue Full-length Clone

A NaN-specific cDNA sequence from a full-length clone is used as a probe in Northern blot analysis to determine the messenger RNA size in human tissue for comparison with the rat and mouse messenger RNA size. Confirmation of biological activity of the cloned cDNA is carried out using methods similar to those described for the rat NaN.

Example 9

Polymerase Chain Reaction (PCR) Approaches to Clone Other Full Length Human NaN Sodium Channels Using DNA Sequences Derived from Rat, Mouse or Human Amino Acid Sequences Total RNA and poly A+RNA is isolated from human dorsal root ganglia or trigerninal ganglia or other cranial ganglia from post-mortem human material or foetuses or biopsy/surgical tissues as described above. Preparation of cDNA and PCR-based methods are then used as described previously in Example 1.

Using degenerate PCR primers derived from the rat, mouse or human NaN-specific coding sequence (see FIGS. 2, 7B, 8B and 11B) (SEQ ID NO: 3, 5, 8 and 42, respectively), the cDNA is amplified using the polymerase chain reaction [69]. A skilled artisan could utilize the many variables which can be manipulated in a PCR reaction to derive the homologous sequences required. These include, but are not limited to, varying cycle and step temperatures, cycle and step times, number of cycles, thermostable polymerase, and $Mg_{2+}$ concentration. A greater specificity can be achieved using nested primers derived from further conserved sequences from the NaN sodium channel.

Amplification is typically performed in 60 μl volume using 1 μl of the first strand cDNA, 0.8 mM of each primer and 1.75 units of Expand Long Template DNA polymerase enzyme mixture (Boehringer Mannheim). Compared to conventional and thermostable DNA polymerases, Expand Long Template enzyme mixture increases the yield of the PCR products without an increase in non-specific amplification [49,50]. The PCR reaction buffer consists of 50 mM Tris-HCl (pH 9.2), 16 mM $(NH14)_2SO_4$, 2.25 mM $MgCl_2$, 2% (v/v) DMSO and 0.1% Tween 20. As described previously [46], amplification is carried out in two stages using a programmable thermal cycler (PTC-200, MJ Research, Cambridge, Mass.). First, a denaturation step at 94° C. for 4 min, an annealing step at 60° C. for 2 min and an elongation step at 72° C. for 90 sec. Second, a denaturation step at 94° C. for 1 min, an annealing step at 60° C. for 1 min and an elongation step at 72° C. for 90 sec. The second stage is repeated 33 times for a total of 35 cycles, with the elongation step in the last cycle extended to 10 min. In addition, control reactions are performed alongside the samples. These should be: 1) all components without cDNA, (negative control) and 2) all reaction components with primers for constitutively expressed product, e.g, GAPDH.

The products of the PCR reactions are examined on 1–1.6% (w/v) agarose gels. Bands on the gel (visualized by staining with ethidium bromide and viewing under UV light) representing amplification products of the approximate predicted size are then cut from the gel and the DNA purified.

The resulting DNA may be sequenced directly or is ligated into suitable vectors such as, but not limited to, pCR II (Invitrogen) or pGEMT (Promega). Clones are then sequenced to identify those containing sequence with similarity to the rat, mouse or partial human NaN sodium channel sequence.

Example 10

Clone Analysis

Candidate clones from Example 9 are further characterized by conventional techniques. The biological activity of expression products is also confirmed using conventional techniques.

Example 11

Isolation of Full Length NaN Sequences from Human Fetal Tissues

Commercially available human fetal cDNA libraries and/or cDNA pools are screened with NaN-specific primers (by PCR) or probes (library screening) using PCR standard PCR protocols- and standard library screening procedures as described above.

Example 12

Northern Blot of Rat DRG or Trigeminal Neurons with Fragments of Rat NaN

10–30 μg total DRG and/or RNA from DRG or trigeminal (for positive tissues) and cerebral hemisphere, cerebellum and liver (for negative tissues) is electrophoresed in denaturing 1% agarose-formaldehyde gel or agarose-glyoxal gel, and then is transferred to a nylon membrane as described in achieved in multiple steps, as detailed in standard molecular biology manuals [59, 60]. Radiolabeled (specific activity of >$10^8$ dpm/ug) or Digixoginen-labeled RNA probes are typically used for Northern analysis. An antisense RNA probe (see Example 20, which describes in situ hybridization with a NaN-specific probe) is created by in vitro synthesis from a sense DNA fragment. The membrane carrying the immobilized RNA in wetted with 6×SSC, and the membrane is placed RNA-side-up in a hybridization tube. One ml formamide prehybridization/hybridization solution per 10 $cm^2$ of membrane is added. Prehybridization and hybridization are usually carried out in glass tubes in a commercial hybridization oven. The tubes are place in a hybridization oven and incubated, with rotation, at 60° C. for 15 min to 1 hr. The desired volume of probe is pipeted into the hybridization tube, and the incubation is continued with rotation overnight at 60° C. The probe concentration in the hybridization solution should be 10 ng/ml if the specific activity is $10^8$ dpm/ug or 2 ng/ml if the specific activity is $10^9$ dpm/ug (use 2–10 ng/ml of Digixogenin labeled probe).

The hybridization solution is poured off and an equal volume of 2×SSC/0.1% SDS is added. Incubation with rotation for 5 min at room temperature is carried out. The wash solution is changed, and this step is repeated. To reduce background, it may be beneficial to double the volume of the wash solutions. The wash solution is replaced with an equal volume of 0.2×SSC/0.1% SDS and the tube. is incubated for 5 min with rotation at room temperature. The wash solution is changed and this step is repeated (this is a low-stringency wash). For moderate or high stringency conditions, further washes are done with wash solutions pre-warmed to moderate (42° C.) or high (68° C.) temperatures. The final wash solution is removed and the membrane rinsed in 2×SSC at room temperature. Autoradiography is then performed for up to 1 week. Alternatively, signal is detected using chemiluminescence technology (Amersham) if non-radioactive probes are used. The transcript size is calculated from the signal from the gel in comparison with gel molecular weight standard markers.

Example 13

Tissue Specific Distribution of NaN by RT-PCR

NaN-specific forward (5'CCCTGCTGCGCTCGGT-GAAGAA 3') (SEQ ID NO: 39) and reverse primer (5'GA- CAAAGTAGATCCCAGAGG 3') (SEQ ID NO: 25), were used in RT-PCR assays using cDNA template prepared from multiple rat. These primers amplify NaN sequence between nucleotides 765 and 1156 (392 bp) and are NaN-specific as judged by lack of similarity to sequences in the database (using programs like BLASTN from the National Library of Medicine). Amplification was typically performed in a 60 μl volume using 1 μl of the first strand of cDNA, 0.8 μM of each primer and 1.75 units of Expand Long Template DNA polymerase enzyme mixture (Boehringer Mannheim). Compared to conventional and thermostable DNA polymerases, Expand Long Template enzyme mixture increases the yield of the PCR products without an increase in non-specific amplification [49, 50]. The PCR reaction buffer consisted of 50 mM Tris-HCl (pH 9.2), 16 mM $(NH4)_2SO_4$, 2.25 mM $MgCl_2$, 2% (v/v) DMSO and 0.1% Tween 20. As described previously [71], amplification was carried out in two stages using a programmable thermal cycler (PTC-200, MJ Research, Cambridge, Mass.). First, a denaturation step is performed at 94° C. for 4 mm., followed by an annealing step at 60° C. for 2 mm, and then an elongation step at 72° C. for 90 sec. Second, a denaturation step is performed at 94° C. for 1 mm, followed by an annealing step at 60° C. for 1 min, and then an elongation step at 72° C. for 90 sec. The second stage was repeated 33 times for a total of 25–35 cycles, with the elongation step in the last cycle extended to 10 min.

Glyceraldehyde-3-phosphate dehydrogenase (GAPDH) was used as an internal control to ensure that a lack of NaN signals in different tissues was not due to degraded templates or presence of PCR inhibitors. Rat GAPDH sequences were co-amplified using primers which amplify a 66 bp product that corresponds to nucleotides 328–994 (accession number: M17701). The amplified product spans multiple exon/intron splice sites, based on the structure of the human gene [72]. Dnase I treatment was routinely performed prior to reverse transcription to prevent amplification of GAPDH sequences from genomic processed pseudogenes that may have contaminated the total RNA preparation [73].

NaN is primarily and preferentially expressed in DRG and trigeminal ganglia neurons. FIG. 4 shows the results of screening by RT-PCR for the expression of NaN in various neuronal and non-neuronal tissues. Lanes 1, 2, 4, 9 and 16 show a single amplification product co-migrating with the 400 bp marker, consistent with NaN-specific product of 392 bp. Lanes 1 and 16, 2, 4 and 9 contain products using DRG, cerebral hemisphere, retina, and trigeminal ganglia, respectively. Using this assay, NaN was not detected in cerebellum, optic nerve, spinal cord, sciatic nerve, superior cervical ganglia, skeletal muscle, cardiac muscle, adrenal gland, uterus, liver or kidney (lanes 3, 5–8, and 10–15, respectively). The attenuated NaN signal in cerebral hemisphere and retina, and the absence of this signal in the remaining tissues is not due to degraded RNA or the presence of PCR inhibitors in the cDNA templates as comparable GAPDH amplification products were obtained in a parallel set of PCR reaction (data not shown).

Example 14

Transformation of a Host Cell with the NaN Coding Sequence

Transformed host cells for the measurement of $Na^+$ current or intracellular $Na^+$ levels are usually prepared by co-transfecting constructs into cells such as HEK293 cells with a fluorescent reporter plasmid (pGreen Lantern-1, Life Technologies, Inc.) using the calcium-phosphate precipitation technique [27]. HEK293 cells are typically grown in high glucose DMEM (Life Technologies, Inc.) supplemented with 10% fetal calf serum (Life Technologies, Inc). After 48 hrs, cells with green fluorescence are selected for recording [28].

For preparation of cell lines continuously expressing recombinant channels, the NaN construct is cloned into other vectors that carry a selectable marker in mammalian cells. Transfections are carried out using the calcium phosphate precipitation technique [27]. Human embryonic kidney (HEK-293), chinese hamster ovary (CHO) cells, or other suitable cell lines are grown under standard tissue culture conditions in Dulbeccos's modified Eagle's medium supplemented with 10% fetal bovine serum. The calcium phosphate-DNA mixture is added to the cell culture medium and left for 15–20 hr, after which time the cells are washed with fresh medium. After 48 hrs, antibiotic (G418, Geneticin, Life Technologies) is added to select for cells which have acquired neomycin resistance. After 2–3 weeks in G418, 10–20 isolated cell colonies are harvested using sterile 10 ml pipette tips. Colonies are grown for another 4–7 days, split and subsequently tested for channel expression using whole-cell patch-clamp recording techniques and RT-PCR.

Example 15

Production of NaN Specific Antibodies

Antibodies specific to the rat, mouse or human NaN are produced with an immunogenic NaN-specific peptide by raising polyclonal antibodies in rabbits. In one example, the peptide CGPNPASNKDCFEKEKDSED (SEQ ID NO: 40) (rat amino acids 285–304) was selected because it fits the criteria for immunogenecity and surface accessibility. This peptide sequence does not match any peptide in the public databases. The underlined cysteine (C) residue was changed to Alanine (A) to prevent disulfide bond formation. This amino acid change is not expected to significantly affect the specificity of the antibodies.

Peptide synthesis, rabbit immunization, and affinity purification of the antipeptide antibodies were performed using standard procedures. Purified antibodies were then tested on DRG neurons in culture. Immunostaining procedures using these antibodies before and after blocking with excess peptide were performed according to standard procedures.

DRG neurons after 16–24 h in culture were processed for immunocytochemical detection of NaN protein as follows. Coverslips were washed with complete saline solution (137 mM NaCl, 5.3 mM KCl, 1 ITIM M902 25 mM sorbitol, 10 mM HEPES, 3 mM CaCl2 pH 7.2), fixed with 4% paraformaldehyde in 0.14 M phosphate buffer for 10 min at 4° C., washed with three 5-min with phosphate-buffered saline (PBS), and blocked with PBS containing 20% normal goat serum, 1% bovine serum albumin and 0.1% Triton X-100 for 15 minutes. The coverslips were incubated in anti-NaN antibody (1:100 dilution) at 4° C. overnight. Following overnight incubation, coverslips were washed extensively in PBS and then incubated with goat anti-rabbit IgG-conjugated to Cy3 (1:3000; Amersham) for 2 h at room temperature. The coverslips were rinsed with PBS and mounted onto glass slides with Aqua-poly-mount. The neurons were examined with a Leitz Aristoplan light microscope equipped with epifluorescence and images were captured with a Dage DC330T color camera and Scion CG-7 color PCI frame grabber (see FIG. 7).

Example 16

NaN Expression is Altered in a Neuropathic Pain Model

The CCI model of neuropathic pain (Bennett and Xie) was used to study the plasticity of sodium channel expression in DRG neurons. Twenty two adult, femal Sprague-Dawley rats, weighing 240–260 g, were anesthetized with pentobarbital sodium (50 mg/kg ip) and the right sciatic nerve exposed at the mid-thigh. Four chromic gut (4–0) ligatures were tied loosely around the nerve as described by Bennett and Xie (1988) *Pain* 33, 87–107. The incision site was closed in layers and a bacteriostatic agent administered intramuscularly.

Previous studies have shown that transection of the sciatic nerve induces dramatic changes in sodium currents of axotomized DRG neurons, which is paralleled by significant changes to transcripts of various sodium channels expressed in these neurons. Sodium currents that are TTX-R and the transcripts of two TTX-R sodium channels (SNS/PN3 and NaN) are significantly attenuated while a rapidly repriming silent TTX-S current emerges and the transcript of α-III sodium channel, which produces a TTX-S current, is up-regulated. We have discovered that CCI-induced changes in DRG neurons, 14 days post-surgery, mirror those of axotomy. Transcripts of NaN and SNS, the two sensory neuron-specific TTX-R channels, are significantly down-regulated as is the TTX-R sodium current, while transcripts of the TTX-S α-III sodium channel are up-regulated, in small diameter DRG neurons. These changes may be partly responsible for making DRG neurons hyperexcitable, that contributes to the hyperalgesia that results from this injury.

Example 17

Assays for Agents which Modulate the Activity of the NaN Channel Using Patch Clamp Methods Cells lines expressing the cloned $Na^+$ channel are used to assay for agents which modulate the activity of the NaN channel, e.g., agents which block or inhibit the channel or enhance channel opening. Since the channel activation is voltage dependent, depolarizing conditions may be used for observation of baseline activity that is modified by the agent to be tested. Depolarization may be achieved by any means available, for example, by raising the extracellular potassium ion concentration to about 20 to 40 nM, or by repeated electrical pulses.

The agent to be tested is incubated with HEK 293 or other transformed cells that express the $Na^+$ channel [28]. After incubation for a sufficient period of time, the agent induced changes in $Na^+$ channel activity can be measured by patch-clamp methods [29]. Data for these measurements are acquired on a MacIntosh Quadra 950, or similar computer, using a program such as Pulse (v 7.52, HEKA, German). Fire-polished electrodes (0.8–1.5 MW) are fabricated from capillary glass using a Sutter P-87 puller or a similar instrument. Cells are usually only considered for analysis if initial seal resistance is <5 Gohm, they have high leakage currents (holding current <0.1 nA at −80 mV), membrane blebs, and an access resistance <5 Mohm. Access resistance is monitored and data is not used if resistance changes occur. Voltage errors are minimized using series resistance compensation and the capacitance artifact will be canceled as necessary using computer-controlled amplifier circuitry or other similar methods.

For comparisons of the voltage dependence of activation and inactivation, cells with a maximum voltage error of 10 mV after compensation are usually used. Linear leak subtraction is used for voltage clamp recordings. Membrane currents are typically filtered at 5 KHz and sampled at 20 KHz. The pipette solution contains a standard solution such as: 140 mM CsF, 2 mM $MgCl_2$, 1 mM EGTA, and 10 mM Na-HEPES (pH 7.3). The standard bathing solution is a standard solution such as 140 mM NaCl, 3 mM KCl, 2 mM $MgCl_2$, 1 mM $CaCl_2$, 10 mM HEPES, and 10 mM glucose (pH 7.3).

Tetrodotoxin (TTX)-resistant and TTX-sensitive $Na^+$ currents are measured by exposure to appropriate concentrations of TTX and/or by pre-pulse protocols which distinguish between TTX-sensitive and TTX-resistant currents on the basis of their distinct steady-state inactivation properties [22,55].

Data are collected using standard pulse protocols and are analyzed to measure sodium current properties that include voltage-dependence, steady-state characteristics, kinetics, and re-priming. Measurements of current amplitude and cell capacitance provides an estimate of $Na^+$ current density, thereby permitting comparisons of channel density under different conditions [22,30]. Cells are studied in the current clamp mode to study patterns of spontaneous and evoked action potential generation, threshold for firing, frequency response characteristics, and response to de- and hyperpolarization, and other aspects of electrogenesis [55]. These measurements are carried out both in control cells expressing NaN and in cells expressing NaN that also have been exposed to the agent to be tested.

Example 18

Assays for Agents which Modulate the Activity of the NaN Channel by the Measurement of Intracellular Sodium [$Na^+$]

The agent to be tested is incubated with cells exhibiting NaN channel activity. After incubation for a sufficient period of time, the agent induced changes in $Na^+$ channel are measured by ratiometric imaging of $[Na^+]_i$ using SBFI. In this method, cytosolic-free $Na^+$ is measured using an indicator for $Na^+$, such as SBFI (sodium-binding benzofuran isophthalate; [33]) or a similar dye. Cells are first loaded with the membrane-permeable acetoxymethyl ester form of SBFI (SBFI/AM) or a similar dye (usually dissolved in dimethyl sulfoxide (DMSO) at a stock concentration of 10 mM). Recordings are obtained on the stage of a microscope using a commercially available ratiometric imaging setup (e.g., from Georgia Instruments). Excitation light is provided at appropriate wavelengths (e.g., 340:385 nm). Excitation light is passed to the cells through a dichroic reflector (400 nm) and emitted light above 450 nm was collected. Fluorescence signals are amplified, e.g., by an image intensifier (GenIISyS) and collected with a CCD camera, or similar device, interfaced to a frame grabber. To account for fluorescence rundown, the fluorescence ratio 340:385 is used to assay cytosolic-free $Na^+$.

For calibration of SBFI's fluorescence, cells are perfused with calibration solutions containing known $Na^+$ concentrations (typically 0 and 30 mM, or 0, 30, and 50 mM [$Na^+$], and gramicidin and monensin. As reported by Rose and Ransom [34], the 345/390 nm fluorescence ratio of intracellular SBFI changes monotonically with changes in $[Na^+]_i$. Experiments are repeated on multiple (typically at least 4) different coverslips, providing statistically significant measurements of intracellular sodium in control cells, and in cells exposed to various concentrations of agents that may block, inhibit or enhance the activity of the channel. Use of this method is illustrated in Sontheimer et al. [32].

Example 19

Assays for Agents which Modulate the Activity of the NaN Channel by Scintigraphic Imaging Cells lines expressing the cloned $Na^+$ channel are used to assay for agents which modulate the activity of the NaN channel, e.g., agents which block the channel or enhance channel opening. For example, the agent to be tested is incubated with HEK 293 or other transformed cells that express the $Na^+$ channel [28]. After incubation for a sufficient period of time, the agent induced changes in $Na^{++}$ channel activity are detected by the measurement of $Na^+$ influx by isotopic methods. $^{22}Na$ is a gamma emitter and can be used to measure $Na^+$ flux [31] and $^{86}Rb^+$ can be used to measure $Na^+/K^+$ATPase activity which provides a measure of Na channel activity [32] $^{86}Rb^+$ ions are taken up by the $Na^+/K+$ATPase like K+ ions, but have the advantage of a much longer half-life than $^{42}K^+$ [35]. Thus, measurement of the unidirectional ouabain-sensitive $^{86}Rb^+$ uptake provides a quantitative method for assaying $Na^+/K^+$-ATPase activity which follows action potentials.

Following incubation of cell expressing NaN to the isotope, the cellular content of the isotope is measured by liquid scintillation counting or a similar method, and cell protein is determined using a method such as the bicinchoninic acid protein assay [36] following the modifications [37] for cultured cells. $^{22}Na$ and $^{86}Rb^+$ fluxes are determined in the presence and absence of agents that may block, inhibit, or enhance $Na^+$. This permits determination of the actions of these agents on NaN.

Example 20

In Situ Hybridization a. Probes
Probes are prepared as described above in Example 5.
b. DRG Neuron Culture
Cultures of DRG neurons from adult rats were established as described previously [70]. Briefly, lumbar ganglia (L4, L5) from adult Sprague Dawley female rats were freed from their connective sheaths and incubated sequentially in enzyme solutions containing collagenase and then papain. The tissue was triturated in culture medium containing 1:1 Dulbecco's modified Eagle's medium (DMEM) and Hank's F12 medium and 10% fetal calf serum, 1.5 mg/ml trypsin inhibitor, 1.5 mg/ml bovine serum albumin, 100 U/ml penicillin and 0.1 mg/ml streptomycin and plated at a density of 500–1000 cells/mm² on polyornithine/laminin coated coverslips. The cells were maintained at 37° C. in a humidified 95% air/5% $CO_2$ incubator overnight and then processed for in situ hybridization cytochemistry as described previously [56, 57]. Trigeminal ganglia can be cultured by a skilled artisan using similar methods.

c. Tissue Preparation
Adult female Sprague Dawley rats were deeply anesthetized, e.g., with chloral hydrate and perfused through the heart, first with a phosphate-buffered saline (PBS) solution and then with a 4% paraformaldehyde in 0.14 M Sorensen's phosphate buffer, pH 7.4, at 4° C. Following perfusion fixation, dorsal root ganglia at levels L4 and L5 and trigeminal ganglia were collected and placed in fresh fixative at 4° C. After 2–4 hours, the tissue was transferred to a solution containing 4% paraformaldehyde and 30% sucrose in 0.14 M phosphate buffer and stored overnight at 4° C. Fifteen μm sections were cut and placed on poly-L-lysine-coated slides. The slides were processed for in situ hybridization cytochemistry as previously described [24, 56]. Following in situ hybridization cytochemistry, the slides were dehydrated, cleared and mounted with Permount. The results are shown in FIG. 5.

Sections of DRG hybridized with NaN sense riboprobe showed no specific labeling (panel C, FIG. 5). In DRG (panel A, FIG. 5) and trigeminal (panel B) sections hybridized with a NaN antisense riboprobe, with the NaN signal present in most small (<30 mm diam.) neurons; in contrast, most large (>30 mm diam.) neurons did not exhibit NaN hybridization signal. Sections of spinal cord, cerebellum and liver hybridized with an antisense NaN riboprobe showed no specific signal (panels D, E and F respectively).

Example 21

Microsatellite Sequences

The following are the murine intronic microsatellite sequences. These microsatellites may be polymorphic in the human SCN11a gene and could be used as markers to screen for mutant alleles that are associated with a disease. Such screening methods, for instance, hybridization or amplification assays, are readily available. See Sambrook et al. or Ausubel et al.

Intron 4; microsatellite is dTdG (SEQ ID NO: 29)

AGTTTAATGTTGAGTGAATTGTGGTGGTGATTTCCCACTTGAGGCCTTTG

TGTTAAAGCCCAATGTGTGTGTGTGTGTGTGTGTGTGTGTGTGTGTGTGT

GTGTGTGTGTGTGTGTGGTTGGGGGGTGGTGGCAGAGTCTGGTATTGGTA

AGGTGAGAGCAATCCCAGAACGTCCACCTGCTCTTCCATTTTATTAATCA

GGCAGGCCTCT

Intron 5; microsatellite is dCdTdG $(dNdG2)_x$(X5-30) (SEQ ID NO: 30)

GTAAGCCACTGGCTCTTAACTAAAATGCTCGTTGGCATTAGAACATTTCT

GAGCTGGGGTGGTGGTGGTGGTGGTGGTGGTGGTGGTGGTGGTGGTGGTG

GTGGTGGTGGTGATGGTGGTGGTGGAGGTGGNGGTGGAGGTGGTGGCTGT

GGTGGTGGNGGTGGTGGTGGTGGANGTGGANGTGGTGGCGTGGTGGT

GGNGGTGGTGGTGGAGGTGGTGGCTGTGGTGGTNGTGGTGGC

Intron 6; microsatellite is dCdA (SEQ ID NO: 31)

TGTGCATGCTTGATTCCCAGCTCCTATGGTCTGATTACTCGGTCCTTAGG

AGCAAGGCCAGACTGTCCACCCTGACACACACACACACACACACACACAC

ACACACACACACACACACACAGTGTAGAGAATTACCTCATTCTTGGAG

TTTCTCTGGAAAAGGAATGTCTCAAAGCCAAGTTCACAGAGC

Intron 8; 5' microsatellite is dTdC followed by a stretch of dT (SEQ ID NO: 32)

TGTTAGAAACTCTAAGACAATGAAGCACCATGCTGGAAATAAGAGCACAA

ACTCTTTCTTCATGCATTACCCACTGCTTGTGCTTTCACCTTAGTGCTCG

TGCTCTCTCTTTCTCTCTCTCTCTCTCTCTCTCTCTCTCTCTCTCTCTCT

CTCTCTCTCTCTCTCTCTTTTTTTTTTTTTT

Intron 8; 3' microsatellite is dCdA (SEQ ID NO: 33)

CACACACACACACACACACACACACACACACACACACACAGAGAAACACT

GTCGCAGTCATACATATAAAGATAAATACATCTTAAAAAAAGAACCATGT

GATTGAGTTATAAAATATTCCAACTTAT

Intron 10B; microsatellite is dCdA followed, three nucleotides downstream by dCdA$_3$ (SEQ ID NO: 34)

AGGTCATTTCCTCTGCAGTGTGCTTGGCAGGAAAAACTTCCTGGCTATTC

AAGTCAGTGCCCTGCTTGATCATCCATGTATCACACACACAAAACAAA

CAAACAAACAAACAAAACCCTGGGGAAGAAGGAAGAGGTTAAGCACATAG

GCAGAGAGCAGCCAGGCTGACTCAGAGCAAACACCTGATCATTCTTCCAT

Intron 12; microsatellite is dPydG (dT/dCdG) (SEQ ID NO: 35)

GTGCTGGGATCAAAGGCGTGCGCCGCCACCACGCCCGGCCCCTTTTTATG

TTTCAAATTTACTTTTATCATGTGCACGTGTGTGGGTGCGTGCATGTGTG

TGCGTGCGTGTGCGTGTGNGTGTGNGTGTGTGTGTGTGTGTGTGTGTGTG

TGTGTGTG

Intron 14; microsatellite is dCdA (SEQ ID NO: 36)

CACACACACACACACACACACACACACACACACACACACACACACACACA

CACACACTTGCATCTTTGAGTTAATTGGATAGGCTGAGTCTTACACCGGA

ATCATACTGTTGC

Intron 15A; microsatellige is dCdA (SEQ ID NO: 37)

CCAATGAGAGACTCTTGTCTCAAAAAAGCCATGGTGTCCAGATCCTGAGG

AATAACACCTAAGAATGTGCTCTGGCCTGAAAACACACACACACACAC

ACACACACACACACACACAGTTTTATTTATTTATTTAAAAAAATATGT

CTCTAGGCATTGCTGAAATGTCTCCTACAGGATTAAGTCAACCAGAGCCA

It should be understood that the foregoing discussion and examples merely present a detailed description of certain preferred embodiments. It will be apparent to those of ordinary skill in the art that various modification and equivalents can be made without departing from the spirit and scope of the invention.

REFERENCES CITED

The following documents were cited and discussed above. These and any other documents referred to in this patent specification are hereby incorporated by reference in their entirety.

[1] Catterall, W. A. (1993) Trends in Neurosciences 16: 500–6.
[2] Isom, L. L., De Jongh, K. S. and Catterall, W. A. (1994) Neuron 12: 1183–94.
[3] Goldin, A. L. (1995) in: Handbook of receptors and channels, pp. 73–100 (North, R. A., Ed.) CRC press, Boca Raton, Fla.
[4] Akopian, A. N., Sivilotti, L. and Wood, J. N. (1996) Nature 379: 257–62.
[5] Akopian, A. N., Souslova, V., Sivilotti, L. and Wood, J. N. (1997) FEBS Letters 400: 183–187.
[6] Sangameswaran, L. et al. (1996) J. Biol. Chem. 271: 5953–6.
[7] Beckh, S., Noda, M., Lubbert, H. and Numa, S. (1989) EMBO J. 8: 3611–6.
[8] Mandel, G. (1992) J. Membrane Biology 125: 193–205.
[9] Roden, D. M. and George, A. L., Jr. (1997) Am. J. Physiol. 273: H511–25.
[10] Ptacek, L. J. (1997) Neuromuscul. Disord. 7: 250–5.
[11] Cannon, S. C. (1997) Neuromuscul. Disord. 7: 241–9.
[12] Cannon, S. C. (1996) Trends Neurosci. 19: 3–10.
[13] Rizzo, M. A., Kocsis, J. D. and Waxman, S. G. (1996) European Neurology 36: 3–12.
[14] Felipe, A., Knittle, T. J., Doyle, K. L. and Tamkun, M. M. (1994) J. Biol. Chem. 269: 30125–31.
[15] Eccles, J. C., Libet, B. and Young, R. R. (1958) J. Physiol. 143: 11–40.
[16] Gallego, R., Ivorra, I. and Morales, A. (1987) J. Physiol. (Lond) 391: 39–56.
[17] Kuno, M. and Llinas, R. (1970) J. Physiol. (Lond.) 210: 807–821.
[18] Dodge, F. A. and Cooley, J. W. (1973) IBM J. Res. Dev. 17: 219–229.
[19] Titmus, M. J. and Faber, D. S. (1986) J. Neurophysiol. 55: 1440–1454.
[20] Semagor, E., Yarom, Y. and Werman, R. (1986) Proc. Natl. Acad. Sci. (USA) 83: 7966–70.
[21] Rizzo, M. A., Kocsis, J. D. and Waxman, S. G. (1995) Neurobiol. Dis. 2: 87–96.
[22] Cummins, T. R. and Waxman, S. G. (1997) J. Neurophysiology 17: 3503–3514.
[23] Dib-Hajj, S., Black, J. A., Felts, P. and Waxman, S. G. (1996) Proc. Natl. Acad. Sci. (USA) 93: 14950–4.
[24] Waxman, S. G., Kocsis, J. D. and Black, J. A. (1994) J. Neurophysiology 72: 466–70.
[25] Gold, M. S., Reichling, D. B., Shuster, M. J. and Levine, J. D. (1996) Proc. Natl. Acad. Sci. (USA) 93: 1108–12.
[26] England, S., Bevan, S. and Docherty, R. J. (1996) J. Physiology 495: 429–40.
[27] Ukomadu, C., Zhou, J., Sigworth, F. J. and Agnew, W. S. (1992) Neuron 8: 663–76.
[28] Dib-Hajj, S. D., Ishikawa, K., Cummins, T. R. and Waxman, S. G. (1997) FEBS Letters 416: 11–14.
[29] Hamill, O. P., Neher, M. A., Sakmann, B. and Sigworth, F. J. (1981) Pflugers Arch. 391: 85–100.
[30] Rizzo, M. A., Kocsis, J. D. and Waxman, S. G. (1994) J. Neurophysiology 72: 2796–815.
[31] Kimelberg, H. K. and Waltz, W. (1988) (Boulton, A., Baker, G. and Walz, W., Eds.).
[32] Sontheimer, H., Fernandez-Marques, E., Ullrich, N., Pappas, C. A. and Waxman, S. G. (1994) J. Neuroscience 14: 2464–75.
[33] Harootunian, A., Kao, J. P. Y., Ecker, B. K. and Tsien, R. Y. (1989) J. Biol. Chem. 264: 19458–19467.

[34] Rose, C. R. and Ransom, B. R. (1996) J. Physiol. (Lond) 491: 291–305.

[35] Kimelberg, H. K. and Mayhew, E. (1975) J. Biol. Chem. 250: 100–104.

[36] Smith, P. K. et al. (1985) Anal. Biochem. 150: 76–85.

[37] Goldschmidt, R. C. and Kimelberg, H. K. (1989) Analytical Biochemistry 177: 41–45.

[38] Dubner, R. (1994) in: Textbook of Pain (Wall, P. D. and Melzack, R., Eds.) Churchill Livingstone Publishers.

[39] Dubuisson, D. and Dennis, S. G. (1977) Pain 4: 161–74.

[40] Iadarola, M. J., Brady, L. S., Draisci, G. and Dubner, R. (1988) Pain 35: 313–26.

[41] Bennett, G. J. and Xie, Y. K. (1988) Pain 33: 87–107.

[42] Kim, S. H. and Chung, J. M. (1992) Pain 50: 355–63.

[43] Seltzer, Z., Dubner, R. and Shir, Y. (1990) Pain 43: 205–18.

[44] Stys, P. K., Ransom, B. R. and Waxman, S. G. (1992) J. Neurophysiology 67: 236–40.

[45] Chomczynski, P. a. S., N (1987) Anal. Bioch. 162: 156–159.

[46] Dib-Hajj, S. D., Hinson, A. W., Black, J. A. and Waxman, S. G. (1996) FEBS Letters 384: 78–82.

[47] Gu, X. Q., Dibhajj, S., Rizzo, M. A. and Waxman, S. G. (1997) J. Neurophysiology 77: 236–246.

[48] Fjell, J., Dibhajj, S., Fried, K., Black, J. A. and Waxman, S. G. (1997) Molecular Brain Research 50: 197–204.

[49] Barnes, W. M. (1994) Proc. Natl. Acad. Sci. (USA) 91: 2216–2220.

[50] Cheng, S., Fockler, C. Barnes W. M. and Higuchi, R. (1994) Proc. Natl. Acad. Sci. (USA) 91: 5695–5699.

[51] George, A. L., Jr., Iyer, G. S., Kleinfield, R., Kallen, R. G. and Barchi, R. L. (1993) Genomics 15: 598–606.

[52] Souslova, V. A., Fox, M., Wood, J. N. and Akopian, A. N. (1997) Genomics 41: 201–209.

[53] McClatchey, A. I., Lin, C. S., Wang, J., Hoffman, E. P., Rojas, C. and Gusella, J. F. (1992) Hum. Mol. Genet. 1: 521–7.

[54] Wang, Q., Li, Z., Shen, J. and Keating, M. T. (1996) Genomics 34: 9–16.

[55] Sontheimer, H. and Waxman, S. G. (1992) J. Neurophysiology 68: 1001–11.

[56] Black, J. A., Yokoyama, S., Waxman, S. G., Oh, Y., Zur, K. B., Sontheimer, H., Higashida, H. and Ransom, B. R. (1994) Brain Research. Molecular Brain Research 23: 235–45.

[57] Zur, K. B., Oh, Y., Waxman, S. G. and Black, J. A. (1995) Brain Research. Molecular Brain Research 30: 97–105.

[58] Tanaka et al., unpublished.

[59] Sambrook et al., *Molecular Cloning: A Laboratory Approach*, Cold Spring Harbor Press, NY, 1989.

[60] Ausubel et al., *Current Protocols in Molecular Biology*, Greene Publishing Co., NY, 1995.

[61] Cohen et al., *Proc Acad Sci USA* (1972) 69: 2110.

[62] Maniatis et al., *Molecular Cloning*, Cold Spring Harbor Laboratory, Cold Spring Harbor, N.Y. 1982.

[63] Graham et al., Virol. (1973) 52: 456.

[64] Wigler et al., Proc. Natl. Acad. Sci. USA (1979) 76: 1373–76.

[65] Southern, *J. Mol. Biol.* (1975) 98: 503.

[66] Berent et al., *Biotech* (1985) 3: 208.

[67] Rose; et al., *J. Neurophysiology*, 1997 in press.

[68] Dib-Hajj and Waxman, unpublished.

[69] Saiki et al. (1985) *Science* 230: 1350.

[70] Rizzo, M. A., Kocsis, J. D., and Waxman, S. G. (1994). Slow sodium conductances of dorsal root ganglion neurons: intraneuronal homogeneity and interneuronal heterogeneity. Journal of Neurophysiology 72, 2796–815.

[71] Dib-Hajj, S. D., Hinson, A. W., Black, J. A., and Waxman, S. G. (1996). Sodium channel mRNA in the B 104 neuroblastoma cell line. FEBS Letters 384, 78–82.

[72] Benham, C. D., and Tsien, R. W. (1987). A novel receptor-operated Ca2+-permeable channel activated by ATP in smooth muscle. Nature 328, 275–8.

[73] Ercolani, L., Florence, B., Denaro, M., and Alexander, M. (1988). Isolation and complete sequence of a functional human glyceraldehyde-3-phosphate dehydrogenase gene. J Biol Chem 263, 15335–41.

The invention claimed is:

1. An isolated protein capable of producing a sodium current and encoded by a nucleic acid with at least 80% sequence identity to a nucleotide sequence comprising SEQ ID NO: 41.

2. The isolated protein of claim 1, wherein the percent nucleotide sequence identity to SEQ ID NO: 41 is at least 90%.

3. The isolated protein of claim 1, wherein the percent nucleotide sequence identity to SEQ ID NO: 41 is at least 95%.

4. The isolated protein of claim 1, wherein the percent nucleotide sequence identity to SEQ ID NO: 41 is at least 99%.

5. The isolated protein of claim 1, wherein the isolated protein is encoded by a nucleotide sequence comprising SEQ ID NO: 41.

6. The isolated protein of claim 1, wherein the isolated protein is encoded by a nucleotide sequence comprising nucleotides 31 to 5403 of SEQ ID NO: 41.

7. The isolated protein of claim 1, wherein the isolated protein is encoded by a nucleotide sequence consisting of nucleotides 31 to 5403 of SEQ ID NO: 41.

8. The isolated protein of claim 1, wherein the isolated protein is a membrane-bound sodium channel.

9. The isolated protein of claim 1, wherein the isolated protein comprises an amino acid sequence of SEQ ID NO: 42.

10. The isolated protein of claim 1, wherein the isolated protein consists essentially of an amino acid sequence of SEQ ID NO: 42.

11. The isolated protein of claim 1, wherein the isolated protein consists of an amino acid sequence of SEQ ID NO: 42.

12. An isolated protein comprising an amino acid sequence of SEQ ID NO: 42 or a peptide fragment thereof capable of producing a sodium current.

13. The isolated protein of claim 12, wherein the peptide fragment comprises an amino acid sequence of SEQ ID NO: 8.

14. The isolated protein of claim 12, wherein the peptide fragment consists essentially of an amino acid sequence of SEQ ID NO: 8.

15. The isolated protein of claim 12, wherein the peptide fragment consists of an amino acid sequence of SEQ ID NO: 8.

16. The isolated protein of claim 13, wherein the peptide fragment is encoded by a nucleotide sequence comprising SEQ ID NO: 6.

17. The isolated protein of claims 1 or 12, wherein the protein is recombinantly produced.

18. The isolated protein of claim 17, wherein the protein is expressed by a recombinant host cell.

19. An isolated protein comprising an amino acid sequence of SEQ ID NO: 42.

* * * * *

SEQUENCE LISTING

<160> NUMBER OF SEQ ID NOS: 44

<210> SEQ ID NO 1
<211> LENGTH: 5875
<212> TYPE: DNA
<213> ORGANISM: Rattus norvegicus
<220> FEATURE:
<221> NAME/KEY: CDS
<222> LOCATION: (41)..(5335)
<223> OTHER INFORMATION: cDNA sequence for rat NaN
<220> FEATURE:
<221> NAME/KEY: unsure
<222> LOCATION: (1996)..(4042)
<223> OTHER INFORMATION: n = a or c or g or t. Xaa at amino acid
      position 652 is Leu; Xaa at amino acid position 1334 is Asn
      or Lys.

<400> SEQUENCE: 1
acggtgccct gatcctctgt accaggaaga cagggtgaag atg gag gag agg tac    55
                                              Met Glu Glu Arg Tyr
                                                1               5

-continued

| | |
|---|---|
| tac ccg gtg atc ttc ccg gac gag cgg aat ttc cgc ccc ttc act tcc<br>Tyr Pro Val Ile Phe Pro Asp Glu Arg Asn Phe Arg Pro Phe Thr Ser<br>          10                      15                20 | 103 |
| gac tct ctg gct gcc ata gag aag cgg att gct atc caa aag gag agg<br>Asp Ser Leu Ala Ala Ile Glu Lys Arg Ile Ala Ile Gln Lys Glu Arg<br>          25                      30                      35 | 151 |
| aag aag tcc aaa gac aag gcg gca gct gag ccc cag cct cgg cct cag<br>Lys Lys Ser Lys Asp Lys Ala Ala Ala Glu Pro Gln Pro Arg Pro Gln<br>              40                      45                  50 | 199 |
| ctt gac cta aag gcc tcc agg aag tta cct aag ctt tat ggt gac att<br>Leu Asp Leu Lys Ala Ser Arg Lys Leu Pro Lys Leu Tyr Gly Asp Ile<br>55                      60                      65 | 247 |
| ccc cct gag ctt gta gcg aag cct ctg gaa gac ctg gac cca ttc tac<br>Pro Pro Glu Leu Val Ala Lys Pro Leu Glu Asp Leu Asp Pro Phe Tyr<br>70                      75                      80                  85 | 295 |
| aaa gac cat aag aca ttc atg gtg ttg aac aag aag aga aca att tat<br>Lys Asp His Lys Thr Phe Met Val Leu Asn Lys Lys Arg Thr Ile Tyr<br>              90                      95                      100 | 343 |
| cgc ttc agc gcc aag cgg gcc ttg ttc att ctg ggg cct ttt aat ccc<br>Arg Phe Ser Ala Lys Arg Ala Leu Phe Ile Leu Gly Pro Phe Asn Pro<br>          105                     110                   115 | 391 |
| ctc aga agc tta atg att cgt atc tct gtc cat tca gtc ttt agc atg<br>Leu Arg Ser Leu Met Ile Arg Ile Ser Val His Ser Val Phe Ser Met<br>          120                     125                   130 | 439 |
| ttc atc atc tgc acg gtg atc atc aac tgt atg ttc atg gcg aat tct<br>Phe Ile Ile Cys Thr Val Ile Ile Asn Cys Met Phe Met Ala Asn Ser<br>          135                     140                   145 | 487 |
| atg gag aga agt ttc gac aac gac att ccc gaa tac gtc ttc att ggg<br>Met Glu Arg Ser Phe Asp Asn Asp Ile Pro Glu Tyr Val Phe Ile Gly<br>150                      155                      160                  165 | 535 |
| att tat att tta gaa gct gtg att aaa ata ttg gca aga ggc ttc att<br>Ile Tyr Ile Leu Glu Ala Val Ile Lys Ile Leu Ala Arg Gly Phe Ile<br>          170                     175                   180 | 583 |
| gtg gat gag ttt tcc ttc ctc cga gat ccg tgg aac tgg ctg gac ttc<br>Val Asp Glu Phe Ser Phe Leu Arg Asp Pro Trp Asn Trp Leu Asp Phe<br>          185                     190                   195 | 631 |
| att gtc att gga aca gcg atc gca act tgt ttt ccg ggc agc caa gtc<br>Ile Val Ile Gly Thr Ala Ile Ala Thr Cys Phe Pro Gly Ser Gln Val<br>          200                     205                   210 | 679 |
| aat ctt tca gct ctt cgt acc ttc cga gtg ttc aga gct ctg aag gcg<br>Asn Leu Ser Ala Leu Arg Thr Phe Arg Val Phe Arg Ala Leu Lys Ala<br>          215                     220                   225 | 727 |
| att tca gtt atc tca ggt ctg aag gtc atc gta ggt gcc ctg ctg cgc<br>Ile Ser Val Ile Ser Gly Leu Lys Val Ile Val Gly Ala Leu Leu Arg<br>230                      235                      240                  245 | 775 |
| tcg gtg aag aag ctg gta gac gtg atg gtc ctc act ctc ttc tgc ctc<br>Ser Val Lys Lys Leu Val Asp Val Met Val Leu Thr Leu Phe Cys Leu<br>          250                     255                   260 | 823 |
| agc atc ttt gcc ctg gtc ggt cag cag ctg ttc atg gga att ctg aac<br>Ser Ile Phe Ala Leu Val Gly Gln Gln Leu Phe Met Gly Ile Leu Asn<br>          265                     270                   275 | 871 |
| cag aag tgt att aag cac aac tgt ggc ccc aac cct gca tcc aac aag<br>Gln Lys Cys Ile Lys His Asn Cys Gly Pro Asn Pro Ala Ser Asn Lys<br>          280                     285                   290 | 919 |
| gat tgt ttt gaa aag gaa aaa gat agc gaa gac ttc ata atg tgt ggt<br>Asp Cys Phe Glu Lys Glu Lys Asp Ser Glu Asp Phe Ile Met Cys Gly<br>295                      300                      305 | 967 |
| acc tgg ctc ggc agc aga ccc tgt ccc aat ggt tct acg tgc gat aaa<br>Thr Trp Leu Gly Ser Arg Pro Cys Pro Asn Gly Ser Thr Cys Asp Lys<br>310                      315                      320                  325 | 1015 |

```
acc aca ttg aac cca gac aat aat tat aca aag ttt gac aac ttt ggc      1063
Thr Thr Leu Asn Pro Asp Asn Asn Tyr Thr Lys Phe Asp Asn Phe Gly
            330                 335                 340 tgg tcc ttt ctc gcc atg ttc cgg gtt atg act caa gac tcc tgg gag      1111
Trp Ser Phe Leu Ala Met Phe Arg Val Met Thr Gln Asp Ser Trp Glu
            345                 350                 355 agg ctt tac cga cag atc ctg cgg acc tct ggg atc tac ttt gtc ttc      1159
Arg Leu Tyr Arg Gln Ile Leu Arg Thr Ser Gly Ile Tyr Phe Val Phe
            360                 365                 370 ttc ttc gtg gtg gtc atc ttc ctg ggc tcc ttc tac ctg ctt aac cta      1207
Phe Phe Val Val Val Ile Phe Leu Gly Ser Phe Tyr Leu Leu Asn Leu
            375                 380                 385 acc ctg gct gtt gtc acc atg gct tat gaa gaa cag aac aga aat gta      1255
Thr Leu Ala Val Val Thr Met Ala Tyr Glu Glu Gln Asn Arg Asn Val
390                 395                 400                 405 gct gct gag aca gag gcc aag gag aaa atg ttt cag gaa gcc cag cag      1303
Ala Ala Glu Thr Glu Ala Lys Glu Lys Met Phe Gln Glu Ala Gln Gln
            410                 415                 420 ctg tta agg gag gag aag gag gct ctg gtt gcc atg gga att gac aga      1351
Leu Leu Arg Glu Glu Lys Glu Ala Leu Val Ala Met Gly Ile Asp Arg
            425                 430                 435 agt tcc ctt aat tcc ctt caa gct tca tcc ttt tcc ccg aag aag agg      1399
Ser Ser Leu Asn Ser Leu Gln Ala Ser Ser Phe Ser Pro Lys Lys Arg
            440                 445                 450 aag ttt ttc ggt agt aag aca aga aag tcc ttc ttt atg aga ggg tcc      1447
Lys Phe Phe Gly Ser Lys Thr Arg Lys Ser Phe Phe Met Arg Gly Ser
            455                 460                 465 aag acg gcc caa gcc tca gcg tct gat tca gag gac gat gcc tct aaa      1495
Lys Thr Ala Gln Ala Ser Ala Ser Asp Ser Glu Asp Asp Ala Ser Lys
470                 475                 480                 485 aat cca cag ctc ctt gag cag acc aaa cga ctg tcc cag aac ttg cca      1543
Asn Pro Gln Leu Leu Glu Gln Thr Lys Arg Leu Ser Gln Asn Leu Pro
            490                 495                 500 gtg gat ctc ttt gat gag cac gtg gac ccc ctc cac agg cag aga gcg      1591
Val Asp Leu Phe Asp Glu His Val Asp Pro Leu His Arg Gln Arg Ala
            505                 510                 515 ctg agc gct gtc agt atc tta acc atc acc atg cag gaa caa gaa aaa      1639
Leu Ser Ala Val Ser Ile Leu Thr Ile Thr Met Gln Glu Gln Glu Lys
            520                 525                 530 ttc cag gag cct tgt ttc cca tgt ggg aaa aat ttg gcc tct aag tac      1687
Phe Gln Glu Pro Cys Phe Pro Cys Gly Lys Asn Leu Ala Ser Lys Tyr
            535                 540                 545 ctg gtg tgg gac tgt agc cct caa tgg ctg tgc ata aag aag gtc ctg      1735
Leu Val Trp Asp Cys Ser Pro Gln Trp Leu Cys Ile Lys Lys Val Leu
550                 555                 560                 565 cgg acc atc atg acg gat ccc ttt act gag ctg gcc atc acc atc tgc      1783
Arg Thr Ile Met Thr Asp Pro Phe Thr Glu Leu Ala Ile Thr Ile Cys
            570                 575                 580 atc atc atc aat acc gtt ttc tta gcc gtg gag cac cac aac atg gat      1831
Ile Ile Ile Asn Thr Val Phe Leu Ala Val Glu His His Asn Met Asp
            585                 590                 595 gac aac tta aag acc ata ctg aaa ata gga aac tgg gtt ttc acg gga      1879
Asp Asn Leu Lys Thr Ile Leu Lys Ile Gly Asn Trp Val Phe Thr Gly
            600                 605                 610 att ttc ata gcg gaa atg tgt ctc aag atc atc gcg ctc gac cct tac      1927
Ile Phe Ile Ala Glu Met Cys Leu Lys Ile Ile Ala Leu Asp Pro Tyr
            615                 620                 625 cac tac ttc cgg cac ggc tgg aat gtt ttt gac agc atc gtg gcc ctc      1975
His Tyr Phe Arg His Gly Trp Asn Val Phe Asp Ser Ile Val Ala Leu
630                 635                 640                 645
```

```
                                              -continued ctg agt ctc gct gat gtg ctn tac aac aca ctg tct gat aac aat agg    2023
Leu Ser Leu Ala Asp Val Xaa Tyr Asn Thr Leu Ser Asp Asn Asn Arg
            650                 655                 660 tct ttc ttg gct tcc ctc aga gtg ctg agg gtc ttc aag tta gcc aaa    2071
Ser Phe Leu Ala Ser Leu Arg Val Leu Arg Val Phe Lys Leu Ala Lys
        665                 670                 675 tcc tgg ccc acg tta aac act ctc att aag atc atc ggc cac tcc gtg    2119
Ser Trp Pro Thr Leu Asn Thr Leu Ile Lys Ile Ile Gly His Ser Val
    680                 685                 690 ggc gcg ctt gga aac ctg act gtg gtc ctg act atc gtg gtc ttc atc    2167
Gly Ala Leu Gly Asn Leu Thr Val Val Leu Thr Ile Val Val Phe Ile
695                 700                 705 ttt tct gtg gtg ggc atg cgg ctc ttc ggc acc aag ttt aac aag acc    2215
Phe Ser Val Val Gly Met Arg Leu Phe Gly Thr Lys Phe Asn Lys Thr
710                 715                 720                 725 gcc tac gcc acc cag gag cgg ccc agg cgg cgc tgg cac atg gat aat    2263
Ala Tyr Ala Thr Gln Glu Arg Pro Arg Arg Arg Trp His Met Asp Asn
                730                 735                 740 ttc tac cac tcc ttc ctg gtg gtg ttc cgc atc ctc tgt ggg gaa tgg    2311
Phe Tyr His Ser Phe Leu Val Val Phe Arg Ile Leu Cys Gly Glu Trp
            745                 750                 755 atc gag aac atg tgg ggc tgc atg cag gat atg gac ggc tcc ccg ttg    2359
Ile Glu Asn Met Trp Gly Cys Met Gln Asp Met Asp Gly Ser Pro Leu
        760                 765                 770 tgc atc att gtc ttt gtc ctg ata atg gtg atc ggg aag ctt gtg gtg    2407
Cys Ile Ile Val Phe Val Leu Ile Met Val Ile Gly Lys Leu Val Val
    775                 780                 785 ctt aac ctc ttc att gcc ttg ctc ctc aat tcc ttc agc aat gag gag    2455
Leu Asn Leu Phe Ile Ala Leu Leu Leu Asn Ser Phe Ser Asn Glu Glu
790                 795                 800                 805 aag gat ggg agc ctg gaa gga gag acc agg aaa acc aaa gtg cag cta    2503
Lys Asp Gly Ser Leu Glu Gly Glu Thr Arg Lys Thr Lys Val Gln Leu
                810                 815                 820 gcc ctg gat cgg ttc cgc cgg gcc ttc tcc ttc atg ctg cac gct ctt    2551
Ala Leu Asp Arg Phe Arg Arg Ala Phe Ser Phe Met Leu His Ala Leu
            825                 830                 835 cag agt ttt tgt tgc aag aaa tgc agg agg aaa aac tcg cca aag cca    2599
Gln Ser Phe Cys Cys Lys Lys Cys Arg Arg Lys Asn Ser Pro Lys Pro
        840                 845                 850 aaa gag aca aca gaa agc ttt gct ggt gag aat aaa gac tca atc ctc    2647
Lys Glu Thr Thr Glu Ser Phe Ala Gly Glu Asn Lys Asp Ser Ile Leu
    855                 860                 865 ccg gat gcg agg ccc tgg aag gag tat gat aca gac atg gct ttg tac    2695
Pro Asp Ala Arg Pro Trp Lys Glu Tyr Asp Thr Asp Met Ala Leu Tyr
870                 875                 880                 885 act gga cag gcc ggg gct ccg ctg gcc cca ctc gca gag gta gag gac    2743
Thr Gly Gln Ala Gly Ala Pro Leu Ala Pro Leu Ala Glu Val Glu Asp
                890                 895                 900 gat gtg gaa tat tgt ggt gaa ggc ggt gcc cta ccc acc tca caa cat    2791
Asp Val Glu Tyr Cys Gly Glu Gly Gly Ala Leu Pro Thr Ser Gln His
            905                 910                 915 agt gct gga gtt cag gcc ggt gac ctc cct cca gag acc aag cag ctc    2839
Ser Ala Gly Val Gln Ala Gly Asp Leu Pro Pro Glu Thr Lys Gln Leu
        920                 925                 930 act agc ccg gat gac caa ggg gtt gaa atg gaa gta ttt tct gaa gaa    2887
Thr Ser Pro Asp Asp Gln Gly Val Glu Met Glu Val Phe Ser Glu Glu
    935                 940                 945 gat ctg cat tta agc ata cag agt cct cga aag aag tct gac gca gtg    2935
Asp Leu His Leu Ser Ile Gln Ser Pro Arg Lys Lys Ser Asp Ala Val
950                 955                 960                 965
```

| | |
|---|---|
| agc atg ctc tcg gaa tgc agc aca att gac ctg aat gat atc ttt aga<br>Ser Met Leu Ser Glu Cys Ser Thr Ile Asp Leu Asn Asp Ile Phe Arg<br>970                 975               980 | 2983 |
| aat tta cag aaa aca gtt tcc ccc aaa aag cag cca gat aga tgc ttt<br>Asn Leu Gln Lys Thr Val Ser Pro Lys Lys Gln Pro Asp Arg Cys Phe<br>    985               990               995 | 3031 |
| ccc aag ggc ctt agt tgt cac ttt cta tgc cac aaa aca gac aag aga<br>Pro Lys Gly Leu Ser Cys His Phe Leu Cys His Lys Thr Asp Lys Arg<br>1000                1005              1010 | 3079 |
| aag tcc ccc tgg gtc ctg tgg tgg aac att cgg aaa acc tgc tac caa<br>Lys Ser Pro Trp Val Leu Trp Trp Asn Ile Arg Lys Thr Cys Tyr Gln<br>1015                1020              1025 | 3127 |
| atc gtg aag cac agc tgg ttt gag agt ttc ata atc ttt gtt att ctg<br>Ile Val Lys His Ser Trp Phe Glu Ser Phe Ile Ile Phe Val Ile Leu<br>1030                1035              1040              1045 | 3175 |
| ctg agc agt gga gcg ctg ata ttt gaa gat gtc aat ctc ccc agc cgg<br>Leu Ser Ser Gly Ala Leu Ile Phe Glu Asp Val Asn Leu Pro Ser Arg<br>              1050              1055              1060 | 3223 |
| ccc caa gtt gag aaa tta cta agg tgt acc gat aat att ttc aca ttt<br>Pro Gln Val Glu Lys Leu Leu Arg Cys Thr Asp Asn Ile Phe Thr Phe<br>                1065              1070              1075 | 3271 |
| att ttc ctc ctg gaa atg atc ctg aag tgg gtg gcc ttt gga ttc cgg<br>Ile Phe Leu Leu Glu Met Ile Leu Lys Trp Val Ala Phe Gly Phe Arg<br>1080                1085              1090 | 3319 |
| agg tat ttc acc agt gcc tgg tgc tgg ctt gat ttc ctc att gtg gtg<br>Arg Tyr Phe Thr Ser Ala Trp Cys Trp Leu Asp Phe Leu Ile Val Val<br>    1095              1100              1105 | 3367 |
| gtg tct gtg ctc agt ctc atg aat cta cca agc ttg aag tcc ttc cgg<br>Val Ser Val Leu Ser Leu Met Asn Leu Pro Ser Leu Lys Ser Phe Arg<br>1110                1115              1120              1125 | 3415 |
| act ctg cgg gcc ctg aga cct ctg cgg gcg ctg tcc cag ttt gaa gga<br>Thr Leu Arg Ala Leu Arg Pro Leu Arg Ala Leu Ser Gln Phe Glu Gly<br>              1130              1135              1140 | 3463 |
| atg aag gtt gtc gtc tac gcc ctg atc agc gcc ata cct gcc att ctc<br>Met Lys Val Val Val Tyr Ala Leu Ile Ser Ala Ile Pro Ala Ile Leu<br>                1145              1150              1155 | 3511 |
| aat gtc ttg ctg gtc tgc ctc att ttc tgg ctc gta ttt tgt atc ttg<br>Asn Val Leu Leu Val Cys Leu Ile Phe Trp Leu Val Phe Cys Ile Leu<br>1160                1165              1170 | 3559 |
| gga gta aat tta ttt tct ggg aag ttt gga agg tgc att aac ggg aca<br>Gly Val Asn Leu Phe Ser Gly Lys Phe Gly Arg Cys Ile Asn Gly Thr<br>    1175              1180              1185 | 3607 |
| gac ata aat atg tat ttg gat ttt acc gaa gtt ccg aac cga agc caa<br>Asp Ile Asn Met Tyr Leu Asp Phe Thr Glu Val Pro Asn Arg Ser Gln<br>1190                1195              1200              1205 | 3655 |
| tgt aac att agt aat tac tcg tgg aag gtc ccg cag gtc aac ttt gac<br>Cys Asn Ile Ser Asn Tyr Ser Trp Lys Val Pro Gln Val Asn Phe Asp<br>              1210              1215              1220 | 3703 |
| aac gtg ggg aat gcc tat ctc gcc ctg ctg caa gtg gca acc tat aag<br>Asn Val Gly Asn Ala Tyr Leu Ala Leu Leu Gln Val Ala Thr Tyr Lys<br>                1225              1230              1235 | 3751 |
| ggc tgg ctg gaa atc atg aat gct gct gtc gat tcc aga gag aaa gac<br>Gly Trp Leu Glu Ile Met Asn Ala Ala Val Asp Ser Arg Glu Lys Asp<br>1240                1245              1250 | 3799 |
| gag cag ccg gac ttt gag gcg aac ctc tac gcg tat ctc tac ttt gtg<br>Glu Gln Pro Asp Phe Glu Ala Asn Leu Tyr Ala Tyr Leu Tyr Phe Val<br>    1255              1260              1265 | 3847 |
| gtt ttt atc atc ttc ggc tcc ttc ttt acc ctg aac ctc ttt atc ggt<br>Val Phe Ile Ile Phe Gly Ser Phe Phe Thr Leu Asn Leu Phe Ile Gly<br>1270                1275              1280              1285 | 3895 |

-continued

| | |
|---|---|
| gtt att att gac aac ttc aat cag cag cag aaa aag tta ggt ggc caa<br>Val Ile Ile Asp Asn Phe Asn Gln Gln Gln Lys Lys Leu Gly Gly Gln<br>          1290                    1295                    1300 | 3943 |
| gac att ttt atg aca gaa gaa cag aag aaa tat tac aat gca atg aaa<br>Asp Ile Phe Met Thr Glu Glu Gln Lys Lys Tyr Tyr Asn Ala Met Lys<br>1305                    1310                    1315 | 3991 |
| aag tta gga acc aag aaa cct caa aag ccc atc cca agg ccc ctg aac<br>Lys Leu Gly Thr Lys Lys Pro Gln Lys Pro Ile Pro Arg Pro Leu Asn<br>1320                    1325                    1330 | 4039 |
| aan tgt caa gcc ttt gtg ttc gac ctg gtc aca agc cat gtc ttt gac<br>Xaa Cys Gln Ala Phe Val Phe Asp Leu Val Thr Ser His Val Phe Asp<br>          1335                    1340                    1345 | 4087 |
| gtc atc att ctg ggt ctt att gtc tta aat atg att atc atg atg gct<br>Val Ile Ile Leu Gly Leu Ile Val Leu Asn Met Ile Ile Met Met Ala<br>1350                    1355                    1360                    1365 | 4135 |
| gaa tct gcc gac cag ccc aaa gat gtg aag aaa acc ttt gat atc ctc<br>Glu Ser Ala Asp Gln Pro Lys Asp Val Lys Lys Thr Phe Asp Ile Leu<br>                  1370                    1375                    1380 | 4183 |
| aac ata gcc ttc gtg gtc atc ttt acc ata gag tgt ctc atc aaa gtc<br>Asn Ile Ala Phe Val Val Ile Phe Thr Ile Glu Cys Leu Ile Lys Val<br>1385                    1390                    1395 | 4231 |
| ttt gct ttg agg caa cac tac ttc acc aat ggc tgg aac tta ttt gat<br>Phe Ala Leu Arg Gln His Tyr Phe Thr Asn Gly Trp Asn Leu Phe Asp<br>          1400                    1405                    1410 | 4279 |
| tgt gtg gtc gtg gtt ctt tct atc att agt acc ctg gtt tcc cgc ttg<br>Cys Val Val Val Leu Ser Ile Ile Ser Thr Leu Val Ser Arg Leu<br>              1415                    1420                    1425 | 4327 |
| gag gac agt gac att tct ttc ccg ccc acg ctc ttc aga gtc gtc cgc<br>Glu Asp Ser Asp Ile Ser Phe Pro Pro Thr Leu Phe Arg Val Val Arg<br>1430                    1435                    1440                    1445 | 4375 |
| ttg gct cgg att ggt cga atc ctc agg ctg gtc cgg gct gcc cgg gga<br>Leu Ala Arg Ile Gly Arg Ile Leu Arg Leu Val Arg Ala Ala Arg Gly<br>                  1450                    1455                    1460 | 4423 |
| atc agg acc ctc ctc ttt gct ttg atg atg tct ctc ccc tct ctc ttc<br>Ile Arg Thr Leu Leu Phe Ala Leu Met Met Ser Leu Pro Ser Leu Phe<br>1465                    1470                    1475 | 4471 |
| aac atc ggt ctg ctg ctc ttc ctg gtg atg ttc att tac gcc atc ttt<br>Asn Ile Gly Leu Leu Leu Phe Leu Val Met Phe Ile Tyr Ala Ile Phe<br>                  1480                    1485                    1490 | 4519 |
| ggg atg agc tgg ttt tcc aaa gtg aag aag ggc tcc ggg atc gac gac<br>Gly Met Ser Trp Phe Ser Lys Val Lys Lys Gly Ser Gly Ile Asp Asp<br>1495                    1500                    1505 | 4567 |
| atc ttc aac ttc gag acc ttt acg ggc agc atg ctg tgc ctc ttc cag<br>Ile Phe Asn Phe Glu Thr Phe Thr Gly Ser Met Leu Cys Leu Phe Gln<br>1510                    1515                    1520                    1525 | 4615 |
| ata acc act tcg gct ggc tgg gat acc ctc ctc aac ccc atg ctg gag<br>Ile Thr Thr Ser Ala Gly Trp Asp Thr Leu Leu Asn Pro Met Leu Glu<br>                  1530                    1535                    1540 | 4663 |
| gca aaa gaa cac tgc aac tcc tcc tcc caa gac agc tgt cag cag ccg<br>Ala Lys Glu His Cys Asn Ser Ser Ser Gln Asp Ser Cys Gln Gln Pro<br>1545                    1550                    1555 | 4711 |
| cag ata gcc gtc gtc tac ttc gtc agt tac atc atc atc tcc ttc ctc<br>Gln Ile Ala Val Val Tyr Phe Val Ser Tyr Ile Ile Ile Ser Phe Leu<br>          1560                    1565                    1570 | 4759 |
| atc gtg gtc aac atg tac atc gct gtg atc ctc gag aac ttc aac aca<br>Ile Val Val Asn Met Tyr Ile Ala Val Ile Leu Glu Asn Phe Asn Thr<br>              1575                    1580                    1585 | 4807 |
| gcc acg gag gag agc gag gac cct ctg gga gag gac gac ttt gaa atc<br>Ala Thr Glu Glu Ser Glu Asp Pro Leu Gly Glu Asp Asp Phe Glu Ile<br>1590                    1595                    1600                    1605 | 4855 |

```
ttc tat gag gtc tgg gag aag ttt gac ccc gag gcg tcg cag ttc atc      4903
Phe Tyr Glu Val Trp Glu Lys Phe Asp Pro Glu Ala Ser Gln Phe Ile
            1610             1615                 1620 cag tat tcg gcc ctc tct gac ttt gcg gac gcc ctg ccg gag ccg ttg      4951
Gln Tyr Ser Ala Leu Ser Asp Phe Ala Asp Ala Leu Pro Glu Pro Leu
        1625                 1630                 1635 cgt gtg gcc aag ccg aat aag ttt cag ttt cta gtg atg gac ttg ccc      4999
Arg Val Ala Lys Pro Asn Lys Phe Gln Phe Leu Val Met Asp Leu Pro
    1640                 1645                 1650 atg gtg atg ggc gac cgc ctc cat tgc atg gat gtt ctc ttt gct ttc      5047
Met Val Met Gly Asp Arg Leu His Cys Met Asp Val Leu Phe Ala Phe
1655                 1660                 1665 act acc agg gtc ctc ggg gac tcc agc ggc ttg gat acc atg aaa acc      5095
Thr Thr Arg Val Leu Gly Asp Ser Ser Gly Leu Asp Thr Met Lys Thr
1670                 1675                 1680                 1685 atg atg gag gag aag ttt atg gag gcc aac cct ttt aag aag ctc tac      5143
Met Met Glu Glu Lys Phe Met Glu Ala Asn Pro Phe Lys Lys Leu Tyr
        1690                 1695                 1700 gag ccc ata gtc acc acc acc aag agg aag gag gag gag caa ggc gcc      5191
Glu Pro Ile Val Thr Thr Thr Lys Arg Lys Glu Glu Glu Gln Gly Ala
            1705                 1710                 1715 gcc gtc atc cag agg gcc tac cgg aaa cac atg gag aag atg gtc aaa      5239
Ala Val Ile Gln Arg Ala Tyr Arg Lys His Met Glu Lys Met Val Lys
        1720                 1725                 1730 ctg agg ctg aag gac agg tca agt tca tcg cac cag gtg ttt tgc aat      5287
Leu Arg Leu Lys Asp Arg Ser Ser Ser Ser His Gln Val Phe Cys Asn
    1735                 1740                 1745 gga gac ttg tcc agc ttg gat gtg gcc aag gtc aag gtt cac aat gac      5335
Gly Asp Leu Ser Ser Leu Asp Val Ala Lys Val Lys Val His Asn Asp
1750                 1755                 1760                 1765 tgaaccctca tctccacccc tacctcactg cctcacagct tagcctccag cctctggcga   5395
gcaggcggca gactcactga acacaggccg ttcgatctgt gtttttggct gaacgaggtg   5455
acaggttggc gtccattttt aaatgactct tggaaagatt tcatgtagag agatgttaga   5515
agggactgca aaggacaccg accataacgg aaggcctgga ggacagtcca acttacataa   5575
agatgagaaa caagaaggaa agatcccagg aaaacttcag attgtgttct cagtacattc   5635
cccaatgtgt ctgttcggtg ttttgagtat gtgacctgcc acatgtagct ctttttttgca  5695 tgtacgtcaa aaccctgcag taagttaata gcttgctacg ggtgttccta ccagcatcac   5755
agaattgggt gtatgactca aacctaaaag catgactctg acttgtcagt cagcaccccg   5815
actttcagac gctccaatct ctgtcccagg tgtctaacga ataaataggt aaagaaaaa    5875

<210> SEQ ID NO 2
<211> LENGTH: 1765
<212> TYPE: PRT
<213> ORGANISM: Rattus norvegicus
<220> FEATURE:
<221> NAME/KEY: UNSURE
<222> LOCATION: (652)..(1334)
<223> OTHER INFORMATION: Xaa at position 652 is Leu; Xaa at position
      1334 is Asn or Lys.  Xaa's result from n's in SEQ ID NO: 1.

<400> SEQUENCE: 2

Met Glu Glu Arg Tyr Tyr Pro Val Ile Phe Pro Asp Glu Arg Asn Phe
1               5                  10                  15

Arg Pro Phe Thr Ser Asp Ser Leu Ala Ala Ile Glu Lys Arg Ile Ala
            20                  25                  30

Ile Gln Lys Glu Arg Lys Lys Ser Lys Asp Lys Ala Ala Ala Glu Pro
        35                  40                  45
```

-continued

```
Gln Pro Arg Pro Gln Leu Asp Leu Lys Ala Ser Arg Lys Leu Pro Lys
     50                  55                  60

Leu Tyr Gly Asp Ile Pro Glu Leu Val Ala Lys Pro Leu Glu Asp
 65              70                  75                  80

Leu Asp Pro Phe Tyr Lys Asp His Lys Thr Phe Met Val Leu Asn Lys
                 85                  90                  95

Lys Arg Thr Ile Tyr Arg Phe Ser Ala Lys Arg Ala Leu Phe Ile Leu
                100                 105                 110

Gly Pro Phe Asn Pro Leu Arg Ser Leu Met Ile Arg Ile Ser Val His
            115                 120                 125

Ser Val Phe Ser Met Phe Ile Ile Cys Thr Val Ile Ile Asn Cys Met
    130                 135                 140

Phe Met Ala Asn Ser Met Glu Arg Ser Phe Asp Asn Asp Ile Pro Glu
145                 150                 155                 160

Tyr Val Phe Ile Gly Ile Tyr Ile Leu Glu Ala Val Ile Lys Ile Leu
                165                 170                 175

Ala Arg Gly Phe Ile Val Asp Glu Phe Ser Phe Leu Arg Asp Pro Trp
            180                 185                 190

Asn Trp Leu Asp Phe Ile Val Ile Gly Thr Ala Ile Ala Thr Cys Phe
        195                 200                 205

Pro Gly Ser Gln Val Asn Leu Ser Ala Leu Arg Thr Phe Arg Val Phe
    210                 215                 220

Arg Ala Leu Lys Ala Ile Ser Val Ile Ser Gly Leu Lys Val Ile Val
225                 230                 235                 240

Gly Ala Leu Leu Arg Ser Val Lys Lys Leu Asp Val Met Val Leu
                245                 250                 255

Thr Leu Phe Cys Leu Ser Ile Phe Ala Leu Val Gly Gln Gln Leu Phe
            260                 265                 270

Met Gly Ile Leu Asn Gln Lys Cys Ile Lys His Asn Cys Gly Pro Asn
        275                 280                 285

Pro Ala Ser Asn Lys Asp Cys Phe Glu Lys Glu Lys Asp Ser Glu Asp
    290                 295                 300

Phe Ile Met Cys Gly Thr Trp Leu Gly Ser Arg Pro Cys Pro Asn Gly
305                 310                 315                 320

Ser Thr Cys Asp Lys Thr Thr Leu Asn Pro Asp Asn Asn Tyr Thr Lys
                325                 330                 335

Phe Asp Asn Phe Gly Trp Ser Phe Leu Ala Met Phe Arg Val Met Thr
            340                 345                 350

Gln Asp Ser Trp Glu Arg Leu Tyr Arg Gln Ile Leu Arg Thr Ser Gly
        355                 360                 365

Ile Tyr Phe Val Phe Phe Val Val Ile Phe Leu Gly Ser Phe
    370                 375                 380

Tyr Leu Leu Asn Leu Thr Leu Ala Val Val Thr Met Ala Tyr Glu Glu
385                 390                 395                 400

Gln Asn Arg Asn Val Ala Ala Glu Thr Glu Ala Lys Glu Lys Met Phe
                405                 410                 415

Gln Glu Ala Gln Gln Leu Leu Arg Glu Glu Lys Glu Ala Leu Val Ala
            420                 425                 430

Met Gly Ile Asp Arg Ser Ser Leu Asn Ser Leu Gln Ala Ser Ser Phe
        435                 440                 445

Ser Pro Lys Lys Arg Lys Phe Phe Gly Ser Lys Thr Arg Lys Ser Phe
    450                 455                 460
```

-continued

```
Phe Met Arg Gly Ser Lys Thr Ala Gln Ala Ser Ala Ser Asp Ser Glu
465                 470                 475                 480

Asp Asp Ala Ser Lys Asn Pro Gln Leu Leu Glu Gln Thr Lys Arg Leu
                485                 490                 495

Ser Gln Asn Leu Pro Val Asp Leu Phe Asp Glu His Val Asp Pro Leu
            500                 505                 510

His Arg Gln Arg Ala Leu Ser Ala Val Ser Ile Leu Thr Ile Thr Met
        515                 520                 525

Gln Glu Gln Glu Lys Phe Gln Glu Pro Cys Phe Pro Cys Gly Lys Asn
    530                 535                 540

Leu Ala Ser Lys Tyr Leu Val Trp Asp Cys Ser Pro Gln Trp Leu Cys
545                 550                 555                 560

Ile Lys Lys Val Leu Arg Thr Ile Met Thr Asp Pro Phe Thr Glu Leu
                565                 570                 575

Ala Ile Thr Ile Cys Ile Ile Asn Thr Val Phe Leu Ala Val Glu
            580                 585                 590

His His Asn Met Asp Asp Asn Leu Lys Thr Ile Leu Lys Ile Gly Asn
        595                 600                 605

Trp Val Phe Thr Gly Ile Phe Ile Ala Glu Met Cys Leu Lys Ile Ile
    610                 615                 620

Ala Leu Asp Pro Tyr His Tyr Phe Arg His Gly Trp Asn Val Phe Asp
625                 630                 635                 640

Ser Ile Val Ala Leu Leu Ser Leu Ala Asp Val Xaa Tyr Asn Thr Leu
                645                 650                 655

Ser Asp Asn Asn Arg Ser Phe Leu Ala Ser Leu Arg Val Leu Arg Val
            660                 665                 670

Phe Lys Leu Ala Lys Ser Trp Pro Thr Leu Asn Thr Leu Ile Lys Ile
        675                 680                 685

Ile Gly His Ser Val Gly Ala Leu Gly Asn Leu Thr Val Val Leu Thr
    690                 695                 700

Ile Val Val Phe Ile Phe Ser Val Val Gly Met Arg Leu Phe Gly Thr
705                 710                 715                 720

Lys Phe Asn Lys Thr Ala Tyr Ala Thr Gln Glu Arg Pro Arg Arg
                725                 730                 735

Trp His Met Asp Asn Phe Tyr His Ser Phe Leu Val Val Phe Arg Ile
            740                 745                 750

Leu Cys Gly Glu Trp Ile Glu Asn Met Trp Gly Cys Met Gln Asp Met
        755                 760                 765

Asp Gly Ser Pro Leu Cys Ile Ile Val Phe Val Leu Ile Met Val Ile
    770                 775                 780

Gly Lys Leu Val Val Leu Asn Leu Phe Ile Ala Leu Leu Leu Asn Ser
785                 790                 795                 800

Phe Ser Asn Glu Glu Lys Asp Gly Ser Leu Glu Gly Glu Thr Arg Lys
                805                 810                 815

Thr Lys Val Gln Leu Ala Leu Asp Arg Phe Arg Arg Ala Phe Ser Phe
            820                 825                 830

Met Leu His Ala Leu Gln Ser Phe Cys Cys Lys Cys Arg Arg Lys
        835                 840                 845

Asn Ser Pro Lys Pro Lys Glu Thr Thr Glu Ser Phe Ala Gly Glu Asn
    850                 855                 860

Lys Asp Ser Ile Leu Pro Asp Ala Arg Pro Trp Lys Glu Tyr Asp Thr
865                 870                 875                 880
```

-continued

```
Asp Met Ala Leu Tyr Thr Gly Gln Ala Gly Ala Pro Leu Ala Pro Leu
                885                 890                 895

Ala Glu Val Glu Asp Val Glu Tyr Cys Gly Gly Gly Ala Leu
            900                 905                 910

Pro Thr Ser Gln His Ser Ala Gly Val Gln Ala Gly Asp Leu Pro Pro
            915                 920                 925

Glu Thr Lys Gln Leu Thr Ser Pro Asp Asp Gln Gly Val Glu Met Glu
        930                 935                 940

Val Phe Ser Glu Glu Asp Leu His Leu Ser Ile Gln Ser Pro Arg Lys
945                 950                 955                 960

Lys Ser Asp Ala Val Ser Met Leu Ser Glu Cys Ser Thr Ile Asp Leu
                965                 970                 975

Asn Asp Ile Phe Arg Asn Leu Gln Lys Thr Val Ser Pro Lys Lys Gln
            980                 985                 990

Pro Asp Arg Cys Phe Pro Lys Gly Leu Ser Cys His Phe Leu Cys His
            995                 1000                1005

Lys Thr Asp Lys Arg Lys Ser Pro Trp Val Leu Trp Trp Asn Ile Arg
        1010                1015                1020

Lys Thr Cys Tyr Gln Ile Val Lys His Ser Trp Phe Glu Ser Phe Ile
1025                1030                1035                1040

Ile Phe Val Ile Leu Leu Ser Ser Gly Ala Leu Ile Phe Glu Asp Val
            1045                1050                1055

Asn Leu Pro Ser Arg Pro Gln Val Glu Lys Leu Leu Arg Cys Thr Asp
            1060                1065                1070

Asn Ile Phe Thr Phe Ile Phe Leu Leu Glu Met Ile Leu Lys Trp Val
        1075                1080                1085

Ala Phe Gly Phe Arg Arg Tyr Phe Thr Ser Ala Trp Cys Trp Leu Asp
        1090                1095                1100

Phe Leu Ile Val Val Ser Val Leu Ser Leu Met Asn Leu Pro Ser
1105                1110                1115                1120

Leu Lys Ser Phe Arg Thr Leu Arg Ala Leu Arg Pro Leu Arg Ala Leu
            1125                1130                1135

Ser Gln Phe Glu Gly Met Lys Val Val Val Tyr Ala Leu Ile Ser Ala
            1140                1145                1150

Ile Pro Ala Ile Leu Asn Val Leu Leu Val Cys Leu Ile Phe Trp Leu
        1155                1160                1165

Val Phe Cys Ile Leu Gly Val Asn Leu Phe Ser Gly Lys Phe Gly Arg
        1170                1175                1180

Cys Ile Asn Gly Thr Asp Ile Asn Met Tyr Leu Asp Phe Thr Glu Val
1185                1190                1195                1200

Pro Asn Arg Ser Gln Cys Asn Ile Ser Asn Tyr Ser Trp Lys Val Pro
            1205                1210                1215

Gln Val Asn Phe Asp Asn Val Gly Asn Ala Tyr Leu Ala Leu Leu Gln
            1220                1225                1230

Val Ala Thr Tyr Lys Gly Trp Leu Glu Ile Met Asn Ala Ala Val Asp
        1235                1240                1245

Ser Arg Glu Lys Asp Glu Gln Pro Asp Phe Glu Ala Asn Leu Tyr Ala
        1250                1255                1260

Tyr Leu Tyr Phe Val Val Phe Ile Ile Phe Gly Ser Phe Phe Thr Leu
1265                1270                1275                1280

Asn Leu Phe Ile Gly Val Ile Ile Asp Asn Phe Asn Gln Gln Gln Lys
            1285                1290                1295
```

```
Lys Leu Gly Gly Gln Asp Ile Phe Met Thr Glu Glu Gln Lys Lys Tyr
            1300                1305                1310

Tyr Asn Ala Met Lys Lys Leu Gly Thr Lys Lys Pro Gln Lys Pro Ile
        1315                1320                1325

Pro Arg Pro Leu Asn Xaa Cys Gln Ala Phe Val Phe Asp Leu Val Thr
        1330                1335                1340

Ser His Val Phe Asp Val Ile Ile Leu Gly Leu Ile Val Leu Asn Met
1345                1350                1355                1360

Ile Ile Met Met Ala Glu Ser Ala Asp Gln Pro Lys Asp Val Lys Lys
            1365                1370                1375

Thr Phe Asp Ile Leu Asn Ile Ala Phe Val Val Ile Phe Thr Ile Glu
        1380                1385                1390

Cys Leu Ile Lys Val Phe Ala Leu Arg Gln His Tyr Phe Thr Asn Gly
        1395                1400                1405

Trp Asn Leu Phe Asp Cys Val Val Val Leu Ser Ile Ile Ser Thr
        1410                1415                1420

Leu Val Ser Arg Leu Glu Asp Ser Asp Ile Ser Phe Pro Pro Thr Leu
1425                1430                1435                1440

Phe Arg Val Val Arg Leu Ala Arg Ile Gly Arg Ile Leu Arg Leu Val
            1445                1450                1455

Arg Ala Ala Arg Gly Ile Arg Thr Leu Leu Phe Ala Leu Met Met Ser
        1460                1465                1470

Leu Pro Ser Leu Phe Asn Ile Gly Leu Leu Leu Phe Leu Val Met Phe
        1475                1480                1485

Ile Tyr Ala Ile Phe Gly Met Ser Trp Phe Ser Lys Val Lys Lys Gly
        1490                1495                1500

Ser Gly Ile Asp Asp Ile Phe Asn Phe Glu Thr Phe Thr Gly Ser Met
1505                1510                1515                1520

Leu Cys Leu Phe Gln Ile Thr Thr Ser Ala Gly Trp Asp Thr Leu Leu
            1525                1530                1535

Asn Pro Met Leu Glu Ala Lys Glu His Cys Asn Ser Ser Gln Asp
        1540                1545                1550

Ser Cys Gln Gln Pro Gln Ile Ala Val Val Tyr Phe Val Ser Tyr Ile
        1555                1560                1565

Ile Ile Ser Phe Leu Ile Val Val Asn Met Tyr Ile Ala Val Ile Leu
        1570                1575                1580

Glu Asn Phe Asn Thr Ala Thr Glu Glu Ser Glu Asp Pro Leu Gly Glu
1585                1590                1595                1600

Asp Asp Phe Glu Ile Phe Tyr Glu Val Trp Glu Lys Phe Asp Pro Glu
            1605                1610                1615

Ala Ser Gln Phe Ile Gln Tyr Ser Ala Leu Ser Asp Phe Ala Asp Ala
        1620                1625                1630

Leu Pro Glu Pro Leu Arg Val Ala Lys Pro Asn Lys Phe Gln Phe Leu
        1635                1640                1645

Val Met Asp Leu Pro Met Val Met Gly Asp Arg Leu His Cys Met Asp
1650                1655                1660

Val Leu Phe Ala Phe Thr Thr Arg Val Leu Gly Asp Ser Ser Gly Leu
1665                1670                1675                1680

Asp Thr Met Lys Thr Met Met Glu Glu Lys Phe Met Glu Ala Asn Pro
            1685                1690                1695

Phe Lys Lys Leu Tyr Glu Pro Ile Val Thr Thr Thr Lys Arg Lys Glu
        1700                1705                1710
```

```
Glu Glu Gln Gly Ala Ala Val Ile Gln Arg Ala Tyr Arg Lys His Met
    1715                1720                1725
Glu Lys Met Val Lys Leu Arg Leu Lys Asp Arg Ser Ser Ser His
    1730                1735            1740
Gln Val Phe Cys Asn Gly Asp Leu Ser Ser Leu Asp Val Ala Lys Val
1745                1750                1755                1760
Lys Val His Asn Asp
            1765

<210> SEQ ID NO 3
<211> LENGTH: 1765
<212> TYPE: PRT
<213> ORGANISM: Rattus norvegicus
<220> FEATURE:
<223> OTHER INFORMATION: putative amino acid seq. of rat NaN

<400> SEQUENCE: 3

Met Glu Glu Arg Tyr Tyr Pro Val Ile Phe Pro Asp Glu Arg Asn Phe
1               5                   10                  15
Arg Pro Phe Thr Ser Asp Ser Leu Ala Ala Ile Glu Lys Arg Ile Ala
            20                  25                  30
Ile Gln Lys Glu Arg Lys Lys Ser Lys Asp Lys Ala Ala Glu Pro
        35                  40                  45
Gln Pro Arg Pro Gln Leu Asp Leu Lys Ala Ser Arg Lys Leu Pro Lys
    50                  55                  60
Leu Tyr Gly Asp Ile Pro Pro Glu Leu Val Ala Lys Pro Leu Glu Asp
65              70                  75                  80
Leu Asp Pro Phe Tyr Lys Asp His Lys Thr Phe Met Val Leu Asn Lys
                85                  90                  95
Lys Arg Thr Ile Tyr Arg Phe Ser Ala Lys Arg Ala Leu Phe Ile Leu
            100                 105                 110
Gly Pro Phe Asn Pro Leu Arg Ser Leu Met Ile Arg Ile Ser Val His
        115                 120                 125
Ser Val Phe Ser Met Phe Ile Ile Cys Thr Val Ile Ile Asn Cys Met
    130                 135                 140
Phe Met Ala Asn Ser Met Glu Arg Ser Phe Asp Asn Asp Ile Pro Glu
145                 150                 155                 160
Tyr Val Phe Ile Gly Ile Tyr Ile Leu Glu Ala Val Ile Lys Ile Leu
                165                 170                 175
Ala Arg Gly Phe Ile Val Asp Glu Phe Ser Phe Leu Arg Asp Pro Trp
            180                 185                 190
Asn Trp Leu Asp Phe Ile Val Ile Gly Thr Ala Ile Ala Thr Cys Phe
        195                 200                 205
Pro Gly Ser Gln Val Asn Leu Ser Ala Leu Arg Thr Phe Arg Val Phe
    210                 215                 220
Arg Ala Leu Lys Ala Ile Ser Val Ile Ser Gly Leu Lys Val Ile Val
225                 230                 235                 240
Gly Ala Leu Leu Arg Ser Val Lys Lys Leu Val Asp Val Met Val Leu
                245                 250                 255
Thr Leu Phe Cys Leu Ser Ile Phe Ala Leu Val Gly Gln Gln Leu Phe
            260                 265                 270
Met Gly Ile Leu Asn Gln Lys Cys Ile Lys His Asn Cys Gly Pro Asn
        275                 280                 285
Pro Ala Ser Asn Lys Asp Cys Phe Glu Lys Glu Lys Asp Ser Glu Asp
    290                 295                 300
```

```
Phe Ile Met Cys Gly Thr Trp Leu Gly Ser Arg Pro Cys Pro Asn Gly
305                 310                 315                 320

Ser Thr Cys Asp Lys Thr Thr Leu Asn Pro Asp Asn Asn Tyr Thr Lys
                325                 330                 335

Phe Asp Asn Phe Gly Trp Ser Phe Leu Ala Met Phe Arg Val Met Thr
            340                 345                 350

Gln Asp Ser Trp Glu Arg Leu Tyr Arg Gln Ile Leu Arg Thr Ser Gly
        355                 360                 365

Ile Tyr Phe Val Phe Phe Phe Val Val Ile Phe Leu Gly Ser Phe
    370                 375                 380

Tyr Leu Leu Asn Leu Thr Leu Ala Val Val Thr Met Ala Tyr Glu Glu
385                 390                 395                 400

Gln Asn Arg Asn Val Ala Ala Glu Thr Glu Ala Lys Glu Lys Met Phe
                405                 410                 415

Gln Glu Ala Gln Gln Leu Leu Arg Glu Glu Lys Glu Ala Leu Val Ala
            420                 425                 430

Met Gly Ile Asp Arg Ser Ser Leu Asn Ser Leu Gln Ala Ser Ser Phe
        435                 440                 445

Ser Pro Lys Lys Arg Lys Phe Phe Gly Ser Lys Thr Arg Lys Ser Phe
    450                 455                 460

Phe Met Arg Gly Ser Lys Thr Ala Gln Ala Ser Ala Ser Asp Ser Glu
465                 470                 475                 480

Asp Asp Ala Ser Lys Asn Pro Gln Leu Leu Glu Gln Thr Lys Arg Leu
                485                 490                 495

Ser Gln Asn Leu Pro Val Asp Leu Phe Asp Glu His Val Asp Pro Leu
            500                 505                 510

His Arg Gln Arg Ala Leu Ser Ala Val Ser Ile Leu Thr Ile Thr Met
        515                 520                 525

Gln Glu Gln Glu Lys Phe Gln Glu Pro Cys Phe Pro Cys Gly Lys Asn
    530                 535                 540

Leu Ala Ser Lys Tyr Leu Val Trp Asp Cys Ser Pro Gln Trp Leu Cys
545                 550                 555                 560

Ile Lys Lys Val Leu Arg Thr Ile Met Thr Asp Pro Phe Thr Glu Leu
                565                 570                 575

Ala Ile Thr Ile Cys Ile Ile Asn Thr Val Phe Leu Ala Val Glu
            580                 585                 590

His His Asn Met Asp Asp Asn Leu Lys Thr Ile Leu Lys Ile Gly Asn
        595                 600                 605

Trp Val Phe Thr Gly Ile Phe Ile Ala Glu Met Cys Leu Lys Ile Ile
    610                 615                 620

Ala Leu Asp Pro Tyr His Tyr Phe Arg His Gly Trp Asn Val Phe Asp
625                 630                 635                 640

Ser Ile Val Ala Leu Leu Ser Leu Ala Asp Val Leu Tyr Asn Thr Leu
                645                 650                 655

Ser Asp Asn Asn Arg Ser Phe Leu Ala Ser Leu Arg Val Leu Arg Val
            660                 665                 670

Phe Lys Leu Ala Lys Ser Trp Pro Thr Leu Asn Thr Leu Ile Lys Ile
        675                 680                 685

Ile Gly His Ser Val Gly Ala Leu Gly Asn Leu Thr Val Val Leu Thr
    690                 695                 700

Ile Val Val Phe Ile Phe Ser Val Val Gly Met Arg Leu Phe Gly Thr
705                 710                 715                 720
```

-continued

Lys Phe Asn Lys Thr Ala Tyr Ala Thr Gln Glu Arg Pro Arg Arg Arg
            725                 730                 735

Trp His Met Asp Asn Phe Tyr His Ser Phe Leu Val Val Phe Arg Ile
            740                 745                 750

Leu Cys Gly Glu Trp Ile Glu Asn Met Trp Gly Cys Met Gln Asp Met
            755                 760                 765

Asp Gly Ser Pro Leu Cys Ile Ile Val Phe Val Leu Ile Met Val Ile
    770                 775                 780

Gly Lys Leu Val Val Leu Asn Leu Phe Ile Ala Leu Leu Leu Asn Ser
785                 790                 795                 800

Phe Ser Asn Glu Glu Lys Asp Gly Ser Leu Glu Gly Glu Thr Arg Lys
                805                 810                 815

Thr Lys Val Gln Leu Ala Leu Asp Arg Phe Arg Arg Ala Phe Ser Phe
            820                 825                 830

Met Leu His Ala Leu Gln Ser Phe Cys Cys Lys Lys Cys Arg Arg Lys
            835                 840                 845

Asn Ser Pro Lys Pro Lys Glu Thr Thr Glu Ser Phe Ala Gly Glu Asn
850                 855                 860

Lys Asp Ser Ile Leu Pro Asp Ala Arg Pro Trp Lys Glu Tyr Asp Thr
865                 870                 875                 880

Asp Met Ala Leu Tyr Thr Gly Gln Ala Gly Ala Pro Leu Ala Pro Leu
                885                 890                 895

Ala Glu Val Glu Asp Asp Val Glu Tyr Cys Gly Glu Gly Gly Ala Leu
            900                 905                 910

Pro Thr Ser Gln His Ser Ala Gly Val Gln Ala Gly Asp Leu Pro Pro
            915                 920                 925

Glu Thr Lys Gln Leu Thr Ser Pro Asp Asp Gln Gly Val Glu Met Glu
            930                 935                 940

Val Phe Ser Glu Glu Asp Leu His Leu Ser Ile Gln Ser Pro Arg Lys
945                 950                 955                 960

Lys Ser Asp Ala Val Ser Met Leu Ser Glu Cys Ser Thr Ile Asp Leu
                965                 970                 975

Asn Asp Ile Phe Arg Asn Leu Gln Lys Thr Val Ser Pro Lys Lys Gln
            980                 985                 990

Pro Asp Arg Cys Phe Pro Lys Gly Leu Ser Cys His Phe Leu Cys His
            995                 1000                1005

Lys Thr Asp Lys Arg Lys Ser Pro Trp Val Leu Trp Trp Asn Ile Arg
    1010                1015                1020

Lys Thr Cys Tyr Gln Ile Val Lys His Ser Trp Phe Glu Ser Phe Ile
1025                1030                1035                1040

Ile Phe Val Ile Leu Leu Ser Ser Gly Ala Leu Ile Phe Glu Asp Val
                1045                1050                1055

Asn Leu Pro Ser Arg Pro Gln Val Glu Lys Leu Leu Arg Cys Thr Asp
            1060                1065                1070

Asn Ile Phe Thr Phe Ile Phe Leu Leu Glu Met Ile Leu Lys Trp Val
            1075                1080                1085

Ala Phe Gly Phe Arg Arg Tyr Phe Thr Ser Ala Trp Cys Trp Leu Asp
            1090                1095                1100

Phe Leu Ile Val Val Val Ser Val Leu Ser Leu Met Asn Leu Pro Ser
1105                1110                1115                1120

Leu Lys Ser Phe Arg Thr Leu Arg Ala Leu Arg Pro Leu Arg Ala Leu
            1125                1130                1135

-continued

```
Ser Gln Phe Glu Gly Met Lys Val Val Tyr Ala Leu Ile Ser Ala
        1140                1145                1150

Ile Pro Ala Ile Leu Asn Val Leu Val Cys Leu Ile Phe Trp Leu
        1155                1160                1165

Val Phe Cys Ile Leu Gly Val Asn Leu Phe Ser Gly Lys Phe Gly Arg
1170                1175                1180

Cys Ile Asn Gly Thr Asp Ile Asn Met Tyr Leu Asp Phe Thr Glu Val
1185                1190                1195                1200

Pro Asn Arg Ser Gln Cys Asn Ile Ser Asn Tyr Ser Trp Lys Val Pro
        1205                1210                1215

Gln Val Asn Phe Asp Asn Val Gly Asn Ala Tyr Leu Ala Leu Leu Gln
        1220                1225                1230

Val Ala Thr Tyr Lys Gly Trp Leu Glu Ile Met Asn Ala Ala Val Asp
        1235                1240                1245

Ser Arg Glu Lys Asp Glu Gln Pro Asp Phe Glu Ala Asn Leu Tyr Ala
        1250                1255                1260

Tyr Leu Tyr Phe Val Val Phe Ile Ile Phe Gly Ser Phe Phe Thr Leu
1265                1270                1275                1280

Asn Leu Phe Ile Gly Val Ile Ile Asp Asn Phe Asn Gln Gln Gln Lys
        1285                1290                1295

Lys Leu Gly Gly Gln Asp Ile Phe Met Thr Glu Glu Gln Lys Lys Tyr
        1300                1305                1310

Tyr Asn Ala Met Lys Lys Leu Gly Thr Lys Lys Pro Gln Lys Pro Ile
        1315                1320                1325

Pro Arg Pro Leu Asn Arg Cys Gln Ala Phe Val Phe Asp Leu Val Thr
        1330                1335                1340

Ser His Val Phe Asp Val Ile Ile Leu Gly Leu Ile Val Leu Asn Met
1345                1350                1355                1360

Ile Ile Met Met Ala Glu Ser Ala Asp Gln Pro Lys Asp Val Lys Lys
        1365                1370                1375

Thr Phe Asp Ile Leu Asn Ile Ala Phe Val Val Ile Phe Thr Ile Glu
        1380                1385                1390

Cys Leu Ile Lys Val Phe Ala Leu Arg Gln His Tyr Phe Thr Asn Gly
        1395                1400                1405

Trp Asn Leu Phe Asp Cys Val Val Val Leu Ser Ile Ile Ser Thr
1410                1415                1420

Leu Val Ser Arg Leu Glu Asp Ser Asp Ile Ser Phe Pro Pro Thr Leu
1425                1430                1435                1440

Phe Arg Val Val Arg Leu Ala Arg Ile Gly Arg Ile Leu Arg Leu Val
        1445                1450                1455

Arg Ala Ala Arg Gly Ile Arg Thr Leu Leu Phe Ala Leu Met Met Ser
        1460                1465                1470

Leu Pro Ser Leu Phe Asn Ile Gly Leu Leu Leu Phe Leu Val Met Phe
        1475                1480                1485

Ile Tyr Ala Ile Phe Gly Met Ser Trp Phe Ser Lys Val Lys Lys Gly
        1490                1495                1500

Ser Gly Ile Asp Asp Ile Phe Asn Phe Glu Thr Phe Thr Gly Ser Met
1505                1510                1515                1520

Leu Cys Leu Phe Gln Ile Thr Thr Ser Ala Gly Trp Asp Thr Leu Leu
        1525                1530                1535

Asn Pro Met Leu Glu Ala Lys Glu His Cys Asn Ser Ser Ser Gln Asp
        1540                1545                1550
```

-continued

```
Ser Cys Gln Gln Pro Gln Ile Ala Val Val Tyr Phe Val Ser Tyr Ile
    1555                1560                1565

Ile Ile Ser Phe Leu Ile Val Val Asn Met Tyr Ile Ala Val Ile Leu
 1570                1575                1580

Glu Asn Phe Asn Thr Ala Thr Glu Glu Ser Asp Pro Leu Gly Glu
1585                1590                1595                1600

Asp Asp Phe Glu Ile Phe Tyr Glu Val Trp Glu Lys Phe Asp Pro Glu
                1605                1610                1615

Ala Ser Gln Phe Ile Gln Tyr Ser Ala Leu Ser Asp Phe Ala Asp Ala
            1620                1625                1630

Leu Pro Glu Pro Leu Arg Val Ala Lys Pro Asn Lys Phe Gln Phe Leu
        1635                1640                1645

Val Met Asp Leu Pro Met Val Met Gly Asp Arg Leu His Cys Met Asp
    1650                1655                1660

Val Leu Phe Ala Phe Thr Thr Arg Val Leu Gly Asp Ser Ser Gly Leu
1665                1670                1675                1680

Asp Thr Met Lys Thr Met Met Glu Glu Lys Phe Met Glu Ala Asn Pro
                1685                1690                1695

Phe Lys Lys Leu Tyr Glu Pro Ile Val Thr Thr Lys Arg Lys Glu
            1700                1705                1710

Glu Glu Gln Gly Ala Ala Val Ile Gln Arg Ala Tyr Arg Lys His Met
        1715                1720                1725

Glu Lys Met Val Lys Leu Arg Leu Lys Asp Arg Ser Ser Ser Ser His
    1730                1735                1740

Gln Val Phe Cys Asn Gly Asp Leu Ser Ser Leu Asp Val Ala Lys Val
1745                1750                1755                1760

Lys Val His Asn Asp
            1765

<210> SEQ ID NO 4
<211> LENGTH: 5822
<212> TYPE: DNA
<213> ORGANISM: Mus musculus
<220> FEATURE:
<221> NAME/KEY: CDS
<222> LOCATION: (19)..(5313)
<220> FEATURE:
<221> NAME/KEY: unsure
<222> LOCATION: (5804)
<223> OTHER INFORMATION: cDNA sequence of mouse NaN, n = a or c or g
      or t

<400> SEQUENCE: 4
tctgagccaa gggtgaag atg gag gag agg tac tat cca gtg atc ttc cca        51
                    Met Glu Glu Arg Tyr Tyr Pro Val Ile Phe Pro
                     1               5                   10 gac gag agg aat ttc cgc ccc ttc act ttc gac tct ttg gct gca ata        99
Asp Glu Arg Asn Phe Arg Pro Phe Thr Phe Asp Ser Leu Ala Ala Ile
            15                  20                  25 gag aag cgg atc acc atc caa aag gag aag aag aaa tcc aaa gac aag       147
Glu Lys Arg Ile Thr Ile Gln Lys Glu Lys Lys Lys Ser Lys Asp Lys
        30                  35                  40 gca gca act gag ccc cag cct cgg cct cag ctc gac cta aag gcc tcc       195
Ala Ala Thr Glu Pro Gln Pro Arg Pro Gln Leu Asp Leu Lys Ala Ser
    45                  50                  55 agg aag tta cct aag ctc tat ggc gac gtt ccc cct gac ctt ata gcg       243
Arg Lys Leu Pro Lys Leu Tyr Gly Asp Val Pro Pro Asp Leu Ile Ala
60                  65                  70                  75
```

```
aag ccc ctg gaa gat ctg gac cca ttt tac aaa gac cat aag aca ttc      291
Lys Pro Leu Glu Asp Leu Asp Pro Phe Tyr Lys Asp His Lys Thr Phe
            80                  85                  90 atg gta ttg aac aag aag aga aca atc tat cgc ttc agc gcc aag agg      339
Met Val Leu Asn Lys Lys Arg Thr Ile Tyr Arg Phe Ser Ala Lys Arg
                95                 100                 105 gcc ttg ttc att ctg ggg cct ttt aat ccc atc aga agc ttc atg att      387
Ala Leu Phe Ile Leu Gly Pro Phe Asn Pro Ile Arg Ser Phe Met Ile
        110                 115                 120 cgc atc tct gtc cat tca gtc ttc agc atg ttc att atc tgc aca gtg      435
Arg Ile Ser Val His Ser Val Phe Ser Met Phe Ile Ile Cys Thr Val
    125                 130                 135 atc atc aac tgt atg ttc atg gct aat aat tct tct gtg gac agt cgt      483
Ile Ile Asn Cys Met Phe Met Ala Asn Asn Ser Ser Val Asp Ser Arg
140                 145                 150                 155 cct agc agt aac att ccc gaa tac gtc ttc att ggg att tat gtt tta      531
Pro Ser Ser Asn Ile Pro Glu Tyr Val Phe Ile Gly Ile Tyr Val Leu
                160                 165                 170 gaa gct gtg att aaa ata ttg gca aga ggc ttc att gtg gat gag ttt      579
Glu Ala Val Ile Lys Ile Leu Ala Arg Gly Phe Ile Val Asp Glu Phe
            175                 180                 185 tcc tac ctc cga gat cct tgg aac tgg ctg gac ttc att gtc atc gga      627
Ser Tyr Leu Arg Asp Pro Trp Asn Trp Leu Asp Phe Ile Val Ile Gly
        190                 195                 200 aca gcg ata gcg cct tgt ttt ctc ggt aac aaa gtc aat aat ctt tcc      675
Thr Ala Ile Ala Pro Cys Phe Leu Gly Asn Lys Val Asn Asn Leu Ser
    205                 210                 215 act cta cgt acc ttc cga gtg ttg aga gct ctg aaa gcc att tct gta      723
Thr Leu Arg Thr Phe Arg Val Leu Arg Ala Leu Lys Ala Ile Ser Val
220                 225                 230                 235 atc tca ggt ctg aag gtc atc gtg ggt gcc ctg ctg cgc tcc gtg aag      771
Ile Ser Gly Leu Lys Val Ile Val Gly Ala Leu Leu Arg Ser Val Lys
                240                 245                 250 aag cta gtg gac gtg atg gtc ctc act ctc ttt tgc ctc agc atc ttt      819
Lys Leu Val Asp Val Met Val Leu Thr Leu Phe Cys Leu Ser Ile Phe
            255                 260                 265 gcc ctg gtt ggt cag cag ctc ttc atg gga att ctg agc cag aaa tgt      867
Ala Leu Val Gly Gln Gln Leu Phe Met Gly Ile Leu Ser Gln Lys Cys
        270                 275                 280 att aag gac gac tgt ggc cct aac gct ttt tcc aac aag gat tgc ttt      915
Ile Lys Asp Asp Cys Gly Pro Asn Ala Phe Ser Asn Lys Asp Cys Phe
    285                 290                 295 gta aaa gaa aat gat agc gag gac ttc ata atg tgt ggc aac tgg ctc      963
Val Lys Glu Asn Asp Ser Glu Asp Phe Ile Met Cys Gly Asn Trp Leu
300                 305                 310                 315 ggc aga aga tcc tgc ccc gat ggt tcc acg tgc aat aaa acc aca ttt     1011
Gly Arg Arg Ser Cys Pro Asp Gly Ser Thr Cys Asn Lys Thr Thr Phe
                320                 325                 330 aac cca gat tat aat tat aca aac ttt gac agc ttt ggc tgg tct ttt     1059
Asn Pro Asp Tyr Asn Tyr Thr Asn Phe Asp Ser Phe Gly Trp Ser Phe
            335                 340                 345 ctc gcc atg ttc cgg gtt atg act caa gac tcc tgg gag aag ctt tat     1107
Leu Ala Met Phe Arg Val Met Thr Gln Asp Ser Trp Glu Lys Leu Tyr
        350                 355                 360 cga cag atc ctt cgc acc tcc ggg atc tac ttt gtc ttc ttc ttc gtg     1155
Arg Gln Ile Leu Arg Thr Ser Gly Ile Tyr Phe Val Phe Phe Phe Val
    365                 370                 375 gtc gtc atc ttc ctg ggc tct ttc tac ctg ctt aac tta acc ctg gct     1203
Val Val Ile Phe Leu Gly Ser Phe Tyr Leu Leu Asn Leu Thr Leu Ala
380                 385                 390                 395
```

-continued

```
gtc gtc acc atg gct tac gag gaa cag aac aga aat gtc gct gcc gag    1251
Val Val Thr Met Ala Tyr Glu Glu Gln Asn Arg Asn Val Ala Ala Glu
            400                 405                 410 aca gag gcc aag gag aag atg ttt cag gaa gcc cag cag ctg ttg agg    1299
Thr Glu Ala Lys Glu Lys Met Phe Gln Glu Ala Gln Gln Leu Leu Arg
        415                 420                 425 gag gaa aag gag gct ctg gtt gcc atg gga att gac aga act tcc ctt    1347
Glu Glu Lys Glu Ala Leu Val Ala Met Gly Ile Asp Arg Thr Ser Leu
    430                 435                 440 aat tcc ctc caa gct tcg tcc ttt tcc cca aag aag agg aag ttt ttt    1395
Asn Ser Leu Gln Ala Ser Ser Phe Ser Pro Lys Lys Arg Lys Phe Phe
445                 450                 455 ggc agt aag aca aga aag tcc ttc ttt atg aga ggg tcc aag aca gcc    1443
Gly Ser Lys Thr Arg Lys Ser Phe Phe Met Arg Gly Ser Lys Thr Ala
460                 465                 470                 475 cga gcc tca gcg tcc gat tca gag gac gat gcc tct aaa aac cca caa    1491
Arg Ala Ser Ala Ser Asp Ser Glu Asp Asp Ala Ser Lys Asn Pro Gln
            480                 485                 490 ctc ctt gag caa aca aaa cga cta tcc cag aac ttg ccc gta gaa ctc    1539
Leu Leu Glu Gln Thr Lys Arg Leu Ser Gln Asn Leu Pro Val Glu Leu
        495                 500                 505 ttt gat gag cac gtg gac ccc ctc cat agg cag aga gcg ctg agt gcc    1587
Phe Asp Glu His Val Asp Pro Leu His Arg Gln Arg Ala Leu Ser Ala
    510                 515                 520 gtc agt atc tta acc atc acc atg cag gaa caa gaa aaa tcc cag gag    1635
Val Ser Ile Leu Thr Ile Thr Met Gln Glu Gln Glu Lys Ser Gln Glu
525                 530                 535 cct tgt ttc ccg tgt ggg aaa aac ttg gca tcc aag tac ctg gtg tgg    1683
Pro Cys Phe Pro Cys Gly Lys Asn Leu Ala Ser Lys Tyr Leu Val Trp
540                 545                 550                 555 gaa tgt agc cct ccg tgg ctg tgc ata aag aag gtc ctg cag act atc    1731
Glu Cys Ser Pro Pro Trp Leu Cys Ile Lys Lys Val Leu Gln Thr Ile
            560                 565                 570 atg aca gac ccc ttc act gag ctg gcc atc acc atc tgc atc atc gtc    1779
Met Thr Asp Pro Phe Thr Glu Leu Ala Ile Thr Ile Cys Ile Ile Val
        575                 580                 585 aat act gtc ttc ttg gcc atg gaa cac cac aat atg gat aac tct tta    1827
Asn Thr Val Phe Leu Ala Met Glu His His Asn Met Asp Asn Ser Leu
    590                 595                 600 aaa gac ata ctg aaa ata gga aac tgg gtt ttc act gga att ttc ata    1875
Lys Asp Ile Leu Lys Ile Gly Asn Trp Val Phe Thr Gly Ile Phe Ile
605                 610                 615 gcg gaa atg tgt ctc aag atc att gcg cta gac cct tac cac tac ttc    1923
Ala Glu Met Cys Leu Lys Ile Ile Ala Leu Asp Pro Tyr His Tyr Phe
620                 625                 630                 635 cgg cac ggc tgg aac atc ttt gac agc att gtg gcc ctt gtg agt ctc    1971
Arg His Gly Trp Asn Ile Phe Asp Ser Ile Val Ala Leu Val Ser Leu
            640                 645                 650 gct gac gtg ctc ttc cac aaa ctg tct aaa aac ctc tcc ttc ttg gct    2019
Ala Asp Val Leu Phe His Lys Leu Ser Lys Asn Leu Ser Phe Leu Ala
        655                 660                 665 tcc ctc aga gtg ctg agg gtc ttc aag tta gcc aaa tcc tgg ccc aca    2067
Ser Leu Arg Val Leu Arg Val Phe Lys Leu Ala Lys Ser Trp Pro Thr
    670                 675                 680 tta aac act ctc att aag atc atc ggc cac tcc gtg ggt gcg ctc gga    2115
Leu Asn Thr Leu Ile Lys Ile Ile Gly His Ser Val Gly Ala Leu Gly
685                 690                 695 aac ctg act gtg gtc cta acg atc gtg gtc ttc atc ttt tcc gtg gtt    2163
Asn Leu Thr Val Val Leu Thr Ile Val Val Phe Ile Phe Ser Val Val
700                 705                 710                 715
```

```
ggc atg cgg ctc ttt ggt gcc aag ttt aac aag act tgc tcc acc tct      2211
Gly Met Arg Leu Phe Gly Ala Lys Phe Asn Lys Thr Cys Ser Thr Ser
            720                 725                 730 ccg gag tcc ctc cgg cgc tgg cac atg ggt gat ttc tac cat tcc ttc      2259
Pro Glu Ser Leu Arg Arg Trp His Met Gly Asp Phe Tyr His Ser Phe
        735                 740                 745 ctg gtg gtg ttc cgc atc ctc tgt ggg gag tgg atc gag aac atg tgg      2307
Leu Val Val Phe Arg Ile Leu Cys Gly Glu Trp Ile Glu Asn Met Trp
    750                 755                 760 gaa tgc atg cag gag atg gaa ggc tcc ccg ctg tgt gtc atc gtc ttt      2355
Glu Cys Met Gln Glu Met Glu Gly Ser Pro Leu Cys Val Ile Val Phe
765                 770                 775 gtg ctg atc atg gtg gtc ggg aag ctc gtg gtg ctt aac ctc ttc att      2403
Val Leu Ile Met Val Val Gly Lys Leu Val Val Leu Asn Leu Phe Ile
780                 785                 790                 795 gcc ttg ctg ctc aat tcc ttc agc aat gag gaa aag gat ggg aac cca      2451
Ala Leu Leu Leu Asn Ser Phe Ser Asn Glu Glu Lys Asp Gly Asn Pro
            800                 805                 810 gaa gga gag acc agg aaa acc aaa gtg cag cta gcc ctg gat cgg ttc      2499
Glu Gly Glu Thr Arg Lys Thr Lys Val Gln Leu Ala Leu Asp Arg Phe
        815                 820                 825 agc cga gcg ttc tac ttc atg gcg cgc gct ctt cag aat ttc tgt tgc      2547
Ser Arg Ala Phe Tyr Phe Met Ala Arg Ala Leu Gln Asn Phe Cys Cys
    830                 835                 840 aag aga tgc agg agg caa aac tcg cca aag cca aat gag gca aca gaa      2595
Lys Arg Cys Arg Arg Gln Asn Ser Pro Lys Pro Asn Glu Ala Thr Glu
845                 850                 855 agc ttt gct ggt gag agt aga gac aca gcc acc ctg gat aca agg tcc      2643
Ser Phe Ala Gly Glu Ser Arg Asp Thr Ala Thr Leu Asp Thr Arg Ser
860                 865                 870                 875 tgg aag gag tat gat tca gaa atg act ctg tac act ggg cag gcc ggg      2691
Trp Lys Glu Tyr Asp Ser Glu Met Thr Leu Tyr Thr Gly Gln Ala Gly
            880                 885                 890 gct cca ctg gcc cca ctg gca aaa gaa gag gac gat atg gaa tgt tgt      2739
Ala Pro Leu Ala Pro Leu Ala Lys Glu Glu Asp Asp Met Glu Cys Cys
        895                 900                 905 ggt gaa tgt gat gcc tca cct acc tca cag cct agt gag gaa gct cag      2787
Gly Glu Cys Asp Ala Ser Pro Thr Ser Gln Pro Ser Glu Glu Ala Gln
    910                 915                 920 gcc tgt gac ctc cct ctg aag acc aag cgg ctc ccc agc cca gat gac      2835
Ala Cys Asp Leu Pro Leu Lys Thr Lys Arg Leu Pro Ser Pro Asp Asp
925                 930                 935 cac ggg gtt gaa atg gaa gtg ttt tcc gaa gaa gat ccg aat tta acc      2883
His Gly Val Glu Met Glu Val Phe Ser Glu Glu Asp Pro Asn Leu Thr
940                 945                 950                 955 ata cag agt gct cga aag aag tct gat gcg gca agc atg ctc tca gaa      2931
Ile Gln Ser Ala Arg Lys Lys Ser Asp Ala Ala Ser Met Leu Ser Glu
            960                 965                 970 tgc agc aca ata gac ctg aat gat atc ttt aga aat tta cag aaa aca      2979
Cys Ser Thr Ile Asp Leu Asn Asp Ile Phe Arg Asn Leu Gln Lys Thr
        975                 980                 985 gtt tcc ccc caa aag caa cca gat cga tgc ttt ccc aag ggc ctc agt      3027
Val Ser Pro Gln Lys Gln Pro Asp Arg Cys Phe Pro Lys Gly Leu Ser
    990                 995                 1000 tgt atc ttt cta tgt tgc aaa aca atc aaa aaa aag tcc ccc tgg gtc      3075
Cys Ile Phe Leu Cys Cys Lys Thr Ile Lys Lys Lys Ser Pro Trp Val
    1005                1010                1015 ctg tgg tgg aat ctt cgg aaa acc tgc tac caa atc gtg aag cat agc      3123
Leu Trp Trp Asn Leu Arg Lys Thr Cys Tyr Gln Ile Val Lys His Ser
1020                1025                1030                1035
```

| | |
|---|---|
| tgg ttt gag agc ttc ata att ttt gtc atc ctg ctg agc agc gga gca<br>Trp Phe Glu Ser Phe Ile Ile Phe Val Ile Leu Leu Ser Ser Gly Ala<br>           1040                  1045                1050 | 3171 |
| ctg ata ttc gaa gat gtc aat ctt ccc agc cgg ccc caa gtt gaa aaa<br>Leu Ile Phe Glu Asp Val Asn Leu Pro Ser Arg Pro Gln Val Glu Lys<br>           1055                  1060                1065 | 3219 |
| tta ctg aag tgt acc gat aat att ttc aca ttt att ttt ctc ctg gaa<br>Leu Leu Lys Cys Thr Asp Asn Ile Phe Thr Phe Ile Phe Leu Leu Glu<br>           1070                  1075                1080 | 3267 |
| atg att ttg aag tgg gtg gcc ttt gga ttc cgg aag tat ttc acc agt<br>Met Ile Leu Lys Trp Val Ala Phe Gly Phe Arg Lys Tyr Phe Thr Ser<br>           1085                  1090                1095 | 3315 |
| gcc tgg tgc tgg ctc gat ttc ctc att gtg gtg gtg tct gtg ctc agc<br>Ala Trp Cys Trp Leu Asp Phe Leu Ile Val Val Val Ser Val Leu Ser<br>1100                1105                1110                1115 | 3363 |
| ctc acg aac tta cca aac ttg aag tcc ttc cgg aat ctg cga gcg ctg<br>Leu Thr Asn Leu Pro Asn Leu Lys Ser Phe Arg Asn Leu Arg Ala Leu<br>           1120                  1125                1130 | 3411 |
| aga cct ctg cgg gca ctg tct cag ttt gaa gga atg aag gtt gtt gtc<br>Arg Pro Leu Arg Ala Leu Ser Gln Phe Glu Gly Met Lys Val Val Val<br>                 1135                  1140                1145 | 3459 |
| aat gcc ctc atg agt gcc ata cct gcc atc ctc aat gtc ttg ctg gtc<br>Asn Ala Leu Met Ser Ala Ile Pro Ala Ile Leu Asn Val Leu Leu Val<br>           1150                  1155                1160 | 3507 |
| tgc ctc att ttc tgg ctc ata ttt tgt atc ctg gga gta aat ttt ttt<br>Cys Leu Ile Phe Trp Leu Ile Phe Cys Ile Leu Gly Val Asn Phe Phe<br>           1165                  1170                1175 | 3555 |
| tct ggg aag ttt gga aga tgc att aat gga aca gac ata aat aaa tat<br>Ser Gly Lys Phe Gly Arg Cys Ile Asn Gly Thr Asp Ile Asn Lys Tyr<br>1180                1185                1190                1195 | 3603 |
| ttc aac gct tcc aat gtt cca aac caa agc caa tgt tta gtt agt aat<br>Phe Asn Ala Ser Asn Val Pro Asn Gln Ser Gln Cys Leu Val Ser Asn<br>           1200                  1205                1210 | 3651 |
| tac acg tgg aaa gtc ccg aat gtc aac ttt gac aac gtg ggg aat gcc<br>Tyr Thr Trp Lys Val Pro Asn Val Asn Phe Asp Asn Val Gly Asn Ala<br>           1215                  1220                1225 | 3699 |
| tac ctt gcc ctg ctg caa gtg gcg acc tat aag ggc tgg ctg gac att<br>Tyr Leu Ala Leu Leu Gln Val Ala Thr Tyr Lys Gly Trp Leu Asp Ile<br>           1230                  1235                1240 | 3747 |
| atg aat gca gct gtt gat tcc aga ggg aaa gat gag cag ccg gcc ttt<br>Met Asn Ala Ala Val Asp Ser Arg Gly Lys Asp Glu Gln Pro Ala Phe<br>           1245                  1250                1255 | 3795 |
| gag gcg aat cta tac gca tac ctt tac ttc gtg gtt ttt atc atc ttc<br>Glu Ala Asn Leu Tyr Ala Tyr Leu Tyr Phe Val Val Phe Ile Ile Phe<br>1260                1265                1270                1275 | 3843 |
| ggc tca ttc ttt acc ctg aac ctc ttt atc ggt gtt att att gac aac<br>Gly Ser Phe Phe Thr Leu Asn Leu Phe Ile Gly Val Ile Ile Asp Asn<br>           1280                  1285                1290 | 3891 |
| ttc aat cag cag cag aaa aag tta ggt ggc caa gac att ttt atg aca<br>Phe Asn Gln Gln Gln Lys Lys Leu Gly Gly Gln Asp Ile Phe Met Thr<br>           1295                  1300                1305 | 3939 |
| gaa gaa cag aag aaa tat tac aat gca atg aaa aag tta gga acc aag<br>Glu Glu Gln Lys Lys Tyr Tyr Asn Ala Met Lys Lys Leu Gly Thr Lys<br>           1310                  1315                1320 | 3987 |
| aag cct caa aag ccc atc cca agg ccc ctg aac aaa tgt caa gcc ttc<br>Lys Pro Gln Lys Pro Ile Pro Arg Pro Leu Asn Lys Cys Gln Ala Phe<br>           1325                  1330                1335 | 4035 |
| gtg ttc gat ttg gtc aca agc cag gtc ttt gac gtc atc att ctg ggt<br>Val Phe Asp Leu Val Thr Ser Gln Val Phe Asp Val Ile Ile Leu Gly<br>1340                1345                1350                1355 | 4083 |

```
ctt att gtc aca aac atg att atc atg atg gct gaa tct gaa ggc cag      4131
Leu Ile Val Thr Asn Met Ile Ile Met Met Ala Glu Ser Glu Gly Gln
            1360                1365                1370 ccc aac gaa gtg aag aaa atc ttt gat att ctc aac ata gtc ttc gtg      4179
Pro Asn Glu Val Lys Lys Ile Phe Asp Ile Leu Asn Ile Val Phe Val
        1375                1380                1385 gtc atc ttt acc gta gag tgt ctc atc aaa gtc ttt gct ttg agg caa      4227
Val Ile Phe Thr Val Glu Cys Leu Ile Lys Val Phe Ala Leu Arg Gln
        1390                1395                1400 cac tac ttc acc aat ggc tgg aac tta ttt gat tgt gtg gtc gtg gtt      4275
His Tyr Phe Thr Asn Gly Trp Asn Leu Phe Asp Cys Val Val Val Val
        1405                1410                1415 ctt tcc atc att agt acc ttg gtt tct ggc ttg gag aac agc aac gtc      4323
Leu Ser Ile Ile Ser Thr Leu Val Ser Gly Leu Glu Asn Ser Asn Val
1420                1425                1430                1435 ttc ccg ccc aca ctc ttc agg att gtc cgc ttg gct cgg atc ggt cga      4371
Phe Pro Pro Thr Leu Phe Arg Ile Val Arg Leu Ala Arg Ile Gly Arg
            1440                1445                1450 atc ctc aga ctg gtc cgg gcg gct cga gga atc agg aca ctc ctt ttc      4419
Ile Leu Arg Leu Val Arg Ala Ala Arg Gly Ile Arg Thr Leu Leu Phe
        1455                1460                1465 gcg ttg atg atg tct ctc ccc tct ctc ttc aac att ggt ctg ctt ctc      4467
Ala Leu Met Met Ser Leu Pro Ser Leu Phe Asn Ile Gly Leu Leu Leu
        1470                1475                1480 ttt ctg gtg atg ttc att tat gcc atc ttt ggg atg aac tgg ttt tcc      4515
Phe Leu Val Met Phe Ile Tyr Ala Ile Phe Gly Met Asn Trp Phe Ser
        1485                1490                1495 aaa gtg aag aga ggc tct ggg att gat gac atc ttc aac ttt gac act      4563
Lys Val Lys Arg Gly Ser Gly Ile Asp Asp Ile Phe Asn Phe Asp Thr
1500                1505                1510                1515 ttc tcg ggc agc atg ctc tgc ctc ttc cag ata acc act tca gcc ggc      4611
Phe Ser Gly Ser Met Leu Cys Leu Phe Gln Ile Thr Thr Ser Ala Gly
            1520                1525                1530 tgg gat gct ctc ctc aac ccc atg ctg gaa tca aaa gcc tct tgc aat      4659
Trp Asp Ala Leu Leu Asn Pro Met Leu Glu Ser Lys Ala Ser Cys Asn
        1535                1540                1545 tcc tcc tcc caa gag agc tgt cag cag ccg cag ata gcc ata gtc tac      4707
Ser Ser Ser Gln Glu Ser Cys Gln Gln Pro Gln Ile Ala Ile Val Tyr
        1550                1555                1560 ttc gtc agc tac atc atc atc tcc ttt ctc att gtg gtt aac atg tac      4755
Phe Val Ser Tyr Ile Ile Ile Ser Phe Leu Ile Val Val Asn Met Tyr
        1565                1570                1575 ata gct gtg att cta gag aac ttc aac aca gcc aca gag gag agc gag      4803
Ile Ala Val Ile Leu Glu Asn Phe Asn Thr Ala Thr Glu Glu Ser Glu
1580                1585                1590                1595 gac ccc ctg ggc gaa gac gac ttt gag atc ttc tat gag atc tgg gag      4851
Asp Pro Leu Gly Glu Asp Asp Phe Glu Ile Phe Tyr Glu Ile Trp Glu
            1600                1605                1610 aag ttt gac ccc gaa gca aca cag ttc atc cag tac tca tcc ctc tct      4899
Lys Phe Asp Pro Glu Ala Thr Gln Phe Ile Gln Tyr Ser Ser Leu Ser
            1615                1620                1625 gac ttc gcc gac gcc ctg ccc gag ccg ttg cgt gtg gcc aag ccc aac      4947
Asp Phe Ala Asp Ala Leu Pro Glu Pro Leu Arg Val Ala Lys Pro Asn
        1630                1635                1640 agg ttt cag ttt ctc atg atg gac ttg ccc atg gtg atg ggt gat cgc      4995
Arg Phe Gln Phe Leu Met Met Asp Leu Pro Met Val Met Gly Asp Arg
        1645                1650                1655 ctc cat tgc atg gat gtt ctc ttt gct ttc acc acc agg gtc ctc ggg      5043
Leu His Cys Met Asp Val Leu Phe Ala Phe Thr Thr Arg Val Leu Gly
1660                1665                1670                1675
```

-continued

| | | |
|---|---|---|
| aac tcc agc ggc ttg gat acc atg aaa gcc atg atg gag gag aag ttc<br>Asn Ser Ser Gly Leu Asp Thr Met Lys Ala Met Met Glu Glu Lys Phe<br>          1680                 1685                 1690 | 5091 |
| atg gag gcc aat cct ttc aag aag ttg tac gag ccc att gtc acc acc<br>Met Glu Ala Asn Pro Phe Lys Lys Leu Tyr Glu Pro Ile Val Thr Thr<br>1695                 1700                 1705 | 5139 |
| aca aag agg aag gag gag gag gaa tgt gcc gct gtc atc cag agg gcc<br>Thr Lys Arg Lys Glu Glu Glu Glu Cys Ala Ala Val Ile Gln Arg Ala<br>          1710                 1715                 1720 | 5187 |
| tac cgg aga cac atg gag aag atg atc aag ctg aag ctg aaa ggc agg<br>Tyr Arg Arg His Met Glu Lys Met Ile Lys Leu Lys Leu Lys Gly Arg<br>   1725                 1730                 1735 | 5235 |
| tca agt tca tcg ctc cag gtg ttt tgc aat gga gac ttg tct agc ttg<br>Ser Ser Ser Ser Leu Gln Val Phe Cys Asn Gly Asp Leu Ser Ser Leu<br>1740                 1745                 1750                 1755 | 5283 |
| gat gtg ccc aag atc aag gtt cat tgt gac tgaaacccc acctgcacgc<br>Asp Val Pro Lys Ile Lys Val His Cys Asp<br>          1760                 1765 | 5333 |
| ctacctcaca gcctcacagc tcagccccca gcctctggcg aacaagcggc ggactcaccg | 5393 |
| aacaggccgt tcaacttgtt tttttgggtg aaagaggtga taggttggtg tccatttta | 5453 |
| aatgattctt ggaaagattg aacgtcggaa catgttagaa aggactgcca aggacatcca | 5513 |
| cagtaacgga aggcctgaag gacagttcaa attatgtaaa gaaacgagaa ggaaaggtca | 5573 |
| catgtctgtt cagttttaag tatgtgacct gccacatgta gctcctttgc atgttaagtg | 5633 |
| agaagtcaaa accctgccat aagtaaatag ctttgttgca ggtgtttcta ccagtgctgc | 5693 |
| ggatttgggt gtatggctca aacctgaaag catgactctg acttgtcagc ccccaactt | 5753 |
| tcagaagctc tgatctctgt cctaggtgtt tgacaaataa atacataaaa naaaaaaaa | 5813 |
| aaaaaaaaa | 5822 |

<210> SEQ ID NO 5
<211> LENGTH: 1765
<212> TYPE: PRT
<213> ORGANISM: Mus musculus

<400> SEQUENCE: 5

Met Glu Glu Arg Tyr Tyr Pro Val Ile Phe Pro Asp Glu Arg Asn Phe
1               5                   10                  15

Arg Pro Phe Thr Phe Asp Ser Leu Ala Ala Ile Glu Lys Arg Ile Thr
            20                  25                  30

Ile Gln Lys Glu Lys Lys Ser Lys Asp Lys Ala Ala Thr Glu Pro
        35                  40                  45

Gln Pro Arg Pro Gln Leu Asp Leu Lys Ala Ser Arg Lys Leu Pro Lys
    50                  55                  60

Leu Tyr Gly Asp Val Pro Pro Asp Leu Ile Ala Lys Pro Leu Glu Asp
65                  70                  75                  80

Leu Asp Pro Phe Tyr Lys Asp His Lys Thr Phe Met Val Leu Asn Lys
                85                  90                  95

Lys Arg Thr Ile Tyr Arg Phe Ser Ala Lys Arg Ala Leu Phe Ile Leu
            100                 105                 110

Gly Pro Phe Asn Pro Ile Arg Ser Phe Met Ile Arg Ile Ser Val His
        115                 120                 125

Ser Val Phe Ser Met Phe Ile Ile Cys Thr Val Ile Ile Asn Cys Met
    130                 135                 140

Phe Met Ala Asn Asn Ser Ser Val Asp Ser Arg Pro Ser Ser Asn Ile
145                 150                 155                 160

```
Pro Glu Tyr Val Phe Ile Gly Ile Tyr Val Leu Glu Ala Val Ile Lys
            165                 170                 175

Ile Leu Ala Arg Gly Phe Ile Val Asp Glu Phe Ser Tyr Leu Arg Asp
            180                 185                 190

Pro Trp Asn Trp Leu Asp Phe Ile Val Ile Gly Thr Ala Ile Ala Pro
            195                 200                 205

Cys Phe Leu Gly Asn Lys Val Asn Asn Leu Ser Thr Leu Arg Thr Phe
            210                 215                 220

Arg Val Leu Arg Ala Leu Lys Ala Ile Ser Val Ile Ser Gly Leu Lys
225                 230                 235                 240

Val Ile Val Gly Ala Leu Leu Arg Ser Val Lys Lys Leu Val Asp Val
                245                 250                 255

Met Val Leu Thr Leu Phe Cys Leu Ser Ile Phe Ala Leu Val Gly Gln
            260                 265                 270

Gln Leu Phe Met Gly Ile Leu Ser Gln Lys Cys Ile Lys Asp Asp Cys
            275                 280                 285

Gly Pro Asn Ala Phe Ser Asn Lys Asp Cys Phe Val Lys Glu Asn Asp
            290                 295                 300

Ser Glu Asp Phe Ile Met Cys Gly Asn Trp Leu Gly Arg Arg Ser Cys
305                 310                 315                 320

Pro Asp Gly Ser Thr Cys Asn Lys Thr Thr Phe Asn Pro Asp Tyr Asn
                325                 330                 335

Tyr Thr Asn Phe Asp Ser Phe Gly Trp Ser Phe Leu Ala Met Phe Arg
            340                 345                 350

Val Met Thr Gln Asp Ser Trp Glu Lys Leu Tyr Arg Gln Ile Leu Arg
            355                 360                 365

Thr Ser Gly Ile Tyr Phe Val Phe Phe Val Val Ile Phe Leu
            370                 375                 380

Gly Ser Phe Tyr Leu Leu Asn Leu Thr Leu Ala Val Val Thr Met Ala
385                 390                 395                 400

Tyr Glu Glu Gln Asn Arg Asn Val Ala Ala Glu Thr Glu Ala Lys Glu
                405                 410                 415

Lys Met Phe Gln Glu Ala Gln Gln Leu Leu Arg Glu Glu Lys Glu Ala
            420                 425                 430

Leu Val Ala Met Gly Ile Asp Arg Thr Ser Leu Asn Ser Leu Gln Ala
            435                 440                 445

Ser Ser Phe Ser Pro Lys Lys Arg Lys Phe Phe Gly Ser Lys Thr Arg
            450                 455                 460

Lys Ser Phe Phe Met Arg Gly Ser Lys Thr Ala Arg Ala Ser Ala Ser
465                 470                 475                 480

Asp Ser Glu Asp Asp Ala Ser Lys Asn Pro Gln Leu Leu Glu Gln Thr
                485                 490                 495

Lys Arg Leu Ser Gln Asn Leu Pro Val Glu Leu Phe Asp Glu His Val
            500                 505                 510

Asp Pro Leu His Arg Gln Arg Ala Leu Ser Ala Val Ser Ile Leu Thr
            515                 520                 525

Ile Thr Met Gln Glu Gln Glu Lys Ser Gln Glu Pro Cys Phe Pro Cys
            530                 535                 540

Gly Lys Asn Leu Ala Ser Lys Tyr Leu Val Trp Glu Cys Ser Pro Pro
545                 550                 555                 560

Trp Leu Cys Ile Lys Lys Val Leu Gln Thr Ile Met Thr Asp Pro Phe
                565                 570                 575
```

```
Thr Glu Leu Ala Ile Thr Ile Cys Ile Ile Val Asn Thr Val Phe Leu
            580                 585                 590

Ala Met Glu His His Asn Met Asp Asn Ser Leu Lys Asp Ile Leu Lys
            595                 600                 605

Ile Gly Asn Trp Val Phe Thr Gly Ile Phe Ile Ala Glu Met Cys Leu
            610                 615                 620

Lys Ile Ile Ala Leu Asp Pro Tyr His Tyr Phe Arg His Gly Trp Asn
625                 630                 635                 640

Ile Phe Asp Ser Ile Val Ala Leu Val Ser Leu Ala Asp Val Leu Phe
                645                 650                 655

His Lys Leu Ser Lys Asn Leu Ser Phe Leu Ala Ser Leu Arg Val Leu
            660                 665                 670

Arg Val Phe Lys Leu Ala Lys Ser Trp Pro Thr Leu Asn Thr Leu Ile
            675                 680                 685

Lys Ile Ile Gly His Ser Val Gly Ala Leu Gly Asn Leu Thr Val Val
            690                 695                 700

Leu Thr Ile Val Val Phe Ile Phe Ser Val Val Gly Met Arg Leu Phe
705                 710                 715                 720

Gly Ala Lys Phe Asn Lys Thr Cys Ser Thr Ser Pro Glu Ser Leu Arg
            725                 730                 735

Arg Trp His Met Gly Asp Phe Tyr His Ser Phe Leu Val Val Phe Arg
            740                 745                 750

Ile Leu Cys Gly Glu Trp Ile Glu Asn Met Trp Glu Cys Met Gln Glu
            755                 760                 765

Met Glu Gly Ser Pro Leu Cys Val Ile Val Phe Val Leu Ile Met Val
            770                 775                 780

Val Gly Lys Leu Val Val Leu Asn Leu Phe Ile Ala Leu Leu Leu Asn
785                 790                 795                 800

Ser Phe Ser Asn Glu Glu Lys Asp Gly Asn Pro Glu Gly Glu Thr Arg
                805                 810                 815

Lys Thr Lys Val Gln Leu Ala Leu Asp Arg Phe Ser Arg Ala Phe Tyr
            820                 825                 830

Phe Met Ala Arg Ala Leu Gln Asn Phe Cys Cys Lys Arg Cys Arg Arg
            835                 840                 845

Gln Asn Ser Pro Lys Pro Asn Glu Ala Thr Glu Ser Phe Ala Gly Glu
850                 855                 860

Ser Arg Asp Thr Ala Thr Leu Asp Thr Arg Ser Trp Lys Glu Tyr Asp
865                 870                 875                 880

Ser Glu Met Thr Leu Tyr Thr Gly Gln Ala Gly Ala Pro Leu Ala Pro
                885                 890                 895

Leu Ala Lys Glu Glu Asp Met Glu Cys Cys Gly Glu Cys Asp Ala
            900                 905                 910

Ser Pro Thr Ser Gln Pro Ser Glu Glu Ala Gln Ala Cys Asp Leu Pro
            915                 920                 925

Leu Lys Thr Lys Arg Leu Pro Ser Pro Asp Asp His Gly Val Glu Met
            930                 935                 940

Glu Val Phe Ser Glu Glu Asp Pro Asn Leu Thr Ile Gln Ser Ala Arg
945                 950                 955                 960

Lys Lys Ser Asp Ala Ala Ser Met Leu Ser Glu Cys Ser Thr Ile Asp
                965                 970                 975

Leu Asn Asp Ile Phe Arg Asn Leu Gln Lys Thr Val Ser Pro Gln Lys
            980                 985                 990
```

-continued

Gln Pro Asp Arg Cys Phe Pro Lys Gly Leu Ser Cys Ile Phe Leu Cys
        995                 1000                1005

Cys Lys Thr Ile Lys Lys Lys Ser Pro Trp Val Leu Trp Trp Asn Leu
    1010                1015                1020

Arg Lys Thr Cys Tyr Gln Ile Val Lys His Ser Trp Phe Glu Ser Phe
1025                1030                1035                1040

Ile Ile Phe Val Ile Leu Leu Ser Ser Gly Ala Leu Ile Phe Glu Asp
            1045                1050                1055

Val Asn Leu Pro Ser Arg Pro Gln Val Glu Lys Leu Leu Lys Cys Thr
        1060                1065                1070

Asp Asn Ile Phe Thr Phe Ile Phe Leu Leu Glu Met Ile Leu Lys Trp
    1075                1080                1085

Val Ala Phe Gly Phe Arg Lys Tyr Phe Thr Ser Ala Trp Cys Trp Leu
    1090                1095                1100

Asp Phe Leu Ile Val Val Ser Val Leu Ser Leu Thr Asn Leu Pro
1105                1110                1115                1120

Asn Leu Lys Ser Phe Arg Asn Leu Arg Ala Leu Arg Pro Leu Arg Ala
            1125                1130                1135

Leu Ser Gln Phe Glu Gly Met Lys Val Val Asn Ala Leu Met Ser
        1140                1145                1150

Ala Ile Pro Ala Ile Leu Asn Val Leu Leu Val Cys Leu Ile Phe Trp
    1155                1160                1165

Leu Ile Phe Cys Ile Leu Gly Val Asn Phe Phe Ser Gly Lys Phe Gly
    1170                1175                1180

Arg Cys Ile Asn Gly Thr Asp Ile Asn Lys Tyr Phe Asn Ala Ser Asn
1185                1190                1195                1200

Val Pro Asn Gln Ser Gln Cys Leu Val Ser Asn Tyr Thr Trp Lys Val
            1205                1210                1215

Pro Asn Val Asn Phe Asp Asn Val Gly Asn Ala Tyr Leu Ala Leu Leu
        1220                1225                1230

Gln Val Ala Thr Tyr Lys Gly Trp Leu Asp Ile Met Asn Ala Ala Val
    1235                1240                1245

Asp Ser Arg Gly Lys Asp Glu Gln Pro Ala Phe Glu Ala Asn Leu Tyr
    1250                1255                1260

Ala Tyr Leu Tyr Phe Val Val Phe Ile Ile Phe Gly Ser Phe Phe Thr
1265                1270                1275                1280

Leu Asn Leu Phe Ile Gly Val Ile Ile Asp Asn Phe Asn Gln Gln Gln
            1285                1290                1295

Lys Lys Leu Gly Gly Gln Asp Ile Phe Met Thr Glu Glu Gln Lys Lys
        1300                1305                1310

Tyr Tyr Asn Ala Met Lys Lys Leu Gly Thr Lys Lys Pro Gln Lys Pro
    1315                1320                1325

Ile Pro Arg Pro Leu Asn Lys Cys Gln Ala Phe Val Phe Asp Leu Val
    1330                1335                1340

Thr Ser Gln Val Phe Asp Val Ile Ile Leu Gly Leu Ile Val Thr Asn
1345                1350                1355                1360

Met Ile Ile Met Met Ala Glu Ser Glu Gly Gln Pro Asn Glu Val Lys
            1365                1370                1375

Lys Ile Phe Asp Ile Leu Asn Ile Val Phe Val Val Ile Phe Thr Val
        1380                1385                1390

Glu Cys Leu Ile Lys Val Phe Ala Leu Arg Gln His Tyr Phe Thr Asn
    1395                1400                1405

-continued

Gly Trp Asn Leu Phe Asp Cys Val Val Val Leu Ser Ile Ile Ser
    1410                1415                1420

Thr Leu Val Ser Gly Leu Glu Asn Ser Asn Val Phe Pro Pro Thr Leu
1425                1430                1435                1440

Phe Arg Ile Val Arg Leu Ala Arg Ile Gly Arg Ile Leu Arg Leu Val
            1445                1450                1455

Arg Ala Ala Arg Gly Ile Arg Thr Leu Leu Phe Ala Leu Met Met Ser
        1460                1465                1470

Leu Pro Ser Leu Phe Asn Ile Gly Leu Leu Leu Phe Leu Val Met Phe
    1475                1480                1485

Ile Tyr Ala Ile Phe Gly Met Asn Trp Phe Ser Lys Val Lys Arg Gly
1490                1495                1500

Ser Gly Ile Asp Asp Ile Phe Asn Phe Asp Thr Phe Ser Gly Ser Met
1505                1510                1515                1520

Leu Cys Leu Phe Gln Ile Thr Thr Ser Ala Gly Trp Asp Ala Leu Leu
            1525                1530                1535

Asn Pro Met Leu Glu Ser Lys Ala Ser Cys Asn Ser Ser Gln Glu
        1540                1545                1550

Ser Cys Gln Gln Pro Gln Ile Ala Ile Val Tyr Phe Val Ser Tyr Ile
    1555                1560                1565

Ile Ile Ser Phe Leu Ile Val Val Asn Met Tyr Ile Ala Val Ile Leu
    1570                1575                1580

Glu Asn Phe Asn Thr Ala Thr Glu Glu Ser Glu Asp Pro Leu Gly Glu
1585                1590                1595                1600

Asp Asp Phe Glu Ile Phe Tyr Glu Ile Trp Glu Lys Phe Asp Pro Glu
            1605                1610                1615

Ala Thr Gln Phe Ile Gln Tyr Ser Ser Leu Ser Asp Phe Ala Asp Ala
        1620                1625                1630

Leu Pro Glu Pro Leu Arg Val Ala Lys Pro Asn Arg Phe Gln Phe Leu
    1635                1640                1645

Met Met Asp Leu Pro Met Val Met Gly Asp Arg Leu His Cys Met Asp
1650                1655                1660

Val Leu Phe Ala Phe Thr Thr Arg Val Leu Gly Asn Ser Ser Gly Leu
1665                1670                1675                1680

Asp Thr Met Lys Ala Met Met Glu Glu Lys Phe Met Glu Ala Asn Pro
            1685                1690                1695

Phe Lys Lys Leu Tyr Glu Pro Ile Val Thr Thr Thr Lys Arg Lys Glu
        1700                1705                1710

Glu Glu Glu Cys Ala Ala Val Ile Gln Arg Ala Tyr Arg Arg His Met
    1715                1720                1725

Glu Lys Met Ile Lys Leu Lys Leu Lys Gly Arg Ser Ser Ser Ser Leu
    1730                1735                1740

Gln Val Phe Cys Asn Gly Asp Leu Ser Ser Leu Asp Val Pro Lys Ile
1745                1750                1755                1760

Lys Val His Cys Asp
            1765

<210> SEQ ID NO 6
<211> LENGTH: 3701
<212> TYPE: DNA
<213> ORGANISM: Homo sapiens
<220> FEATURE:
<221> NAME/KEY: CDS
<222> LOCATION: (1)..(3699)
<223> OTHER INFORMATION: partial human NaN cDNA sequence -continued

```
<220> FEATURE:
<221> NAME/KEY: unsure
<222> LOCATION: (922)
<223> OTHER INFORMATION: y = c or t.  Xaa at amino acid position 308 is
      Leu.

<400> SEQUENCE: 6 tcc att gtc att gga ata gcg att gtg tca tat att cca gga atc acc      48
Ser Ile Val Ile Gly Ile Ala Ile Val Ser Tyr Ile Pro Gly Ile Thr
1               5                   10                  15 atc aaa cta ttg ccc ctg cgt acc ttc cgt gtg ttc aga gct ttg aaa      96
Ile Lys Leu Leu Pro Leu Arg Thr Phe Arg Val Phe Arg Ala Leu Lys
            20                  25                  30 gca att tca gta gtt tca cgt ctg aag gtc atc gtg ggg gcc ttg cta     144
Ala Ile Ser Val Val Ser Arg Leu Lys Val Ile Val Gly Ala Leu Leu
        35                  40                  45 cgc tct gtg aag aag ctg gtc aac gtg att atc ctc acc ttc ttt tgc     192
Arg Ser Val Lys Lys Leu Val Asn Val Ile Ile Leu Thr Phe Phe Cys
    50                  55                  60 ctc agc atc ttt gcc ctg gta ggt cag cag ctc ttc atg gga agt ctg     240
Leu Ser Ile Phe Ala Leu Val Gly Gln Gln Leu Phe Met Gly Ser Leu
65                  70                  75                  80 aac ctg aaa tgc atc tcg agg gac tgt aaa aat atc agt aac ccg gaa     288
Asn Leu Lys Cys Ile Ser Arg Asp Cys Lys Asn Ile Ser Asn Pro Glu
                85                  90                  95 gct tat gac cat tgc ttt gaa aag aaa gaa aat tca cct gaa ttc aaa     336
Ala Tyr Asp His Cys Phe Glu Lys Lys Glu Asn Ser Pro Glu Phe Lys
            100                 105                 110 atg tgt ggc atc tgg atg ggt aac agt gcc tgt tcc ata caa tat gaa     384
Met Cys Gly Ile Trp Met Gly Asn Ser Ala Cys Ser Ile Gln Tyr Glu
        115                 120                 125 tgt aag cac acc aaa att aat cct gac tat aat tat acg aat ttt gac     432
Cys Lys His Thr Lys Ile Asn Pro Asp Tyr Asn Tyr Thr Asn Phe Asp
    130                 135                 140 aac ttt ggc tgg tct ttt ctt gcc atg ttc cgg ctg atg acc caa gat     480
Asn Phe Gly Trp Ser Phe Leu Ala Met Phe Arg Leu Met Thr Gln Asp
145                 150                 155                 160 tcc tgg gag aag ctt tat caa cag acc ctg cgt act act ggg ctc tac     528
Ser Trp Glu Lys Leu Tyr Gln Gln Thr Leu Arg Thr Thr Gly Leu Tyr
                165                 170                 175 tca gtc ttc ttc ttc att gtg gtc att ttc ctg ggc tcc ttc tac ctg     576
Ser Val Phe Phe Phe Ile Val Val Ile Phe Leu Gly Ser Phe Tyr Leu
            180                 185                 190 att aac tta acc ctg gct gtt gtt acc atg gca tat gag gag cag aac     624
Ile Asn Leu Thr Leu Ala Val Val Thr Met Ala Tyr Glu Glu Gln Asn
        195                 200                 205 aag aat gta gct gca gag ata gag gcc aag gaa aag atg ttt cag gaa     672
Lys Asn Val Ala Ala Glu Ile Glu Ala Lys Glu Lys Met Phe Gln Glu
    210                 215                 220 gcc cag cag ctg tta aag gag gaa aag gag gct ctg gtt gcc atg gga     720
Ala Gln Gln Leu Leu Lys Glu Glu Lys Glu Ala Leu Val Ala Met Gly
225                 230                 235                 240 att gac aga agt tca ctt act tcc ctt gaa aca tca tat ttt acc cca     768
Ile Asp Arg Ser Ser Leu Thr Ser Leu Glu Thr Ser Tyr Phe Thr Pro
                245                 250                 255 aaa aag aga aag ctc ttt ggt aat aag aaa agg aag tcc ttc ttt ttg     816
Lys Lys Arg Lys Leu Phe Gly Asn Lys Lys Arg Lys Ser Phe Phe Leu
            260                 265                 270 aga gag tct ggg aaa gac cag cct cct ggg tca gat tct gat gaa gat     864
Arg Glu Ser Gly Lys Asp Gln Pro Pro Gly Ser Asp Ser Asp Glu Asp
        275                 280                 285
```

-continued

| | | |
|---|---|---|
| tgc caa aaa aag cca cag ctc cta gag caa acc aaa cga ctg tcc cag<br>Cys Gln Lys Lys Pro Gln Leu Leu Glu Gln Thr Lys Arg Leu Ser Gln<br>290                       295                       300 | | 912 |
| aat cta tca ytg gac cac ttt gat gag cat gga gat cct ctc caa agg<br>Asn Leu Ser Xaa Asp His Phe Asp Glu His Gly Asp Pro Leu Gln Arg<br>305                       310                       315                     320 | | 960 |
| cag aga gca ctg agt gct gtc agc atc ctc acc atc acc atg aag gaa<br>Gln Arg Ala Leu Ser Ala Val Ser Ile Leu Thr Ile Thr Met Lys Glu<br>                      325                       330                     335 | | 1008 |
| caa gaa aaa tca caa gag cct tgt ctc cct tgt gga gaa aac ctg gca<br>Gln Glu Lys Ser Gln Glu Pro Cys Leu Pro Cys Gly Glu Asn Leu Ala<br>                     340                       345                     350 | | 1056 |
| tcc aag tac ctc gtg tgg aac tgt tgc ccc cag tgg ctg tgc gtt aag<br>Ser Lys Tyr Leu Val Trp Asn Cys Cys Pro Gln Trp Leu Cys Val Lys<br>                355                       360                     365 | | 1104 |
| aag gtc ctg aga act gtg atg act gac ccg ttt act gag ctg gcc atc<br>Lys Val Leu Arg Thr Val Met Thr Asp Pro Phe Thr Glu Leu Ala Ile<br>370                       375                       380 | | 1152 |
| acc atc tgc atc atc atc aac act gtc ttc ttg gcc atg gag cat cac<br>Thr Ile Cys Ile Ile Ile Asn Thr Val Phe Leu Ala Met Glu His His<br>385                       390                       395                     400 | | 1200 |
| aag atg gag gcc agt ttt gag aag atg ttg aat ata ggg aat ttg gtt<br>Lys Met Glu Ala Ser Phe Glu Lys Met Leu Asn Ile Gly Asn Leu Val<br>                     405                       410                     415 | | 1248 |
| ttc act agc att ttt ata gca gaa atg tgc cta aaa atc att gcg ctc<br>Phe Thr Ser Ile Phe Ile Ala Glu Met Cys Leu Lys Ile Ile Ala Leu<br>                     420                       425                     430 | | 1296 |
| gat ccc tac cac tac ttt cgc cga ggc tgg aac att ttt gac agc att<br>Asp Pro Tyr His Tyr Phe Arg Arg Gly Trp Asn Ile Phe Asp Ser Ile<br>                  435                       440                     445 | | 1344 |
| gtt gct ctt ctg agt ttt gca gat gta atg aac tgt gta ctt caa aag<br>Val Ala Leu Leu Ser Phe Ala Asp Val Met Asn Cys Val Leu Gln Lys<br>450                       455                       460 | | 1392 |
| aga agc tgg cca ttc ttg cgt tcc ttc aga gtg ctc agg gtc ttc aag<br>Arg Ser Trp Pro Phe Leu Arg Ser Phe Arg Val Leu Arg Val Phe Lys<br>465                       470                       475                     480 | | 1440 |
| tta gcc aaa tcc tgg cca act ttg aac aca cta att aag ata atc ggc<br>Leu Ala Lys Ser Trp Pro Thr Leu Asn Thr Leu Ile Lys Ile Ile Gly<br>                     485                       490                     495 | | 1488 |
| aac tct gtc gga gcc ctt gga agc ctg act gtg gtc ctg gtc att gtg<br>Asn Ser Val Gly Ala Leu Gly Ser Leu Thr Val Val Leu Val Ile Val<br>                     500                       505                     510 | | 1536 |
| atc ttt att ttc tca gta gtt ggc atg cag ctt ttt ggc cgt agc ttc<br>Ile Phe Ile Phe Ser Val Val Gly Met Gln Leu Phe Gly Arg Ser Phe<br>               515                       520                     525 | | 1584 |
| aat tcc caa aag agt cca aaa ctc tgt aac ccg aca ggc ccg aca gtc<br>Asn Ser Gln Lys Ser Pro Lys Leu Cys Asn Pro Thr Gly Pro Thr Val<br>530                       535                       540 | | 1632 |
| tca tgt tta cgg cac tgg cac atg ggg gat ttc tgg cac tcc ttc cta<br>Ser Cys Leu Arg His Trp His Met Gly Asp Phe Trp His Ser Phe Leu<br>545                       550                       555                     560 | | 1680 |
| gtg gta ttc cgc atc ctc tgc ggg gaa tgg atc gaa aat atg tgg gaa<br>Val Val Phe Arg Ile Leu Cys Gly Glu Trp Ile Glu Asn Met Trp Glu<br>                     565                       570                     575 | | 1728 |
| tgt atg caa gaa gcg aat gca tca tca ttg tgt gtt att gtc ttc<br>Cys Met Gln Glu Ala Asn Ala Ser Ser Ser Leu Cys Val Ile Val Phe<br>                     580                       585                     590 | | 1776 |
| ata ttg atc acg gtg ata gga aaa ctt gtg gtg ctc aac ctc ttc att<br>Ile Leu Ile Thr Val Ile Gly Lys Leu Val Val Leu Asn Leu Phe Ile<br>               595                       600                     605 | | 1824 |

```
                                           -continued gcc tta ctg ctc aat tcc ttt agc aat gag gaa aga aat gga aac tta    1872
Ala Leu Leu Leu Asn Ser Phe Ser Asn Glu Glu Arg Asn Gly Asn Leu
610                 615                 620 gaa gga gag gcc agg aaa act aaa gtc cag tta gca ctg gat cga ttc    1920
Glu Gly Glu Ala Arg Lys Thr Lys Val Gln Leu Ala Leu Asp Arg Phe
625                 630                 635                 640 cgc cgg gct ttt tgt ttt gtg aga cac act ctt gag cat ttc tgt cac    1968
Arg Arg Ala Phe Cys Phe Val Arg His Thr Leu Glu His Phe Cys His
                645                 650                 655 aag tgg tgc agg aag caa aac tta cca cag caa aaa gag gtg gca gga    2016
Lys Trp Cys Arg Lys Gln Asn Leu Pro Gln Gln Lys Glu Val Ala Gly
            660                 665                 670 ggc tgt gct gca caa agc aaa gac atc att ccc ctg gtc atg gag atg    2064
Gly Cys Ala Ala Gln Ser Lys Asp Ile Ile Pro Leu Val Met Glu Met
        675                 680                 685 aaa agg ggc tca gag acc cag gag gag ctt ggt ata cta acc tct gta    2112
Lys Arg Gly Ser Glu Thr Gln Glu Glu Leu Gly Ile Leu Thr Ser Val
690                 695                 700 cca aag acc ctg ggc gtc agg cat gat tgg act tgg ttg gca cca ctt    2160
Pro Lys Thr Leu Gly Val Arg His Asp Trp Thr Trp Leu Ala Pro Leu
705                 710                 715                 720 gcg gag gag gaa gat gac gtt gaa ttt tct ggt gaa gat aat gca cag    2208
Ala Glu Glu Glu Asp Asp Val Glu Phe Ser Gly Glu Asp Asn Ala Gln
                725                 730                 735 cgc atc aca caa cct gag cct gaa caa cag gcc tat gag ctc cat cag    2256
Arg Ile Thr Gln Pro Glu Pro Glu Gln Gln Ala Tyr Glu Leu His Gln
            740                 745                 750 gag aac aag aag ccc acg agc cag aga gtt caa agt gtg gaa att gac    2304
Glu Asn Lys Lys Pro Thr Ser Gln Arg Val Gln Ser Val Glu Ile Asp
        755                 760                 765 atg ttc tct gaa gat gag cct cat ctg acc ata cag gat ccc cga aag    2352
Met Phe Ser Glu Asp Glu Pro His Leu Thr Ile Gln Asp Pro Arg Lys
770                 775                 780 aag tct gat gtt acc agt ata cta tca gaa tgt agc acc att gat ctt    2400
Lys Ser Asp Val Thr Ser Ile Leu Ser Glu Cys Ser Thr Ile Asp Leu
785                 790                 795                 800 cag gat ggc ttt gga tgg tta cct gag atg gtt ccc aaa aag caa cca    2448
Gln Asp Gly Phe Gly Trp Leu Pro Glu Met Val Pro Lys Lys Gln Pro
                805                 810                 815 gag aga tgt ttg ccc aaa ggc ttt ggt tgc tgc ttt cca tgc tgt agc    2496
Glu Arg Cys Leu Pro Lys Gly Phe Gly Cys Cys Phe Pro Cys Cys Ser
            820                 825                 830 gtg gac aag aga aag cct ccc tgg gtc att tgg tgg aac ctg cgg aaa    2544
Val Asp Lys Arg Lys Pro Pro Trp Val Ile Trp Trp Asn Leu Arg Lys
        835                 840                 845 acc tgc tac caa ata gtg aaa cac agc tgg ttt gag agc ttt att atc    2592
Thr Cys Tyr Gln Ile Val Lys His Ser Trp Phe Glu Ser Phe Ile Ile
850                 855                 860 ttt gtg att ctg ctg agc agt ggg gca ctg ata ttt gaa gat gtt cac    2640
Phe Val Ile Leu Leu Ser Ser Gly Ala Leu Ile Phe Glu Asp Val His
865                 870                 875                 880 ctt gag aac caa ccc aaa atc caa gaa tta cta aat tgt act gac att    2688
Leu Glu Asn Gln Pro Lys Ile Gln Glu Leu Leu Asn Cys Thr Asp Ile
                885                 890                 895 att ttt aca cat att ttt atc ctg gag atg gta cta aaa tgg gta gcc    2736
Ile Phe Thr His Ile Phe Ile Leu Glu Met Val Leu Lys Trp Val Ala
            900                 905                 910 ttc gga ttt gga aag tat ttc acc agt gcc tgg tgc tgc ctt gat ttc    2784
Phe Gly Phe Gly Lys Tyr Phe Thr Ser Ala Trp Cys Cys Leu Asp Phe
        915                 920                 925
```

| | | |
|---|---|---|
| atc att gtg att gtc tct gtg acc acc ctc att aac tta atg gaa ttg<br>Ile Ile Val Ile Val Ser Val Thr Thr Leu Ile Asn Leu Met Glu Leu<br>930 935 940 | | 2832 |
| aag tcc ttc cgg act cta cga gca ctg agg cct ctt cgt gcg ctg tcc<br>Lys Ser Phe Arg Thr Leu Arg Ala Leu Arg Pro Leu Arg Ala Leu Ser<br>945 950 955 960 | | 2880 |
| cag ttt gaa gga atg aag gtg gtg gtc aat gct ctc ata ggt gcc ata<br>Gln Phe Glu Gly Met Lys Val Val Val Asn Ala Leu Ile Gly Ala Ile<br>965 970 975 | | 2928 |
| cct gcc att ctg aat gtt ttg ctt gtc tgc ctc att ttc tgg ctc gta<br>Pro Ala Ile Leu Asn Val Leu Leu Val Cys Leu Ile Phe Trp Leu Val<br>980 985 990 | | 2976 |
| ttt tgt att ctg gga gta tac ttc ttt tct gga aaa ttt ggg aaa tgc<br>Phe Cys Ile Leu Gly Val Tyr Phe Phe Ser Gly Lys Phe Gly Lys Cys<br>995 1000 1005 | | 3024 |
| att aat gga aca gac tca gtt ata aat tat acc atc att aca aat aaa<br>Ile Asn Gly Thr Asp Ser Val Ile Asn Tyr Thr Ile Ile Thr Asn Lys<br>1010 1015 1020 | | 3072 |
| agt caa tgt gaa agt ggc aat ttc tct tgg atc aac cag aaa gtc aac<br>Ser Gln Cys Glu Ser Gly Asn Phe Ser Trp Ile Asn Gln Lys Val Asn<br>1025 1030 1035 1040 | | 3120 |
| ttt gac aat gtg gga aat gct tac ctc gct ctg ctg caa gtg gca aca<br>Phe Asp Asn Val Gly Asn Ala Tyr Leu Ala Leu Leu Gln Val Ala Thr<br>1045 1050 1055 | | 3168 |
| ttt aag ggc tgg atg gat att ata tat gca gct gtt gat tcc aca gag<br>Phe Lys Gly Trp Met Asp Ile Ile Tyr Ala Ala Val Asp Ser Thr Glu<br>1060 1065 1070 | | 3216 |
| aaa gaa caa cag cca gag ttt gag agc aat tca ctc ggt tac att tac<br>Lys Glu Gln Gln Pro Glu Phe Glu Ser Asn Ser Leu Gly Tyr Ile Tyr<br>1075 1080 1085 | | 3264 |
| ttc gta gtc ttt atc atc ttt ggc tca ttc ttc act ctg aat ctc ttc<br>Phe Val Val Phe Ile Ile Phe Gly Ser Phe Phe Thr Leu Asn Leu Phe<br>1090 1095 1100 | | 3312 |
| att ggc gtt atc att gac aac ttc aac caa cag cag aaa aag tta ggt<br>Ile Gly Val Ile Ile Asp Asn Phe Asn Gln Gln Gln Lys Lys Leu Gly<br>1105 1110 1115 1120 | | 3360 |
| ggc caa gac att ttt atg aca gaa gaa cag aag aaa tac tat aat gca<br>Gly Gln Asp Ile Phe Met Thr Glu Glu Gln Lys Lys Tyr Tyr Asn Ala<br>1125 1130 1135 | | 3408 |
| atg aaa aaa tta gga tcc aaa aaa cct caa aaa ccc att cca cgg cct<br>Met Lys Lys Leu Gly Ser Lys Lys Pro Gln Lys Pro Ile Pro Arg Pro<br>1140 1145 1150 | | 3456 |
| ctg aac aaa tgt caa ggt ctc gtg ttc gac ata gtc aca agc cag atc<br>Leu Asn Lys Cys Gln Gly Leu Val Phe Asp Ile Val Thr Ser Gln Ile<br>1155 1160 1165 | | 3504 |
| ttt gac atc atc atc ata agt ctc att atc cta aac atg att agc atg<br>Phe Asp Ile Ile Ile Ile Ser Leu Ile Ile Leu Asn Met Ile Ser Met<br>1170 1175 1180 | | 3552 |
| atg gct gaa tca tac aac caa ccc aaa gcc atg aaa tcc atc ctt gac<br>Met Ala Glu Ser Tyr Asn Gln Pro Lys Ala Met Lys Ser Ile Leu Asp<br>1185 1190 1195 1200 | | 3600 |
| cat ctc aac tgg gtc ttt gtg gtc atc ttt acg tta gaa tgt ctc atc<br>His Leu Asn Trp Val Phe Val Val Ile Phe Thr Leu Glu Cys Leu Ile<br>1205 1210 1215 | | 3648 |
| aaa atc ttt gct ttg agg caa tac tac ttc acc aat ggc tgg aat tta<br>Lys Ile Phe Ala Leu Arg Gln Tyr Tyr Phe Thr Asn Gly Trp Asn Leu<br>1220 1225 1230 | | 3696 |
| ttt ga<br>Phe | | 3701 |

```
<210> SEQ ID NO 7
<211> LENGTH: 1233
<212> TYPE: PRT
<213> ORGANISM: Homo sapiens
<220> FEATURE:
<221> NAME/KEY: UNSURE
<222> LOCATION: (308)
<223> OTHER INFORMATION: Xaa is Leu. Xaa results from a "y" in SEQ
      ID NO: 6.

<400> SEQUENCE: 7
```

| Ser | Ile | Val | Ile | Gly | Ile | Ala | Ile | Val | Ser | Tyr | Ile | Pro | Gly | Ile | Thr |
|---|---|---|---|---|---|---|---|---|---|---|---|---|---|---|---|
| 1 | | | | 5 | | | | | 10 | | | | | 15 | |

| Ile | Lys | Leu | Leu | Pro | Leu | Arg | Thr | Phe | Arg | Val | Phe | Arg | Ala | Leu | Lys |
|---|---|---|---|---|---|---|---|---|---|---|---|---|---|---|---|
| | | | 20 | | | | | 25 | | | | | 30 | | |

| Ala | Ile | Ser | Val | Val | Ser | Arg | Leu | Lys | Val | Ile | Val | Gly | Ala | Leu | Leu |
|---|---|---|---|---|---|---|---|---|---|---|---|---|---|---|---|
| | | 35 | | | | | 40 | | | | | 45 | | | |

| Arg | Ser | Val | Lys | Lys | Leu | Val | Asn | Val | Ile | Ile | Leu | Thr | Phe | Phe | Cys |
|---|---|---|---|---|---|---|---|---|---|---|---|---|---|---|---|
| | 50 | | | | | 55 | | | | | 60 | | | | |

| Leu | Ser | Ile | Phe | Ala | Leu | Val | Gly | Gln | Gln | Leu | Phe | Met | Gly | Ser | Leu |
|---|---|---|---|---|---|---|---|---|---|---|---|---|---|---|---|
| 65 | | | | | 70 | | | | | 75 | | | | | 80 |

| Asn | Leu | Lys | Cys | Ile | Ser | Arg | Asp | Cys | Lys | Asn | Ile | Ser | Asn | Pro | Glu |
|---|---|---|---|---|---|---|---|---|---|---|---|---|---|---|---|
| | | | | 85 | | | | | 90 | | | | | 95 | |

| Ala | Tyr | Asp | His | Cys | Phe | Glu | Lys | Lys | Glu | Asn | Ser | Pro | Glu | Phe | Lys |
|---|---|---|---|---|---|---|---|---|---|---|---|---|---|---|---|
| | | | 100 | | | | | 105 | | | | | 110 | | |

| Met | Cys | Gly | Ile | Trp | Met | Gly | Asn | Ser | Ala | Cys | Ser | Ile | Gln | Tyr | Glu |
|---|---|---|---|---|---|---|---|---|---|---|---|---|---|---|---|
| | | 115 | | | | | 120 | | | | | 125 | | | |

| Cys | Lys | His | Thr | Lys | Ile | Asn | Pro | Asp | Tyr | Asn | Tyr | Thr | Asn | Phe | Asp |
|---|---|---|---|---|---|---|---|---|---|---|---|---|---|---|---|
| | 130 | | | | | 135 | | | | | 140 | | | | |

| Asn | Phe | Gly | Trp | Ser | Phe | Leu | Ala | Met | Phe | Arg | Leu | Met | Thr | Gln | Asp |
|---|---|---|---|---|---|---|---|---|---|---|---|---|---|---|---|
| 145 | | | | | 150 | | | | | 155 | | | | | 160 |

| Ser | Trp | Glu | Lys | Leu | Tyr | Gln | Gln | Thr | Leu | Arg | Thr | Thr | Gly | Leu | Tyr |
|---|---|---|---|---|---|---|---|---|---|---|---|---|---|---|---|
| | | | | 165 | | | | | 170 | | | | | 175 | |

| Ser | Val | Phe | Phe | Phe | Ile | Val | Val | Ile | Phe | Leu | Gly | Ser | Phe | Tyr | Leu |
|---|---|---|---|---|---|---|---|---|---|---|---|---|---|---|---|
| | | | 180 | | | | | 185 | | | | | 190 | | |

| Ile | Asn | Leu | Thr | Leu | Ala | Val | Val | Thr | Met | Ala | Tyr | Glu | Glu | Gln | Asn |
|---|---|---|---|---|---|---|---|---|---|---|---|---|---|---|---|
| | | 195 | | | | | 200 | | | | | 205 | | | |

| Lys | Asn | Val | Ala | Ala | Glu | Ile | Glu | Ala | Lys | Glu | Lys | Met | Phe | Gln | Glu |
|---|---|---|---|---|---|---|---|---|---|---|---|---|---|---|---|
| | 210 | | | | | 215 | | | | | 220 | | | | |

| Ala | Gln | Gln | Leu | Leu | Lys | Glu | Glu | Lys | Glu | Ala | Leu | Val | Ala | Met | Gly |
|---|---|---|---|---|---|---|---|---|---|---|---|---|---|---|---|
| 225 | | | | | 230 | | | | | 235 | | | | | 240 |

| Ile | Asp | Arg | Ser | Ser | Leu | Thr | Ser | Leu | Glu | Thr | Ser | Tyr | Phe | Thr | Pro |
|---|---|---|---|---|---|---|---|---|---|---|---|---|---|---|---|
| | | | | 245 | | | | | 250 | | | | | 255 | |

| Lys | Lys | Arg | Lys | Leu | Phe | Gly | Asn | Lys | Lys | Arg | Lys | Ser | Phe | Phe | Leu |
|---|---|---|---|---|---|---|---|---|---|---|---|---|---|---|---|
| | | | 260 | | | | | 265 | | | | | 270 | | |

| Arg | Glu | Ser | Gly | Lys | Asp | Gln | Pro | Pro | Gly | Ser | Asp | Ser | Asp | Glu | Asp |
|---|---|---|---|---|---|---|---|---|---|---|---|---|---|---|---|
| | | 275 | | | | | 280 | | | | | 285 | | | |

| Cys | Gln | Lys | Lys | Pro | Gln | Leu | Leu | Glu | Gln | Thr | Lys | Arg | Leu | Ser | Gln |
|---|---|---|---|---|---|---|---|---|---|---|---|---|---|---|---|
| | 290 | | | | | 295 | | | | | 300 | | | | |

| Asn | Leu | Ser | Xaa | Asp | His | Phe | Asp | Glu | His | Gly | Asp | Pro | Leu | Gln | Arg |
|---|---|---|---|---|---|---|---|---|---|---|---|---|---|---|---|
| 305 | | | | | 310 | | | | | 315 | | | | | 320 |

| Gln | Arg | Ala | Leu | Ser | Ala | Val | Ser | Ile | Leu | Thr | Ile | Thr | Met | Lys | Glu |
|---|---|---|---|---|---|---|---|---|---|---|---|---|---|---|---|
| | | | | 325 | | | | | 330 | | | | | 335 | |

| Gln | Glu | Lys | Ser | Gln | Glu | Pro | Cys | Leu | Pro | Cys | Gly | Glu | Asn | Leu | Ala |
|---|---|---|---|---|---|---|---|---|---|---|---|---|---|---|---|
| | | | 340 | | | | | 345 | | | | | 350 | | |

```
Ser Lys Tyr Leu Val Trp Asn Cys Cys Pro Gln Trp Leu Cys Val Lys
        355                 360                 365

Lys Val Leu Arg Thr Val Met Thr Asp Pro Phe Thr Glu Leu Ala Ile
        370                 375                 380

Thr Ile Cys Ile Ile Ile Asn Thr Val Phe Leu Ala Met Glu His His
385                 390                 395                 400

Lys Met Glu Ala Ser Phe Glu Lys Met Leu Asn Ile Gly Asn Leu Val
                405                 410                 415

Phe Thr Ser Ile Phe Ile Ala Glu Met Cys Leu Lys Ile Ile Ala Leu
                420                 425                 430

Asp Pro Tyr His Tyr Phe Arg Arg Gly Trp Asn Ile Phe Asp Ser Ile
            435                 440                 445

Val Ala Leu Leu Ser Phe Ala Asp Val Met Asn Cys Val Leu Gln Lys
        450                 455                 460

Arg Ser Trp Pro Phe Leu Arg Ser Phe Arg Val Leu Arg Val Phe Lys
465                 470                 475                 480

Leu Ala Lys Ser Trp Pro Thr Leu Asn Thr Leu Ile Lys Ile Ile Gly
                485                 490                 495

Asn Ser Val Gly Ala Leu Gly Ser Leu Thr Val Val Leu Val Ile Val
            500                 505                 510

Ile Phe Ile Phe Ser Val Val Gly Met Gln Leu Phe Gly Arg Ser Phe
        515                 520                 525

Asn Ser Gln Lys Ser Pro Lys Leu Cys Asn Pro Thr Gly Pro Thr Val
        530                 535                 540

Ser Cys Leu Arg His Trp His Met Gly Asp Phe Trp His Ser Phe Leu
545                 550                 555                 560

Val Val Phe Arg Ile Leu Cys Gly Glu Trp Ile Glu Asn Met Trp Glu
                565                 570                 575

Cys Met Gln Glu Ala Asn Ala Ser Ser Ser Leu Cys Val Ile Val Phe
            580                 585                 590

Ile Leu Ile Thr Val Ile Gly Lys Leu Val Val Leu Asn Leu Phe Ile
        595                 600                 605

Ala Leu Leu Leu Asn Ser Phe Ser Asn Glu Glu Arg Asn Gly Asn Leu
        610                 615                 620

Glu Gly Glu Ala Arg Lys Thr Lys Val Gln Leu Ala Leu Asp Arg Phe
625                 630                 635                 640

Arg Arg Ala Phe Cys Phe Val Arg His Thr Leu Glu His Phe Cys His
                645                 650                 655

Lys Trp Cys Arg Lys Gln Asn Leu Pro Gln Gln Lys Glu Val Ala Gly
            660                 665                 670

Gly Cys Ala Ala Gln Ser Lys Asp Ile Ile Pro Leu Val Met Glu Met
        675                 680                 685

Lys Arg Gly Ser Glu Thr Gln Glu Glu Leu Gly Ile Leu Thr Ser Val
        690                 695                 700

Pro Lys Thr Leu Gly Val Arg His Asp Trp Thr Trp Leu Ala Pro Leu
705                 710                 715                 720

Ala Glu Glu Glu Asp Asp Val Glu Phe Ser Gly Glu Asp Asn Ala Gln
                725                 730                 735

Arg Ile Thr Gln Pro Glu Pro Glu Gln Gln Ala Tyr Glu Leu His Gln
            740                 745                 750

Glu Asn Lys Lys Pro Thr Ser Gln Arg Val Gln Ser Val Glu Ile Asp
        755                 760                 765
```

```
Met Phe Ser Glu Asp Glu Pro His Leu Thr Ile Gln Asp Pro Arg Lys
770                 775                 780

Lys Ser Asp Val Thr Ser Ile Leu Ser Glu Cys Ser Thr Ile Asp Leu
785                 790                 795                 800

Gln Asp Gly Phe Gly Trp Leu Pro Glu Met Val Pro Lys Lys Gln Pro
                805                 810                 815

Glu Arg Cys Leu Pro Lys Gly Phe Gly Cys Cys Phe Pro Cys Cys Ser
            820                 825                 830

Val Asp Lys Arg Lys Pro Pro Trp Val Ile Trp Trp Asn Leu Arg Lys
                835                 840                 845

Thr Cys Tyr Gln Ile Val Lys His Ser Trp Phe Glu Ser Phe Ile Ile
    850                 855                 860

Phe Val Ile Leu Leu Ser Ser Gly Ala Leu Ile Phe Glu Asp Val His
865                 870                 875                 880

Leu Glu Asn Gln Pro Lys Ile Gln Glu Leu Leu Asn Cys Thr Asp Ile
                885                 890                 895

Ile Phe Thr His Ile Phe Ile Leu Glu Met Val Leu Lys Trp Val Ala
                900                 905                 910

Phe Gly Phe Gly Lys Tyr Phe Thr Ser Ala Trp Cys Cys Leu Asp Phe
            915                 920                 925

Ile Ile Val Ile Val Ser Val Thr Thr Leu Ile Asn Leu Met Glu Leu
930                 935                 940

Lys Ser Phe Arg Thr Leu Arg Ala Leu Arg Pro Leu Arg Ala Leu Ser
945                 950                 955                 960

Gln Phe Glu Gly Met Lys Val Val Asn Ala Leu Ile Gly Ala Ile
                965                 970                 975

Pro Ala Ile Leu Asn Val Leu Leu Val Cys Leu Ile Phe Trp Leu Val
            980                 985                 990

Phe Cys Ile Leu Gly Val Tyr Phe Phe Ser Gly Lys Phe Gly Lys Cys
        995                 1000                1005

Ile Asn Gly Thr Asp Ser Val Ile Asn Tyr Thr Ile Ile Thr Asn Lys
    1010                1015                1020

Ser Gln Cys Glu Ser Gly Asn Phe Ser Trp Ile Asn Gln Lys Val Asn
1025                1030                1035                1040

Phe Asp Asn Val Gly Asn Ala Tyr Leu Ala Leu Leu Gln Val Ala Thr
            1045                1050                1055

Phe Lys Gly Trp Met Asp Ile Ile Tyr Ala Ala Val Asp Ser Thr Glu
            1060                1065                1070

Lys Glu Gln Gln Pro Glu Phe Glu Ser Asn Ser Leu Gly Tyr Ile Tyr
    1075                1080                1085

Phe Val Val Phe Ile Ile Phe Gly Ser Phe Phe Thr Leu Asn Leu Phe
    1090                1095                1100

Ile Gly Val Ile Ile Asp Asn Phe Asn Gln Gln Lys Lys Leu Gly
1105                1110                1115                1120

Gly Gln Asp Ile Phe Met Thr Glu Glu Gln Lys Lys Tyr Tyr Asn Ala
            1125                1130                1135

Met Lys Lys Leu Gly Ser Lys Lys Pro Gln Lys Pro Ile Pro Arg Pro
            1140                1145                1150

Leu Asn Lys Cys Gln Gly Leu Val Phe Asp Ile Val Thr Ser Gln Ile
        1155                1160                1165

Phe Asp Ile Ile Ile Ile Ser Leu Ile Ile Leu Asn Met Ile Ser Met
    1170                1175                1180
```

```
Met Ala Glu Ser Tyr Asn Gln Pro Lys Ala Met Lys Ser Ile Leu Asp
1185                1190                1195                1200

His Leu Asn Trp Val Phe Val Ile Phe Thr Leu Glu Cys Leu Ile
            1205                1210                1215

Lys Ile Phe Ala Leu Arg Gln Tyr Tyr Phe Thr Asn Gly Trp Asn Leu
        1220                1225                1230

Phe

<210> SEQ ID NO 8
<211> LENGTH: 1243
<212> TYPE: PRT
<213> ORGANISM: Homo sapiens
<220> FEATURE:
<223> OTHER INFORMATION: partial human NaN amino acid seq.

<400> SEQUENCE: 8

Ser Ile Val Ile Gly Ile Ala Ile Val Ser Tyr Ile Pro Gly Ile Thr
 1               5                   10                  15

Ile Lys Leu Leu Pro Leu Arg Thr Phe Arg Val Phe Arg Ala Leu Lys
                20                  25                  30

Ala Ile Ser Val Val Ser Arg Leu Lys Val Ile Val Gly Ala Leu Leu
            35                  40                  45

Arg Ser Val Lys Lys Leu Val Asn Val Ile Ile Leu Thr Phe Phe Cys
 50                  55                  60

Leu Ser Ile Phe Ala Leu Val Gly Gln Gln Leu Phe Met Gly Ser Leu
 65                  70                  75                  80

Asn Leu Lys Cys Ile Ser Arg Asp Cys Lys Asn Ile Ser Asn Pro Glu
                85                  90                  95

Ala Tyr Asp His Cys Phe Glu Lys Lys Glu Asn Ser Pro Glu Phe Lys
            100                 105                 110

Met Cys Gly Ile Trp Met Gly Asn Ser Ala Cys Ser Ile Gln Tyr Glu
        115                 120                 125

Cys Lys His Thr Lys Ile Asn Pro Asp Tyr Asn Tyr Thr Asn Phe Asp
130                 135                 140

Asn Phe Gly Trp Ser Phe Leu Ala Met Phe Arg Leu Met Thr Gln Asp
145                 150                 155                 160

Ser Trp Glu Lys Leu Tyr Gln Gln Thr Leu Arg Thr Thr Gly Leu Tyr
                165                 170                 175

Ser Val Phe Phe Phe Ile Val Val Ile Phe Leu Gly Ser Phe Tyr Leu
            180                 185                 190

Ile Asn Leu Thr Leu Ala Val Val Thr Met Ala Tyr Glu Glu Gln Asn
        195                 200                 205

Lys Asn Val Ala Ala Glu Ile Glu Ala Lys Glu Lys Met Phe Gln Glu
210                 215                 220

Ala Gln Gln Leu Leu Lys Glu Glu Lys Glu Ala Leu Val Ala Met Gly
225                 230                 235                 240

Ile Asp Arg Ser Ser Leu Thr Ser Leu Glu Thr Ser Tyr Phe Thr Pro
                245                 250                 255

Lys Lys Arg Lys Leu Phe Gly Asn Lys Lys Arg Lys Ser Phe Phe Leu
            260                 265                 270

Arg Glu Ser Gly Lys Asp Gln Pro Pro Gly Ser Asp Ser Asp Glu Asp
        275                 280                 285

Cys Gln Lys Lys Pro Gln Leu Leu Glu Gln Thr Lys Arg Leu Ser Gln
290                 295                 300
```

```
                                  -continued

Asn Leu Ser Leu Asp His Phe Asp Glu His Gly Asp Pro Leu Gln Arg
305                 310                 315                 320

Gln Arg Ala Leu Ser Ala Val Ser Ile Leu Thr Ile Thr Met Lys Glu
            325                 330                 335

Gln Glu Lys Ser Gln Glu Pro Cys Leu Pro Cys Gly Glu Asn Leu Ala
        340                 345                 350

Ser Lys Tyr Leu Val Trp Asn Cys Cys Pro Gln Trp Leu Cys Val Lys
    355                 360                 365

Lys Val Leu Arg Thr Val Met Thr Asp Pro Phe Thr Glu Leu Ala Ile
370                 375                 380

Thr Ile Cys Ile Ile Ile Asn Thr Val Phe Leu Ala Met Glu His His
385                 390                 395                 400

Lys Met Glu Ala Ser Phe Glu Lys Met Leu Asn Ile Gly Asn Leu Val
            405                 410                 415

Phe Thr Ser Ile Phe Ile Ala Glu Met Cys Leu Lys Ile Ile Ala Leu
        420                 425                 430

Asp Pro Tyr His Tyr Phe Arg Arg Gly Trp Asn Ile Phe Asp Ser Ile
    435                 440                 445

Val Ala Leu Leu Ser Phe Ala Asp Val Met Asn Cys Val Leu Gln Lys
450                 455                 460

Arg Ser Trp Pro Phe Leu Arg Ser Phe Arg Val Leu Arg Val Phe Lys
465                 470                 475                 480

Leu Ala Lys Ser Trp Pro Thr Leu Asn Thr Leu Ile Lys Ile Ile Gly
            485                 490                 495

Asn Ser Val Gly Ala Leu Gly Ser Leu Thr Val Val Leu Val Ile Val
        500                 505                 510

Ile Phe Ile Phe Ser Val Val Gly Met Gln Leu Phe Gly Arg Ser Phe
    515                 520                 525

Asn Ser Gln Lys Ser Pro Lys Leu Cys Asn Pro Thr Gly Pro Thr Val
530                 535                 540

Ser Cys Leu Arg His Trp His Met Gly Asp Phe Trp His Ser Phe Leu
545                 550                 555                 560

Val Val Phe Arg Ile Leu Cys Gly Glu Trp Ile Glu Asn Met Trp Glu
            565                 570                 575

Cys Met Gln Glu Ala Asn Ala Ser Ser Ser Leu Cys Val Ile Val Phe
        580                 585                 590

Ile Leu Ile Thr Val Ile Gly Lys Leu Val Val Leu Asn Leu Phe Ile
    595                 600                 605

Ala Leu Leu Leu Asn Ser Phe Ser Asn Glu Glu Arg Asn Gly Asn Leu
610                 615                 620

Glu Gly Glu Ala Arg Lys Thr Lys Val Gln Leu Ala Leu Asp Arg Phe
625                 630                 635                 640

Arg Arg Ala Phe Cys Phe Val Arg His Thr Leu Glu His Phe Cys His
            645                 650                 655

Lys Trp Cys Arg Lys Gln Asn Leu Pro Gln Gln Lys Glu Val Ala Gly
        660                 665                 670

Gly Cys Ala Ala Gln Ser Lys Asp Ile Ile Pro Leu Val Met Glu Met
    675                 680                 685

Lys Arg Gly Ser Glu Thr Gln Glu Glu Leu Gly Ile Leu Thr Ser Val
690                 695                 700

Pro Lys Thr Leu Gly Val Arg His Asp Trp Thr Trp Leu Ala Pro Leu
705                 710                 715                 720
```

```
Ala Glu Glu Asp Asp Val Glu Phe Ser Gly Asp Asn Ala Gln
            725                 730                 735

Arg Ile Thr Gln Pro Glu Pro Glu Gln Gln Ala Tyr Glu Leu His Gln
            740                 745                 750

Glu Asn Lys Lys Pro Thr Ser Gln Arg Val Gln Ser Val Glu Ile Asp
            755                 760                 765

Met Phe Ser Glu Asp Glu Pro His Leu Thr Ile Gln Asp Pro Arg Lys
770                 775                 780

Lys Ser Asp Val Thr Ser Ile Leu Ser Glu Cys Ser Thr Ile Asp Leu
785                 790                 795                 800

Gln Asp Gly Phe Gly Trp Leu Pro Glu Met Val Pro Lys Lys Gln Pro
                805                 810                 815

Glu Arg Cys Leu Pro Lys Gly Phe Gly Cys Cys Phe Pro Cys Cys Ser
            820                 825                 830

Val Asp Lys Arg Lys Pro Pro Trp Val Ile Trp Trp Asn Leu Arg Lys
835                 840                 845

Thr Cys Tyr Gln Ile Val Lys His Ser Trp Phe Glu Ser Phe Ile Ile
        850                 855                 860

Phe Val Ile Leu Leu Ser Ser Gly Ala Leu Ile Phe Glu Asp Val His
865                 870                 875                 880

Leu Glu Asn Gln Pro Lys Ile Gln Glu Leu Leu Asn Cys Thr Asp Ile
                885                 890                 895

Ile Phe Thr His Ile Phe Ile Leu Glu Met Val Leu Lys Trp Val Ala
            900                 905                 910

Phe Gly Phe Gly Lys Tyr Phe Thr Ser Ala Trp Cys Cys Leu Asp Phe
        915                 920                 925

Ile Ile Val Ile Val Ser Val Thr Thr Leu Ile Asn Leu Met Glu Leu
    930                 935                 940

Lys Ser Phe Arg Thr Leu Arg Ala Leu Arg Pro Leu Arg Ala Leu Ser
945                 950                 955                 960

Gln Phe Glu Gly Met Lys Val Val Asn Ala Leu Ile Gly Ala Ile
                965                 970                 975

Pro Ala Ile Leu Asn Val Leu Leu Val Cys Leu Ile Phe Trp Leu Val
            980                 985                 990

Phe Cys Ile Leu Gly Val Tyr Phe Phe Ser Gly Lys Phe Gly Lys Cys
        995                 1000                1005

Ile Asn Gly Thr Asp Ser Val Ile Asn Tyr Thr Ile Ile Thr Asn Lys
    1010                1015                1020

Ser Gln Cys Glu Ser Gly Asn Phe Ser Trp Ile Asn Gln Lys Val Asn
1025                1030                1035                1040

Phe Asp Asn Val Gly Asn Ala Tyr Leu Ala Leu Leu Gln Val Ala Thr
            1045                1050                1055

Phe Lys Gly Trp Met Asp Ile Ile Tyr Ala Ala Val Asp Ser Thr Glu
        1060                1065                1070

Lys Glu Gln Gln Pro Glu Phe Glu Ser Asn Ser Leu Gly Tyr Ile Tyr
    1075                1080                1085

Phe Val Val Phe Ile Ile Phe Gly Ser Phe Phe Thr Leu Asn Leu Phe
    1090                1095                1100

Ile Gly Val Ile Ile Asp Asn Phe Asn Gln Gln Gln Lys Lys Leu Gly
1105                1110                1115                1120

Gly Gln Asp Ile Phe Met Thr Glu Glu Gln Lys Lys Tyr Tyr Asn Ala
            1125                1130                1135
```

```
Met Lys Lys Leu Gly Ser Lys Lys Pro Gln Lys Pro Ile Pro Arg Pro
        1140                1145                1150

Leu Asn Lys Cys Gln Gly Leu Val Phe Asp Ile Val Thr Ser Gln Ile
    1155                1160                1165

Phe Asp Ile Ile Ile Ser Leu Ile Ile Leu Asn Met Ile Ser Met
1170                1175                1180

Met Ala Glu Ser Tyr Asn Gln Pro Lys Ala Met Lys Ser Ile Leu Asp
1185                1190                1195                1200

His Leu Asn Trp Val Phe Val Val Ile Phe Thr Leu Glu Cys Leu Ile
            1205                1210                1215

Lys Ile Phe Ala Leu Arg Gln Tyr Tyr Phe Thr Asn Gly Trp Asn Leu
        1220                1225                1230

Phe Asp Cys Val Val Val Leu Leu Ser Ile Val
        1235                1240

<210> SEQ ID NO 9
<211> LENGTH: 20
<212> TYPE: DNA
<213> ORGANISM: Artificial Sequence
<220> FEATURE:
<221> NAME/KEY: variation
<222> LOCATION: (6)
<223> OTHER INFORMATION: r = a or g
<220> FEATURE:
<223> OTHER INFORMATION: Description of Artificial Sequence:   rat NaN
      forward primer no. 1

<400> SEQUENCE: 9
gacccrtgga attggttgga                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:   rat NaN
      forward primer no. 2

<400> SEQUENCE: 10
aatccctgga attggttgga                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:   rat NaN
      forward primer no. 3

<400> SEQUENCE: 11
gacccgtgga actggttaga                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:   rat NaN
      forward primer no. 4

<400> SEQUENCE: 12
gatctttgga actggcttga                                              20
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: rat Nan
      forward primer no. 5

<400> SEQUENCE: 13
aacatagtgc tggagttcag g                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: rat NaN
      forward primer no. 6

<400> SEQUENCE: 14
gtggcctttg gattccggag g                                           21

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: rat NaN
      reverse primer no. 1

<400> SEQUENCE: 15
caagaaggcc cagctgaagg tgtc                                        24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: rat NaN
      reverse primer no. 2

<400> SEQUENCE: 16
gaggaatgcc cacgcaaagg aatc                                        24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: rat NaN
      reverse primer no. 3

<400> SEQUENCE: 17
aagaagggac cagccaaagt tgtc                                        24

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: rat NaN
      reverse primer no. 4
<220> FEATURE:
<221> NAME/KEY: variation
<222> LOCATION: (3)..(13)
<223> OTHER INFORMATION: y at position 3 = c or t; r at position 9 = a
      or g; n at position 12 = a or c or g or t; w at position 13 = a
      or t.

```
<400> SEQUENCE: 18
acytccatrc anwcccacat                                          20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: rat NaN
      reverse primer no. 5, r = a or g
<220> FEATURE:
<221> NAME/KEY: variation
<222> LOCATION: (3)..(15)
<223> OTHER INFORMATION: r at positions 3, 6 and 15 = a or g; n at
      position 9 = a or c or g or t.

<400> SEQUENCE: 19
agraartcna gccarcacca                                          20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: rat NaN
      reverse primer no. 6

<400> SEQUENCE: 20
tctgctgccg agccaggta                                           19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: rat NaN
      reverse primer no. 7

<400> SEQUENCE: 21
ctgagataac tgaaatcgcc                                          20

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: primer,
      Marathon AP-1

<400> SEQUENCE: 22
ccatcctaat acgactcact atagggc                                  27

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: primer,
      Marathon AP-2

<400> SEQUENCE: 23
actcactata gggctcgagc ggc                                      23

<210> SEQ ID NO 24
<211> LENGTH: 23
<212> TYPE: DNA
<213> ORGANISM: Artificial Sequence
```

```
<220> FEATURE:
<223> OTHER INFORMATION: Description of Artificial Sequence: mouse NaN
      forward primer

<400> SEQUENCE: 24
ccctgctgcg ctcggtgaag aag                                                23

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: mouse NaN
      reverse primer

<400> SEQUENCE: 25
gacaaagtag atcccagagg                                                    20

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: human NaN
      forward primer

<400> SEQUENCE: 26
ctcagtagtt ggcatgc                                                       17

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: human NaN
      reverse primer

<400> SEQUENCE: 27
ggaaagaagc acgaccacac agtc                                               24

<210> SEQ ID NO 28
<211> LENGTH: 94
<212> TYPE: PRT
<213> ORGANISM: Rattus norvegicus
<220> FEATURE:
<223> OTHER INFORMATION: C-terminal truncated rat NaN

<400> SEQUENCE: 28

Ala Ala Gly Gln Ala Met Arg Lys Gln Gly Asp Ile Leu Gly Pro Asn
 1               5                  10                  15

Ile His Gln Phe Ser Gln Ser Ser Glu Thr Pro Phe Leu Gly Cys Pro
                20                  25                  30

Gln Gln Arg Thr Cys Val Ser Phe Val Arg Pro Gln Arg Val Leu Arg
            35                  40                  45

Val Pro Trp Phe Pro Ala Trp Arg Thr Val Thr Phe Leu Ser Arg Pro
        50                  55                  60

Arg Ser Ser Glu Ser Ser Ala Trp Leu Gly Leu Val Glu Ser Ser Gly
 65                  70                  75                  80

Trp Ser Gly Leu Pro Gly Glu Ser Gly Pro Ser Ser Leu Leu
                85                  90
```

<210> SEQ ID NO 29
<211> LENGTH: 211
<212> TYPE: DNA
<213> ORGANISM: Mus musculus

<400> SEQUENCE: 29

| | |
|---|---|
| agtttaatgt tgagtgaatt gtggtggtga tttcccactt gaggcctttg tgttaaagcc | 60 |
| caatgtgtgt gtgtgtgtgt gtgtgtgtgt gtgtgtgtgt gtgtgtggtt | 120 |
| gggggtggt ggcagagtct ggtattggta aggtgagagc aatcccagaa cgtccacctg | 180 |
| ctcttccatt ttattaatca ggcaggcctc t | 211 |

<210> SEQ ID NO 30
<211> LENGTH: 242
<212> TYPE: DNA
<213> ORGANISM: Mus musculus
<220> FEATURE:
<221> NAME/KEY: unsure
<222> LOCATION: (132)..(234)
<223> OTHER INFORMATION: n at positions 132, 159, 178, 184, 203 and
      234 = a or c or g or t.

<400> SEQUENCE: 30

| | |
|---|---|
| gtaagccact ggctcttaac taaaatgctc gttggcatta gaacatttct gagctggggt | 60 |
| ggtggtggtg gtggtggtgg tggtggtggt ggtggtggtg gtggtggtgg tgatggtggt | 120 |
| ggtggaggtg gnggtggagg tggtggctgt ggtggtggng gtggtggtgg tggtggangt | 180 |
| ggangtggtg gcgtggtggt ggnggtggtg gtggaggtgg tggctgtggt ggtngtggtg | 240 |
| gc | 242 |

<210> SEQ ID NO 31
<211> LENGTH: 200
<212> TYPE: DNA
<213> ORGANISM: Mus musculus

<400> SEQUENCE: 31

| | |
|---|---|
| tgtgcatgct tgattcccag ctcctatggt ctgattactc ggtccttagg agcaaggcca | 60 |
| gactgtccac cctgacacac acacacacac acacacacac acacacacac acacacacac | 120 |
| acagtgtaga gaattacctc attcttggag tttctctgga aaaggaatgt ctcaaagcca | 180 |
| agttcacaga gcaacagctg | 200 |

<210> SEQ ID NO 32
<211> LENGTH: 181
<212> TYPE: DNA
<213> ORGANISM: Mus musculus

<400> SEQUENCE: 32

| | |
|---|---|
| tgttagaaac tctaagacaa tgaagcacca tgctggaaat aagagcacaa actctttctt | 60 |
| catgcattac ccactgcttg tgctttcacc ttagtgctcg tgctctctct ttctctctct | 120 |
| ctctctctct ctctctctct ctctctctct ctctctctct ctctctcttt ttttttttt | 180 |
| t | 181 |

<210> SEQ ID NO 33
<211> LENGTH: 128
<212> TYPE: DNA
<213> ORGANISM: Mus musculus

```
<400> SEQUENCE: 33
cacacacaca cacacacaca cacacacaca cacacacaca gagaaacact gtcgcagtca    60
tacatataaa gataaataca tcttaaaaaa agaaccatgt gattgagtta taaatattc    120 caacttat                                                            128

<210> SEQ ID NO 34
<211> LENGTH: 200
<212> TYPE: DNA
<213> ORGANISM: Mus musculus

<400> SEQUENCE: 34
aggtcatttc ctctgcagtg tgcttggcag gaaaaacttc ctggctattc aagtcagtgc    60
cctgcttgat catccatgta tcacacacac acaaaacaaa caaacaaaca aacaaaaccc   120
tggggaagaa ggaagaggtt aagcacatag gcagagagca gccaggctga ctcagagcaa   180
acacctgatc attcttccat                                               200

<210> SEQ ID NO 35
<211> LENGTH: 158
<212> TYPE: DNA
<213> ORGANISM: Mus musculus
<220> FEATURE:
<221> NAME/KEY: unsure
<222> LOCATION: (119)..(125)
<223> OTHER INFORMATION: n = a or c or g or t.

<400> SEQUENCE: 35
gtgctgggat caaaggcgtg cgccgccacc acgcccggcc ccttttttatg tttcaaattt    60 acttttatca tgtgcacgtg tgtgggtgcg tgcatgtgtg tgcgtgcgtg tgcgtgtgng   120
tgtgngtgtg tgtgtgtgtg tgtgtgtgtg tgtgtgtg                           158

<210> SEQ ID NO 36
<211> LENGTH: 113
<212> TYPE: DNA
<213> ORGANISM: Mus musculus

<400> SEQUENCE: 36
cacacacaca cacacacaca cacacacaca cacacacaca cacacacaca cacacacttg    60
catctttgag ttaattggat aggctgagtc ttacaccgga atcatactgt tgc          113

<210> SEQ ID NO 37
<211> LENGTH: 200
<212> TYPE: DNA
<213> ORGANISM: Mus musculus

<400> SEQUENCE: 37
ccaatgagag actcttgtct caaaaaagcc atggtgtcca gatcctgagg aataacacct    60
aagaatgtgc tctggcctga aaacacacac acacacacac acacacacac acacacacac   120
agttttattt atttatttaa aaaaatatgt ctctaggcat tgctgaaatg tctcctacag   180
gattaagtca accagagcca                                               200

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: protein
      seq. basis for rat NaN reverse primers
```

```
<220> FEATURE:
<221> NAME/KEY: VARIANT
<222> LOCATION: (3)
<223> OTHER INFORMATION: Xaa = Val or Asp

<400> SEQUENCE: 38

Met Trp Xaa Cys Met Glu Val
 1               5

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence:  rat NaN
      forward primer

<400> SEQUENCE: 39
ccctgctgcg ctcggtgaag aa                                                 22

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence:  a.a. seq.
      used to derive epitope for polyclonal antibody

<400> SEQUENCE: 40

Cys Gly Pro Asn Pro Ala Ser Asn Lys Asp Cys Phe Glu Lys Glu Lys
 1               5                  10                  15

Asp Ser Glu Asp
            20

<210> SEQ ID NO 41
<211> LENGTH: 5860
<212> TYPE: DNA
<213> ORGANISM: Homo sapiens
<220> FEATURE:
<221> NAME/KEY: CDS
<222> LOCATION: (31)..(5403)
<223> OTHER INFORMATION: full length cDNA sequence for human NaN

<400> SEQUENCE: 41
atctgctcaa gccaggaatc tcgggtgaag atg gat gac aga tgc tac cca gta       54
                                Met Asp Asp Arg Cys Tyr Pro Val
                                 1               5 atc ttt cca gat gag cgg aat ttc cgc ccc ttc act tcc gac tct ctg       102
Ile Phe Pro Asp Glu Arg Asn Phe Arg Pro Phe Thr Ser Asp Ser Leu
        10                  15                  20 gct gca att gag aag cgg att gcc atc caa aag gag aaa aag aag tct       150
Ala Ala Ile Glu Lys Arg Ile Ala Ile Gln Lys Glu Lys Lys Lys Ser
 25                  30                  35                  40 aaa gac cag aca gga gaa gta ccc cag cct cgg cct cag ctt gac cta       198
Lys Asp Gln Thr Gly Glu Val Pro Gln Pro Arg Pro Gln Leu Asp Leu
                45                  50                  55 aag gcc tcc agg aag ttg ccc aag ctc tat ggc gac att cct cgt gag       246
Lys Ala Ser Arg Lys Leu Pro Lys Leu Tyr Gly Asp Ile Pro Arg Glu
            60                  65                  70 ctc ata gga aag cct ctg gaa gac ttg gac cca ttc tac cga aat cat       294
Leu Ile Gly Lys Pro Leu Glu Asp Leu Asp Pro Phe Tyr Arg Asn His
        75                  80                  85 aag aca ttt atg gtg tta aac aga aag agg aca atc tac cgc ttc agt       342
Lys Thr Phe Met Val Leu Asn Arg Lys Arg Thr Ile Tyr Arg Phe Ser
 90                  95                 100
```

-continued

| | | |
|---|---|---|
| gcc aag cat gcc ttg ttc att ttt ggg cct ttc aat tca atc aga agt<br>Ala Lys His Ala Leu Phe Ile Phe Gly Pro Phe Asn Ser Ile Arg Ser<br>105              110              115              120 | 390 |
| tta gcc att aga gtc tca gtc cat tca ttg ttc agc atg ttc att atc<br>Leu Ala Ile Arg Val Ser Val His Ser Leu Phe Ser Met Phe Ile Ile<br>              125              130              135 | 438 |
| ggc acc gtt atc atc aac tgc gtg ttc atg gct aca ggg cct gct aaa<br>Gly Thr Val Ile Ile Asn Cys Val Phe Met Ala Thr Gly Pro Ala Lys<br>           140               145              150 | 486 |
| aac agc aac agt aac aat act gac att gca gag tgt gtc ttc act ggg<br>Asn Ser Asn Ser Asn Asn Thr Asp Ile Ala Glu Cys Val Phe Thr Gly<br>              155              160              165 | 534 |
| att tat att ttt gaa gct ttg att aaa ata ttg gca aga ggt ttc att<br>Ile Tyr Ile Phe Glu Ala Leu Ile Lys Ile Leu Ala Arg Gly Phe Ile<br>170              175              180 | 582 |
| ctg gat gag ttt tct ttc ctt cga gat cca tgg aac tgg ctg gac tcc<br>Leu Asp Glu Phe Ser Phe Leu Arg Asp Pro Trp Asn Trp Leu Asp Ser<br>185              190              195              200 | 630 |
| att gtc att gga ata gcg att gtg tca tat att cca gga atc acc atc<br>Ile Val Ile Gly Ile Ala Ile Val Ser Tyr Ile Pro Gly Ile Thr Ile<br>                  205              210              215 | 678 |
| aaa cta ttg ccc ctg cgt acc ttc cgt gtg ttc aga gct ttg aaa gca<br>Lys Leu Leu Pro Leu Arg Thr Phe Arg Val Phe Arg Ala Leu Lys Ala<br>            220               225              230 | 726 |
| att tca gta gtt tca cgt ctg aag gtc atc gtg ggg gcc ttg cta cgc<br>Ile Ser Val Val Ser Arg Leu Lys Val Ile Val Gly Ala Leu Leu Arg<br>              235              240              245 | 774 |
| tct gtg aag aag ctg gtc aac gtg att atc ctc acc ttc ttt tgc ctc<br>Ser Val Lys Lys Leu Val Asn Val Ile Ile Leu Thr Phe Phe Cys Leu<br>250              255              260 | 822 |
| agc atc ttt gcc ctg gta ggt cag cag ctc ttc atg gga agt ctg aac<br>Ser Ile Phe Ala Leu Val Gly Gln Gln Leu Phe Met Gly Ser Leu Asn<br>265              270              275              280 | 870 |
| ctg aaa tgc atc tcg agg gac tgt aaa aat atc agt aac ccg gaa gct<br>Leu Lys Cys Ile Ser Arg Asp Cys Lys Asn Ile Ser Asn Pro Glu Ala<br>                  285              290              295 | 918 |
| tat gac cat tgc ttt gaa aag aaa gaa aat tca cct gaa ttc aaa atg<br>Tyr Asp His Cys Phe Glu Lys Lys Glu Asn Ser Pro Glu Phe Lys Met<br>            300               305              310 | 966 |
| tgt ggc atc tgg atg ggt aac agt gcc tgt tcc ata caa tat gaa tgt<br>Cys Gly Ile Trp Met Gly Asn Ser Ala Cys Ser Ile Gln Tyr Glu Cys<br>              315              320              325 | 1014 |
| aag cac acc aaa att aat cct gac tat aat tat acg aat ttt gac aac<br>Lys His Thr Lys Ile Asn Pro Asp Tyr Asn Tyr Thr Asn Phe Asp Asn<br>330              335              340 | 1062 |
| ttt ggc tgg tct ttt ctt gcc atg ttc cgg ctg atg acc caa gat tcc<br>Phe Gly Trp Ser Phe Leu Ala Met Phe Arg Leu Met Thr Gln Asp Ser<br>345              350              355              360 | 1110 |
| tgg gag aag ctt tat caa cag acc ctg cgt act act ggg ctc tac tca<br>Trp Glu Lys Leu Tyr Gln Gln Thr Leu Arg Thr Thr Gly Leu Tyr Ser<br>                  365              370              375 | 1158 |
| gtc ttc ttc ttc att gtg gtc att ttc ctg ggc tcc ttc tac ctg att<br>Val Phe Phe Phe Ile Val Val Ile Phe Leu Gly Ser Phe Tyr Leu Ile<br>              380               385              390 | 1206 |
| aac tta acc ctg gct gtt gtt acc atg gca tat gag gag cag aac aag<br>Asn Leu Thr Leu Ala Val Val Thr Met Ala Tyr Glu Glu Gln Asn Lys<br>            395               400              405 | 1254 |
| aat gta gct gca gag ata gag gcc aag gaa aag atg ttt cag gaa gcc<br>Asn Val Ala Ala Glu Ile Glu Ala Lys Glu Lys Met Phe Gln Glu Ala<br>410              415              420 | 1302 |

```
cag cag ctg tta aag gag gaa aag gag gct ctg gtt gcc atg gga att          1350
Gln Gln Leu Leu Lys Glu Glu Lys Glu Ala Leu Val Ala Met Gly Ile
425                 430                 435                 440 gac aga agt tca ctt act tcc ctt gaa aca tca tat ttt acc cca aaa          1398
Asp Arg Ser Ser Leu Thr Ser Leu Glu Thr Ser Tyr Phe Thr Pro Lys
            445                 450                 455 aag aga aag ctc ttt ggt aat aag aaa agg aag tcc ttc ttt ttg aga          1446
Lys Arg Lys Leu Phe Gly Asn Lys Lys Arg Lys Ser Phe Phe Leu Arg
        460                 465                 470 gag tct ggg aaa gac cag cct cct ggg tca gat tct gat gaa gat tgc          1494
Glu Ser Gly Lys Asp Gln Pro Pro Gly Ser Asp Ser Asp Glu Asp Cys
    475                 480                 485 caa aaa aag cca cag ctc cta gag caa acc aaa cga ctg tcc cag aat          1542
Gln Lys Lys Pro Gln Leu Leu Glu Gln Thr Lys Arg Leu Ser Gln Asn
490                 495                 500 cta tca ctg gac cac ttt gat gag cat gga gat cct ctc caa agg cag          1590
Leu Ser Leu Asp His Phe Asp Glu His Gly Asp Pro Leu Gln Arg Gln
505                 510                 515                 520 aga gca ctg agt gct gtc agc atc ctc acc atc acc atg aag gaa caa          1638
Arg Ala Leu Ser Ala Val Ser Ile Leu Thr Ile Thr Met Lys Glu Gln
            525                 530                 535 gaa aaa tca caa gag cct tgt ctc cct tgt gga gaa aac ctg gca tcc          1686
Glu Lys Ser Gln Glu Pro Cys Leu Pro Cys Gly Glu Asn Leu Ala Ser
        540                 545                 550 aag tac ctc gtg tgg aac tgt tgc ccc cag tgg ctg tgc gtt aag aag          1734
Lys Tyr Leu Val Trp Asn Cys Cys Pro Gln Trp Leu Cys Val Lys Lys
    555                 560                 565 gtc ctg aga act gtg atg act gac ccg ttt act gag ctg gcc atc acc          1782
Val Leu Arg Thr Val Met Thr Asp Pro Phe Thr Glu Leu Ala Ile Thr
570                 575                 580 atc tgc atc atc atc aac act gtc ttc ttg gcc atg gag cat cac aag          1830
Ile Cys Ile Ile Ile Asn Thr Val Phe Leu Ala Met Glu His His Lys
585                 590                 595                 600 atg gag gcc agt ttt gag aag atg ttg aat ata ggg aat ttg gtt ttc          1878
Met Glu Ala Ser Phe Glu Lys Met Leu Asn Ile Gly Asn Leu Val Phe
            605                 610                 615 act agc att ttt ata gca gaa atg tgc cta aaa atc att gcg ctc gat          1926
Thr Ser Ile Phe Ile Ala Glu Met Cys Leu Lys Ile Ile Ala Leu Asp
        620                 625                 630 ccc tac cac tac ttt cgc cga ggc tgg aac att ttt gac agc att gtt          1974
Pro Tyr His Tyr Phe Arg Arg Gly Trp Asn Ile Phe Asp Ser Ile Val
    635                 640                 645 gct ctt ctg agt ttt gca gat gta atg aac tgt gta ctt caa aag aga          2022
Ala Leu Leu Ser Phe Ala Asp Val Met Asn Cys Val Leu Gln Lys Arg
650                 655                 660 agc tgg cca ttc ttg cgt tcc ttc aga gtg ctc agg gtc ttc aag tta          2070
Ser Trp Pro Phe Leu Arg Ser Phe Arg Val Leu Arg Val Phe Lys Leu
665                 670                 675                 680 gcc aaa tcc tgg cca act ttg aac aca cta att aag ata atc ggc aac          2118
Ala Lys Ser Trp Pro Thr Leu Asn Thr Leu Ile Lys Ile Ile Gly Asn
            685                 690                 695 tct gtc gga gcc ctt gga agc ctg act gtg gtc ctg gtc att gtg atc          2166
Ser Val Gly Ala Leu Gly Ser Leu Thr Val Val Leu Val Ile Val Ile
        700                 705                 710 ttt att ttc tca gta gtt ggc atg cag ctt ttt ggc cgt agc ttc aat          2214
Phe Ile Phe Ser Val Val Gly Met Gln Leu Phe Gly Arg Ser Phe Asn
    715                 720                 725 tcc caa aag agt cca aaa ctc tgt aac ccg aca ggc ccg aca gtc tca          2262
Ser Gln Lys Ser Pro Lys Leu Cys Asn Pro Thr Gly Pro Thr Val Ser
730                 735                 740
```

-continued

| | |
|---|---|
| tgt tta cgg cac tgg cac atg ggg gat ttc tgg cac tcc ttc cta gtg<br>Cys Leu Arg His Trp His Met Gly Asp Phe Trp His Ser Phe Leu Val<br>745                                     750                            755                          760 | 2310 |
| gta ttc cgc atc ctc tgc ggg gaa tgg atc gaa aat atg tgg gaa tgt<br>Val Phe Arg Ile Leu Cys Gly Glu Trp Ile Glu Asn Met Trp Glu Cys<br>               765                            770                           775 | 2358 |
| atg caa gaa gcg aat gca tca tca ttg tgt gtt att gtc ttc ata<br>Met Gln Glu Ala Asn Ala Ser Ser Ser Leu Cys Val Ile Val Phe Ile<br>         780                              785                           790 | 2406 |
| ttg atc acg gtg ata gga aaa ctt gtg gtg ctc aac ctc ttc att gcc<br>Leu Ile Thr Val Ile Gly Lys Leu Val Val Leu Asn Leu Phe Ile Ala<br>             795                            800                         805 | 2454 |
| tta ctg ctc aat tcc ttt agc aat gag gaa aga aat gga aac tta gaa<br>Leu Leu Leu Asn Ser Phe Ser Asn Glu Glu Arg Asn Gly Asn Leu Glu<br>810                                 815                            820 | 2502 |
| gga gag gcc agg aaa act aaa gtc cag tta gca ctg gat cga ttc cgc<br>Gly Glu Ala Arg Lys Thr Lys Val Gln Leu Ala Leu Asp Arg Phe Arg<br>825                                 830                            835             840 | 2550 |
| cgg gct ttt tgt ttt gtg aga cac act ctt gag cat ttc tgt cac aag<br>Arg Ala Phe Cys Phe Val Arg His Thr Leu Glu His Phe Cys His Lys<br>                       845                           850                         855 | 2598 |
| tgg tgc agg aag caa aac tta cca cag caa aaa gag gtg gca gga ggc<br>Trp Cys Arg Lys Gln Asn Leu Pro Gln Gln Lys Glu Val Ala Gly Gly<br>             860                            865                         870 | 2646 |
| tgt gct gca caa agc aaa gac atc att ccc ctg gtc atg gag atg aaa<br>Cys Ala Ala Gln Ser Lys Asp Ile Ile Pro Leu Val Met Glu Met Lys<br>875                                 880                            885 | 2694 |
| agg ggc tca gag acc cag gag gag ctt ggt ata cta acc tct gta cca<br>Arg Gly Ser Glu Thr Gln Glu Glu Leu Gly Ile Leu Thr Ser Val Pro<br>         890                              895                         900 | 2742 |
| aag acc ctg ggc gtc agg cat gat tgg act tgg ttg gca cca ctt gcg<br>Lys Thr Leu Gly Val Arg His Asp Trp Thr Trp Leu Ala Pro Leu Ala<br>905                                 910                            915             920 | 2790 |
| gag gag gaa gat gac gtt gaa ttt tct ggt gaa gat aat gca cag cgc<br>Glu Glu Glu Asp Asp Val Glu Phe Ser Gly Glu Asp Asn Ala Gln Arg<br>                       925                           930                         935 | 2838 |
| atc aca caa cct gag cct gaa caa cag gcc tat gag ctc cat cag gag<br>Ile Thr Gln Pro Glu Pro Glu Gln Gln Ala Tyr Glu Leu His Gln Glu<br>             940                            945                         950 | 2886 |
| aac aag aag ccc acg agc cag aga gtt caa agt gtg gaa att gac atg<br>Asn Lys Lys Pro Thr Ser Gln Arg Val Gln Ser Val Glu Ile Asp Met<br>                 955                            960                           965 | 2934 |
| ttc tct gaa gat gag cct cat ctg acc ata cag gat ccc cga aag aag<br>Phe Ser Glu Asp Glu Pro His Leu Thr Ile Gln Asp Pro Arg Lys Lys<br>970                                 975                            980 | 2982 |
| tct gat gtt acc agt ata cta tca gaa tgt agc acc att gat ctt cag<br>Ser Asp Val Thr Ser Ile Leu Ser Glu Cys Ser Thr Ile Asp Leu Gln<br>985                                 990                            995             1000 | 3030 |
| gat ggc ttt gga tgg tta cct gag atg gtt ccc aaa aag caa cca gag<br>Asp Gly Phe Gly Trp Leu Pro Glu Met Val Pro Lys Lys Gln Pro Glu<br>                     1005                          1010                        1015 | 3078 |
| aga tgt ttg ccc aaa ggc ttt ggt tgc tgc ttt cca tgc tgt agc gtg<br>Arg Cys Leu Pro Lys Gly Phe Gly Cys Cys Phe Pro Cys Cys Ser Val<br>                  1020                         1025                        1030 | 3126 |
| gac aag aga aag cct ccc tgg gtc att tgg tgg aac ctg cgg aaa acc<br>Asp Lys Arg Lys Pro Pro Trp Val Ile Trp Trp Asn Leu Arg Lys Thr<br>              1035                         1040                       1045 | 3174 |
| tgc tac caa ata gtg aaa cac agc tgg ttt gag agc ttt att atc ttt<br>Cys Tyr Gln Ile Val Lys His Ser Trp Phe Glu Ser Phe Ile Ile Phe<br>     1050                         1055                       1060 | 3222 |

```
gtg att ctg ctg agc agt ggg gca ctg ata ttt gaa gat gtt cac ctt   3270
Val Ile Leu Leu Ser Ser Gly Ala Leu Ile Phe Glu Asp Val His Leu
1065                1070                1075                1080 gag aac caa ccc aaa atc caa gaa tta cta aat tgt act gac att att   3318
Glu Asn Gln Pro Lys Ile Gln Glu Leu Leu Asn Cys Thr Asp Ile Ile
            1085                1090                1095 ttt aca cat att ttt atc ctg gag atg gta cta aaa tgg gta gcc ttc   3366
Phe Thr His Ile Phe Ile Leu Glu Met Val Leu Lys Trp Val Ala Phe
1100                1105                1110 gga ttt gga aag tat ttc acc agt gcc tgg tgc tgc ttg gat ttc atc   3414
Gly Phe Gly Lys Tyr Phe Thr Ser Ala Trp Cys Cys Leu Asp Phe Ile
        1115                1120                1125 att gtg att gtc tct gtg acc acc ctc att aac tta atg gaa ttg aag   3462
Ile Val Ile Val Ser Val Thr Thr Leu Ile Asn Leu Met Glu Leu Lys
1130                1135                1140 tcc ttc cgg act cta cga gca ctg agg cct ctt cgt gcg ctg tcc cag   3510
Ser Phe Arg Thr Leu Arg Ala Leu Arg Pro Leu Arg Ala Leu Ser Gln
1145                1150                1155                1160 ttt gaa gga atg aag gtg gtg gtc aat gct ctc ata ggt gcc ata cct   3558
Phe Glu Gly Met Lys Val Val Val Asn Ala Leu Ile Gly Ala Ile Pro
            1165                1170                1175 gcc att ctg aat gtt ttg ctt gtc tgc ctc att ttc tgg ctc gta ttt   3606
Ala Ile Leu Asn Val Leu Leu Val Cys Leu Ile Phe Trp Leu Val Phe
1180                1185                1190 tgt att ctg gga gta tac ttc ttt tct gga aaa ttt ggg aaa tgc att   3654
Cys Ile Leu Gly Val Tyr Phe Phe Ser Gly Lys Phe Gly Lys Cys Ile
        1195                1200                1205 aat gga aca gac tca gtt ata aat tat acc atc att aca aat aaa agt   3702
Asn Gly Thr Asp Ser Val Ile Asn Tyr Thr Ile Ile Thr Asn Lys Ser
1210                1215                1220 caa tgt gaa agt ggc aat ttc tct tgg atc aac cag aaa gtc aac ttt   3750
Gln Cys Glu Ser Gly Asn Phe Ser Trp Ile Asn Gln Lys Val Asn Phe
1225                1230                1235                1240 gac aat gtg gga aat gct tac ctc gct ctg ctg caa gtg gca aca ttt   3798
Asp Asn Val Gly Asn Ala Tyr Leu Ala Leu Leu Gln Val Ala Thr Phe
            1245                1250                1255 aag ggc tgg atg gat att ata tat gca gct gtt gat tcc aca gag aaa   3846
Lys Gly Trp Met Asp Ile Ile Tyr Ala Ala Val Asp Ser Thr Glu Lys
        1260                1265                1270 gaa caa cag cca gag ttt gag agc aat tca ctc ggt tac att tac ttc   3894
Glu Gln Gln Pro Glu Phe Glu Ser Asn Ser Leu Gly Tyr Ile Tyr Phe
1275                1280                1285 gta gtc ttt atc atc ttt ggc tca ttc ttc act ctg aat ctc ttc att   3942
Val Val Phe Ile Ile Phe Gly Ser Phe Phe Thr Leu Asn Leu Phe Ile
1290                1295                1300 ggc gtt atc att gac aac ttc aac caa cag cag aaa aag tta ggt ggc   3990
Gly Val Ile Ile Asp Asn Phe Asn Gln Gln Gln Lys Lys Leu Gly Gly
1305                1310                1315                1320 caa gac att ttt atg aca gaa gaa cag aag aaa tac tat aat gca atg   4038
Gln Asp Ile Phe Met Thr Glu Glu Gln Lys Lys Tyr Tyr Asn Ala Met
            1325                1330                1335 aaa aaa tta gga tcc aaa aaa cct caa aaa ccc att cca cgg cct ctg   4086
Lys Lys Leu Gly Ser Lys Lys Pro Gln Lys Pro Ile Pro Arg Pro Leu
        1340                1345                1350 aac aaa tgt caa ggt ctc gtg ttc gac ata gtc aca agc cag atc ttt   4134
Asn Lys Cys Gln Gly Leu Val Phe Asp Ile Val Thr Ser Gln Ile Phe
1355                1360                1365 gac atc atc atc ata agt ctc att atc cta aac atg att agc atg atg   4182
Asp Ile Ile Ile Ile Ser Leu Ile Ile Leu Asn Met Ile Ser Met Met
1370                1375                1380
```

```
gct gaa tca tac aac caa ccc aaa gcc atg aaa tcc atc ctt gac cat       4230
Ala Glu Ser Tyr Asn Gln Pro Lys Ala Met Lys Ser Ile Leu Asp His
1385                1390                1395                1400 ctc aac tgg gtc ttt gtg gtc atc ttt acg tta gaa tgt ctc atc aaa       4278
Leu Asn Trp Val Phe Val Val Ile Phe Thr Leu Glu Cys Leu Ile Lys
        1405                1410                1415 atc ttt gct ttg agg caa tac tac ttc acc aat ggc tgg aat tta ttt       4326
Ile Phe Ala Leu Arg Gln Tyr Tyr Phe Thr Asn Gly Trp Asn Leu Phe
1420                1425                1430 gac tgt gtg gtc gtg ctt ctt tcc att gtt agt aca atg att tct acc       4374
Asp Cys Val Val Val Leu Leu Ser Ile Val Ser Thr Met Ile Ser Thr
        1435                1440                1445 ttg gaa aat cag gag cac att cct ttc cct ccg acg ctc ttc aga att       4422
Leu Glu Asn Gln Glu His Ile Pro Phe Pro Pro Thr Leu Phe Arg Ile
1450                1455                1460 gtc cgc ttg gct cgg att ggc cga atc ctg agg ctt gtc cgg gct gca       4470
Val Arg Leu Ala Arg Ile Gly Arg Ile Leu Arg Leu Val Arg Ala Ala
1465                1470                1475                1480 cga gga atc agg act ctc ctc ttt gct ctg atg atg tcg ctt cct tct       4518
Arg Gly Ile Arg Thr Leu Leu Phe Ala Leu Met Met Ser Leu Pro Ser
        1485                1490                1495 ctg ttc aac att ggt ctt cta ctc ttt ctg att atg ttt atc tat gcc       4566
Leu Phe Asn Ile Gly Leu Leu Leu Phe Leu Ile Met Phe Ile Tyr Ala
1500                1505                1510 att ctg ggt atg aac tgg ttt tcc aaa gtg aat cca gag tct gga atc       4614
Ile Leu Gly Met Asn Trp Phe Ser Lys Val Asn Pro Glu Ser Gly Ile
        1515                1520                1525 gat gac ata ttc aac ttc aag act ttt gcc agc agc atg ctc tgt ctc       4662
Asp Asp Ile Phe Asn Phe Lys Thr Phe Ala Ser Ser Met Leu Cys Leu
1530                1535                1540 ttc cag ata agc aca tca gca ggt tgg gat tcc ctg ctc agc ccc atg       4710
Phe Gln Ile Ser Thr Ser Ala Gly Trp Asp Ser Leu Leu Ser Pro Met
1545                1550                1555                1560 ctg cga tca aaa gaa tca tgt aac tct tcc tca gaa aac tgc cac ctc       4758
Leu Arg Ser Lys Glu Ser Cys Asn Ser Ser Ser Glu Asn Cys His Leu
        1565                1570                1575 cct ggc ata gcc aca tcc tac ttt gtc agt tac att atc atc tcc ttt       4806
Pro Gly Ile Ala Thr Ser Tyr Phe Val Ser Tyr Ile Ile Ile Ser Phe
1580                1585                1590 ctc att gtt gtc aac atg tac att gct gtg att tta gag aac ttc aat       4854
Leu Ile Val Val Asn Met Tyr Ile Ala Val Ile Leu Glu Asn Phe Asn
        1595                1600                1605 aca gcc act gaa gaa agt gag gac cct ttg ggt gaa gat gac ttt gac       4902
Thr Ala Thr Glu Glu Ser Glu Asp Pro Leu Gly Glu Asp Asp Phe Asp
1610                1615                1620 ata ttt tat gaa gtg tgg gaa aag ttt gac cca gaa gca aca caa ttt       4950
Ile Phe Tyr Glu Val Trp Glu Lys Phe Asp Pro Glu Ala Thr Gln Phe
1625                1630                1635                1640 atc aaa tat tct gcc ctt tct gac ttt gct gat gcc ttg cct gag cct       4998
Ile Lys Tyr Ser Ala Leu Ser Asp Phe Ala Asp Ala Leu Pro Glu Pro
        1645                1650                1655 ttg cgt gtc gca aag cca aat aaa tat caa ttt cta gta atg gac ttg       5046
Leu Arg Val Ala Lys Pro Asn Lys Tyr Gln Phe Leu Val Met Asp Leu
1660                1665                1670 ccc atg gtg agt gaa gat cgc ctc cac tgc atg gat att ctt ttc gcc       5094
Pro Met Val Ser Glu Asp Arg Leu His Cys Met Asp Ile Leu Phe Ala
        1675                1680                1685 ttc acc gct agg gta ctc ggt ggc tct gat ggc cta gat agt atg aaa       5142
Phe Thr Ala Arg Val Leu Gly Gly Ser Asp Gly Leu Asp Ser Met Lys
1690                1695                1700
```

-continued

```
gca atg atg gaa gag aag ttc atg gaa gcc aat cct ctc aag aag ttg      5190
Ala Met Met Glu Glu Lys Phe Met Glu Ala Asn Pro Leu Lys Lys Leu
1705                1710                1715                1720 tat gaa ccc ata gtc acc acc acc aag aga aag gaa gag gaa aga ggt      5238
Tyr Glu Pro Ile Val Thr Thr Thr Lys Arg Lys Glu Glu Glu Arg Gly
            1725                1730                1735 gct gct att att caa aag gcc ttt cga aag tac atg atg aag gtg acc      5286
Ala Ala Ile Ile Gln Lys Ala Phe Arg Lys Tyr Met Met Lys Val Thr
        1740                1745                1750 aag ggt gac caa ggt gac caa aat gac ttg gaa aac ggg cct cat tca      5334
Lys Gly Asp Gln Gly Asp Gln Asn Asp Leu Glu Asn Gly Pro His Ser
    1755                1760                1765 cca ctc cag act ctt tgc aat gga gac ttg tct agc ttt ggg gtg gcc      5382
Pro Leu Gln Thr Leu Cys Asn Gly Asp Leu Ser Ser Phe Gly Val Ala
1770                1775                1780 aag ggc aag gtc cac tgt gac tgagccctca cctccacgcc tacctcatag         5433
Lys Gly Lys Val His Cys Asp
1785            1790 cttcacagcc ttgccttcag cctctgagct ccaggggtca gcagcttagt gtatcaacag    5493
ggagtggatt caccaaatta gccattccat tttcttttct ggctaaaata aatgatattt    5553
caatttcatt ttaaatgata cttacagaga tataagataa ggctacttga caaccagtgg    5613
tactattata ataaggaaga agacaccagg aaggactgta aaaggacata ccaattttag    5673
gattgaaata gttcaggccg ggcgcagtgg ctcatgcctg taatcccagc actttgagag    5733
gccaaggcag gtggatcacg aggtcaagag atcgagacca tcctggccaa catgatgaaa    5793
ctccgtctct ctaaaaatac aaaaattagc tgggcatggt ggcgtgcgcc tgtagtccca    5853
ctacttg                                                             5860
```

<210> SEQ ID NO 42
<211> LENGTH: 1791
<212> TYPE: PRT
<213> ORGANISM: Homo sapiens

<400> SEQUENCE: 42

```
Met Asp Asp Arg Cys Tyr Pro Val Ile Phe Pro Asp Glu Arg Asn Phe
1               5                   10                  15

Arg Pro Phe Thr Ser Asp Ser Leu Ala Ala Ile Glu Lys Arg Ile Ala
                20                  25                  30

Ile Gln Lys Glu Lys Lys Lys Ser Lys Asp Gln Thr Gly Glu Val Pro
            35                  40                  45

Gln Pro Arg Pro Gln Leu Asp Leu Lys Ala Ser Arg Lys Leu Pro Lys
        50                  55                  60

Leu Tyr Gly Asp Ile Pro Arg Glu Leu Ile Gly Lys Pro Leu Glu Asp
65                  70                  75                  80

Leu Asp Pro Phe Tyr Arg Asn His Lys Thr Phe Met Val Leu Asn Arg
                85                  90                  95

Lys Arg Thr Ile Tyr Arg Phe Ser Ala Lys His Ala Leu Phe Ile Phe
            100                 105                 110

Gly Pro Phe Asn Ser Ile Arg Ser Leu Ala Ile Arg Val Ser Val His
        115                 120                 125

Ser Leu Phe Ser Met Phe Ile Ile Gly Thr Val Ile Ile Asn Cys Val
    130                 135                 140

Phe Met Ala Thr Gly Pro Ala Lys Asn Ser Asn Ser Asn Asn Thr Asp
145                 150                 155                 160
```

-continued

```
Ile Ala Glu Cys Val Phe Thr Gly Ile Tyr Ile Phe Glu Ala Leu Ile
                165                 170                 175
Lys Ile Leu Ala Arg Gly Phe Ile Leu Asp Glu Phe Ser Phe Leu Arg
            180                 185                 190
Asp Pro Trp Asn Trp Leu Asp Ser Ile Val Ile Gly Ile Ala Ile Val
        195                 200                 205
Ser Tyr Ile Pro Gly Ile Thr Ile Lys Leu Leu Pro Leu Arg Thr Phe
    210                 215                 220
Arg Val Phe Arg Ala Leu Lys Ala Ile Ser Val Val Ser Arg Leu Lys
225                 230                 235                 240
Val Ile Val Gly Ala Leu Leu Arg Ser Val Lys Lys Leu Val Asn Val
                245                 250                 255
Ile Ile Leu Thr Phe Phe Cys Leu Ser Ile Phe Ala Leu Val Gly Gln
            260                 265                 270
Gln Leu Phe Met Gly Ser Leu Asn Leu Lys Cys Ile Ser Arg Asp Cys
        275                 280                 285
Lys Asn Ile Ser Asn Pro Glu Ala Tyr Asp His Cys Phe Glu Lys Lys
    290                 295                 300
Glu Asn Ser Pro Glu Phe Lys Met Cys Gly Ile Trp Met Gly Asn Ser
305                 310                 315                 320
Ala Cys Ser Ile Gln Tyr Glu Cys Lys His Thr Lys Ile Asn Pro Asp
                325                 330                 335
Tyr Asn Tyr Thr Asn Phe Asp Asn Phe Gly Trp Ser Phe Leu Ala Met
            340                 345                 350
Phe Arg Leu Met Thr Gln Asp Ser Trp Glu Lys Leu Tyr Gln Gln Thr
        355                 360                 365
Leu Arg Thr Thr Gly Leu Tyr Ser Val Phe Phe Ile Val Val Ile
    370                 375                 380
Phe Leu Gly Ser Phe Tyr Leu Ile Asn Leu Thr Leu Ala Val Val Thr
385                 390                 395                 400
Met Ala Tyr Glu Glu Gln Asn Lys Asn Val Ala Ala Glu Ile Glu Ala
                405                 410                 415
Lys Glu Lys Met Phe Gln Glu Ala Gln Gln Leu Leu Lys Glu Glu Lys
            420                 425                 430
Glu Ala Leu Val Ala Met Gly Ile Asp Arg Ser Ser Leu Thr Ser Leu
        435                 440                 445
Glu Thr Ser Tyr Phe Thr Pro Lys Lys Arg Lys Leu Phe Gly Asn Lys
    450                 455                 460
Lys Arg Lys Ser Phe Phe Leu Arg Glu Ser Gly Lys Asp Gln Pro Pro
465                 470                 475                 480
Gly Ser Asp Ser Asp Glu Asp Cys Gln Lys Pro Gln Leu Leu Glu
                485                 490                 495
Gln Thr Lys Arg Leu Ser Gln Asn Leu Ser Leu Asp His Phe Asp Glu
            500                 505                 510
His Gly Asp Pro Leu Gln Arg Gln Arg Ala Leu Ser Ala Val Ser Ile
        515                 520                 525
Leu Thr Ile Thr Met Lys Glu Gln Glu Lys Ser Gln Glu Pro Cys Leu
    530                 535                 540
Pro Cys Gly Glu Asn Leu Ala Ser Lys Tyr Leu Val Trp Asn Cys Cys
545                 550                 555                 560
Pro Gln Trp Leu Cys Val Lys Lys Val Leu Arg Thr Val Met Thr Asp
                565                 570                 575
```

```
Pro Phe Thr Glu Leu Ala Ile Thr Ile Cys Ile Ile Asn Thr Val
            580                 585                 590

Phe Leu Ala Met Glu His His Lys Met Glu Ala Ser Phe Glu Lys Met
        595                 600                 605

Leu Asn Ile Gly Asn Leu Val Phe Thr Ser Ile Phe Ile Ala Glu Met
    610                 615                 620

Cys Leu Lys Ile Ile Ala Leu Asp Pro Tyr His Tyr Phe Arg Arg Gly
625                 630                 635                 640

Trp Asn Ile Phe Asp Ser Ile Val Ala Leu Leu Ser Phe Ala Asp Val
                645                 650                 655

Met Asn Cys Val Leu Gln Lys Arg Ser Trp Pro Phe Leu Arg Ser Phe
            660                 665                 670

Arg Val Leu Arg Val Phe Lys Leu Ala Lys Ser Trp Pro Thr Leu Asn
        675                 680                 685

Thr Leu Ile Lys Ile Ile Gly Asn Ser Val Gly Ala Leu Gly Ser Leu
    690                 695                 700

Thr Val Val Leu Val Ile Val Ile Phe Ile Phe Ser Val Val Gly Met
705                 710                 715                 720

Gln Leu Phe Gly Arg Ser Phe Asn Ser Gln Lys Ser Pro Lys Leu Cys
                725                 730                 735

Asn Pro Thr Gly Pro Thr Val Ser Cys Leu Arg His Trp His Met Gly
            740                 745                 750

Asp Phe Trp His Ser Phe Leu Val Val Phe Arg Ile Leu Cys Gly Glu
        755                 760                 765

Trp Ile Glu Asn Met Trp Glu Cys Met Gln Glu Ala Asn Ala Ser Ser
    770                 775                 780

Ser Leu Cys Val Ile Val Phe Ile Leu Ile Thr Val Ile Gly Lys Leu
785                 790                 795                 800

Val Val Leu Asn Leu Phe Ile Ala Leu Leu Asn Ser Phe Ser Asn
                805                 810                 815

Glu Glu Arg Asn Gly Asn Leu Glu Gly Glu Ala Arg Lys Thr Lys Val
            820                 825                 830

Gln Leu Ala Leu Asp Arg Phe Arg Arg Ala Phe Cys Phe Val Arg His
        835                 840                 845

Thr Leu Glu His Phe Cys His Lys Trp Cys Arg Lys Gln Asn Leu Pro
    850                 855                 860

Gln Gln Lys Glu Val Ala Gly Gly Cys Ala Ala Gln Ser Lys Asp Ile
865                 870                 875                 880

Ile Pro Leu Val Met Glu Met Lys Arg Gly Ser Glu Thr Gln Glu Glu
                885                 890                 895

Leu Gly Ile Leu Thr Ser Val Pro Lys Thr Leu Gly Val Arg His Asp
            900                 905                 910

Trp Thr Trp Leu Ala Pro Leu Ala Glu Glu Asp Val Glu Phe
        915                 920                 925

Ser Gly Glu Asp Asn Ala Gln Arg Ile Thr Gln Pro Glu Pro Glu Gln
    930                 935                 940

Gln Ala Tyr Glu Leu His Gln Glu Asn Lys Pro Thr Ser Gln Arg
945                 950                 955                 960

Val Gln Ser Val Glu Ile Asp Met Phe Ser Glu Asp Glu Pro His Leu
                965                 970                 975

Thr Ile Gln Asp Pro Arg Lys Lys Ser Asp Val Thr Ser Ile Leu Ser
            980                 985                 990
```

-continued

```
Glu Cys Ser Thr Ile Asp Leu Gln Asp Gly Phe Gly Trp Leu Pro Glu
        995                 1000                1005

Met Val Pro Lys Lys Gln Pro Glu Arg Cys Leu Pro Lys Gly Phe Gly
    1010                1015                1020

Cys Cys Phe Pro Cys Cys Ser Val Asp Lys Arg Lys Pro Pro Trp Val
1025                1030                1035                1040

Ile Trp Trp Asn Leu Arg Lys Thr Cys Tyr Gln Ile Val Lys His Ser
                1045                1050                1055

Trp Phe Glu Ser Phe Ile Ile Phe Val Ile Leu Leu Ser Ser Gly Ala
            1060                1065                1070

Leu Ile Phe Glu Asp Val His Leu Glu Asn Gln Pro Lys Ile Gln Glu
        1075                1080                1085

Leu Leu Asn Cys Thr Asp Ile Ile Phe Thr His Ile Phe Ile Leu Glu
    1090                1095                1100

Met Val Leu Lys Trp Val Ala Phe Gly Phe Gly Lys Tyr Phe Thr Ser
1105                1110                1115                1120

Ala Trp Cys Cys Leu Asp Phe Ile Ile Val Ile Val Ser Val Thr Thr
                1125                1130                1135

Leu Ile Asn Leu Met Glu Leu Lys Ser Phe Arg Thr Leu Arg Ala Leu
            1140                1145                1150

Arg Pro Leu Arg Ala Leu Ser Gln Phe Glu Gly Met Lys Val Val Val
        1155                1160                1165

Asn Ala Leu Ile Gly Ala Ile Pro Ala Ile Leu Asn Val Leu Leu Val
    1170                1175                1180

Cys Leu Ile Phe Trp Leu Val Phe Cys Ile Leu Gly Val Tyr Phe Phe
1185                1190                1195                1200

Ser Gly Lys Phe Gly Lys Cys Ile Asn Gly Thr Asp Ser Val Ile Asn
                1205                1210                1215

Tyr Thr Ile Ile Thr Asn Lys Ser Gln Cys Glu Ser Gly Asn Phe Ser
            1220                1225                1230

Trp Ile Asn Gln Lys Val Asn Phe Asp Asn Val Gly Asn Ala Tyr Leu
        1235                1240                1245

Ala Leu Leu Gln Val Ala Thr Phe Lys Gly Trp Met Asp Ile Ile Tyr
    1250                1255                1260

Ala Ala Val Asp Ser Thr Glu Lys Glu Gln Gln Pro Glu Phe Glu Ser
1265                1270                1275                1280

Asn Ser Leu Gly Tyr Ile Tyr Phe Val Val Phe Ile Ile Phe Gly Ser
                1285                1290                1295

Phe Phe Thr Leu Asn Leu Phe Ile Gly Val Ile Ile Asp Asn Phe Asn
            1300                1305                1310

Gln Gln Gln Lys Lys Leu Gly Gly Gln Asp Ile Phe Met Thr Glu Glu
        1315                1320                1325

Gln Lys Lys Tyr Tyr Asn Ala Met Lys Lys Leu Gly Ser Lys Lys Pro
    1330                1335                1340

Gln Lys Pro Ile Pro Arg Pro Leu Asn Lys Cys Gln Gly Leu Val Phe
1345                1350                1355                1360

Asp Ile Val Thr Ser Gln Ile Phe Asp Ile Ile Ile Ile Ser Leu Ile
                1365                1370                1375

Ile Leu Asn Met Ile Ser Met Met Ala Glu Ser Tyr Asn Gln Pro Lys
            1380                1385                1390

Ala Met Lys Ser Ile Leu Asp His Leu Asn Trp Val Phe Val Val Ile
        1395                1400                1405
```

```
Phe Thr Leu Glu Cys Leu Ile Lys Ile Phe Ala Leu Arg Gln Tyr Tyr
    1410                1415                1420

Phe Thr Asn Gly Trp Asn Leu Phe Asp Cys Val Val Leu Leu Ser
1425                1430                1435                1440

Ile Val Ser Thr Met Ile Ser Thr Leu Glu Asn Gln Glu His Ile Pro
            1445                1450                1455

Phe Pro Pro Thr Leu Phe Arg Ile Val Arg Leu Ala Arg Ile Gly Arg
        1460                1465                1470

Ile Leu Arg Leu Val Arg Ala Ala Arg Gly Ile Arg Thr Leu Leu Phe
    1475                1480                1485

Ala Leu Met Met Ser Leu Pro Ser Leu Phe Asn Ile Gly Leu Leu Leu
1490                1495                1500

Phe Leu Ile Met Phe Ile Tyr Ala Ile Leu Gly Met Asn Trp Phe Ser
1505                1510                1515                1520

Lys Val Asn Pro Glu Ser Gly Ile Asp Asp Ile Phe Asn Phe Lys Thr
            1525                1530                1535

Phe Ala Ser Ser Met Leu Cys Leu Phe Gln Ile Ser Thr Ser Ala Gly
        1540                1545                1550

Trp Asp Ser Leu Leu Ser Pro Met Leu Arg Ser Lys Glu Ser Cys Asn
    1555                1560                1565

Ser Ser Ser Glu Asn Cys His Leu Pro Gly Ile Ala Thr Ser Tyr Phe
1570                1575                1580

Val Ser Tyr Ile Ile Ile Ser Phe Leu Ile Val Val Asn Met Tyr Ile
1585                1590                1595                1600

Ala Val Ile Leu Glu Asn Phe Asn Thr Ala Thr Glu Glu Ser Glu Asp
            1605                1610                1615

Pro Leu Gly Glu Asp Asp Phe Asp Ile Phe Tyr Glu Val Trp Glu Lys
        1620                1625                1630

Phe Asp Pro Glu Ala Thr Gln Phe Ile Lys Tyr Ser Ala Leu Ser Asp
    1635                1640                1645

Phe Ala Asp Ala Leu Pro Glu Pro Leu Arg Val Ala Lys Pro Asn Lys
1650                1655                1660

Tyr Gln Phe Leu Val Met Asp Leu Pro Met Val Ser Glu Asp Arg Leu
1665                1670                1675                1680

His Cys Met Asp Ile Leu Phe Ala Phe Thr Ala Arg Val Leu Gly Gly
            1685                1690                1695

Ser Asp Gly Leu Asp Ser Met Lys Ala Met Met Glu Glu Lys Phe Met
        1700                1705                1710

Glu Ala Asn Pro Leu Lys Lys Leu Tyr Glu Pro Ile Val Thr Thr Thr
    1715                1720                1725

Lys Arg Lys Glu Glu Glu Arg Gly Ala Ala Ile Ile Gln Lys Ala Phe
1730                1735                1740

Arg Lys Tyr Met Met Lys Val Thr Lys Gly Asp Gln Gly Asp Gln Asn
1745                1750                1755                1760

Asp Leu Glu Asn Gly Pro His Ser Pro Leu Gln Thr Leu Cys Asn Gly
            1765                1770                1775

Asp Leu Ser Ser Phe Gly Val Ala Lys Gly Lys Val His Cys Asp
        1780                1785                1790

<210> SEQ ID NO 43
<211> LENGTH: 8
<212> TYPE: PRT
<213> ORGANISM: Artificial Sequence
```

```
<220> FEATURE:
<223> OTHER INFORMATION: Description of Artificial Sequence:  protein
      seq. basis for rat NaN reverse primer no. 5

<400> SEQUENCE: 43

Ala Trp Cys Trp Leu Asp Phe Leu
  1               5

<210> SEQ ID NO 44
<211> LENGTH: 23
<212> TYPE: DNA
<213> ORGANISM: Artificial Sequence
<220> FEATURE:
<223> OTHER INFORMATION: human NaN reverse primer

<400> SEQUENCE: 44
gtgccgtaaa catgagactg tcg                                              23
```